(12) United States Patent
Selemidis et al.

(10) Patent No.: US 11,319,343 B2
(45) Date of Patent: May 3, 2022

(54) METHOD OF TREATMENT

(71) Applicants: ROYAL MELBOURNE INSTITUTE OF TECHNOLOGY, Melbourne (AU); UNIVERSITY OF SOUTH AUSTRALIA, South Australia (AU); THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE); MONASH UNIVERSITY, Clayton (AU)

(72) Inventors: Stavros Selemidis, Forest Hill (AU); Doug A. Brooks, Cheltenham (AU); John O'Leary, Enniskerry (IE)

(73) Assignees: ROYAL MELBOURNE INSTITUTE OF TECHNOLOGY, Melbourne (AU); UNIVERSITY OF SOUTH AUSTRALIA, South Australia (AU); THE PROVOST, FELLOWS, FOUNDATION SCHOLARS AND THE OTHER MEMBERS OF BOARD, OF THE COLLEGE OF THE HOLY & UNDIVIDED TRINITY OF QUEEEN ELIZABETH NEAR DUBLIN, Dublin (IE); MONASH UNIVERSITY, Clayton (AU)

( * ) Notice: Subject to any disclaimer, the term of this patent is extended or adjusted under 35 U.S.C. 154(b) by 0 days.

(21) Appl. No.: 16/624,367

(22) PCT Filed: Jun. 29, 2018

(86) PCT No.: PCT/AU2018/050667
§ 371 (c)(1),
(2) Date: Dec. 19, 2019

(87) PCT Pub. No.: WO2019/000045
PCT Pub. Date: Jan. 3, 2019

(65) Prior Publication Data
US 2020/0216494 A1    Jul. 9, 2020

(30) Foreign Application Priority Data

Jun. 30, 2017 (AU) .................... 2017902545

(51) Int. Cl.
*C07K 7/06* (2006.01)
*A61K 38/00* (2006.01)
*A61P 37/00* (2006.01)
*A61P 31/00* (2006.01)
*A61P 29/00* (2006.01)
*A61P 35/00* (2006.01)
*C07K 14/705* (2006.01)

(52) U.S. Cl.
CPC ............... *C07K 7/06* (2013.01); *A61P 29/00* (2018.01); *A61P 31/00* (2018.01); *A61P 35/00* (2018.01); *A61P 37/00* (2018.01); *C07K 14/70596* (2013.01); *A61K 38/00* (2013.01); *C07K 2319/10* (2013.01)

(58) Field of Classification Search
CPC ............ C07K 7/06; C07K 38/00; C07P 37/00
See application file for complete search history.

(56) References Cited

U.S. PATENT DOCUMENTS

2013/0156814 A1* 6/2013 Barrat .................. C12N 15/117
424/278.1

FOREIGN PATENT DOCUMENTS

| EP | 2 050 762 A2 | | 4/2009 | |
| EP | 2 990 419 A1 | | 3/2016 | |
| EP | 3 006 460 | * | 4/2016 | ........... C07K 14/745 |
| WO | 02/22809 A2 | | 3/2002 | |
| WO | WO 2014/190860 | * | 4/2014 | ........... C07K 14/745 |

OTHER PUBLICATIONS

Bolhassani et al., 2016 (online Nov. 22, 2016), In vitro and in vivo delivery of therapeutic proteins using cell penetrating peptides, Peptides, 87: 50-63.*
Aguirre, et al., "Nox enzymes from fungus to fly to fish and what they tell us about Nox function in mammals", Free Radical Biology & Medicine, 49(9), pp. 1342-1353, 2010.
Allen, et al., "The NLRP3 inflammasome mediates in vivo innate immunity to influenza A virus through recognition of viral RNA", Immunity, 30(4), pp. 556-565, 2009.
Altschul, et al., "Gapped BLAST and PSI-BLAST: A new generation of protein database search programs", Nucleic Acids Research, 25(17), pp. 3389-3402, 1997.

(Continued)

*Primary Examiner* — Amber D Steele
(74) *Attorney, Agent, or Firm* — BakerHostetler

(57) ABSTRACT

The present invention relates generally to the field of immunomodulation. Taught herein is an agent for inhibiting immunostimulation mediated by a Toll-like receptor useful in the treatment of viral and microbial pathogenesis, diseases involving elements of autoimmunity and inflammation as well as cancer. The agent antagonizes disulfide bond formation between C98 and C475 of Toll-like receptor 7 (TLR7) thereby preventing TLR7 activation. Pharmaceutical compositions are also enabled herein.

14 Claims, 49 Drawing Sheets

Specification includes a Sequence Listing.

(56) References Cited

OTHER PUBLICATIONS

Bedard, et al., "The NOX family of ROS-generating NADPH oxidases: physiology and pathophysiology", Physiological Reviews, 87(1), pp. 245-313, 2007.

Campbell, et al., "NADPH oxidases inhibits the pathogenesis of systemic lupus erythematosus", Science Translational Medicine, 4(157), pp. 157ra141, 2012.

Cossart, et al., "Endocytosis of viruses and bacteria", Cold Spring Harbor Perspectives in Biology, 6(8), a016972, 2014.

Diebold, et al., "Innate antiviral responses by means of TLR7-mediated recognition of single-stranded RNA", Science, 303(5663), pp. 1529-1531, 2004.

Drummond, et al., "Combating oxidative stress in vascular disease: NADPH oxidases as therapeutic targets", Nature Reviews. Drug Discovery, 10(6), pp. 453-471, 2011.

Gill, et al, "Linking oxidative stress to inflammation: Toll-like receptors", Free Radical Biology & Medicine, 48(9), pp. 1121-1132, 2010.

Guidotti, et al., "Cell-penetrating peptides: from basic research to clinics", Trends in Pharmacological Science, 38(4), pp. 406-424, 2017.

Halls, et al., "Detection and quantification of intracellular signalling using FRET-based biosensors and high content imaging", Methods in molecular biology, 1335, pp. 131-161, 2015.

Hipp et al., "The processed amino-terminal fragment of human TLR7 acts as chaperone to direct human TLR7 into endosomes", Journal of Immunology, 194(11), pp. 5417-5425, 2015.

Hu, et al., "Multimerization and interaction of Toll and Spätzle in *Drosophila*", Proceedings of the National Academy of Sciences of the United States of America, 101(25), pp. 9369-9374, 2004.

Ichinohe, et al., "Inflammasome recognition of influenza virus is essential for adaptive immune responses", Journal of Experimental Medicine, 206(1), pp. 79-87, 2009.

Imai, et al., "Identification of oxidative stress and Toll-like receptor 4 signalling as a key pathway of acute lung injury", Cell, 133(2), pp. 235-249, 2008.

Iwasaki, et al., "Innate immunity to influenza virus infection", Nature Reviews. Immunology, 14(5), pp. 315-328, 2014.

Jensen, et al., "Endothelin-converting enzyme 1 and β-arrestins exert spatiotemporal control of substance P-induced inflammatory signals", Journal of Biological Chemistry, 289(29), pp. 20283-20294, 2014.

Johnson, et al., "Peptide Turn Mimetics", Biotechnology and Pharmacy, pp. 366-378, 1993.

Judkins, et al., "Direct evidence of a role of Nox2 in superoxide production, reduced nitric oxide bioavailability, and early atherosclerotic plaque formation in ApoE-/- mice", American Journal of Physiology. Heart and Circulatory Physiology, 298(1), pp. H24-H32, 2010.

Kanno, et al., "Essential role for Toll-like receptor 7 (TLR7)-unique cysteines in an inlramolecular disulfide bond, proteolytic cleavage and RNA sensing", International Immunology, 25(7), pp. 413-422, 2013.

Kawahara, et al., "Molecular evolution of the reactive oxygen-generating NADPH oxidase (Nox/Duox) family of enzymes", BMC Evolutionary Biology, 7:109, 2007.

Kelkka et al., "Reactive oxygen species deficiency induces autoimmunity with type 1 interferon signature", Antioxidants & Redox Signalling, 21(16), pp. 2231-2245, 2014.

King, et al., "Lung T-cell responses to nontypeable Haemophilus influenzae in patients with chronic obstructive pulmonary disease", Journal of Allergy and Clinical Immunology, 131(5), pp. 1314-1321, 2015.

Lamphier, et al., "Novel small molecule inhibitors of TLR7 and TLR9: mechanism of action and efficacy in vivo", Molecular Pharmacology, 85(3), pp. 429-440, 2014.

Lund, et al., "Recognition of single-stranded RNA viruses by Toll-like receptor 7", Proceedings of the National Academy of Sciences of the United States of America, 101(15), pp. 5598-5603, 2004.

Ma, et al., "The neurotoxic effect of astrocytes activated with toll-like receptor ligands", Journal of Neuroimmunology, 254(1-2), pp. 10-18, 2013.

Pollock, et al., "Mouse model of X-linked chronic granulomatous disease, an inherited defect in phagocyte superoxide production", Nature Genetics, 9(2), pp. 202-209, 1995.

Prinz, et al., "Antiphospholipid antibodies induce translocation of TLR7 and TLR8 to the endosome in human monocytes and plasmacytoid dendritic cells", Blood, 118(8), pp. 2322-2332, 2011.

Rajendran, et al., "Efficient inhibition of the alzheimer's disease β-secretase by membrane targeting", Science. 320 (5875), pp. 520-523, 2008.

Sah, et al., "Effects of human mesenchymal stem cells transduced with superoxide disumatase on imiquimod-induced psoriasis-like skin inflammation in mice", Antioxidants & Redox Signalling, 24(5), pp. 233-248, 2016.

Selemidis, et al., "NADPH oxidases in the vasculature: molecular features, roles in disease and pharmacological inhibition", Pharmacology & Therapeutics, 120(3), pp. 254-291, 2008.

Snelgrove, et al., "An absence of reactive oxygen species improves the resolution of lung infection", European Journal of Immunology, 36(6), pp. 1364-1373, 2006.

To, et al., "Influenza A virus and TLR7 activation potentiate NOX2 oxidase-dependent ROS production in macrophages", Free Radical Research, 48(8), pp. 940-947, 2014.

To, et al., "Endosomal NOX2 oxidase exacerbates virus pathogenicity and is a target for antiviral therapy", Nature Communications, 8(1), Article No. 69, 2017.

To, et al., "Nox2 oxidase expressed in endosomes exacerbates influenza pathogenicity", European Respiratory Journal, vol. 48, Supplement 60, Abstract No. PA2600, 2016.

Violin, et al., "A genetically encoded fluorescent reporter reveals oscillatory phosphorylation by protein kinase C", Journal of Cell Biology, 161(5), pp. 899-909, 2003.

Vlahos, et al., "NADPH oxidases as novel pharmacologic targets against influenza A virus infection", Molecular Pharmacology, 86(6), pp. 747-759, 2014.

Vlahos, et al., "Inhibition of Nox2 oxidase activity ameliorates influenza A virus-induced lung inflammation", PLoS Pathogens 7(2), p. e1001271, 2011.

Vlahos, et al., "Suppressing production of reactive oxygen species (ROS) for influenza A virus therapy", Trends in Pharmacological Sciences, 33(1), pp. 3-8, 2012.

West, et al., "TLR signalling augments macrophage bactericidal activity through mitochrondrial ROS", Nature, 472 (7344), pp. 476-480, 2011.

GenBank Accession No. ACK58672.1, Toll-like receptor 7, partial [Sigmodon hispidus], Jul. 24, 2016.

GenBank Accession No. AES08222.1, Toll-like receptor 7, partial [Mustela putorius furo], Mar. 8, 2013.

European Search Report issued in European Patent Application No. 18823595.6 dated Mar. 19, 2021.

Petes, et al., "The Toll for Trafficking: Toll-Like Receptor 7 Delivery to the endosome", Front Immunol., vol. 8, Article 1075, Sep. 2017.

\* cited by examiner

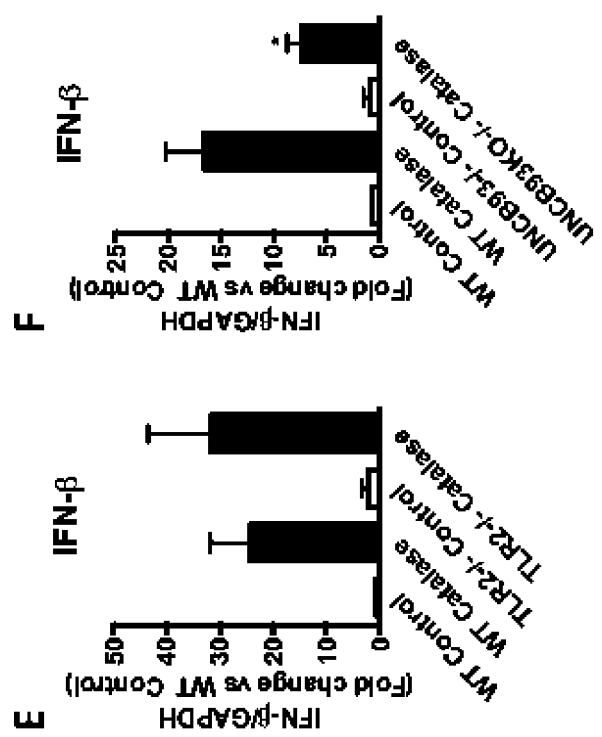

FIG. 7B

| | | | | | | | | | | |
|---|---|---|---|---|---|---|---|---|---|---|
| Human | 95 | D | F | R | C | N | C | V | 101 | |
| Mouse | 95 | D | L | R | C | N | C | V | 101 | SEQ ID NO:49 |
| Rat | 95 | D | L | R | C | N | C | V | 101 | SEQ ID NO:50 |
| Chicken | 103 | D | L | R | C | N | C | V | 109 | SEQ ID NO:51 |
| Frog | 101 | D | F | R | C | N | C | V | 107 | SEQ ID NO:52 |
| Pig | 95 | D | F | R | C | N | C | – | 95 | SEQ ID NO:53 |
| Salmon | 103 | D | F | R | C | N | C | – | 106 | SEQ ID NO:54 |
| Zebrafish | 90 | D | L | R | C | N | C | V | 96 | SEQ ID NO:55 |
| | | | | | | | | | | SEQ ID NO:56 |

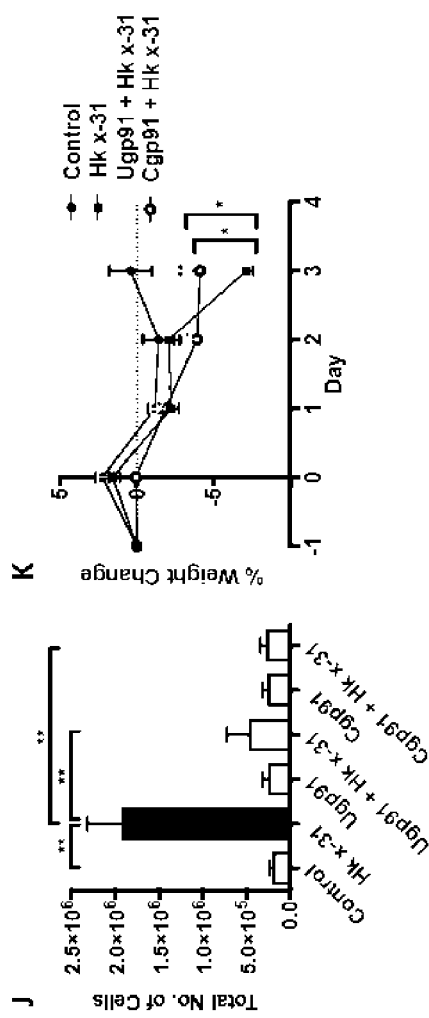
FIG. 9K
FIG. 9J
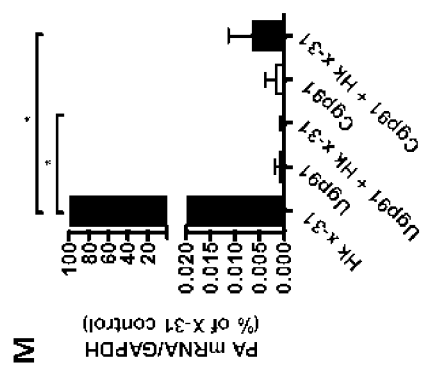
FIG. 9L
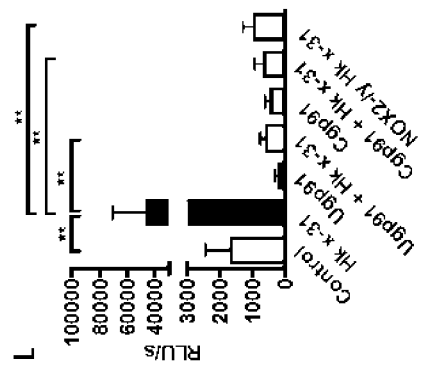
FIG. 9M

FIG. 10A

```
                                                                                             C36                C51
TLR3       ------------------------MRQTLPCIY---------FWGGLLPF-------GML              20
TLR9       -------MGFCRSA----LHP---LS-----LLVQAIMLAMTLALGTLPA-------FLP               34
TLR7       -----------------MVFPMWTLKRLILILF-NIILISKLLGARWFPK-------TLP               35
TLR8       MKESSLQNSSCSLGKETKKENMFLQSSMLTCIFLLISGSCELCAEENFSR-------SYP               53
TLR5       ------------------------MGDHLDLL--LGVVLMAGPVFG-------IPS                  23
TLR4       --------------------MMSASRLAGTL---I--PAMAFLSCVRPE------SWEP               28
TLR2       --------------------------MP----HT--LWMVWVLGVIISLSKEESSNQA               26
TLR10      ------------------------MRLIRNIYIFC--SIVMTAEGDAPE----------              23
TLR1       --------------------------MTSIFHFA--IIFMLILQIRIQ----------               20
TLR6       --------------------MTKDKEPIVKSFHFV--CLMIIIVGTRIQ----------              27

C36                C51
TLR3       CASSTTKCTVSHEVADCSHLKLTQVPD----DLPTNITVLNLTHNQLRRLPAANFTRYSQ              76
TLR9       CEL-QP-----HGLVNCNWLFLKSVPHFSMAAPRGNVTSLSLSSNRIHHLHDSDFAHLPS              88
TLR7       CDV-TLDVPKNHVIVDCTDKHLTEIPG----GIPTNTTNLTLTINHIPDISPASFHRLDH              90
TLR8       CDE-KK--QNDSVIAECSNRRLQEVPQ----TVGKYVTELDLSDNFITHITNESFQGLQN             106
TLR5       CSF-----DGRIAFYR--FCNLTQVPQ----VL-NTTERLLLSFNYIRTVTASSFPFLEQ              71
TLR4       CVE-----VVPNITYQCMELNFYKIPD----NLPFSTKNLDLSFNPLRHLGSYSFFSFPE              79
TLR2       SLS-----CDRNGICKGSSGSLNSIPS----GLTEAVKSLDLSNNRITYISNSDLQRCVN              77
TLR10      -LP-----EERELMTNCSNMSLRKVPA----DLTPATTTLDLSYNLLFQLQSSDFHSVSK              73
TLR1       -LS-----EESEFLVDRSKNGLIHVPK----DLSQKTTILNISQNYISELWTSDILSLSK              70
TLR6       -FS-----DGNEFAVDKSKRGLIHVPK----DLPLKTKVLDMSQNYIAELQVSDMSFLSE              77
                  :  :*                *   ::  *  :    .:

C98 C100        C112
TLR3       LTSLDVGFNTISK-------------LEPELCQKLPMLKVLNLQHNELSQLSDKTFAFC              122
TLR9       LRHLNLKWNCPPVGLSPMH--FPCHMTIEPSTFLAVPTLEELNLSYNNIMTVP----ALP             142
TLR7       LVEIDFRCNCVPIPLGSKNNMCIKRLQIKPRSFSGLTYLKSLYLDGNQLLEIPQ---GLP             147
TLR8       LTKINLNHNPNVQHQNGNPGIQSNGLNITDGAFLNLKNLRELLLEDNQLPQIPS---GLP             163
TLR5       LQLLELGSQYTPL-------------TIDKEAFRNLPNLRILDLGSSKIYFLHPDAFQGL            118
TLR4       LQVLDLSRC-EIQ-------------TIEDGAYQSLSHLSTLILTGNPIQSLALGAFSGL            125
TLR2       LQALVLTSN-GIN-------------TIEEDSFSSLGSLEHLDLSYNYLSNLSSSWFKPL            123
TLR10      LRVLILCHN-RIQ-------------QLDLKTFEFNKELRYLDLSNNRLKSVT---WYLL            116
TLR1       LRILIISHN-RIQ-------------YLDISVFKFNQELEYLDLSHNKLVKIS---CHPT            113
TLR6       LTVLRLSHN-RIQ-------------LLDLSVFKFNQDLEYLDLSHNQLQKIS---CHPI            120
            *  :  .                    :       *  *  *   . :   :

C183  C189
TLR3       TNLTELHLMSNSIQKIKNNPFVK---------------------QKNLI                       150
TLR9       KSLISLSLSHTNILMLDSASLAGLHALRFLFMDGNCYYKNPCRQALEVAPGALLGLGNLT             202
TLR7       PSLQLLSLEANNIFSIRKENLTELANIEILYLGQNCYYRNPCYVSYSIEKDAFLNLTKLK             207
TLR8       ESLTELSLIQNNIYNITKEGISRLINLKNLYLAWNCYFNKVCEK-TNIEDGVFETLTNLE             222
TLR5       FHLFELRLYFCGL-----------------------SDAVLKDGYFRNLKALT                   148
TLR4       SSLQKLVAVET-------------------------NLASLENFPIGHLKTLK                   153
TLR2       ------------------------------------SSLT                                127
TLR10      ------------------------------------AGLR                                120
TLR1       ------------------------------------VNLK                                117
TLR6       ------------------------------------VSFR                                124
                                                  :

TLR3       TLDLSHNGLSSTKLGTQVQLENLQELLLSNNKIQALKSEELDIFANSSLKKLELSSNQIK             210
TLR9       HLSLKYNNLTVVP---RNLPSSLEYLLLSYNRIVKLAPEDLANLTA--LRVLDVGG----             253
TLR7       VLSLKDNNVTAVP---TVLPSTLTELYLYNNMIAKIQEDDFNNLNQ--LQILDLSG----             258
TLR8       LLSLSFNSLSHVP---PKLPSSLRKLFLSNTQIKYISEEDFKGLIN--LTLLDLSG----             273
TLR5       RLDLSKNQIRSLY----------------------LHPSFGKLNS--LKSIDFSSNQIF             183
TLR4       ELNVAHNLIQSFK----------------------LPEYFSNLTN--LEHLDLSSN---             185
TLR2       FLNLLGNPYKTLG----------------------ETSLFSHLTK--LQILRVGNMDTF             162
TLR10      YLDLSFNDFDTMP----------------------ICEEAGNMSH--LEILGLSGA---             152
TLR1       HLDLSFNAFDALP----------------------ICKEFGNMSQ--LKFLGLSTT---             149
TLR6       HLDLSFNDFKALP----------------------ICKEFGNLSQ--LNFLGLSAM---             156
            *.: *                                     :   *  : ..
```

FIG. 10B

```
         C260  C263    C270 C273
TLR3   EFSPGCFHAIGRLFGLFLNN-VQLGPSLTEKLCLELANTSIRNLSLSNSQL-STTSNTTF   268
TLR9   -NCRRCDHAPNPCMECPRHFPQ-LHPDT------FSHLSRLEGLVLKDSSL-SWLNASWF   304
TLR7   -NCPRCYNAPFPCAPCKNNSPLQIPVNA------FDALTELKVLRLHSNSL-QHVPPRWF   310
TLR8   -NCPRCFNAPFPCVPCDGGASINIDRFA------FQNLTQLRYLNLSSTSL-RKINAAWF   325
TLR5   LVCE-----HELEPLQGK---------------------TLSFFSLAANSLYSRVSVDWG   217
TLR4   -KIQSIYCTDLRVLHQM----------------------PLLNLSLDLSLNPMNF-IQ-P   220
TLR2   TKIQRKDFAGLTFLE-------------------------EL----EIDASDLQS-YE-P   191
TLR10  -KIQKSDFQKIAHLH-------------------------LNTVFLGFRTL--PH-YE-E   182
TLR1   -HLEKSSVLPIAHLN-------------------------ISKVLLVLGETYGEK-ED-P   181
TLR6   -KLQKLDLLPIAHLH-------------------------LSYILLDLRNYYIKE-NE-T   188

TLR3   LGLKWTNLT----MLDLSYNNLN--VVGNDSFAWLPQLEYFFLEYNNIQHLFSHSL----   318
TLR9   RGL--GNLR----VLDLSENFLYKCITKTKAFQGLTQLRKLNLSFNYQKRVSFAHLSLAP   358
TLR7   KNI--NKLQ----ELDLSQNFLAKEIGDAKFLHFLPSLIQLDLSFNFELQVYRASMNLSQ   364
TLR8   KNM--PHLK----VLDLEFNYLVGEIASGAFTLMLPRLEILDLSFNYIKGSYPQHINISR   379
TLR5   KCMNPFRNMVLEI-LDVSGNGWTVDIT--------------------GNFSNAISKSQ   254
TLR4   GAFKEIRLHKLTL----RNNFDSLNVMKT-CIQGLAGLEVHRL----VLGEFRNE-GNLE   270
TLR2   KSLKSIQNV-SHLILHMKQHILLLEIFVD-VTSSVECLELRDT----DLDT--------F   237
TLR10  GSLPILNTTKLHIVLPMDTNFW--VLLRD-GIKTSKILEMTNI----DGKS---------   226
TLR1   GGLQDFNTESLHIVFPTNKEFH--FILDV-SVKTVANLELSNI----KCVL--ED-SKCS   231
TLR6   ESLQILNAKTLHLVFHPTSLFA--IQVNI-SVNTLGCLQLTNI----K--L---ND-DNCQ   236
              :    .

TLR3   --HGLFNVRYLNLKRSFTKQSISLASLPKIDDFSFQWLKCLEHLN-MEDNDIPGIKSNMF   375
TLR9   SFGSLVALKELDMHGIF------FRSLDETTLRPLARLPMLQTLR-LQMNFINQAQLGIF   411
TLR7   AFSSLKSLKILRIRGYV------FKELKSFNLSPLHNLQNLEVLD-LGTNFIKIANLSMF   417
TLR8   NFSKLLSLRALHLRGYV------FQELREDDFQPLMQLPNLSTIN-LGINFIKQIDFKLF   432
TLR5   AFSLILA------HHIM-GAGFGFHNIKDPDQ---------------------------   279
TLR4   KFDKSA---LEGLCNLT-IEEFRLAYLDYYLDDIIDLFNCLTNVSSFSLVSVTIERVKDF   326
TLR2   HF-SELS---TGEETNSL-IKKFTFRNVKITDESLFQVMKLLNQIS-------------   277
TLR10  QFVSYEMQRNLSLEHAK-TSVLLLNKVDLLWDDLFLILQFVWHTS---------------   270
TLR1   YFLSILAK---LQTNPK-LSSLTLNNIETTWNSFIRILQLVWHTT---------------   272
TLR6   VFIKFLSE---LTRGPT-LLNFTLNHIETTWKCLVRVFQFLWPKP---------------   277
              :    :
                        C445
TLR3   TGLINLKYLSLSNSFTSLRT-L----------------------------------   396
TLR9   RAFPGLRYVDLSDNRISGASELTATMGEADGGEKV-WLQPG-------DL---------   453
TLR7   KQFKRLKVIDLSVNKISPSGDSSEVGFCSNARTSVESYEPQVL-EQLHYFRYDKY-----   471
TLR8   QNFSNLEIIYLSENRISPLVKDTRQSYANSSSF-----QRHIRKRRSTDFEFDPH-----   482
TLR5   -------------NTFAGL---------------------------------ARS   288
TLR4   SYNFGWQHLELVNCKFGQFPTLKL---------------------KS-------------   352
TLR2   ----GLLELEFDDCTLNGVGNFRA----------------SDNDRVIDPGKVETL   312
TLR10  -----VEHFQIRNVTFGGKAYLDH-------------------NS--FDYSNTVMRTI   302
TLR1   -----VWYSSISNVKLQGQ--LDF----------------RD--FDYSGTSLKAL   302
TLR6   -----VEYLNIYNLTIIES--IRE----------------ED--FTYSKTTLKAL   307

C475          C491                      C521
TLR3   ----------------TNETFVSIAHSPLHILNLTKNKISKIESDAFSWLGHLEVLDL   438
TLR9   ----------APAPVDTPSSEDFRPNCSTLNFTLDLSRNNLVTVQPEMFAQLSHLQCLRL   503
TLR7   --------ARSCRFKNKEASFMSVNESCYKYGQTLDLSKNSIFFVKSSDFQHLSFLKCLNL   524
TLR8   --------SNFYHF-----TRPLIKPQCAAYGKALDLSLNSIFFIGPNQFENLPDIACLNL   530
TLR5   SVRHLDLSHGFVFSLN-----SRVFETLKDLKVLNLAYNKINKIADEAFYGLDNLQVLNL   343
TLR4   -------------------------LKRLTFTSNK--GGNAFSEVDLPSLEFLDL   380
TLR2   TIRRLHIPRFYLFYDL-----STLYSLTERVKRITVENSKVFLVPCLLSQHLKSLEYLDL   367
TLR10  KLEHVHFRVFYI--QQ-----DKIYILLTKMDIENLTISNAQMPHMLFPNYPTKFQYLNF   355
TLR1   SIHQVVSDVFGF--PQ-----SYIYEIFSNMNIKNFTVSGTRMVHMLCPSKISPFLHLDF   355
TLR6   TIEHITNQVFLF--SQ-----TALYTVFSEMNIMMLTISDTPFIHMLCPHAPSTFKFLNF   360
                                                      :  *  :
```

FIG. 10C

```
TLR3     GLNEIGQELTG----QEWRGLENIFEIYLSYNKYLQLTRNSFALVPSLQRLMLRR----V      490
TLR9     SHNCISQAVNG----SQFLPLTGLQVLDLSHNKLDLYHEHSFTELPRLEALDLSYNSQPF    559
TLR7     SGNLISQTLNG----SEFQPLAELRYLDFSNNRLDLLHSTAFEELHKLEVLDISSNSHYF    580
TLR8     SANSNAQVLSG----TEFSAIPHVKYLDLTNNRLDFDNASALTELSDLEVLDLSYNSHYF    586
TLR5     SYNLLGELYSS-----NFYGLPKVAYIDLQKNHIAIIQDQTFKFLEKLQTLDLRDNALTT    398
TLR4     SRNGLS---FKGCCSQSDFGTTSLKYLDLSFNGVIT-MSSNFLGLEQLEHLDFQHSNLKQ    436
TLR2     SENLMVEEYLKNSACED------------------------AWPSLQTLILRQNHLAS    401
TLR10    ANNILTDELFKRT---L------------------------QLPHLKTLILNGNKLET    386
TLR1     SNNLLTDTVFENC---G------------------------HLTELETLILQMNQLKE    386
TLR6     TQNVFTDSIFEKC---S------------------------TLVKLETLILQKNGLKD    391
                 *                               *: *  :

TLR3     ALKNVDSSPSPFQPLRNLTILDLSNNNIANIN-DDMLEGLEKLEILDLQHNNLARLWKHA    549
TLR9     GMQGVGHNFSFVAHLRTLRHLSLAHNNIHSQ--VSQQLCSTSLRALDFSGNALGHMWAEG    617
TLR7     QSEGITHMLNFTKNLKVLQKLMMNDNDISSS--TSRTMESESLRTLEFRGNHLDVLWREG    638
TLR8     RIAGVTHHLEFIQNFTNLKVLNLSHNNIYTLT-DKYNLESKSLVELVFSGNRLDILWNDD    645
TLR5     I-HFIPSIP----------DIFLSGNKLVTLPKINLTANLIHLSE---N--------R-L    435
TLR4     M-SE---------------------------FSVFLSLRNLIYLDISH-------T-H    458
TLR2     L-EK---------------------------TGET-----------------------    408
TLR10    L-SL---------------------------VSCF-----------------------    393
TLR1     L-SK---------------------------IAEM-----------------------    393
TLR6     L-FK---------------------------VGLM-----------------------    398

TLR3     NPGGPIYFLKGLSHLILNLESNGFDEIPVEVFKDLF----------------------    586
TLR9     D--LYLHFFQGLSGLIWLDLSQNRLHTLLPQTLRNLPKSLQVLRLRDNYLA-----FFKW    670
TLR7     DN-RYLQLFKNLLKLEELDISKNSLSFLPSGVFDGMPPNLKNLSLAKNGLK-----SFSW    692
TLR8     DN-RYISIFKGLKNLTRLDLSLNRLKHIPNEAFLNLPASLTELHINDNMLK-----FFNW    699
TLR5     ENLDILYFLLRVPHLQILILNQNRFSSCSGDQTPSENPSLEQLFLGENMLQLAWETELCW    495
TLR4     TRVAFNGIFNGLSSLEVLKMAGNSFQENFLPDIFTEL---------------------    495
TLR2     --------LLTLKNLTNIDISKNSF--HSMPETCQWPEKMKYLNLSSTRI---------H    449
TLR10    --------ANN-TPLEHLDLSQNLLQ-HKNDENCSWPETVVNMNLSYNKL--------SD    435
TLR1     --------TTQMKSLQQLDISQNSVSYDEKKGDCSWTKSLLSLNMSSNIL--------TD    437
TLR6     --------TKDMPSLEILDVSWNSLESGRHKENCTWVESIVVLNLSSNML--------TD    442
                     *  :   *
                 C697              C721
TLR3     ----:----ELKIIDLG-----------:----------LNNLNTLPASVFNNQVSLKS    614
TLR9     WSLHFL-PKLEVLDLAGNQLKALTNGSLPAGTRLRRLDVSCNSISFVAPGFFSKAKELRE    729
TLR7     KKLQCL-KNLETLDLSHNQLTTVPERLSNCSRSLKNLILKNNQIRSLTKYFLQDAFQLRY    751
TLR8     TLLQQF-PRLELLDLRGNKLLFLTDSLSDFTSSLRTLLLSHNRISHLPSGFLSEVSSLKH    758
TLR5     DVFEGL-SHLQVLYLNHNYLNSLPPGVFSHLTALRGLSLNSNRLTVLSH--NDLPANLEI    552
TLR4     ----:--RNLTFLDLSQCQLEQLSPTAFNSLSSLQVLNMSHNNFFSLDTFPYKCLNSLQV    548
TLR2     SVTGCIPKTLEILDVSNNNLNLF-S---INLPQLKELYISRNKLMTLPD--ASLLPMLLV    503
TLR10    SVFRCLPKSIQILDLNNNQIQTV-PKETIHLMALRELNIAFNFLTDLPG--CSHFSRLSV    492
TLR1     TIFRCLPPRIKVLDLHSNKIKSI-PKQVVKLEALQELNVAFNSLTDLPG--CGSFSSLSV    494
TLR6     SVFRCLPPRIKVLDLHSNKIKSV-PKQVVKLEALQELNVAFNSLTDLPG--CGSFSSLSV    499
                : : :                        * :  :         *
                              C787 789
TLR3     LNLQKNLITSVEKKVFGP-AFRNLTELDMRFNPFDCICESIAWFVNWINE-THTNIPELS    672
TLR9     LNLSANALKTVDHSWFGP-LASALQILDVSANPLHCACG-AAFMDFLLE--VQAAVPGLP    785
TLR7     LDLSSNKIQMIQKTSFPENVLNNLKMLLLHHNRFLCICD-AVWFVWWVNH-TEVTIPYLA    809
TLR8     LDLSSNLLKTINKSALETKTTTKLSMLELHGNPFECICD-IGDFRRWMDEHLNVKIPR-L    816
TLR5     LDISRNQLLAPNPDVFV-----SLSVLDITHNKFICECE-LSTFINWLNHT-NVTIAGPP    605
TLR4     LDYSLNHIMTSKKQELQH-FPSSLAFLNLTQNDFACICE-HQSFLQWIKDQRQLL--VEV    604
TLR2     LKISRNAITTFSKEQLDS-FH-TLKTLEAGGNNPICSCE-FLSFTQE-QQALAKVLIDWP    559
TLR10    LNIEMNFILSPSLDFVQS-CQ-EVKTLNAGRNPFRCICE-LKNFIQ-LETYSEVMMVGWS    548
TLR1     LIIDHNSVSHPSADFFQS-CQ-KMRSIKAGDNPFQCICE-LGEFVKNIDQVSSEVLEGWP    551
TLR6     LIIDHNSVSHPSADFFQS-CQ-KMRSIKAGDNPFQCICE-LREFVKNIDQVSSEVLEGWP    556
             *    *  :  .    .          :  :     * : * *         :
```

FIG. 10D

```
            C814                    C833
TLR3   SHYLCNTPPHYHGFPVRLFDTS--SCKDSAPFELFFMINTSILLIFIFIVLLIHFEGWRI   730
TLR9   SRVKCGSPGQLQGLSIFAQDLR--LCLDEALSWDCFALSLLAVALGLGVPMLHHLCGWDL   843
TLR7   TDVTCVGPGAHKGQSVISLDLY--TCELDLTNLILFSLSISVSLFLMVMMTASHLYFWDV   867
TLR8   VDVICASPGDQRGKSIVSLELT--TCVSDVTAVILFFFTFFITTMVMLAALAHHLFYWDV   874
TLR5   ADIYCVYPDSFSGVSLFSLS--TEGCDEEEVLKSLKFSLFIVCT---VTLTLFLMTILTV   660
TLR4   ERMECATPSDKQGMPVLSLNI---TCQMNKTIIGVSVLSVLVVS---VVAVLVYKFYFHL   658
TLR2   ANYLCDSPSHVRGQQVQDVRLSVSECHRTALVSGMCCALFLL-----ILLTGVLCHRFHG   614
TLR10  DSYTCEYPLNLRGTRLKDVHLELSCNTALLIVTIVVIMLVL-----GLAVAFCCLHFDL   603
TLR1   DSYKCDYPESYRGTLLKDFHMSELSCNITLLIVTIVATMLVL-----AVTVTSLCIYLDL   606
TLR6   DSYKCDYPESYRGSPLKDFHMSELSCNITLLIVTIGATMLVL-----AVTVTSLCIYLDL   611
            *    *    *    :         *
            C874                    C889 890
TLR3   SFYWNVSVHRVLGFKEID-R------QTEQFEYAAYIIHAYKD---KDWVWEHFSSMEKE   780
TLR9   WYCFHLCLAWLPWRGRQSGR------DEDALPYDAFVVFDKTQSAVADWVYNELRGQLEE   897
TLR7   WYIYHFCKAKIKGYQRLI---------SPDCCYDAFIVYDTKDPAVTEWVLAELVAKLED   918
TLR8   WFIYNVCLAKVKGYRSLS---------TSQTFYDAYISYDTKDASVTDWVINELRYHLEE   925
TLR5   TKFRGFCFICYKTAQRLVFKDHPQGTEPDMYKYDAYLCFSSKD---FTWVQNALLKHLDT   717
TLR4   ----MLLAGCIKY--G-----------RGENIYDAFVIYSSQD---EDWVRNELVKNLEE   698
TLR2   LWYMKMMWAWLQA--KRKPRKAP----SRNICYDAFVSYSERD---AYWVENLMVQELEN   665
TLR10  PWYLRMLGQCTQT--WHRVRKTTQEQLKRNVRFHAFISYSEHD---SLWVKNELIPNLEK   658
TLR1   PWYLRMVCQWTQT--RRRARNIPLEELQRNLDFHAFISYSGHD---SFWMKNELLPNLEK   661
TLR6   PWYLRMVCQWTQT--RRRARNIPLEELQRNLDFHAFISYSEHD---SAWVKSELVPYLEK   666
            .                    : *::  .   :    *:  :   .
            C927
TLR3   ----DQSLKFCLEERDFEAGVFELEAIVN-SIKRSRKIIFVITHHLLKDPLCKRFKVHHA   835
TLR9   CR-GRWALRLCLEERDWLPGKTLFENLWA-SVYGSRKTLFVLAHTDRVSGLLR-ASFLLA   954
TLR7   PR-EK-HFNLCLEERDWLPGQPVLENLSQ-SIQLSKKTVFVMTDKYAKTENFK-IAFYLS   974
TLR8   SR-DK-NVLLCLEERDWDPGLAIIDNLMQ-SINQSKKTVFVLTKKYAKSWNFK-TAFYLA   981
TLR5   QYSDQNRFNLCFEERDFVPGENRIANIQD-AIWNSRKIVCLVSRHFLRDGWCL-EAFSYA   775
TLR4   G---VPPFQLCLHYRDFIPGVAIAANIIHEGFHKSRKVIVVVSQHFIQSRWCI-FEYEIA   754
TLR2   F---NPPFKLCLHKRDFIPGKWIIDNIID-SIEKSHKTVFVLSENFVKSEWCK-YELDFS   720
TLR10  E---DGSILICLYESYFDPGKSISENIVS-FIEKSYKSIFVLSPNFVQNEWCH-YEFYFA   713
TLR1   E---G--MQICLHERNFVPGKSIVENIIT-CIEKSYKSIFVLSPNFVQSEWCH-YELYFA   714
TLR6   E---D--IQICLHERNFVPGKSIVENIIN-CIEKSYKSIFVLSPNFVQSEWCH-YELYFA   719
            . :*:   :  *          :    . * * : :::              :
            C1008                   C1028
TLR3   VQQAIEQNLDSIILVFLEEIPDYKLNHALCLRRGMFKSHCILNWPVQKERIGAFRHKLQV   895
TLR9   QQRLLEDRKDVVVLVILSPD--GRRSRYVRLRQRLC-RQSVLLWPHQPSGQRSFWAQLGM   1011
TLR7   HQRLMDEKVDVIILIFLEKP--FQKSKFLQLRKRLC-GSSVLEWPTNPQAHPYFWQCLKN   1031
TLR8   LQRLMDENMDVIIFILLEPV--LQHSQYLRLRQRIC-KSSILQWPDNPKAEGLFWQTLRN   1038
TLR5   QGRCLSDLNSALIMVVGSLSQYQLMKH-QSIRGFVQKQQYLRWPEDLQDVGWFLHKLSQ   834
TLR4   QTWQFLSSRAGIIFIVLQKVEKTLLRQQ-VELYRLLSRNTYLEWEDSVLGRHIFWRRLRK   813
TLR2   HFRLFDENNDAAILILLEPIEKKAIPQRFCKLRKIMNTKTYLEWPMDEAQREGFWVNLRA   780
TLR10  HHNLFHENSDHIILILLEPIPFYCIPTRYHKLKALLEKKAYLEWPKDRRKCGLFWANLRA   773
TLR1   HHNLFHEGSNSLILILLEPIPQYSIPSSYHKLKSLMARRTYLEWPKEKSKRGLFWANLRA   774
TLR6   HHNLFHEGSNNLILILLEPIPQNSIPNKYHKLKALMTQRTYLQWPKEKSKRGLFWANIRA   779
            :  .   ::::.:           :      * *  .     *    :

TLR3   ALGSKNSVH------------------------- 904
TLR9   ALTRDNHHFYNRNFCQGPTAE------------- 1032
TLR7   ALATDNHVAYSQVFKETV---------------- 1049
TLR8   VVLTENDSRYNNMYVDSIKQY------------- 1059
TLR5   QILKKEKEKKKDNNIPLQT-------VATIS---- 858
TLR4   ALLDGKSWNPEGTV-GTGCNWQE---ATSI----- 839
TLR2   AIKS------------------------------ 784
TLR10  AINVNVLATREMYELQTFTELNEESRGSTISLMRTDCL 811
TLR1   AINIKLTEQAKK---------------------- 786
TLR6   AFNMKLTLVTENNDVKS----------------- 796
```

FIG. 11A

```
                                                                    C36
[Salmo      MLSRMT------RSECASFHVCGVILLGLWCSSVLAAGSWYPKTLPCDVTLDSNDTMVNV  54
[Xenopus    MHGKTFKV-----FYFGMRRQLLFFLISILSFSGLLATNWFPKSLPCDVEQNAKGNVIVV  55
[Gallus     -MTNLSEVAAHRKMVHHARTSNALLFVLLFLFPMLLSGRWFPKTLPCDVEA--FESTVRV  57
[Mus        ---------MV--FSMWTRKRQILIFLNMLLVSRVFGFRWFPKTLPCEVKVNIPEAHVIV  49
[Rattus     ---------MV--FPMWTLKRQSFIFLNMILVSRVLGFRWYPKTLPCDVSLDSTNTHVIV  49
[Homo       ---------MV--FPMWTLKRLILILFNIILISKLLGARWFPKTLPCDVTLDVPKNHVIV  49
[Sus        ---------MV--FPVWTLKRQFLILFNIVLISELLGARWFPKTLPCDVSLDAPNAHVIV  49
[Bos        -MGDLFLYFQV--FPMWTLKRQFPILFNMILISGLLGARWFPKTLPCDVTLDAPNTHVIV  57
                         ::. :        : .  *:**:***:*        :  *
             C51                                       C98 C100
[Salmo      DCTERGLLEVPKDIPRNTTNLTLTINHIPHINSTSFQGLENLTEIDMRCNCVPIKIGPKD 114
[Xenopus    DCSDRHLTSIPWGIPTNVTNLTLTINHIPRISVDSFAEFTNLVELDFRCNCVPAKVGPKD 115
[Gallus     DCSDRRLKEVPRGIPGNATNLTLTINHIPRISPASFTQLENLVEIDFRCNCVPPRLGPKD 117
[Mus        DCTDKHLTEIPEGIPTNTTNLTLTINHIPSISPDSFRRLNHLEEIDLRCNCVPVLLGSKA 109
[Rattus     DCTDKHLTEIPEGIPTNTTNLTLTINHIPSISPDSFHRLKHLEELDLRCNCVPILLGSKA 109
[Homo       DCTDKHLTEIPGGIPTNTTNLTLTINHIPDISPASFHRLDHLVEIDFRCNCVPIPLGSKN 109
[Sus        DCTDKHLTAIPGGIPTNATNLTLTINHIASITPASFQQLDHLVEIDFRCNCIPVRLGPKD 109
[Bos        DCTDKHLTEIPGGIPANATNLTLTINHIAGISPASFHRLDHLVEIDFRCNCVPVRLGPKD 117
            **::: *  :*  ** *.********** *.  **   : .* *:*:****:* :* *
              C112
[Salmo      RMCTESVTIKTNTFKDLRNLKALYLDGNQLSSIPKGLPPNLILLSLEVNKIYTILKRNLS 174
[Xenopus    HVCTKRLDVEDRSFASLYNLRSLYLDGNQLIEFPKGLPPNLQLLSLEINNIISISRNNLS 175
[Gallus     NVCVTPPSIENGSFAALTRLKSLYLDANQLSKIPRGLPATLRLLSLEANNIFSIKKNTFS 177
[Mus        NVCTKRLQIRPGSFSGLSDLKALYLDGNQLLEIPQDLPSSLHLLSLEANNIFSITKENLT 169
[Rattus     NVCTKRLQIRPGSFSGLSDLKSLYLDGNQLLEIPQDLPSSLQLLSLEANNIFSITKENLS 169
[Homo       NMCIKRLQIKPRSFSGLTYLKSLYLDGNQLLEIPQGLPPSLQLLSLEANNIFSIRKENLT 169
[Sus        NLCTRRLQIKPSSFSKLTYLKALYLDGNQLLEIPRDLPPSLQLLSLEANNIFWIMKENLT 169
[Bos        NVCTKRLQIKPNSFSKLTYLKSLYLDGNQLLEIPQDLPPSLQLLSLEANNIFLIMKENLT 177
            .:*          :.   :*   *  *::****.***  .:*: **  .*  *****  *:*   *  :...::
              C183    C189
[Salmo      DITNVQILYLGQNCYYRNECNVSYQIEEGAFLQLGNMTLLSLKSNNLSYIPPRLPTSLRE 234
[Xenopus    ELSNIQMLYLGQNCYHRNECSDSFKIEKDAFKDLKNLSILSMKSNNLSFVPGGLSDSLKE 235
[Gallus     ELRNIELLYLGQNCYYRNECNVSFEIEETAFLNLKNLTVLSLKSNNLTFIPPNLSSTLKE 237
[Mus        ELVNIETLYLGQNCYYRNECNVSYSIEKDAFLVMRNLKVLSLKDNNVTAVPTTLPPNLLE 229
[Rattus     ELVNIESLYLGQNCYYRNECNVSYSIEKDAFLVMKNLKVLSLKDNNVTAVPTILPPNLLE 229
[Homo       ELANIEILYLGQNCYYRNECYVSYSIEKDAFLNLTKLKVLSLKDNNVTAVPTVLPSTLTE 229
[Sus        ELANLEMLYLGQNCYYRNECNVSFSIEKDAFLSLRNLKLLSLKDNNISAVPTVLPSTLTE 229
[Bos        ELANLEILYLGQNCYYRNECNVSFTIEKDAFLNMRNLKLLSLKDNNISAVPTVLPSSLTE 237
            :: *::  ****** *:****:  *: **: **   : ::.:**:*.**:: :*   *   .* *
                                            C260 C263   C270 C273
[Salmo      LYLYNNKIEMVTDKDFHNLTQLEILDLCGNCPRCYNAPFECIPCPNN-SLQIDPSTFKTL 293
[Xenopus    LYLYNNAIQYIEEHDLENLINLEILDLSGNCPRCYNSPFECTPCPNNAPIQIHPKAFSSL 295
[Gallus     LYIYNNRIQEVQEHDLSNLVNLEILDLSGNCPRCYNAPYECTPCPNI-SKIHSKAFYSL 296
[Mus        LYLYNNIIKKIQENDFNNLNELQVLDLSGNCPRCYNVPYECTPCENNSPLQIHDNAFNSL 289
[Rattus     LYLYNNIIKRIQEHDFNKLSQLQVLDLSGNCPRCYNVPYECTPCENNSPLQIHDNAFDSL 289
[Homo       LYLYNNMIAKIQEDDFNNLNQLQILDLSGNCPRCYNAPFECAECKNNSPLQIPVNAFDAL 289
[Sus        LFLYNNIIAKIQEDDFNNLSQLQVLDLSGNCPRCYNVPFECTPCENNAPLQIHLHAFDAL 289
[Bos        LYLYNNIITKIQEDDFNNLSQLQVLDLSGNCPRCYNVPFECTPCENNSPLQIDPNAFDAL 297
            *::***  *   :  .*:  :*  :*::***.*****:*** *: ** *   ::*    :*  :*

[Salmo      TKLRILRLHSNSLTYVLREWFQNCKELRVLDLSTNFLAREIAITYFPRALPNLEELDLSF 353
[Xenopus    KNLQVLRLHSNSLRSIPEQWFKNNRNLQVLDLSENFLASEISTANFLKYIPSLKSLDLSF 355
[Gallus     KKLRILRLHSNSLQSIPSSWFKNIKNLKNLDLSQNFLIKEIGDAEFLKLIPSLVELDLSF 356
[Mus        TELKVLRLHSNSLQHVPPTWFKNMRNLQELDLSQNYLAREIEEAKFLHFLPNLVELDFSF 349
[Rattus     TELKVLRLHSNSLQHVPAEWFKNMSNLQELDLSQNYLAREIEEAKFLNSLPNLVQLDLSF 349
[Homo       TELKVLRLHSNSLQHVPPRWFKNINKLQELDLSQNFLAKEIGDAKFLHFLPSLIQLDLSF 349
[Sus        TELQVLRLHSNSLQYVPQRWFQNLNKLKELDLSQNFLAKEIGDAKFLHLLPNLVKLDLSF 349
[Bos        TELQVLRLHSNSLQHVPQRWFKNINKLKELDLSQNFLAKEIGDAKFLHLLHNLVNLDLSF 357
            .:*:: ********   :   **:*  :*: ****  *:*   **  :  *  . :  .*  .**:**

[Salmo      NYELQRYPATLHLSPSFSSLKSLKVLRIRAFVFQQLTLEDISPLIHLKNLEVIDLGTNFI 413
[Xenopus    NFELQVYPSDLKLSSIFSSLASLETLRIRGYVFQNLKKNNLMPLVHLPNLTLLDLSTNFI 415
[Gallus     NFELQMYSPFLNLSKTFSCLSNLETLRIKGYVFKELREENLDPLLNLRNLTVLDLGTNFI 416
[Mus        NYELQVYHASITLPHSLSSLENLKIRVKGYVFKELKNSSLSVLHKLPRLEVLDLGTNFI 409
[Rattus     NYELQVYHASITLPHSLSSLTKLKNLYIKGYVFKELKDSSLSVLHNLSNLEVLDLGTNFI 409
[Homo       NFELQVYRASMNLSQAFSSLKSLKILRIRGYVFKELKSFNLSPLHNLQNLEVLDLGTNFI 409
[Sus        NYELQVYHTFMNLSDSFSSLKNLKVLRIKGYVFKELKSLNLSPLRNLPNLEVLDLGTNFI 409
[Bos        NYDLQVYHAVINLSDAFSSLKKLKVLRIKGYVFKELNSLNLFPLHNLPNLEVLDLGTNFI 417
            *::** *    :  *    :*.* .*: *   ::.:**::*    .:   *  .*   :* ::**.****
```

FIG. 11B

```
                                            C445
[Salmo     KITNLSILMELKSFKIINLSDNKISSPSESGQSVAFSGGEAIHGSPMSDAGHNRNGEVRE 473
[Xenopus   KVADFSLFPKFKSLQTIILSNNKISPSSEA--NIDSCBASQV------SSGHYIGRTFQE 467
[Gallus    KIADLRVFKKFRSLKIIDLSMNKISPSSGEGNFYGECBDHRI------TVEQYSRHVLQE 470
[Mus       KIADLNIFKHFENLKLIDLSVNKISPS-EESREVGECPNAQT------SVDRHGPQVLEA 462
[Rattus    KIADLNIFQQFENLKFIDLSVNKISPS-EESREVGLCPNAQT------SVDWHGPQVLEA 462
[Homo      KIANLSMFKQFKRLKVIDLSVNKISPS-GDSSEVGECSNART------SVESYEPQVLEQ 462
[Sus       KIANLSIFKQFKTLKFIDLSVNKISPS-GDSSESGECSGMRT------SAESHGPQVLES 462
[Bos       KIANLSIFNQFKTLKFIDLSVNKISPS-GDSPEGGECSNRRT------SVEGHGPQVLET 470
           *::::  ::  .    *  ** ****                                  ..
                       C475                C491
[Salmo     IHYFRYDEYARSCKYKDKEDGTLNSFVNTQCSKFGKTLDISRNNIFFLHS-RFLNLADLR 532
[Xenopus   VHYFEYDENARKCKAKDKENFTFKLFLNESCQAYGQSLDLSQNNIFFVKATDFTNLSFLK 527
[Gallus    MHYFRYDEYGRSCKSKDKEADSYQPLVNGDCMSYGETLDLSRNNIFFVNSIDFQDLSFLK 530
[Mus       LHYFRYDEYARSCRFKNKEPPSFLPL-NADCHIYGQTLDLSRNNIFFIKPSDFQHLSFLK 521
[Rattus    LHYFRYDEYARSCRFKNKEPPTFLPL-NADCHTYGKTLDLSRNNIFFIKPSDFKHLSFLK 521
[Homo      LHYFRYDKYARSCRFKNKEA-SFMSV-NESCYKYGQTLDLSKNSIFFVKSSDFQHLSFLK 520
[Sus       LHYFRYDEYARSCRFKNKEPSSSLPL-NEDCSMYGQTLDLSRNNIFFIRSSEFQHLTFLK 521
[Bos       LHYFRYDEYARSCRSKSKEPPSFLPL-NEDCYMYGQTLDLSRNNIFFIKPSDFQHLSFLK 529
           .**: .*:*: *.**   :  . * :*  :*::**:*:*.***:.  * .*: *:
           C521
[Salmo     CLNLSGNAMSQSLNGSEFTFLTKLQYLDFSFNRLDLLYSSAFQELENLVILDISNNNHYF 592
[Xenopus   CLNLSGNAISQTLNGSEFRNLNRLKYLDFSNNRIDLLYSTAFQELTELEVLDISNNDHYF 587
[Gallus    CLNLSGNAISQTLNGSEFYYLSGLKYLDFSNNRIDLLYSTAFKELKFLEILDLSNNKHYF 590
[Mus       CLNLSGNTIGQTLNGSELWPLRELRYLDFSNNRLDLLYSTAFEELQSLEVLDLSSNHYF 581
[Rattus    CLNLSGNAIGQTLNGSELQPLRELRYLDFSNNRLDLLYSTAFEELQNLEILDLSSNSHYF 581
[Homo      CLNLSGNLISQTLNGSEFQPLAELRYLDFSNNRLDLLHSTAFEELHKLEVLDLSSNSHYF 580
[Sus       CLNLSGNSISQALNGSEFQPLVELKYLDFSNNRLDLLHSTAFEELRNLEVLDISSNSHYF 581
[Bos       CLNLSGNSISQTLNGSEFQPLVELKYLDFSNNRLDLLYSTAFEELHNLEVLDISSNSHYF 589
           :****** :.*:*****:  * *:***** **:***:*:**:**  * :**:*.*.***

[Salmo     ESEGLTHMLNFTKNLTKLKILLMNYNKISTSTNTELESRSLEKLEFKGNRLDMLWRDGDT 652
[Xenopus   LAEGITHVFNFTKNLEKLTKLMMNNNQISTSTNRHLVSQSLRILEFKGNYLNILWKDGDT 647
[Gallus    LAEGVSHVLSFMKNLAYLKKLMMNENEISTSISTGMESQSLQTLEFRGNRLDIFWSDGKK 650
[Mus       QAEGITHMLNFTKKLRLLDKLMMNDNDISTSASRTMESDSLRILEFRGNHLDVLWRDGDN 641
[Rattus    QAEGITHMLNFTKKLRHLEKLMMNDNDISTSASRTMESESLRVLEFRGNHLDVLWRDGDN 641
[Homo      QSEGITHMLNFTKNLKVLQKLMMNDNDISSSTSRTMESESLRTLEFRGNHLDVLWREGDN 640
[Sus       QSEGITHMLDFTKNLKVLKKLMMNNNDIATSTSTTMESESLRILEFRGNHLDILWRDGDN 641
[Bos       QSEGITHMLNFTKNLKVLRKLMMNYNDIATSTSRTMESESLQILEFRGNHLDILWRDGDN 649
            :**:  *: *:   * *: *   *.:** *.*:*   . :  * **. ***:**  *:::
                                                                    C697
[Salmo     RYIDYFKKLLNLRVLDISHNNLNFIPQQVFQGLPDKLTNLYINNNRLKIFSWEKLIILQY 712
[Xenopus   RYLNFFKNLNKLYKLDISENSLTFVPPGVFEGMPPDLLELYLARNKLKTFSWDKLHLLEK 707
[Gallus    EYLSFFKNLTNLEQLDISSNMLNFLPPDVFEAMPPELKILNLTSNRLHTFNWGKLHLLTK 710
[Mus       RYLDFFKNLFNLEVLDISRNSLNSLPPEVFEGMPPNLKNLSLAKNGLKSFFWDRLQLLKH 701
[Rattus    RYLDFFKNLLNLEELDISRNSLNSVPPGVFEGMPPNLTTLSLAKNGLRSFSWGRLQLLKH 701
[Homo      RYLQLFKNLLKLEELDISKNSLSFLPSGVFDGMPPNLKNLSLAKNGLKSFSWKKLQCLKN 700
[Sus       RYLKFFKNLHKLEELDISENSLSFLPSGVFDGMPPNLKTLSLAKNGLKSFNWGKLQYLQN 701
[Bos       RYLKFFKNLLNLEELDISENSLSFLPLGVFDSMPPNLKTLSLAKNGLKSFSWERLQSLKN 709
           .*:. **:* :*  ****   ::    :*  **:: :*  .*  * *: * *  :*  *
                        C721
[Salmo     LEVLDLSSNSISTVPPELSNCTKSLKTLLLRRNQISKLSAYFLKDAFSLKYLDLSFNHIQ 772
[Xenopus   LSVLDLSNNYLTTVPRELSNCTSSIKKLILSNNKIKKLTPFFLRGSVSLKYLDLSDNLIQ 767
[Gallus    LITLDLSNNLLTTVPRKLSNCTSTLQELILRNNRITRITKYFLRGAIQLTYLDLSSNKIQ 770
[Mus       LEILDLSHNQLTKVPERLANCSKSLTTLILKMNQIRQLTKYFLEDALQLRYLDISSNKIQ 761
[Rattus    LKNLDLSHNQLTTVPARLANCSKSLTKLILNHNQIRQLTKYFLEDALQLRYLDISSNKIQ 761
[Homo      LETLDLSHNQLTTVPERLSNCSRSLKNLILKNNQIRSLTKYFLQDAFQLRYLDLSSNKIQ 760
[Sus       LETLDLSYNQLKTVPERLSNCSRSLKKLILKNNEIRNLTKYFLQDAFQLRHLDLSSNKIQ 761
[Bos       LETLDLSFNQLKTVPERLSNCSRSLKKLILKNNQIRCLTKYFLQGAFQLRHLDLSSNKIQ 769
           *  **** *  :..**  .*:*:  :     *.*  .*     :: :*..   * ** **
                           C787 C789                        C814
[Salmo     NIEQTSIPDDVVDQMDTLVLNNNKFMCNCNALMFVMWLNRTMVNIPRLATAVVCAAPGAQ 832
[Xenopus   NIGHSSFPEDVLDNLTELLLQGNPFFKCNCNLVWLVSWINQTKVYIPNLVTGVICSGPGAH 827
[Gallus    IIKKSSFPENIINNLRMLLLHNNPFKCNCDAVWFVGWINQTQVAIPLLATDVTCAGPGAH 830
[Mus       VIQKTSFPENVLNNLEMLVLHHNRFLCNCDAVWFVWWVNHTDVTIPYLATDVTCVGPGAH 821
[Rattus    VIQKTSFPENVLNNLNMLLLHHNRFLCNCDAVWFVWWVNHTDVTIPYLATDVTCAGPGAH 821
[Homo      MIQKTSFPENVLNNLKMLLLHHNRFLCICDAVWFVWWVNHTEVTIPYLATDVTCVGPGAH 820
[Sus       VIQKTSFPENVLNNLQILFLHHNRFLCNCDAVWLVWWVNHTEVTIPYLATDVTCMGPGAH 821
[Bos       VIQKTSFPENVLNNLNILFLHHNRFLCNCDAVWFVWWVNHTEVTIPYLATDVTCMGPGAH 829
           * ::*:*:::::::::  *.*. *  *:*: : :* *:*:* * ** *.*  *:*  .***:
```

FIG. 11C

```
[Salmo     RGHPVISLDLELQACQHNYLSIILYILLTSLVLSFVTLPISSHLFLWDVWYLYHFLLAKF 892
[Xenopus   RGQSLVLLDL--YTCEQYHLNLILQALSASFIICLMVVSVSSHLFYWDFWFIYHLFKAKI 885
[Gallus    KGRSLVFLDL--NTCELDTSYFIMYALSTSAVLCLMMFAVMSHLYFWDVWYSYHYCTAKL 888
[Mus       KGQSVISLDL--YTCELDLTNLILFSVSISSVLFLMVVMTTSHLFFWDMWYIYYFWKAKI 879
[Rattus    KGQSVISLDL--YTCELDLTNLILFSVSISSVLFLMIVMTTSHLFFWDMWYIYYFWKAKI 879
[Homo      KGQSVISLDL--YTCELDLTNLILFSLSISVSLFLMVMMTASHLYFWDVWYIYHFCKAKI 878
[Sus       KGQSVVSLDL--YTCELDLTNFVLFSLSLSAVLFLIVITIANHLYFWDVWYSYHFCKAKI 879
[Bos       KGQSVVSLDL--YTCELDLTNFILFSLSISAVLSLMMITIANHLYFWDVWYSYHFCKAKI 887
           :*: ::       ::: : * : :: .  .**:      *:    **:
              C8898 C890                            C927

[Salmo     KGYRRLSSPSAAYDAFVVYDKKDPEVSEWVLKELLVQLEEHGDHPLQLCLEERDWIPGCP 952
[Xenopus   HGYKRF--PKCCYDALIMYDTKDSAVSDWVFNDLVNILEKQGNKMLNLCLEERDFLAGQP 943
[Gallus    KGYRRIPLPDACYDAFIAYDNTDLAVNEWVMTELVEKLEDQKARQFNLCLEERDWLPGQP 948
[Mus       KGYQHLQSMESCYDAFIVYDTKNSAVTEWVLQELVAKLEDPREKHFNLCLEERDWLPGQP 939
[Rattus    KGYQHLQSMESCYDAFIVYDTKNSAVTEWVLQELVVKLEDPREKHFNLCLEERDWLPGQP 939
[Homo      KGYQRLISPDCCYDAFIVYDTKDPAVTEWVLAELVAKLEDPREKHFNLCLEERDWLPGQP 938
[Sus       KGYQRLISPNSCYDAFIVYDTKDPAVTEWVLDELVAKLEDPREKHFNLCLEERDWLPGQP 939
[Bos       KGYRRLISPNSCYDAFIVYDTKDPAVTEWVLDELVAKLEDPREKCFNLCLEERDWLPGQP 947
           :**:::   .:.:***:: **..: *.:**: :*: **.    : ::********:: * *

[Salmo     LIDNLSQSIHQSKRTVFILTNKYIKSGDFKTAFYMAHQRLMDERDDIVLIFLEKVPSHS 1012
[Xenopus   FLDNLSESIQISRKTVFVLTRKYVKKGHFKTAFYMAHQRLIEEKVDVIILILLEKTLQRS 1003
[Gallus    VFDNLSQSIQLSKKTIFVLTNKYIKSGTFKTTFYMAHQRLLDEKIDVIILIFLEKVLQKS 1008
[Mus       VLENLSQSIQLSKKTVFVMTQKYAKTESFKMAFYLSHQRLLDEKVDVIILIFLEKPLQKS 999
[Rattus    VLENLSQSIQLSRKTVFVMTQKYAKTESFKMAFYLSHQRLLDEKVDVIILIFLEKPLQKS 999
[Homo      VLENLSQSIQLSKKTVFVMTDKYAKTENFKIAFYLSHQRLMDEKVDVIILIFLEKPFQKS 998
[Sus       VLENLSQSIQLSKKTVFVMTDKYAKTEKFKIAFYLSHQRLMDEKVDVIILIFLEKPLQKS 999
[Bos       VLENLSQSIQLSKKTVFVMTDKYAKTENFKIAFYLSHQRLMDEKVDVIILIFLEKPLQKS 1007
           .::***:    :*:*::*  ** *.       *:::****::*: ***:**:***  .:*
              C1008              C1029

[Salmo     KYLRLRKRLYRRSVIEWPTNPQAQQYFWFSLRSVLVTDSQKQYSNLFKETR       1063
[Xenopus   RYLRLRKRLCANSVLYWPSNPNSQSYFWHCLKSAIATENQMAYDKLFKDHT       1054
[Gallus    RYVQLRKRLCRSSVLEWPTNPRSQPYFWQRLKNAIAMNNTLSYNKLLQETV       1059
[Mus       KFLQLRKRLCRSSVLEWPANPQAHPYFWQCLKNALTTDNHVAYSQMFKETV       1050
[Rattus    KFLQLRKRLCSSSVLEWPTNPQAHPYFWQCLKNALTTDNHVAYSQMFKETV       1050
[Homo      KFLQLRKRLCGSSVLEWPTNPQAHPYFWQCLKNALATDNHVAYSQVFKETV       1049
[Sus       KFFQLRKRLCGSSVLEWPTNPQAHPYFWQCLKNALATDNHVTYSQVFKETA       1050
[Bos       KFLQLRKRLCGSSVLEWPTNPQAHPYFWQCLKNALATDNHVTYSQVFKETA       1058
           ::..:*****:    **: **:**.:: ***  *:..:. :.    *.:::::
```

METHOD OF TREATMENT

CROSS-REFERENCE TO RELATED APPLICATIONS

This application is the National Stage Application of International Patent Application No. PCT/AU2018/050667, filed 29 Jun. 2018, which claims priority from Australian Provisional Patent Application No. 2017902545, filed on 30 Jun. 2017, entitled "A method of treatment", the entire contents of each of which are incorporated herein by reference, in their entirety.

SEQUENCE LISTING

The instant application contains a Sequence Listing which has been submitted electronically in ANSI format and is hereby incorporated by reference in its entirety. The ANSI copy is named ST25.txt and is 152 kB in size.

FIELD

The present invention relates generally to the field of immunomodulation. Taught herein is an agent for inhibiting immunostimulation mediated by a Toll-like receptor useful in the treatment of viral and microbial pathogenesis, diseases involving elements of autoimmunity and inflammation as well as cancer. Pharmaceutical compositions are also enabled herein.

BACKGROUND

Bibliographic details of the publications referred to by author in this specification are collected alphabetically at the end of the description.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavor to which this specification relates.

Immune stimulation is a major component in the prevention of viral and microbial pathogenesis. However, the regulation of the immune system is complex, sensitive and multifaceted. Unwarranted stimulation can lead to autoimmune diseases. A fuller understanding of the regulatory processes controlling the immune response is required if medical professionals are to deal with the imminent threat of viral epidemics and pandemics and to control autoimmunity. There is an urgent need for novel therapeutic approaches to target pathology irrespective of the infecting strain or autoimmune condition.

The production of reactive oxygen species (ROS) is a highly coordinated process achieved by enzymes of the NADPH oxidase (NOX) family. NOX enzymes evolved in single cell eukaryotes over 1.5 billion years ago and are present in most eukaryotic groups including amoeba, fungi, algae and plants, nematodes, echinoderms, urochordates, insects, fish, reptiles and mammals (Kawahara et al. (2007) *BMC Evolutionary Biology* 7:109; Aguirre (2010) *Free Radical Biology and Medicine* 49(9):1342-1353). The functions of NADPH oxidases within eukaryotes are diverse, however, a common function is the generation of ROS by innate immune cells in response to pathogens. Indeed, orthologs of NADPH oxidase in plants (ArtbohD and ArtbohF), fungi (NOXA/B), and invertebrates Celegans (Duox orthologs), *Drosophila* melongaster (NOX5 homolog, d-NOX and DUOX) and mosquito *Aedes aegypti* (NOXM and DUOX) generate ROS with bactericidal activity that protects the host (Kawahara et al. (2007) supra; Aguirre (2010) supra). Vertebrates including teleosts, amphibians, birds and mammals possess a NOX2 NADPH oxidase that generates a burst of ROS within phagosomes to kill invading pathogens especially bacteria. However, the impact of ROS on virus infection is largely unknown.

ROS, such as superoxide anion and hydrogen peroxide ($H_2O_2$), are produced by mouse and human inflammatory cells in response to viral infection and enhance the pathology caused by viruses of low to high pathogenicity, including influenza A viruses (Imai et al. (2008) *Cell* 133(2):235-249; Snelgrove et al. (2006) *Eur J Immunol* 36(6):1364-1373; To et al. (2014) *Free Radical Research* 48(8):940-947; Vlahos et al. (2011) *PLoS Pathogens* 7(2):e1001271; Vlahos et al. (2012) *Trends in Pharmacological Sciences* 33(1):308; Vlahos and Selemidis (2014) *Molecular Pharmacology* 86(6):747-759) The primary source of inflammatory cell ROS is the NOX2 oxidase enzyme (Vlahos and Selemidis (2014) supra; Selemidis et al. (2008) *Pharmacology & Therapeutics* 120(3):254-291; Drummond et al. (2011) *Nature Reviews Drug Discovery* 10(6):453-471; Bedard and Krause (2007) *Physiological Reviews* 87(1):245-313). Although NOX2 oxidase plays a role in the killing of bacteria and fungi via phagosomal ROS production, NOX2 oxidase does not appear to eliminate viruses in a manner analogous to that for bacteria. In fact, in the absence of NOX2, influenza A virus causes substantially less lung injury and dysfunction, and leads to lower viral burden suggesting that NOX2 oxidase-derived ROS promotes rather than inhibits viral infection Imai et al. (2008) supra; Snelgrove et al. (2006) supra; To et al. (2014) supra; Vlahos et al. (2011) supra; Vlahos et al. (2012) supra; Vlahos and Selemidis (2014) supra) However, identifying how viruses cause ROS production has been allusive, as is how these highly reactive oxygen molecules, which appear to be largely confined to their site of generation, contribute to disease.

After binding to the plasma membrane (Cossart and Helenius (2014) *Cold Spring Harbor Perspectives in Biology* 6(8)), viruses enter cells and ultimately endosomes by a variety of mechanisms resulting in viral RNA detection by endosomal pattern recognition receptors, including Toll-like receptor 3 (TLR3), TLR7 and TLR9 (Iwasaki and Pillai (2014) *Nature Reviews Immunology* 14(5):315-328). The specific receptor interaction depends upon either the Group (I to V) or genomic orientation (i.e. ssRNA, dsRNA or DNA) of the virus and triggers an immune response characterized by Type I IFN and IL-1β production, and B-cell-dependent antibody production (Iwasaki and Pillai (2014) supra). Host nucleic acids and self-antigens are also detected by endosomal TLRs, and in autoimmune disease, mediate similar Type I IFN responses and stimulate antibody production against self-RNA and antigen. Notably, mice that are chronically deficient in NOX2 oxidase have an increased tendency to develop self-antibodies (Campbell et al. (2012) *Science Translational Medicine* 4(157):157ra141) and patients with chronic granulomatous disease, who have a defective capacity to generate ROS via the NOX2 oxidase, have elevated circulating Type I IFNs and autoantibodies (Kelkka et al. (2014) *Antioxidants & Redox Signaling* 21(16):2231-2245). These observations are supportive of the notion that low levels of ROS result in an enhanced immune response. However, until the advent of the present invention, it was unknown how ROS modulate inflammation and the pathology caused by pathogens and whether targeted (and acute) abrogation of ROS may actually be beneficial in treating infection as well as other immune response-related conditions such as autoimmune disease conditions.

SUMMARY

Reactive oxygen species (ROS) promote the pathogenicity of viruses and microorganisms and other parasites. In work leading up to the present invention, the site and enzymatic source of subcellular ROS generation were determined together with the impact on ROS on immunostimulation. In accordance with the present invention, it is determined that TLR7 protein is activated by a disulfide bond forming between cysteine residues at positions 98 (C98) and 475 (C475) of TLR7 and this leads to toxic ROS production via NADPH oxidase (NOX2). The ROS in turn suppress antiviral and antimicrobial activity. The present invention therefore validates TLR7 as a therapeutic target. Reduction in TLR7 activity also enables treatment of autoimmune disease, inflammation and cancer and other conditions exacerbated by TLR7 activity.

Enabled herein is a method for inhibiting TLR7-mediated immunostimulatory activity in a subject, the method comprising contacting a cell from the subject expressing TLR7 with an effective amount of an agent which antagonizes disulfide bond formation between C98 and C475 of human (or murine) TLR7 or their corresponding positions in other TLR7s. Further taught herein is a method for treating a subject for autoimmune disease, viral or microbial pathogenesis, inflammation or cancer, the method comprising contacting a cell from the subject expressing TLR7 with an effective amount of an agent which antagonizes disulfide bond formation between C98 and C475 of TLR7 human (or murine) or their corresponding positions in other TLR7s. The present invention also enables a reduction in hypoimmunostimulation induced by ROS and ameliorates conditions associated with or exacerbated by TLR7 activity. In an embodiment, the agent suppresses TLR7 activity and is useful in the treatment of autoimmune disease condition.

In an embodiment, the agent comprises a peptide, referred to herein as a "decoy peptide" of from about 4 to about 190 amino acids in length and having an amino acid sequence with at least 70% amino acid sequence similarity to up to 190 contiguous amino acids between amino acids 4 to 194 of TLR7 human (or murine) which includes a peptide having an amino acid sequence with at least 70% amino acid sequence similarity to up to 100 contiguous amino acids between amino acids 48 to 148 of TLR7 and which also includes a peptide having an amino acid sequence with at least 70% amino acid sequence similarity to up to 40 contiguous amino acids between amino acid 78 to 118 of TLR7 with the proviso that the peptide comprises a cysteine residue at the equivalent of position 98 of TLR7 (C98).

In an embodiment, the decoy peptide comprises the amino acid sequence RCNC (SEQ ID NO:45) (using single amino acid code) corresponding to amino acids R97 to C100 of TLR7. In an embodiment, the decoy peptide comprises 10 amino acids in length from positions 95 to 104 of human TLR and has an amino acid sequence with at least 70% similarity to $DX_1RCNCX_2PX_3X_4$ (SEQ ID NO:27) wherein:

$X_1$ is L, F or M;
$X_2$ is V or I;
$X_3$ is V or I or A or P; and
$X_4$ is P or L or K or R.

In an embodiment, the decoy peptide is DFRCNCVPIP (SEQ ID NO:26) corresponding to human TLR7 between D95 and P104.

In another embodiment, the peptide comprises the amino acid sequence DLRCNCVPVL (SEQ ID NO:1) corresponding to D95 to L104 of murine TLR7.

To facilitate uptake of the peptide into the cell, the peptide may further comprise a moiety attached to the N-terminal or C-terminal end of the peptide which moiety includes a hydrophilic or cationic peptide, an amphiphilic or amphipathic peptide or a peptide with a periodic amino acid sequence. Alternatively, the peptide is conjugated to cholestanol.

Examples of a hydrophilic peptide include a peptide is selected from the group consisting of TAT (SEQ ID NO:2), SynB1 (SEQ ID NO:3), SynB3 (SEQ ID NO:4), PTD-4 (SEQ ID NO:5), PTD-5 (SEQ ID NO:6), FHV coat (SEQ ID NO:7), BMV Gag-(7-25) (SEQ ID NO:8), HTLV-II Rex-(4-16) (SEQ ID NO:9), D-Tat (SEQ ID NO:10) and R9-Tat (SEQ ID NO:11).

Examples of an amphiphilic peptide include a peptide is selected from the group consisting of Transportan chimera (SEQ ID NO:12), MAP (SEQ ID NO:13), SBP (SEQ ID NO:14), FBP (SEQ ID NO:15), MPG [MPGac] (SEQ ID NO:16), MPG (ΔNLS) (SEQ ID NO:17), Pep-1 (SEQ ID NO:18) and Pep-2 (SEQ ID NO:19).

Examples of a peptide with a periodic amino acid sequence include a peptide with a polyarginine or a polylysine sequence. Other examples are provided in Table 1 of Guidotti et al. (2017) *Trends in Pharmacological Sciences* 38(4):406-424, the contents of which are incorporated by reference. Cell uptake can also be facilitated by a NOX2-cholestanol-linker (PEG)-gp91ds-TAT construct. Linking cholestanol and PEG to gp91ds-TAT facilities delivery of gp91ds-TAT to the endosome.

In an embodiment, the subject is a human or non-human mammal.

Further enabled herein is use of an agent which antagonizes disulfide bond formation between C98 and C475 of TLR7 or their corresponding positions in the manufacture of a medicament to inhibit autoimmune disease, viral or microbial pathogenesis, inflammation or cancer in a subject. In a related embodiment, the present invention teaches an agent which antagonizes disulfide bond formation between C98 and C475 of TLR7 or their corresponding positions for use in inhibiting autoimmune disease, viral or microbial pathogenesis, inflammation or cancer in a subject.

Taught herein is a pharmaceutical composition comprising an agent which antagonizes disulfide bond formation between C98 and C475 of TLR7 or their corresponding positions and one or more pharmaceutical carriers, excipients and/or diluents. Such an agent, in an embodiment, includes an agent which comprises a peptide of from about 4 to 190 amino acids in length and having an amino acid sequence with at least 70% amino acid sequence similarity to up to 190 contiguous amino acids between amino acids 4 and 194 of TLR7. In another embodiment the agent comprises a peptide of from about 4 to 100 amino acids in length and having an amino acid sequence with at least 70% amino acid sequence similarity to up to 100 contiguous amino acids between amino acids 48 and 148 of TLR7. In another embodiment, the agent comprises a peptide of from about 4 to 40 amino acids in length and having an amino acid sequence with at least 70% amino acid sequence similarity to up to 40 contiguous amino acids between amino acids 78 and 118 of TLR7. Each of these embodiments is with the proviso that the peptide comprises a cysteine residue at the equivalent of position 98 of TLR7 (C98). Alternatively, or in addition, the peptide comprises the amino acid sequence RCNC (SEQ ID NO:45) corresponding to R97 to C100 of TLR7. Extraneous amino acids totalling, with RCNC (SEQ ID NO:45), from 5 to 500 may be included on the N- and/or C-terminal ends of $H_2N$—RCNC—COOH. Chemical mimetics of the TLR7-inhibitory peptides also form part of the present invention.

Abbreviations used herein are defined in Table 1.

TABLE 1

Abbreviations

| Abbreviation | Definition |
|---|---|
| AA | Amino acid |
| BMDM | Bone marrow derived macrophage |
| C98i | Decoy peptide corresponding to amino acids 95 to 104 of TLR7 |
| EEA1 | Early endosome antigen 1 |
| $H_2O_2$ | Hydrogen peroxide |
| HIV-TAT | TAT from Human immunodeficiency virus |
| IAV | Influenza A virus |
| IFN | Interferon |
| MOI | Multiplicity of infection |
| NOX | NADPH oxidase |
| NP | Nucleoprotein |
| PFU | Plaque forming units |
| ROS | Reactive oxygen species |
| TAT | Trans-activating transcriptional activator |
| TLR | Toll-like receptor |
| TLR1 | Toll-like receptor 1 |
| TLR2 | Toll-like receptor 2 |
| TLR3 | Toll-like receptor 3 |
| TLR4 | Toll-like receptor 4 |
| TLR5 | Toll-like receptor 5 |
| TLR6 | Toll-like receptor 6 |
| TLR7 | Toll-like receptor 7 |
| TLR8 | Toll-like receptor 8 |
| TLR9 | Toll-like receptor 9 |
| TLR10 | Toll-like receptor 10 |
| WT | Wildtype |
| X31 | Mouse adapted Hong Kong H3N2 influenza A virus |

Amino acid sequences are referred to by a sequence identifier number (SEQ ID NO). The SEQ ID NOs correspond numerically to the sequence identifiers <400>1 (SEQ ID NO:1), <400>2 (SEQ ID NO:3), etc. An amino acid sequence in 3 or single letter code or written in full is provided in the N-terminal to C-terminal direction (left to right, respectively), unless otherwise specified.

A summary of sequence identifiers used throughout the subject specification is provided in Table 2.

TABLE 2

Summary of sequence identifiers

| SEQUENCE ID NO: | DESCRIPTION |
|---|---|
| 1 | Peptide decoy from D95 to L104 of murine TLR7 |
| 2 | Cell penetrating peptide TAT |
| 3 | Cell penetrating peptide SynB1 |
| 4 | Cell penetrating peptide SynB3 |
| 5 | Cell penetrating peptide PTD-4 |
| 6 | Cell penetrating peptide PTD-5 |
| 7 | Cell penetrating peptide FHV coat |
| 8 | Cell penetrating peptide BMV Gag-(7-25) |
| 9 | Cell penetrating peptide HTLV-II Rex-(4-16) |
| 10 | Cell penetrating peptide D-Tat |
| 11 | Cell penetrating peptide R9-Tat |
| 12 | Cell penetrating peptide Transportan chimera |
| 13 | Cell penetrating peptide MAP |

TABLE 2-continued

Summary of sequence identifiers

| SEQUENCE ID NO: | DESCRIPTION |
|---|---|
| 14 | Cell penetrating peptide SBP |
| 15 | Cell penetrating peptide FBP |
| 16 | Cell penetrating peptide MPGac |
| 17 | Cell penetrating peptide $MPG^{(NLS)}$ |
| 18 | Cell penetrating peptide Pep-1 |
| 19 | Cell penetrating peptide Pep-2 |
| 20 | Human TLR7 |
| 21 | Influenza polymerase forward primer |
| 22 | Influenza polymerase reverse primer |
| 23 | Gp91 ds-TAT peptide |
| 24 | Sgp91 ds-TAT peptide |
| 25 | Murine TLR7 |
| 26 | Peptide decoy from D95 to P104 of human TLR7 |
| 27 | Consensus peptide decoy from positions 95 to 104 of TLR |
| 28 | Human TLR3 |
| 29 | Human TLR9 |
| 30 | Human TLR8 |
| 31 | Human TLR5 |
| 32 | Human TLR4 |
| 33 | Human TLR2 |
| 34 | Human TLR10 |
| 35 | Human TLR1 |
| 36 | Human TLR6 |
| 37 | *Salmo salar* TLR7 |
| 38 | *Xenopus tropicalis* TLR7 |
| 39 | *Gallus gallus* TLR7 |
| 40 | *Rattus norvegius* TLR7 |
| 41 | Human TLR7 |
| 42 | *Sus scrofa* TLR7 |
| 43 | *Bos Taurus* TLR7 |
| 44 | Amino acid sequence of scrambled C98i amino acid sequence |
| 45 | Amino acid sequence of C98i motif RCNC |
| 46 | Amino acid sequence of RANC |
| 47 | Amino acid sequence RANA |
| 48 | Amino acid sequence of RCNA |
| 49 | Amino acid sequence of human TLR7 motif starting at AA95 |
| 50 | Amino acid sequence of mouse TLR7 motif starting at AA95 |
| 51 | Amino acid sequence of rat TLR7 motif starting at AA95 |
| 52 | Amino acid sequence of chicken TLR7 motif starting at AA103 |
| 53 | Amino acid sequence of frog TLR7 motif starting at AA101 |
| 54 | Amino acid sequence of pig TLR7 motif starting at AA95 |
| 55 | Amino acid sequence of salmon TLR7 motif starting at AA103 |
| 56 | Amino acid sequence of zebrafish TLR7 motif starting at AA90 |
| 57 | Amino acid sequence of C98i with TAT |

Single and three letter codes for amino acids used herein are defined in Table 3.

TABLE 3

Amino acid three and single letter

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |

TABLE 3-continued

Amino acid three and single letter

| Amino Acid | Three-letter Abbreviation | One-letter Symbol |
| --- | --- | --- |
| Serine | Ser | S |
| Threonine | Thr | T |
| Tryptophan | Trp | W |
| Tyrosine | Tyr | Y |
| Valine | Val | V |
| Pyrrolysine | Pyl | O |
| Selenocysteine | Sec | U |
| Any residue | Xaa | X |

List of primers and their sources and reference sequences are shown in Table 4. The influenza polymerase primers were custom synthesized and the sequences are shown.

Table 4

Primers

| Gene | Company | Gene expression assay | Catalog no. | Ref Seq |
| --- | --- | --- | --- | --- |
| Mouse IL-1β TaqMan Primer | Applied Biosystems | Mm00434226_m1 | 4331182 | NM_008361.3 |
| Mouse CYBB TaqMan Primer | Applied Biosystems | Mm01287743_m1 | 4331182 | NM_007807.5 |
| Mouse IFNB1 TaqMan Primer | Applied Biosystems | Mm00439552_s1 | 4331182 | NM_010510.1 |
| Mouse TNFα TaqMan Primer | Applied Biosystems | Mm00443258_m1 | 4331182 | NM_001278601.1 |
| Mouse IL6 TaqMan Primer | Applied Biosystems | Mm00446190_m1 | 4331182 | NM_031168.1 |
| Mouse TLR7 TaqMan Primer | Applied Biosystems | Mm00446590_m1 | 4331182 | NM_016562.3 |
| Mouse GAPDH (X20) | Applied Biosystems | | 4352339E | |
| Influenza polymerase forward primer | Appied Biosystems | 5'-CGGTCCAAATTCCT GCTGCTGA-3' | | SEQ ID NO: 21 |
| Influenza polymerase reverse primer | Appied Biosystems | 5'-CATTGGGTTCCTTC CATCCA-3-3' | | SEQ ID NO: 22 |

BRIEF DESCRIPTION OF THE FIGURES

Some figures contain color representations or entities. Color photographs are available from the Patentee upon request or from an appropriate Patent Office. A fee may be imposed if obtained from a Patent Office.

FIG. 4A and FIG. 4B are photographic and graphic representations showing bacteria-induced ROS production is distinct from virus-dependent ROS mechanisms (A) Phagosomal superoxide production to *Haemophilus influenzae* and *Streptococcus pneumoniae* as assessed by OxyBURST (100 μM) fluorescence microscopy in WT and TLR7$^{-/-}$ immortalized bone marrow derived macrophages. Images are representative of >150 cells analyzed over each experiment. Original magnification ×100. (B) Is the quantification of the results (n=5). All data are represented as mean±SEM. One-way ANOVA followed by Dunnett's post hoc test for multiple comparisons. *P<0.05 compared to WT control.

FIG. 6A, FIG. 6B, FIG. 6C, FIG. 6D, FIG. 6E, FIG. 6F, FIG. 6G, FIG. 6H, FIG. 6I, FIG. 6J, FIG. 6K, and FIG. 6L are photographic and graphic representations showing endosomal NOX2 oxidase-derived hydrogen peroxide ($H_2O_2$) inhibits cytokine expression in response to TLR7 activation in vitro and in vivo. (A) WT mouse primary alveolar macrophages were either left untreated or treated with FITC-labeled catalase for 5 min prior to infection with HKx31 virus (MOI of 10). Cells were labeled for Lysotracker (50 nM) and colocalization of Lysotracker and FITC catalase assessed by confocal microscopy. Images are representative of >100 cells analyzed over each experiment. Original magnification ×100 (n=3). (B) WT and TLR7$^{-/-}$ immortalized bone marrow-derived macrophages (BMDMs) were left untreated or treated for 1 hr with catalase (1000 U/mL) and IFN-β and IL-1β, mRNA expression determined by QPCR after 24 hr (n=7). (C) WT BMDMs were left untreated or treated for 1 hr with imiquimod (Imiq) in the absence or presence of catalase (1000 U/mL), IFN-β and IL-1β, mRNA expression assessed 24 hr later by QPCR (n=6). (D) WT BMDMs were treated for 30 mins with either DMSO (0.1%) or dynasore (Dyna; 100 μM) and then with catalase (1000 U/mL) for 1 hr. Cytokine mRNA expression determined by QPCR after 24 h (n=6). (E) WT and TLR2$^{-/-}$ immortalized BMDMs were treated with catalase (1000 U/mL) for 1 hr and cytokine mRNA expression determined by QPCR after 24 h (n=6). (F) WT and UNCB93$^{-/-}$ immortalized BMDMs were treated with catalase (1000 U/mL) for 1 hr and cytokine mRNA expression determined by QPCR after 24 h (n=6). (G-I) WT BMDMs were treated for 1 hr with either catalase or imiquimod (10 μg/ml) and G) TLR7, H) NLRP3 or I) TREML4 mRNA expression determined by QPCR after 24h (n=6). (J) Mice were intranasally treated with catalase (1000U/mouse) and then lung expression of TREML4 was determined by QPCR (n=5). (K and L) Catalase (1000 U/mouse, intranasal) was administered to WT mice and K) total BALF airway inflammation and L) lung cytokine expression assessed 24h later (n=5). (B-H and L) Responses are relative to GAPDH and then expressed as a foldchange above WT controls. (B-H and L) Kruskal-Wallis test with Dunn's post hoc for multiple comparisons. (I and J) Mann-Whitney Wilcoxon test. All data are represented as mean±SEM. Statistical significance was taken when the P<0.05. *P<0.05.

FIG. 7A and FIG. 7B are graphic representations showing C98 on TLR7 regulates activity of the receptor and is a target for endosomal $H_2O_2$ (A) TLR7$^{-/-}$ BMDMs were transfected with empty vector, WT TLR7 or with either TLR7 with cysteines 98, 260, 263, 270, 273 and 445 mutated to alanine (TLR7 6 mut), TLR7 with cysteines 98 and 445 mutated to alanine (TLR7C98A/445A) or with TLR7 with cysteines 445 (TLR7C445A) or 98 (TLR7C98A) mutated to alanine. After 48 h, cells were left untreated or treated for 1 hr with either catalase (1000 U/mL) or imiquimod (Imiq, 10 µg/ml) and cytokine expression assessed 24h later (n=6). Responses are relative to GAPDH and then expressed as a fold-change above TLR7$^{-/-}$ controls. Data are represented as mean±SEM. One-way ANOVA followed by Dunnett's post hoc test for multiple comparisons. Statistical significance was accepted when P<0.05. *P<0.05. (n.$) Denotes not significant. (B) Multiple sequence alignment with CLUSTAL OMEGA showing across species conservation of Cys 98 on TLR7.

FIG. 9A, FIG. 9B, FIG. 9C, FIG. 9D, FIG. 9E, FIG. 9F, FIG. 9G, FIG. 9H, FIG. 9I, FIG. 9J, FIG. 9K, FIG. 9L, and FIG. 9M are photographic and graphic representations showing endosome targeted delivery of a NOX2 oxidase inhibitor protects mice following influenza A virus infection in vivo (A-E) Alveolar macrophages from WT mice were treated with the Cy5 cholestanol-PEG linker fluorophore (Cy5-chol; 100 nM) for 30 min and infected with HKx31 influenza A virus (MOI of 10). Cells were then counter labeled with antibodies to either: A) and B) EEA1, C) NOX2 or D) influenza A nucleoprotein (NP). All cells were then stained with 4',6'-diamidino-2-phenylindole (DAPI) and imaged with confocal microscopy. B) Cells were pre-treated with dynasore (100 µM) for 30 mins prior to exposure to Cy5-cholestanol. E) Quantification of data from (A-D, n=5). (F) RAW 264.7 macrophages were either untreated or treated with various concentrations of cholestanol-conjugated gp91ds-TAT (Cgp91), ethyl conjugated gp91ds-TAT (Egp91) or unconjugated gp91ds-TAT (Ugp91) for 30 mins prior to quantifying ROS production by L-O12 (100 µM)-enhanced chemiluminescence (n=7). (G) Superoxide production via the xanthine/xanthine oxidase cell-free assay in the absence or presence of Ugp91ds-TAT, (1 µM) or Cgp91ds-TAT (1 µM) (n=6). (H-I) Ugp91ds-TAT (0.02 mg/kg/day) or Cgp91ds-TAT (0.02 mg/kg/day) were delivered intranasally to WT mice once daily for 4 days. At 24 h after the first dose of inhibitor, mice were either treated with saline or infected with HKx31 influenza A virus (1×105 PFU per mouse). Mice were culled at day 3 post-infection and H) airway inflammation was assessed by BALF cell counts and I) lung IFN-β mRNA was determined by QPCR (n=7). (n.s) denotes not significant. (J-M) Mice were subjected to the NOX2 inhibitor treatment regime and virus infection protocol as in H) except NOX2 inhibitors were delivered at a dose of 0.2 mg/kg/day (n=7). Analysis of J) airway inflammation by BALF counts, K) body weight (% weight change from the value measured at Day −1), L) ROS production by BALF inflammatory cells with L-O12 enhanced chemiluminescence and M) viral mRNA by QPCR. Data are represented as mean±SEM. E) Unpaired t-test; statistical significance taken when the P<0.05. (F, G, H, J, K, L) One-way ANOVA followed by Dunnett's post hoc test for multiple comparisons. (I and M) Kruskal-Wallis test with Dunn's post hoc for multiple comparisons. Statistical significance was accepted when P<0.05. *P<0.05; **P<0.01.

FIG. 10A, FIG. 10B, FIG. 10C, and FIG. 10D show multiple sequence alignment analysis demonstrating the position of all cysteine residues on human TLR7. Individual sequences of human TLRs were obtained from NCBI GenBank protein databases with the following accession numbers TLR1 (CAG38593.1; SEQ ID NO:35), TLR2 (AAH33756.1; SEQ ID NO:33), TLR3 (ABC86910.1; SEQ ID NO:28), TLR4 (AAF07823.1; SEQ ID NO:32), TLR5 (AAI09119.1; SEQ ID NO:31), TLR6 (BAA78631.1; SEQ ID NO:36), TLR7 (AAZ99026.1; SEQ ID NO:20), TLR8 (AAZ95441.1; SEQ ID NO:30), TLR9 (AAZ95520.1; SEQ ID NO:29) and TLR10 (AAY78491.1; SEQ ID NO:34) and then sequence alignment was performed with CLUSTAL OMEGA (EMBL-EBI). Shown in red dotted rectangular boxes are the cysteines on human TLR7 and the respective position indicated.

FIG. 11A, FIG. 11B, and FIG. 11C show multiple sequence alignment analysis of vertebrate TLR7. Individual sequences of TLRs were obtained from NCBI GenBank protein databases with the following accession numbers *Salmo salar* (CCX35457.1; SEQ ID NO:37), *Xenopus tropicalis* (AAI66280.1; SEQ ID NO:38), *Gallus gallus* (ACR26243.1; SEQ ID NO:39), *Mus musculus* (AAI32386.1; SEQ ID NO:25), *Rattus norvegicus* (NP_001091051.1; SEQ ID NO:40), *Homo sapiens* (AAZ99026.1; SEQ ID NO:41), *Sus scrofa* (ABQ52583.1; SEQ ID NO:42) and *Bos Taurus* (NP_001028933.1; SEQ ID NO:43) and then sequence alignment was performed with CLUSTAL OMEGA (EMBL-EBI). Shown in red dotted rectangular boxes are the cysteines on human TLR7 and the respective position indicated.

DETAILED DESCRIPTION

Figure 1A:
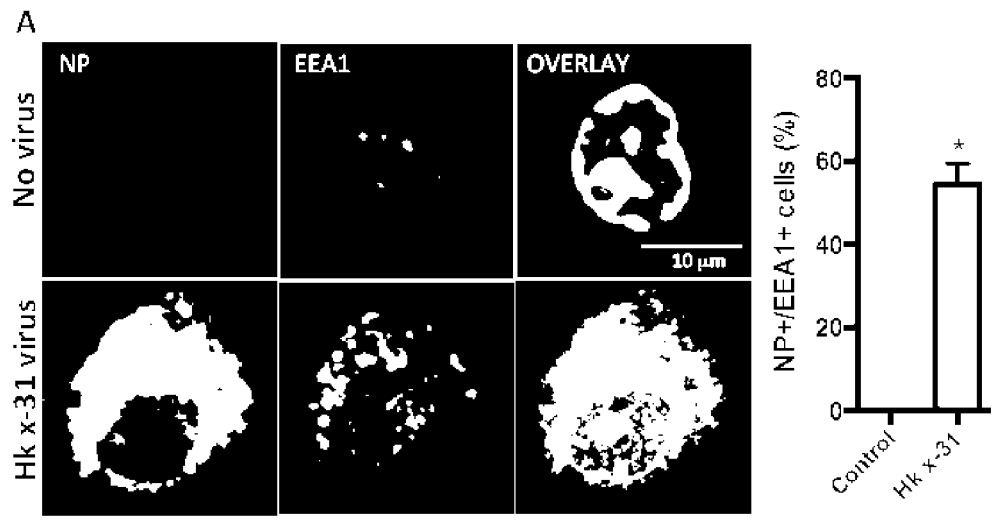
FIG. 1A, FIG. 1B, FIG. 1C, FIG. 1D, FIG. 1E, FIG. 1F, FIG. 1G, FIG. 1H, FIG. 1I, and FIG. 1J are photographic and graphic representations showing seasonal and pandemic influenza A viruses induce endosomal ROS production via activation of NOX2 oxidase. (A-B) Confocal microscopy of wild-type (WT) mouse primary alveolar macrophages that were infected with influenza A virus strain HKx31 (MOI of 10) for 1 hr and labeled with antibody to the early endosome antigen 1 (EEA1) and antibodies to either A) influenza A virus nucleoprotein (NP) or B) NOX2, and then with 4',6'-diamidino-2-phenylindole (DAPI; blue). Also shown is the quantification of results (n=5). (C-D) Time-dependent elevation in endosomal ROS Control levels in mouse primary alveolar macrophages as assessed by OxyBURST (100 μM) confocal fluorescence microscopy and labeled with DAPI (n=5). (E-F) Endosomal ROS production in WT, NOX2$^{-/y}$ and superoxide dismutase (SOD; 300U/mL)-treated WT mouse primary alveolar macrophages as assessed by Oxy-BURST confocal fluorescence microscopy in the absence or presence of HKx31 virus and labeled with DAPI (n=5). (G) Uninfected and HKx31 virus-infected mouse primary alveolar macrophages were labeled with OxyBURST and the acidified endosome marker Lysotracker (50 nM). Some cells were treated with bafilomycin A (Baf-A; 100 nM) to suppress acidification of endosomes (n=4). (H) Human alveolar macrophages infected with seasonal H3N2 (A/New York/55/2004, A/Brisbane/9/2007), seasonal H1N1 (A/New Caledonia/20/1999, A/Solomon Islands/3/2006) and pandemic A(H1N1) pdm09 strains (A/California/7/2009, A/Auckland/1/2009) and labeled with OxyBURST for endosomal ROS (n=4). (I-J) Endosomal ROS production in WT mouse primary alveolar macrophages as assessed by OxyBURST fluorescence microscopy exposed to either heat (56OC)-inactivated HKx-31 virus (to block virus fusion) or UV-inactivated HKx-31 virus (to block replication) and labeled with DAPI (n=4). (A, B, C, E, G, H and I) Images are representative of >150 cells analyzed over each experiment. Original magnification X100. (A, B, D, F and J) Data are represented as mean±SEM. (A and B) Students' unpaired t-test *P<0.05. (D, F and J) One-way ANOVA followed by Dunnett's post hoc test for multiple comparisons. *P<0.05 and **P<0.01.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method step or group of elements or integers or method steps.

As used in the subject specification, the singular forms "a", "an" and "the" include plural aspects unless the context clearly dictates otherwise. Thus, for example, reference to "a pathogen" includes a single pathogen, as well as two or more pathogens; reference to "an agent" includes a single agent, as well as two or more agents; reference to "the disclosure" includes single and multiple aspects taught by the disclosure; and so forth. Aspects taught and enabled herein are encompassed by the term "invention". Any variants and derivatives contemplated herein are encompassed by "forms" of the invention. All aspects of the invention are enabled across the width of the claims.

The present invention is predicated in part on the determination that virus entry into the endosomal compartment of a cell triggers NADPH oxidase (NOX)-dependent production of reactive oxygen species (ROS) in the endosome. It is determined that endosomal ROS are negative regulators of molecular mechanisms conferring antiviral immunity and is dependent on Toll-like receptor 7 (TLR7) activation. The ability to limit ROS production by antagonizing TLR7 activation enables production of a universal antiviral therapy as well as anti-pathogen therapy more generally. Antagonizing TLR7 activation limits production of ROS which would otherwise antagonize immunostimulation. Given that TLR7 is itself associated with forms of inflammation, the present invention has wider implications in the treatment of microbial infection (e.g. bacteria and fungal microorganisms), autoimmune disease conditions, inflammation and cancer. Hence, antagonizing TLR7 activation assists in ameliorating diseases and conditions associated with or exacerbated by TLR7 activation.

Hence, the present invention enables a reduction in levels of activated TLR7 which leads to:

(i) reduced endosomal ROS production via NOX2;

(ii) reduced active TLR7 leading to reduced inflammatory conditions;

(iii) reduced hypoimmunostimulation;

(iv) reduced negative regulation of humoral immune response networks;

(v) reduced capacity for pathogen infection;

(vi) reduced inflammation;

(vii) reduced capacity for cancer growth; and/or (viii) amelioration of autoimmune conditions or diseases arising therefrom.

Accordingly, enabled herein is a method for inhibiting TLR7-mediated immunostimulatory activity in a subject, the method comprising contacting a cell from the subject expressing TLR7 with an effective amount of an agent which antagonizes disulfide bond formation between C98 and C475 of TLR7 or their corresponding positions.

Further enabled herein is a method for treating a subject for autoimmune disease, viral or microbial pathogenesis, inflammation or cancer, the method comprising contacting a cell from the subject expressing TLR7 with an effective amount of an agent which antagonizes disulfide bond formation between C98 and C475 of TLR7 or their corresponding positions.

Also enabled herein is a method for treating a subject for excessive production of reactive oxygen species, the method comprising contacting a cell from the subject expressing TLR7 with an effective amount of an agent which antagonizes disulfide bond formation between C98 and C475 of TLR7 or their corresponding positions.

Enabled herein is a method for treating a subject for TLR7-mediated inflammation, the method comprising contacting a cell from the subject expressing TLR7 with an effective amount of an agent which antagonizes disulfide bond formation between C98 and C475 of TLR7 or their corresponding positions.

Further enabled herein is a method for treating a subject for an autoimmune condition, the method comprising contacting a cell from the subject expressing TLR7 with an effective amount of an agent which antagonizes disulfide bond formation between C98 and C475 of TLR7 or their corresponding positions.

Still further enabled herein is a method for treating a subject for cancer, the method comprising contacting a cell from the subject expressing TLR7 with an effective amount of an agent which antagonizes disulfide bond formation between C98 and C475 of TLR7 or their corresponding positions.

Reference to TLR7 includes any TLR7 from any species. Generally, the TLR7 referred to is the TLR7 from the subject being treated. Hence, where the subject is a human, the antagonist would be for human TLR7 expressed by the cell. The amino acid sequence of human TLR7 is set forth in SEQ ID NO:20. Comparisons of amino acid sequence of TLR7 form different species is set forth in FIG. 11. Of importance is a cysteine residue (Cys; C) at amino acid position 98 (C98) which forms a disulfide bond with the cysteine at amino acid position 475 (C475), or corresponding positions in a homolog from a different species. These amino acid positions are conserved amongst TLR7 molecules across species. In an embodiment, the present invention antagonizes formation of this disulfide bond leading to reduced levels of activated TLR7. This in turn reduces TLR7-mediated immunostimulation and reduces NADPH oxidase-mediated ROS formation.

It is proposed herein to use an antagonist of this disulfide bond forming pair. The agent may be proteinaceous or non-proteinaceous. In an embodiment, a peptide decoy is proposed to form a disulfide bond with C475 of TLR7 which prevents a C98-C475 disulfide bond forming. In an embodiment, the agent is a chemical mimetic of the peptide decoy.

Examples of microbial pathogens include: *Helicobacter pyloris, Borrelia burgdorferi, Legionella* pneumophilia, Mycobacteria sps (such as. *M. tuberculosis, M. avium, M. intracellulare, M. kansasii* and *M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema* pertenue, Leptospira and *Actinomyces israelii*. Examples of pathogenic fungi include, but are not limited to, *Cryptococcus neoformans, Histoplasma capsulatum, Coccidioides immitis, Blastomyces dermatitidis, Chlamydia trachomatis* and *Candida albicans*.

Examples of viral pathogens include: Retroviridae (including but not limited to human immunodeficiency virus (HIV)); Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bunyaviridae (for example, Hantaan viruses, bunya viruses, phleboviruses, and Nairo viruses); Arena viridae (hemorrhagic fever viruses); Reoviridae (e.g. reoviruses, orbiviurses, and rotaviruses); Birnaviridae; Hepadnaviridae (Hepatitis B virus); Parvoviridae (parvoviruses); Papovaviridae (papilloma viruses, polyoma viruses); Adenoviridae (most adeno viruses); Herpesviridae (herpes simplex virus (HSV) 1 and HSV-2, varicella zoster virus, cytomegalovirus (CMV)); Poxviridae (variola viruses, vaccinia viruses, pox viruses); and Iridoviridae (such as African swine fever virus); and unclassified viruses (for example, the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astro viruses).

Cancers or tumors include acute lymphoblastic leukemia, B cell lymphoma, glioma, bladder cancer, biliary cancer, breast cancer, cervical carcinoma, colon carcinoma, colorectal cancer, choriocarcinoma, epithelial cell cancer, gastric cancer, hepatocellular cancer, Hodgkin's lymphoma, lung cancer, lymphoid cell-derived leukemia, melanoma, myeloma, non-small cell lung carcinoma, nasopharyngeal cancer, ovarian cancer, prostate cancer, pancreatic cancer, renal cancer, squamous cell cancers of cervix and esophagus, testicular cancer, T-cell leukemia and melanoma.

Autoimmune disorders include systemic lupus erythematosus, rheumatoid arthritis, inflammatory bowel disease, Sjogren's syndrome, polymyositis, vasculitis, Wegener's granulomatosis, sarcoidosis, ankylosing spondylitis, Reiter's syndrome, psoriatic arthritis and Behcet's syndrome. In an embodiment, the autoimmune disorder is an immune complex associated disease. Immune complex associated diseases specifically include, without limitation, systemic lupus erythematosus, rheumatoid arthritis, polyarteritis nodosa, poststreptococcal glomerulonephritis, cryoglobulinemia, and acute and chronic serum sickness.

Examples of inflammatory disease conditions contemplated by the present invention include but are not limited to those diseases and disorders which result in a response of redness, swelling, pain, and a feeling of heat in certain areas that is meant to protect tissues affected by injury or disease. Inflammatory diseases which can be treated using the methods of the present invention, include, without being limited to, acne, angina, arthritis, asthma, aspiration pneumonia disease, chronic obstructive pulmonary disease (COPD), colitis, empyema, gastroenteritis, intestinal flu, necrotizing enterocolitis, pelvic inflammatory disease, pharyngitis, pleurisy, raw throat, rubor, sore throat, urinary tract infections, chronic inflammatory demyelinating polyneuropathy, chronic inflammatory demyelinating polyradiculoneuropathy.

The peptide decoy comprises from 4 to 190 amino acids in length and comprises, in an embodiment, the amino acid sequence RCNC (SEQ ID NO:45) corresponding to R97 to C100 of TLR7. This sequence is conserved across species. Critical is C98 in TLR7 or its equivalent or corresponding position in a TLR7 homolog or variant. In an embodiment, the peptide decoy comprises:

(a) from 4 to 190 amino acids in length;

(b) the amino acid sequence RCNC (SEQ ID NO:45) corresponds to R97 to C100 of a TLR7; and (c) a cysteine at a position corresponding to C98 of TLR7.

Amino acids may be substituted for conformationally or functionally equivalent or similar amino acids except for the cysteine corresponding to C98.

In an embodiment, the agent comprises a peptide, referred to herein as a "decoy peptide" of from 4 to 190 amino acids in length and having an amino acid sequence with at least 70% amino acid sequence similarity to up to 190 contiguous amino acids between amino acids 4 and 194 of TLR7 which includes a peptide having an amino acid sequence with at least 70% amino acid sequence similarity to up to 100 contiguous amino acids between amino acids 48 and 148 of TLR7 and which also includes a peptide having an amino acid sequence with at least 70% amino acid sequence similarity to up to 40 contiguous amino acids between amino acids 78 and 118 of TLR7 with the proviso that the peptide comprises a cysteine residue at the equivalent of position 98 of TLR7 (C98). The peptide may be from 4 to 190 amino acids in length.

The expression "4 to 190" in terms of length of the decoy peptide includes 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 and 190 amino acids in length. The region between amino acids 48 and 148 includes positions 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147 and 148. The region between 78 to 118 includes 78, 79, 80, 81, 82, 83, 84, 85, 86, 87, 88, 89, 90, 91, 92, 93, 94, 95, 96, 97, 98, 99, 100, 101, 102, 103, 103, 104, 105, 106, 107, 108, 109, 110, 111, 112, 113, 114, 115, 116, 117 and 118. The expression "at least 70%" in relation to percentage similarity includes 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100%.

The term "similarity" as used herein includes exact identity between compared sequences at the amino acid level. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polypeptides include "reference sequence", "comparison window", "sequence similarity", "sequence identity", "percentage of sequence similarity", "percentage of sequence identity", "substantially similar" and "substantial identity". A "reference sequence" is at least 4 or above, inclusive of amino acid residues, in length. Because two polypeptides may each comprise: (1) a sequence (i.e. only a portion of the complete TLR7 amino acid sequence) that is similar between the two polypeptides; and (2) an amino acid sequence that is divergent between the two polypeptides, sequence comparisons between two (or more) polypeptides are typically performed by comparing sequences over a "comparison window" to identify and compare local regions of sequence similarity. A "comparison window" refers to a conceptual segment of typically 4 contiguous amino acid residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) *Nucl. Acids. Res.* 25:3389. A detailed discussion of sequence analysis can be found in Unit 19.3 of Ausubel et al. (*In: Current Protocols in Molecular Biology*, John Wiley & Sons Inc. 1994-1998. Comparisons of TLR7 amino acid sequence are presented in FIGS. 10a through d.

The terms "sequence similarity" and "sequence identity" as used herein refers to the extent that sequences are identical or functionally or structurally similar on an amino acid-by-amino acid basis over a window of comparison. Thus, a "percentage of sequence identity", for example, is calculated by comparing two optimally aligned sequences over the window of comparison, determining the number of positions at which the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e. the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

In an embodiment, the percentage similarity to the amino acid sequence between amino acids 4 to 194 of human TLR7 is at least about 80% or 85% or 90% or 95% or 99%. This also applies to the percentage similarity between amino acids 48 and 148 and between 78 and 118 of human TLR7.

The agent includes, therefore, a peptide or peptide decoy as well as a non-proteinaceous chemical agent which antagonizes disulfide bond formation between C98 and C475. A non-proteinaceous chemical agent includes a chemical mimetic of C98i. A peptide decoy comprises a cysteine at the equivalent of C98. A peptide decoy may also comprise the amino acid sequence RCNC (SEQ ID NO:45) corresponding to R97 to C100 of human TLR7.

In an embodiment, the peptide decoy comprises 10 amino acids having the amino acid sequence $DX_1RCNCX_2PX_3X_4$ (SEQ ID NO:27) wherein:

$X_1$ is L, F or M;
$X_2$ is V or I;
$X_3$ is V or I or A or P; and
$X_4$ is P or L or K or R, or an amino acid sequence having at least about 70% similarity to SEQ ID NO:27 after optimal alignment which includes at least about 80%, 85%, 90%, 95% or 99% similarity to SEQ ID NO:27. The above sequence corresponds to amino acid positions 95 to 104 of human TLR or its equivalent. Human TLR7 comprises a P at position 104. In murine TLR7, the amino acid L is at position 104. Both have a D at position 95.

In an embodiment, the peptide decoy comprises from 4 to 40 amino acids selected from between amino acids 78 to 118 of human TLR7 with the proviso that either the peptide comprises a cysteine residue at a position corresponding to C98 of human TLR7 or the peptide comprises the amino acid sequence RCNC (SEQ ID NO:45) at positions corresponding to R97 to C100 of human TLR7.

In yet another embodiment, the peptide decoy comprises the amino acid sequence: DFRCNCVPIP (SEQ ID NO:26) which corresponds to D95 to P104 of human TLR7 or an amino acid sequence having at least 70% similarity to SEQ ID NO:20 after optimal alignment with the proviso that the peptide comprises a cysteine at a position corresponding to C98 of TLR7. In a particular embodiment, the peptide decoy comprises the amino acid sequence set forth in SEQ ID NO:20. The corresponding murine TLR7 decoy peptide sequence is DLRCNCVPVL (SEQ ID NO:1) or having 70% similarity to SEQ ID NO:1 after optimal alignment with the proviso that the peptide comprises a cysteine at a position corresponding to C98 of TLR7.

One or more amino acids may be substituted by one or more amino acid analogs or one or more side chains may be modified. Such modifications can improve serum half life and improve stability.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulfides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilize 3D conformations, using homo-bifunctional crosslinkers such as the bifunctional imido esters having $(CH_2)n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogs by introducing covalent bonds such as forming an amide bond between the N and C termini, between two side chains or between a side chain and the N or C terminus.

Mimetics are another useful group of agents to test for an ability to antagonise TLR7 activation via the C98-C475 disulfide bond. The term is intended to refer to a substance which has some chemical similarity to the decoy peptide it mimics but which antagonizes its interaction with a target (i.e. C475 of human (or murine) TLR7). A peptide mimetic may be a peptide-containing molecule that mimics elements of protein secondary structure (Johnson et al. (1993) *Peptide Turn Mimetics in Biotechnology and Pharmacy*, Pezzuto et al, Eds., Chapman and Hall, New York). The underlying rationale behind the use of peptide mimetics is that the peptide backbone of proteins exists chiefly to orient amino acid side chains in such a way as to facilitate molecular interactions with C475 of TLR7. A peptide mimetic, therefore, is designed to permit molecular interactions similar to the decoy peptide. A chemical mimetic is also contemplated herein which is non-proteinaceous yet has the same effect and/or some conformation as C98i.

The peptide decoy may further comprise a moiety to facilitate peptide uptake by a cell. Any number or type of cell uptake moiety may be employed such as but not limited to TAT (SEQ ID NO:2); SynB1 (SEQ ID NO:3), SynB3 (SEQ ID NO:4), PTD-4 (SEQ ID NO:5), AD-5 (SEQ ID NO:6), FHV Coat (SEQ ID NO:7), BMV Gag (7-25) (SEQ ID NO:8), HTLV-III Rex-(4-16) (SEQ ID NO:9), D-Tat (SEQ ID NO:10) and R9-Tat (SEQ ID NO:11). Such moieties are referred to as hydrophilic or cationic peptides. Other uptake peptides include amphiphilic (or amphipathic) peptides such as but not limited to Transportan chimera (SEQ ID NO:12), MAP (SEQ ID NO:13), SBP (SEQ ID NO:14), FBPC (SEQ ID NO:15), MPG [MPGac] (SEQ ID NO:16), MPG (ΔNLS) (SEQ ID NO:17), Pep-1 (SEQ ID NO:18) and Pep-2 (SEQ ID NO:19). In yet another alternative, the uptake moiety comprises a periodic amino acid sequence such as comprising a polyarginine or a polylysine. Other uptake peptides are those listed in Table 1 of Guidotti et al. (2017) supra, the contents of which are incorporated herein by reference.

Whilst the subject to be treated includes a human by targeting hum TLR7, the present invention has a veterinary application such as the treatment of livestock animals (e.g. cows, sheep, pigs, goats, horses), domestic pets (e.g. cats, dogs) as well as captive wild animals and laboratory test animals (e.g. mice, rats, guinea pigs, hamsters, rabbits). In an embodiment, the subject is a human.

Accordingly, enabled herein is method for inhibiting TLR7-mediated immunostimulatory activity in a human subject, the method comprising contacting a cell from the subject expressing TLR7 with an effective amount of an agent which antagonizes disulfide bond formation between C98 and C475 of TLR7 or their corresponding positions.

Further enabled herein is a method for treating a human subject for autoimmune disease, viral or microbial pathogenesis, inflammation or cancer, the method comprising contacting a cell from the subject expressing TLR7 with an effective amount of an agent which antagonizes disulfide bond formation between C98 and C475 of TLR7 or their corresponding positions.

Also enabled herein is a method for treating a human subject for excessive production of reactive oxygen species, the method comprising contacting a cell from the subject expressing TLR7 with an effective amount of an agent which antagonizes disulfide bond formation between C98 and C475 of TLR7 or their corresponding positions.

Enabled herein is a method for treating a human subject for TLR7-mediated inflammation, the method comprising contacting a cell from the subject expressing TLR7 with an effective amount of an agent which antagonizes disulfide bond formation between C98 and C475 of TLR7 or their corresponding positions.

Further enabled herein is a method for treating a human subject for an autoimmune condition, the method comprising contacting a cell from the subject expressing TLR7 with an effective amount of an agent which antagonizes disulfide bond formation between C98 and C475 of TLR7 or their corresponding positions.

Still further enabled herein is a method for treating a human subject for cancer, the method comprising contacting a cell from the subject expressing TLR7 with an effective amount of an agent which antagonizes disulfide bond formation between C98 and C475 of TLR7 or their corresponding positions.

When the agent is a peptide decoy, the amino acid sequence is generally derived from a TLR7 of the same species being treated (e.g. human TLR7 to treat a human subject). This is referred to an autologous treatment. However, wherein there is substantial amino acid sequence similarity between a TLR of some species for use in another species, heterologous treatment is contemplated and encompassed by the present invention.

Further taught herein is use of an agent which antagonizes disulfide bond formation between C98 and C475 of TLR7 or their corresponding positions in the manufacture of a medicament to inhibit autoimmune disease, viral or microbial pathogenesis, inflammation or cancer in a subject.

Enabled herein is an agent which antagonizes disulfide bond formation between C98 and C475 of TLR7 or their corresponding positions for use in inhibiting autoimmune disease, viral or microbial pathogenesis, inflammation or cancer in a subject.

Still further enabled herein is a pharmaceutical composition pharmaceutical composition comprising an agent which antagonizes disulfide bond formation between C98 and C475 of TLR7 or their corresponding positions and one or more pharmaceutical carriers, excipients and/or diluents.

Also enabled herein is the use and agent for treating a subject for excessive production of reactive oxygen species or TLR7-mediated inflammation.

The agent includes a pharmaceutically acceptable salt of the agent. The term "pharmaceutically acceptable salt" refers to physiologically and pharmaceutically acceptable salts of the agents of the present invention: i.e. salts that retain the desired biological activity of the parent agent and do not impart undesired toxicological effects thereto.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g. by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g. intrathecal or intraventricular, administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered.

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g of peptide decoy per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the agent is administered in maintenance doses, ranging from 0.01 µg to 100 g per kg of body weight, over days, weeks or months.

The cells targeted are generally innate and adapted immune cells or any cell which expresses a TLR7. Examples include phagocytic cells (e.g. macrophages, neutrophils and dendritic cells), NK cells, mast cells, eosinophils, basophils, lymphocytes include B- and T-lymphocytes and epithelial cells.

EXAMPLES

Aspects disclosed herein are further described by the following non-limiting Examples.
Materials and Methods
Viruses
The influenza A virus (IAV) vaccine strains HKx31 (H3N2) and BJx109 (H3N2) were provided by the School of Medicine, Deakin University and the Department of Immunology and Microbiology, University of Melbourne, The Peter Doherty Institute for Infection and Immunity. Virus provided at $6.7 \times 10^8$ plaque-forming units/ml (PFU/ml) and stored at −80° C. Aliquots were thawed and diluted on the day of use with phosphate buffered aline (PBS; Sigma Aldrich, St Louis, USA (at No. D837) when required for in vitro infections). Human IAV virus, including seasonal H3N2 (A/New York/55/2004, A/Brisbane/9/2007), seasonal H1N1 (A/Brazil/11/1978, A/New Caledonia/20/1999, A/Solomon Islands/3/2006), A(H1N1)pdm09 strains (A/California/7/2009, A/Auckland/1/2009), rhinovirus (RV16 strain), respiratory synctitial virus (strain A2), human parainfluenza virus type-3 (C243), human metapneumovirus (strain CAN97-83), mumps virus (strain Enders) and Newcastle disease virus (strain V4) were provided by the Department of Immunology and Microbiology, University of Melbourne, The Peter Doherty Institute for Infection and Immunity. Additional viruses were provided by the following Institutions: dengue virus serotype 2 (Vietnam 2005 isolate, Monash University, Clayton, Victoria); rotavirus (Rhesus and UK strains, Department of Microbiology and Immunology, The Peter Doherty Institute for Infection and Immunity); sendai virus (Cantell strain, Hudson Institute of Medical Research, Monash University), herpes simplex virus type-2 (strain 186; Hudson Institute of Medical Research, Monash University), vaccinia virus (Western Reserve strain, WR NIH-TC; Australia National University) and HIV (NL4-3(AD8)-EGFP strain, The Peter Doherty Institute for Infection and Immunity, The University of Melbourne). The viruses were provided in phosphate buffered saline (PBS, Cat #D8537, Sigma, USA) and stored at −80° C. until used. On the day of use, virus was thawed quickly and incubated at 37° C. prior to infection. Where indicated, HKx31 virus was inactivated by heat (56° C.) for 30 min or UV light (30 min).

Bacteria

*Streptococcus pneumoniae* EF3030 (capsular type 19F) was used as the parent *S. pneumoniae* strain in all experiments (provided by University of Melbourne, Australia). Strain EF3030 is a clinical isolate that is frequently used as a model of human carriage as it typically colonizes the nasopharynx in the absence of bacteremia. For infection experiments, pneumococci were grown statically at 37° C. in Todd-Hewitt broth, supplemented with 0.5% w/v yeast extract, to an optical density (600 nm) of 0.4-0.45. Cultures were placed on wet ice for 5 min and frozen in 8% v/v glycerol at −70° C. Live bacterial counts were confirmed prior to each experiment. A defined strain of non-typeable *Haemophilus influenzae* (NTHi; MU/MMC-1) was previously typed and sequenced and demonstrated to be NTHi, as we have previously shown (King et al. (2013) *The Journal of Allergy and Clinical Immunology* 131(5):1314-1321 e1314).

Custom C98i Peptides

The following custom peptides were purchased from GenicBio Limited: YGRKKRRQRRRDLRCNCVPVL-NH2 (SEQ ID NO:57) (C98i-TAT; 10 amino acid TLR7 inhibitor). YGRKKRRQRRRCLVPNDCRLV-NH2 (SEQ ID NO:44) (Scrambled C98i-TAT; 10 amino acid TLR7 inhibitor). DLRCNCVPVL-NH2 (SEQ ID NO:1) (C98i-noTAT; 10 amino acid TLR7 inhibitor excluding HIV-TAT). DFRCNCVPIP-NH2 (SEQ ID NO:26). (Human C98i-noTAT; 10 amino acid TLR7 inhibitor excluding HIV-TAT). RCNC—NH2 (SEQ ID NO:45) (4AA C98i-noTAT; 4 amino acid TLR7 inhibitor excluding HIV-TAT). RANC-NH2 (SEQ ID NO:46) (4AA 98M C98i-noTAT; Cysteine 98 mutation, 4 amino acid TLR7 inhibitor excluding HIV-TAT). RANA-NH2 (SEq ID NO:47) (4AA 98100M C98i-noTAT; Cysteine 98 and 100 mutation, 4 amino acid TLR7 inhibitor excluding HIV-TAT). RCNA-NH2 (SEQ ID NO:48) (4AA 100M C98i-noTAT; Cysteine 100 mutation, 4 amino acid TLR7 inhibitor excluding HIV-TAT). All peptides were dissolved in endotoxin free water and prepared as stock solutions of 10 mM in aliquots of 20 μL, 50 μL and 100 μL and stored at −20° C.

Conjugation of NOX2 Oxidase Inhibitors

Preparation of gp91 ds-tat (YGRKK-RRQRR-RCSTR-IRRQL-NH$_2$— SEQ ID NO:23) was carried out by standard Fmoc solid-phase peptide synthesis (SPPS) on Fmoc-PAL-PEG-PS resin (Life Technologies, USA, loading 0.17 mmol/g). Fmoc deprotection reactions were carried out using 20% v/v piperidine in N,Ndimethylformamide (DMF). Coupling reactions were carried out using Fmoc-protected amino acids with 013 (6-chlorobenzotriazol-1-yl)-N,N,N',N'-tetramethyluronium hexafluorophosphate (HCTU) as coupling agent and N,N-diisopropylethylamine (DIPEA) as activating agent. Reactions were monitored using the 2,4,6-trinitrobenzenesulfonic acid (TNBS) test to indicate the absence or presence of free amino groups. The alternating sequence of deprotection and coupling reactions was carried out manually for all 20 amino acid residues using the appropriate Fmoc- and side-chain protected amino acids. After a final deprotection step, a small portion of the peptide was cleaved from resin using trifluoroacaetic acid (TFA)/triisopropylsilane (TIPS)/1,2-ethanedithiol (EDT)/water (92.5:2.5:2.5:2.5) for 4h, during which time the side-chain protecting groups were simultaneously removed. The crude peptide was then purified by reverse-phase high-pressure liquid chromatography (HPLC) using a Phenomenex Luna 5 C8 (2) 100 Å AXIA column (10 Å, 250×21.2 mm) with 0.1% TFA/water and 0.1% v/v TFA/ACN as the buffer solutions. The purified gp91 ds-tat peptide was confirmed as having the correct molecular weight by ESI-MS analysis: calcd. for $C_{109}H_{207}N_{52}O_{25}S$ [M+5H+] m/z 535.3, obs. m/z 535.7; calcd. for $C_{109}H_{208}N_{52}O_{25}S$ [M+6H+] m/z 446.3, obs. m/z 446.6; calcd. for $C_{109}H_{209}N_{52}O_{25}S$ [M+7H+] m/z 382.7, obs. m/z 382.9.

Preparation of cholestanol-conjugated gp91 ds-tat (cgp91 ds-tat; Ac-Asp(OChol)-PEG4-PEG3-PEG4-gp91-NH$_2$) was carried out by manual SPPS from resin-bound gp91 ds-tat (as described above), using Fmoc-PEG4-OH, Fmoc-PEG3-OH, Fmoc-PEG4-OH and Fmoc-Asp(OChol)-OH as the amino acids. After the final deprotection step, the N-terminus was capped using a mixture of acetic anhydride and DIPEA in DMF and the peptide construct was cleaved from resin using TFA/TIPS/EDT/water (92.5:2.5:2.5:2.5). The crude peptide was purified as described previously to give cgp91 ds-tat: calcd. for $C_{173}H_{319}N_{56}O_{43}S$ [M+5H+] m/z 780.3, obs. m/z 780.6; calcd. for $C_{173}H_{320}N_{56}O_{43}S$ [M+6H+] m/z 650.4, obs. m/z 650.7; calcd. for $C_{173}H_{321}N_{56}O_{43}S$ [M+7H+] m/z 557.6, obs. m/z 558.0.

Preparation of ethyl ester-conjugated gp91 ds-tat (egp91 ds-tat; Ac-Asp(OEt)-PEG4-PEG3-PEG4-gp91-NH$_2$) was carried out in the same way as for cgp91 ds-tat, except for replacement of Fmoc-Asp(OChol)-OH with Fmoc-Asp (OEt)-OH in the final coupling step: calcd. for $C_{148}H_{277}N_{56}O_{43}S$ [M 5H+] m/z 711.8, obs. m/z 712.1; calcd. for $C_{148}H_{278}N_{56}O_{43}S$ [M+6H+] m/z 593.3, obs. m/z 593.7; calcd. for $C_{148}H_{279}N_{56}O_{43}S$ [M+7H+] m/z 508.7, obs. m/z 509.0.

Preparation of the 18 amino acid scrambled gp91 ds-tat (Sgp91 ds-tat; Ac-Asp(OChol)-PEG4-PEG3-PEG4-RKK-RRQRR-RCLRI-TRQSR-NH$_2$— SEQ ID NO:24) peptide was carried out by manual SPPS as described above for unscrambled gp91 ds-tat. The resin-bound sgp91 ds-tat was then conjugated to cholestanol via a PEG linker using the same method described above for unscrambled cgp91 ds-tat. The crude peptide was purified in the same way to give cgp91 ds-tat: calcd. for $C_{162}H_{307}N_{54}O_{40}S$ [M+5H+] m/z 736.3, obs. m/z 736.5; calcd. for $C_{162}H_{308}N_{54}O_{40}S$ [M+6H+] m/z 613.7, obs. m/z 614.0; calcd. for $C_{162}H_{309}N_{54}O_{40}S$ [M+7H+] m/z 526.2, obs. m/z 526.3.

In Vivo Infection with Influenza A Virus and Drug Treatments

Aged matched (6-12 weeks) littermate male naïve WT control and $NOX2^{-/y}$ mice (also known as gp91phox$^{-/-}$ [Pollock et al. (1995) *Nature Genetics* 9(2):202-209]) were anaesthetized by penthrane inhalation and infected intranasally (i.n.) 1×104 or 1×105 plaque forming units (PFU) of Hkx31 in a 35 μL volume, diluted in PBS. Mice were euthanized at Day 1, 3 or 7 following influenza infections. In some experiments, anaesthetized mice were treated via intranasal delivery with either dimethyl sulfoxide (DMSO, control; Sigma), unconjugated gp91dstat (0.02 mg/kg, 0.2 mg/kg), cholestenol conjugated-gp91dstat (0.02 mg/kg, 0.2 mg/kg) or cholestanol conjugated-scrambled gp91ds-TAT (0.02 mg/kg) one day prior to infection with Hk-x31 and everyday thereafter for 3 days. In additional experiments, anaesthetized mice were treated with imiquimod (50 μg/mouse, i.n.) or catalase (1000U/mouse, i.n.) and then euthanized for analysis at Day 1.

Airways Inflammation and Differential Cell Counting

Mice were killed by an intraperitoneal (i.p) injection of ketamine/xylazene (100 mg/kg) mixture. An incision was made from the lower jaw to the top of the rib cage, where the salivary glands were separated to expose the surface of the trachea. The layer of smooth muscle on the trachea was removed, allowing a small incision to be made near the top of the trachea. A sheathed 21-gauge needle was inserted to the lumen and 300-400 μl of PBS was lavaged repeatedly (4 times). The total number cells in the BALF were stained with 0.4% w/v trypan blue solution (Thermofisher Scientific, USA) and viable cells were evaluated using the Countess (Registered Trademark) automated cell counter (Invitrogen, Cat #C10227). Differential cell analysis was prepared from BALF (5×104 cells) that were centrifuged at 3×g for 5 min on the Cytospin 3 (Shandon, UK). Following this, slides were fixed in 100% v/v propanol for one minute and allowed to dry overnight. Finally, samples were stained with Rapid I Aqueous Red Stain™ (AMBER Scientific, Australia) and Rapid II Blue Stain™ (AMBER Scientific, Australia) for 10 mins, then submerged in 70% v/v ethanol and absolute ethanol twice before being placed into xylene for 5 min (2 times). Samples were then mounted in DPX mounting medium (Labchem, NSW, Australia) and coverslips were firmly placed on top. 500 cells per sample from random fields were differentiated into macrophages, neutrophils, eosinophils and lymphocytes by standard morphological criteria. Data are represented as total cell numbers that was calculated by the respective cell type multiplied by the total live cell numbers and as a percentage of the cell population.

Cell Culture and Primary Cell Isolation

Human alveolar macrophages were obtained from subjects undergoing a bronchoscopy at Monash Medical Centre, Monash University, Clayton, Australia, to investigate underlying lung disease. The bronchoscope was wedged in the right middle lobe and 25-50 mL of saline was washed into the airway then aspirated. Cells were washed twice with PBS before being suspended in culture medium (Roswell Park Memorial Institute (RPMI, Life Technologies, Cat #21870-076) with 10% v/v FCS with 100 U/mL penicillin and 100 ug/mL streptomycin) for ~24 h before use.

Alveolar macrophages were isolated by lung lavage from age-matched (6-12 weeks) male C57Bl/6J (WT), $NOX2^{-/y}$, $NOX4^{-/-}$ (provided by Centre for Eye Research, The University of Melbourne, Australia, $TLR7^{-/-}$ (provided by the School of Biomedical Sciences and Pharmacy, Faculty of Health and Medicine, The University of Newcastle, and Hunter Medical research Institute, New South Wales, Australia) $TLR9^{-/-}$ (provided by the Baker IDI Heart & Diabetes Institute, Melbourne, Victoria, Australia) or $SOD3^{-/-}$ mice (provided by the School of Health and Biomedical Sciences, RMIT University). A thin shallow midline incision from the lower jaw to the top of the rib cage was made and the larynx was separated to expose the top of the trachea. The layer of smooth muscle covering the trachea was removed, a small incision made and a sheathed 21-gauge needle was inserted into the lumen. The lungs were repeatedly (3 times) lavaged with 300-400 μL of PBS. Cell suspensions were spun down by centrifugation (200×g at 4° C. for 5 min). Supernatant was removed, then cells were re-suspended in 1 mL of sterile PBS and counted using the Countess (Registered Trademark) automated cell counter (Invitrogen, Cat #C10227). Cells were then seeded into 24-well plates (1×105 cells/well) for immunocytochemistry and fluorescence microscopy, as stated below.

The immortalized cell line RAW 264.7 cells (RAW 264.7 (ATCC (Registered Trademark) TIB-71 (Trademark)) and immortalized bone marrow-derived macrophages (BMDMs; courtesy of the Hudson Institute of Medical Research Monash University and the Institute of Innate Immunity, University of Bonn, Germany) were maintained in Dulbecco's Modified Eagle's Medium (DMEM: Sigma) supplemented with L-glutamine, glucose (4500 mg/L), sodium pyruvate (110 mg/L) and fetal bovine serum (FBS; 10% v/v. The $TLR2^{-/-}$, $TLR3^{-/-}$, $TLR4^{-/-}$, $TLR7^{-/-}$, $MyD88^{-/-}$, $NLRP3^{-/-}$ and $UNC93B1^{-/-}$ immortalized BMDMs were maintained in RPMI medium supplemented with glucose (4500 mg/L), non essential amino acids, sodium pyruvate, streptomycin and FBS (10% v/v) and DMEM (20% v/v) (containing all supplements, as stated above). All cells were kept at 37° C. with a humidified mixture of 5% $CO_2$ and 95% v/v air. The medium was changed two to three times a week, cells were sub-cultured by scraping when ~80-90% confluent, and counted using the Countess (Registered Trademark) automated cell counter.

The immortalized cell line RAW 264.7 cells (derived from mouse peritoneum) and immortalized bone marrow-derived macrophages (BMDMs) were maintained in Dulbecco's Modified Eagle's Medium (DMEM: Sigma) supplemented with L-glutamine, glucose (4500 mg/L), sodium pyruvate (110 mg/L) and fetal bovine serum (FBS; 10%). All cells were kept at 3TC with a humidified mixture of 5% $CO_2$ and 95% air. The medium was changed two to three times a week, cells were sub-cultured by scraping when ~80-90% confluent, and counted using the Countess (Registered trademark) automated cell counter (Invitrogen).

Confocal Fluorescence Microscopy

Cells were seeded onto glass cover slips in 24-well plates, and allowed to adhere for 24 h in DMEM. Cells were then incubated in the absence or presence of HKx31 influenza A virus (MOI 0.1, 1 or 10) in serum16 free medium at varying time points (5 min, 15 min, 30 min and 1 h). In some cases, cells were pretreated for 30 min prior to infection with Dynasore (100 μM) or the vehicle for Dynasore, DMSO (0.1% w/v). Next, the cells were washed with PBS (0.01 M) and fixed with 4% v/v paraformaldehyde (PFA) for 15 min.

Cells were treated for 10 min with PBS-containing Triton X-100 (0.25% v/v) and then washed three times over 15 min with PBS. The samples were then incubated with 10% v/v goat serum-containing PBS for 2 h and/or mouse on mouse IgG blocking reagent (Cat #MKB-2213, Vector Laboratories). This was followed by the addition of a primary antibody for nucleoprotein (1:1000) to localize influenza A virus, purified mouse anti-NOX2 (1:500) to localize NOX2, rabbit anti-TLR7 (1:1000) to localize TLR7, or mouse anti-early endosome antigen 1 (EEA1; 1000) to localize early endosomes for 24 h at 4° C. In some experiments, combinations of antibodies were used at the indicated concentrations to determine protein co-localization. Cells were washed three times over 30 min with PBS (0.01 M). Following the washes, a secondary antibody goat anti-rabbit alexa 594 (1:1000), goat anti rabbit red 647 (1:500, 1:1000) and/or biotinylated anti-mouse IgG was added to appropriate wells in the dark for 2h. Finally, the cells were washed three times over 30 min with PBS (0.01 M); and where appropriate (mouse primary and secondary anti Fluroscein Avidin DCS was applied for 5 minutes). Cover slips were mounted onto microscope slides with 10-20 µL of diamidino-2-phenylindole (DAPI) for 3 min. Slides were viewed and photographed on a Nikon upright inverted confocal fluorescence microscope (Nikon D-eclipse C1). All immunohistochemistry was assessed by two observers blinded as to the treatment groups throughout the analysis process and all of the appropriate controls were performed, in that all combinations of primary and secondary antibodies were used to ensure no cross reactivity occurred.

Figure 2A:
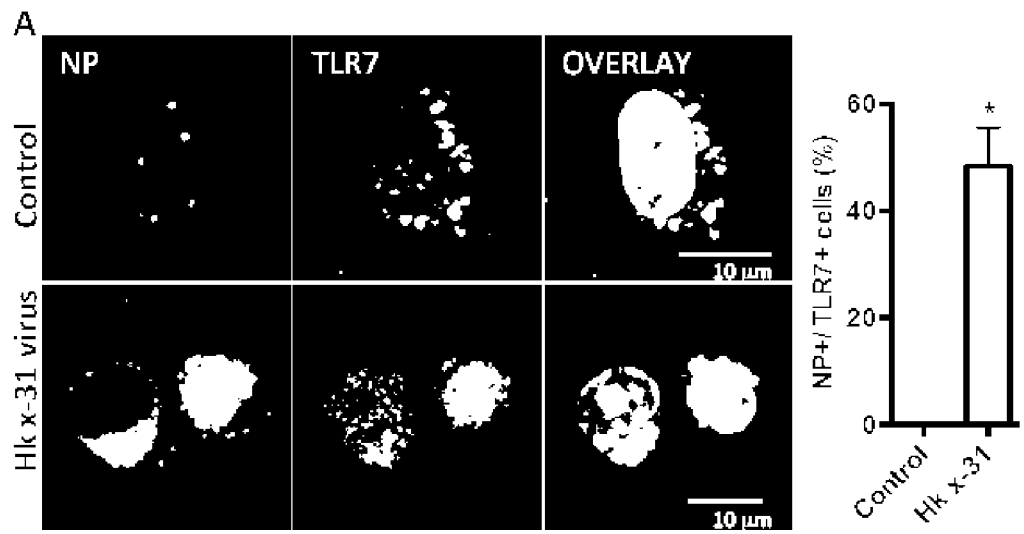
FIG. 2A, FIG. 2B, FIG. 2C, FIG. 2D, FIG. 2E, FIG. 2F, FIG. 2G, FIG. 2H, and FIG. 2I are photographic and graphic representations showing co-localization of TLR7 with influenza A virus, NOX2 and EEA1 is a signaling platform for endosomal ROS generation to influenza A virus via a TLR7 and PKC-dependent mechanism. (A-C) Confocal microscopy of mouse primary alveolar macrophages that were untreated or infected with influenza A virus HKx31 (MOI of 10) and labeled with antibodies to TLR7 and either A) influenza A virus NP, B) NOX2 or C) EEA1, and then with 4',6'-diamidino-2-phenylindole (DAPI). Quantification data from multiple experiments are also shown (n=5). (D) Endosomal ROS production in WT and TLR7$^{-/-}$ mouse primary alveolar macrophages as assessed by Oxyburst (100 μM) fluorescence microscopy in the absence or presence of HKx31 virus and labeled with DAPI (n=6). (E) Immunofluorescence microscopy for assessment of NOX2 and p47phox association. WT and TLR7$^{-/-}$ immortalized bone marrow-derived macrophages (BMDMs) were untreated or infected with HKx31 virus, (MOI of 10) in the absence or presence of bafilomycin A Baf-A; 100 nM) or dynasore (Dyna; 100 μM), and then labeled with antibodies to NOX2 and p47phox. Also shown is the quantification of the results (n=5). (F-I) Endosomal ROS production in WT and NOX2$^{-/y}$ mouse primary alveolar macrophages as assessed by Oxyburst fluorescence microscopy in the absence or presence of F) imiquimod (Imiq; 10 μg/ml) and G) ssRNA (100 μg/ml) and co-labeled with DAPI. (n=5). (H, I) Cytosolic PKC activity as assessed by FRET analysis in WT and TLR7$^{-/-}$ BMDMs. Cells were either treated with vehicle controls or with bafilomycin A (100 nM) or dynasore (100 μM) and then exposed for 25 min to influenza A virus (HKx31, MOI of 10) or imiquimod (10 μg/ml) (n=3). (A-F and H) Images are representative of >150 cells analyzed over each experiment. Original magnification ×100. All data are represented as mean±SEM. (A, B, C, F and G) Student's unpaired t-test *P<0.05. (D, E, H and I) One-way ANOVA followed by Dunnett's post hoc test for multiple comparisons. *P<0.05.
Figure 2B:
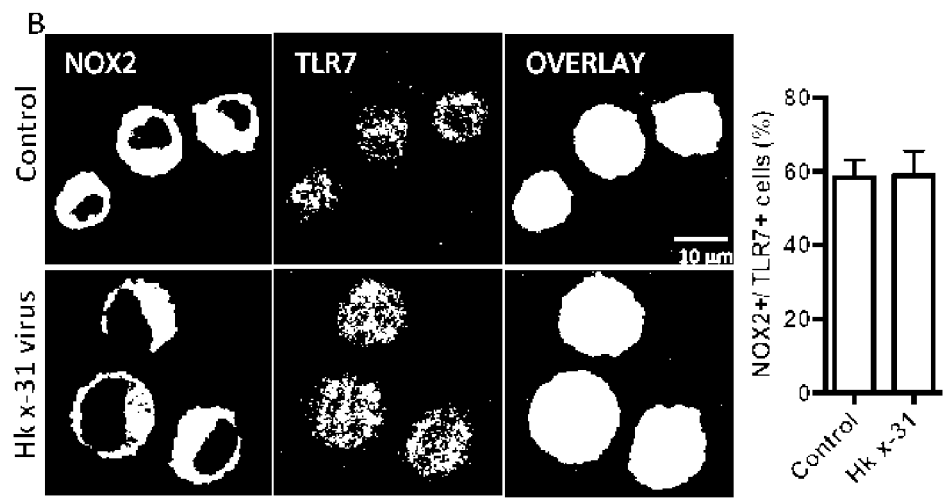
Figure 2C:
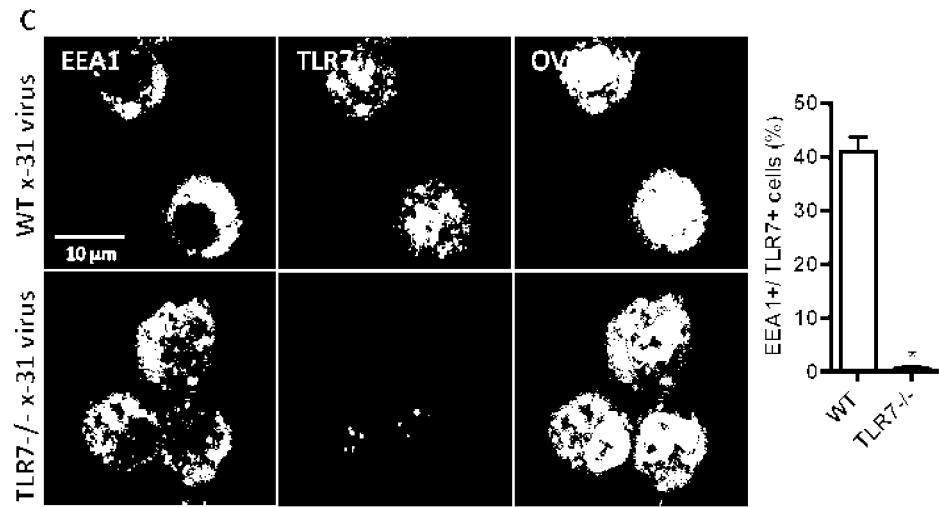

The specificity of both the TLR7 and NOX2 antibodies were verified by examining the degree of staining in alveolar macrophages taken from WT, TLR7$^{-/-}$ and NOX2$^{-/-}$ mice respectively. There was no staining for TLR7 in the TLR7$^{-/-}$ macrophages (FIG. 2c). Similarly with the NOX2 antibody, no staining was observed in alveolar macrophages of NOX2$^{-/y}$ mice compared to the WT cells. Further evidence for the specificity of this NOX2 antibody can be found in Judkins et al. (2010) *American Journal of Physiology Heart and Circulatory Physiology* 298(1):H24-32.

Endosomal ROS Production

Human alveolar macrophages; WT, TLR7$^{-/-}$, TLR2$^{-/-}$, TLR3$^{-/-}$, TLR4$^{-/-}$, MyD88$^{-/-}$, and NLRP3$^{-/-}$ BMDMs; mouse primary WT, NOX2$^{-/y}$, NOX4$^{-/-}$, TLR7$^{-/-}$, TLR9$^{-/-}$ or SOD3$^{-/-}$ alveolar macrophages and RAW264.7 cells were seeded (1×10$^5$ cells/well) onto glass coverslips in 24-well plates allowing the cells to adhere for 24h in DMEM or RPMI medium before being pretreated with OxyBURST Green H2HFF (100 µM) and/or LysoTracker Deep Red (50 nM) for 5 min. This was followed by incubation with PBS (control group; 0.01 M), imiquimod (10 µg/mL), single stranded RNA (ssRNA; 100 µM), or infected with either H3N2 influenza viruses (A/New York/55/2004, A/Brisbane/9/2007), seasonal H1N1 influenza A viruses (A/Brazil/11/1978, A/New Caledonia/20/1999, A/Solomon Islands/3/2006), A(H1N1)pdm influenza A viruses (A/California/7/2009, A/Auckland/1/2009), or with re-assortant vaccine strains HKx31 (MOI 0.1-10) or BJx109 (MOI 10) in serum-free medium at varying time points (5 min, 15 min, 30 min and 1 hr). Other wells were infected with dengue virus (MOI 10), Sendai virus (40 HAU/mL), human parainfluenza virus (MOI 10), human metapneumovirus (MOI 10), rhinovirus (MOI 10), respiratory syncytial virus (MOI 10), HIV (MOI 10), Newcastle disease virus (MOI 10), mumps virus (MOI 10), rhesus or UK rotaviruses (each at MOI 10) or herpes simplex virus-2 (MOI 10) under similar conditions. In some cases, cells were pretreated with superoxide dismutase (SOD; 300 U/mL), apocynin (300 µM), gp91dstat (50 µM) or bafilomycin A (100 nM), for 30 min prior to infection. Next, the cells were washed with PBS (0.01 M) and fixed with 4% PFA for 15 min. After fixation, cells were then washed three times with PBS over 30 min. Cover slips were then mounted onto microscope slides with 10-20 µL of DAPI for 3 min, then analyzed and photographed on an Nikon upright confocal fluorescence microscope (Nikon D-eclipse C1).

NOX2 Oxidase Assembly

To measure NOX2 oxidase activity we assessed p47phox and NOX2 assembly using confocal fluorescence microscopy. Control and HKx31 virus-infected WT and TLR7$^{-/-}$ alveolar macrophages were processed as indicated above under "confocal fluorescence microscopy". In additional experiments, WT cells were treated with Dynasore (100 µM) or bafilomycin A (100 nM) for 30 min prior to virus infection. After exposing samples with 10% v/v goat serum-containing PBS for 2 hr, the rabbit anti-p47phox antibody (1:1000) and the mouse anti-NOX2 antibody (1:500) were added followed by addition of appropriate secondary antibodies, as specified above.

L-O12-Enhanced Chemiluminescence

ROS production was quantified using L-O12-enhanced chemiluminescence.

RAW264.7 cells and primary mouse alveolar macrophages were seeded into a 96-well OptiView plate (5×10$^4$ cells/well). RAW264.7 cells were either treated with DMSO (control, appropriate concentration), unconjugated gp91dstat (100 nM-30 µM), cholestanol-conjugated gp91dstat (100 nM-30 µM) or ethyl-conjugated gp91dstat (100 nM-30 µM) for 1 h. BALF was collected from mice treated with DMSO (control), unconjugated gp91dstat (0.02 mg/kg, 0.2 mg/kg), cholestanol conjugated-gp91dstat (0.02 mg/kg, 0.2 mg/kg) and/or infected with Hkx31 influenza A virus (1λ105 PFUs). Cells were then washed of media with 37° C. Krebs-HEPES buffer, then exposed to a Krebs-HEPES buffer containing L-O12 (10-4 mol/L) in the absence (i.e. basal ROS production) or presence (stimulated ROS production) of the PKC and NADPH oxidase activator phorbol dibutyrate (PDB; 10-6 mol/L). The same treatments were performed in blank wells (i.e. with no cells), which served as controls for background luminescence. All treatment groups were performed in triplicates. Photon emission [relative light units (RLU)/s] was detected using the Chameleon (Trademark) luminescence detector (Hidex, model 425105, Finland) and recorded from each well for 1 s over 60 cycles. Individual data points for each group were derived from the average values of the three replicates minus the respective blank controls. Data are represented as a % of the control in the dose-response curves or as raw values (ex vivo experiments).

To test whether the unconjugated or cholestanol conjugated gp91dstat exhibited ROS scavenging properties, the xanthine oxidase cell free assay was used. Briefly, Krebs-HEPES buffer containing L-O12 (100 µM) was added into a 96-well Optiview plate. Following this, 0.1% w/v DMSO, unconjugated gp91dstat (Ugp91ds-TAT, 1 µM) or cholestanol-conjugated gp91ds-TAT (1 µM) were added in combination with Xanthine (100 µM). Immediately after xanthine oxidase (0.03 U/mL) was added, photon emission [relative light units (RLU)/s] was detected using the Chameleon (Trademark) luminescence detector (Hidex, model 425105, Finland) and recorded from each well for 1 s over 60 cycles. Individual data points for each group were derived from the average values of the three replicates minus the respective blank controls. Data are represented as raw values.

Site Directed Mutagenesis, Sequencing and Transfections

HA-TLR7 cDNA was purchased from Sino Biological (mouse TLR7; Cat #MG50962-NY with Gene Bank Ref Seq number NM_133211.3). Mutation of the key cysteine residues in TLR7 (Cys260, Cys263, Cys270, Cys273, Cys98 and Cys445) to alanine was performed using the QuikChange Multi Site-Directed Mutagenesis kit (Cat #200514, Agilent Technologies). Sequences of WT and mutant HA-TLR7 were confirmed by the Australian Genome Research Facility. Cells were transfected using linear polyethyleneimine (PEI) [Halls et al. (2015) *Methods in Molecular Biology* 1335:131-161].

High-Content Ratiometric FRET Imaging

Cells were plated and transfected in suspension with 200 ng/well FRET biosensor DNA using PEI, in black, optically clear 96-well plates for 48 hr. Prior to the experiment, cells were partially serum-starved overnight in 0.5% v/v FBS media. Fluorescence imaging was performed using a high-content GE Healthcare INCell 2000 Analyzer with a Nikon Plan Fluor ELWD 40× (NA 0.6) objective and FRET module as described (Jensen et al. (2014) *The Journal of Biological Chemistry* 289(29):20283-20294). For CFP/YFP (CKAR) emission ratio analysis, cells were sequentially excited using a CFP filter (430/24) with emission measured using YFP (535/30) and CFP (470/24) filters, and a polychroic optimized for the CFP/YFP filter pair (Quad3). For GFP/RFP (EKAR) emission ratio analysis, cells were sequentially excited using a FITC filter (490/20) with emission measured using dsRed (605/52) and FITC (525/36) filters, and a polychroic optimized for the FITC/dsRed filter pair (Quad4). Cells were imaged every 100 sec for 20 min (image capture of 2 fields of view in 12 wells per 100 sec). Data were analyzed using in-house scripts written for the FIJI distribution of Image J 34, as described (Halls et al. (2015) supra.

Quantification of mRNA by QPCR

Cells were treated with imiquimod (10 ng/ml), poly I:C (100 ng/ml), CpG (10 µg/mL), ssRNA (500 µg/mL) or catalase (1000 U/ml) for 24 hours. Where indicated, cells were pre-treated with apocynin (300 µM), SOD (300 U/mL) or bafilomycin A (100 nM) for 30 mins. RNA was extracted from the lung tissue of mice that were treated with either DMSO (control), unconjugated gp91dstat (0.02 mg/kg, 0.2 mg/kg), cholestanol conjugated-gp91dstat (0.02 mg/kg, 0.2 mg/kg), scrambled cholestanol conjugated gp91dstat (0.02 mg/kg) and/or infected with Hk-x31 influenza A virus (1λ105 PFUs) 3 days post infection for the assessment of viral mRNA and cytokine expression. The right lung lobe was placed in Eppendorf tubes containing a mixture of Buffer RLT (Qiagen, USA) and β-mercaptoethanol (Sigma; 1%), which was minced into small pieces using curved scissors. Following this, lung samples were homogenized using the ultrasound homogenizer (Hielscher Ultrasonics GmBH, Teltow, Germany) and centrifuged at 14,000 rpm for 5 mins. A 1:1 ratio of lysate was mixed with 70% v/v RNase free ethanol transferred to RNeasy spin columns (RNeasy Minikit; Cat #74104, Qiagen). Samples were spun at 10,000 rpm for 15 seconds and then washed with Buffer RW1. After discarding the flow-through, 5 µl of DNase I (Cat #79254, Qiagen) was mixed with 35 µl of Buffer RDD was pipetted directly onto the membrane of the spin column and incubated at room temperature for 15 mins. Buffer RPE was added and centrifuged for 10,000 rpm for 15 seconds. After discarding the flow-through, Buffer RPE was re-added and spun for 10,000 rpm for 2 mins. An additional spin at 14,000 rpm for 1 min was done to remove residual flow-through from the spin column. Finally, RNase free water was added and centrifuged to elute the RNA into an Eppendorf tube. RNA samples were measured using the Nanodrop 1000 Spectrophotometer (Thermo Scientific, USA). cDNA synthesis was performed using the High-Capacity cDNA Reverse Transcription Kit (Cat #4368814, Applied Biosystems, Foster City, Calif., USA) using 1.0-2.0 µg total RNA. RNA was added to a mixture of reagents in the High-Capacity cDNA RT kit to make a final volume of 20 µl. This was transcribed using the BioRad Mycycler (Trademark) thermal cycler (BioRad, USA) at the following settings: 25° C. for 10 mins, 37° C. for 120 mins, 85° C. for 5 mins and 4° C. at rest. Samples were stored at −20° C. prior to use. Quantitative polymerase chain reaction was carried out using the TaqMan Universal PCR Master Mix (Cat #4304437, Applied Biosystems, Foster City, Calif., USA) or SYBR Green PCR Master Mix (Cat #4367659, Applied Biosystems, Foster City, Calif., USA) and analyzed on ABI Step One™ and StepOnePlus™ Real-time PCR Systems (Perkin-Elmer Applied Biosystems, Foster City, Calif., USA). The PCR primers for TNF-α, IL-1β, IFN-β and IL-6 were included in the Assayon-Demand Gene Expression Assay Mix. Additionally, a custom designed forward and reverse primer of the segment 3 polymerase (PA) of influenza virus was used to measure viral titres (Table 4). The PCR program run settings: 50° C. for 2 min, followed by 95° C. for 1 hr, then 95° C. for 15 s+60° C. for 60 s+plate read (40 cycles). Quantitative values 129 were obtained from the threshold cycle (Ct) number. Target gene expression level was normalized against 18s or GAPDH mRNA expression for each sample and data was expressed relative to the control.

RAW264.7 or BMDM cells were seeded into a 6-well plate (5×10$^5$ cells/well). For all iterations of the C98i peptides, cells were either pre-treated with Phosphate buffered saline (PBS; control, appropriate concentration) or the appropriate peptide for 1 hour. Cells were then treated with imiquimod (10 µg/ml) for an additional hour. After treatments, cells were washed with PBS, media was replenished with fresh DMEM (10% FBS) and left to incubate over 24 hours.

Total RNA was prepared using RNeasy Mini Kit (Qiagen, Hilden, Germany), and then total RNA was purified via extraction with double distilled H2O. Synthesis of cDNA was performed using the High-Capacity cDNA RT kit (P/N4322171, Applied Biosystems, Foster City, Calif., USA) using 1.0-3.0 µg total RNA. Quantitative polymerase chain reaction was carried out using the TaqMan Universal PCR Master Mix (Applied Biosystems, Foster City, Calif., USA) and analyzed on ABI StepOne™ and StepOnePlus™ Real-time PCR Systems (Perkin-Elmer Applied Biosystems, Foster City, Calif., USA). The PCR primers for IL-1 and IL-6 were included in the Assayon-Demand Gene Expression Assay Mix (Applied Biosystems, Foster City, Calif., USA). The PCR program run settings: 50.0 for 2 min, followed by 95.0 for 1 hr, then 95.0 for 15 s+60.0 for 60 s+plate read (40 cycles). Quantitative values were obtained from the threshold cycle (Ct) number. Target gene expression level was normalized against 18s or GAPDH mRNA expression for each sample and data was expressed relative to the WT naïve.

ELISA and Multiplex Immunoassay

Protein levels of IFN-β (VeriKine HM mouse IFN (3 Serum ELISA kit; Cat #42410-1, PBL Assay Science), IL-1β (Quantikine ELISA Mouse IL-1β/IL-IF2; Cat #MLB00C, R & D Systems,), TNF-α (Quantikine ELISA Mouse TNF α, Cat #MTA00B, R & D Systems,) and IL-6 (Quantikine ELISA Mouse IL-6, Cat #M6000B, R & D Systems)

secreted into the BALF of HKx31-infected (1×104 PFUs) wild-type and NOX2$^{-/y}$ mice were measured using ELISAs and performed using commercially available kits according to the manufacturer's instructions. The cytokine titres in samples were determined by plotting the optical densities using a 4-parameter fit for the standard curve.

Antibody Determination

Serum and BALF levels of various antibody isotypes (IgA, IgE, IgG1, Ig2a, IgG2b, IgG3, IgM and total IgG) were quantified in HKx31-infected (1×10$^4$ PFUs) WT and NOX2$^{-/y}$ mice using the ProcartaPlex Multiplex Immunoassay (Mouse Isotyping 7plex, Cat #EPX070-2815-901, eBioscience) according to the manufacturer's instructions. Briefly, antibody-conjugated magnetic beads were added into each well of a 96-well plate. Antibody standards were serially diluted (1:4) in universal assay buffer to construct a 7-point standard curve. Serum and BALF samples (diluted 1:20,000 in universal assay buffer) and/or standards were added to appropriate wells of the 96-well plate containing the antibody-conjugated magnetic beads. Following this, a detection antibody mix was added to each well and the plate was incubated for 30 min at room temperature on a microplate shaker (500 rpm) in the dark. After washing, a reading buffer was added to all wells. The plate was read by a Magpix (Registered Trademark) multiplex reader (Luminex, USA) with xPONENT (Registered Trademark) software (Luminex, USA). Procartaplex (Trademark) Analyst 1.0 software (eBioscience, USA) was used to interpolate serum and BALF antibody concentrations in each sample from the standard curve.

Data were represented as the mean±standard error of the mean (SEM). Cytokine mRNA expression and antibody titres were analyzed using one-way ANOVA followed by Tukey's post hoc test for multiple comparisons. All tests were performed by Graphpad Prism 7.0b (San Diego, Calif., USA) and statistical significance was taken at P<0.05.

Statistical Analysis and Image Analysis

In order to quantify the fluorescence microscopy data, images acquired from confocal systems were analyzed in Image J. Approximately 100-150 cells per treatment group from at least three independent experiments were analyzed unless otherwise stated in the figure legend to calculate the fluorescence in each cell, which was then averaged and expressed as a percentage of the area fluorescence. All statistical tests were performed using GraphPad Prism (GraphPad Software Version 6.0, San Diego Calif., USA). P<0.05 was taken to indicate significance. For isolated cell culture work, n is representative of a separate experiment where cells were used from a different passage.

Chemicals

Imiquimod (Cat #tlrl-imq, Invivogen), H.M.W poly I:C (Cat #tlrl-pic, Invivogen) and CpG ODN (Cat #tlrl-1668, Invivogen) were dissolved in endotoxin-free water and prepared as stock solutions of 5-10 mg/mL in aliquots of 30 µL and 100 pt and stored at −20° C. ssRNA (Cat #tlrl-lma40, Invivogen) was dissolved in endotoxin-free water and prepared as a stock solution of 5 mM in aliquots of 50 µL and stored at −20° C. Dynasore (Cat #D7693, Sigma) (freshly prepared on the day) was dissolved in DMSO (100%) and prepared as 10 mM stock solutions. FBS (Cat #12003C, Sigma) was stored in 50 ml aliquots at −20° C. Penicillin-streptomycin solution (Cat #P4333, Sigma) was stored at −20° C. SOD (Cat #S2515, Sigma) was dissolved in distilled water and prepared as stock solutions (10 µl) of 30,000 units/ml and stored at −20° C. OxyBURST Green H2HFF bovine serum albumin (BSA) (Cat #1329, Molecular probes, Life Technologies) and LysoTracker Deep Red (Cat #L12492, Molecular probes, Life Technologies) in stock solutions (1 mg/mL) were generated immediately before use by dissolving in PBS. Bafilomycin A (from Streptomyces, Cat #B1793, Sigma) was prepared as a stock solution of 100 µM in aliquots of 10 µL and stored at −20° C. Apocynin (4'-Hydroxy-3'-methoxy acetophenone, Cat #A10809; Sigma) made freshly on the day of use and gp91dstat (Cat #AS-63818; Anaspec) were prepared as stock solutions of 100 mM and 50 mM respectively, in 100% v/v DMSO. Phorbol dibutyrate (Cat #P1239; Sigma) was dissolved in 100% v/v DMSO as 10 mM stocks and made fresh on the day of use. Catalase (Cat #C1345, Sigma) was prepared as stock solutions of 10$^6$ U/ml in distilled water and stored at −20° C. MitoSOX (Cat #M3600850; Molecular Probes, Life Technologies) was prepared at 5 mM by dissolving the contents (50 µg) of one vial of MitoSOX (Trademark) mitochondrial superoxide indicator (Component A) in 13 µL of DMSO. Xanthine oxidase (Cat #X1875; Sigma) was prepared fresh on the day by dissolving in distilled water to 30 U/ml and xanthine (Cat #X0626; Sigma) was prepared as a stock of 100 mM in 0.1M NaOH. ML171 (Cat #492002; Calbiochem).

Antibodies for influenza nucleoprotein (mAb to Influenza A Virus Nucleoprotein [AASH]; Cat #120-20343, AbCAM), early endosome antigen 1 (Cat #120-02900, AbCAM), mouse anti-gp91phox (Cat #611415, BD Transduction Laboratories, Purified Mouse Anti gp91[phox] Clone 53/gp91[phox](RUO), rabbit anti-TLR7 (Cat #NBP2-24906, Novus Biologicals), rabbit anti-p47phox antibody (Cat #sc14015, Santa Cruz), FITC goat anti-mouse IgG (Cat #A-11029; Invitrogen), goat anti-rabbit alexa 594 (Cat #A-11037; Invitrogen), goat anti-rabbit far red 647 (Cat #A-21244, Invitrogen) and DAPI (Cat #H-1200, Vector Laboratories) were stored at −20° C.

Example 1

Influenza Viruses Drive Endosomal ROS

Figure 1B:
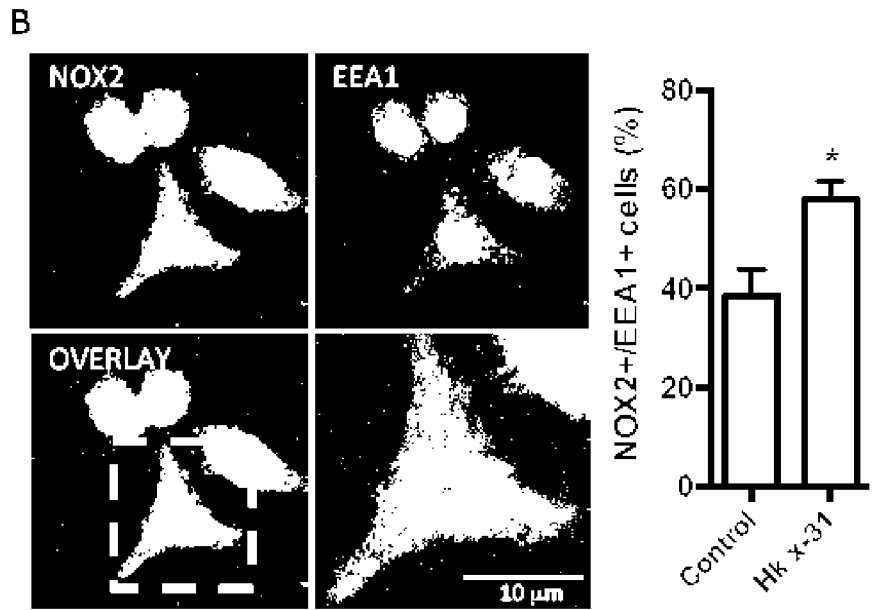
Figure 1C:
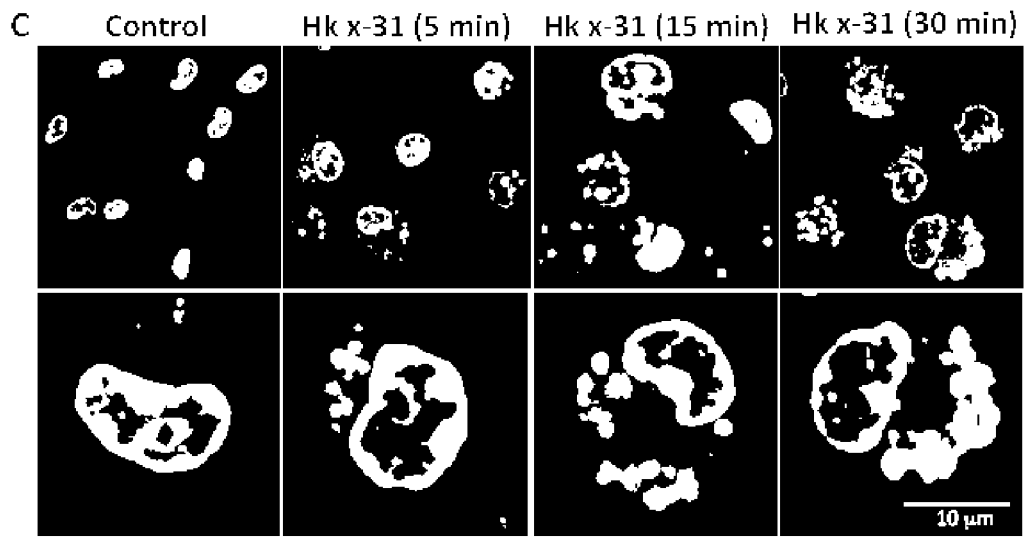
Figure 1D:
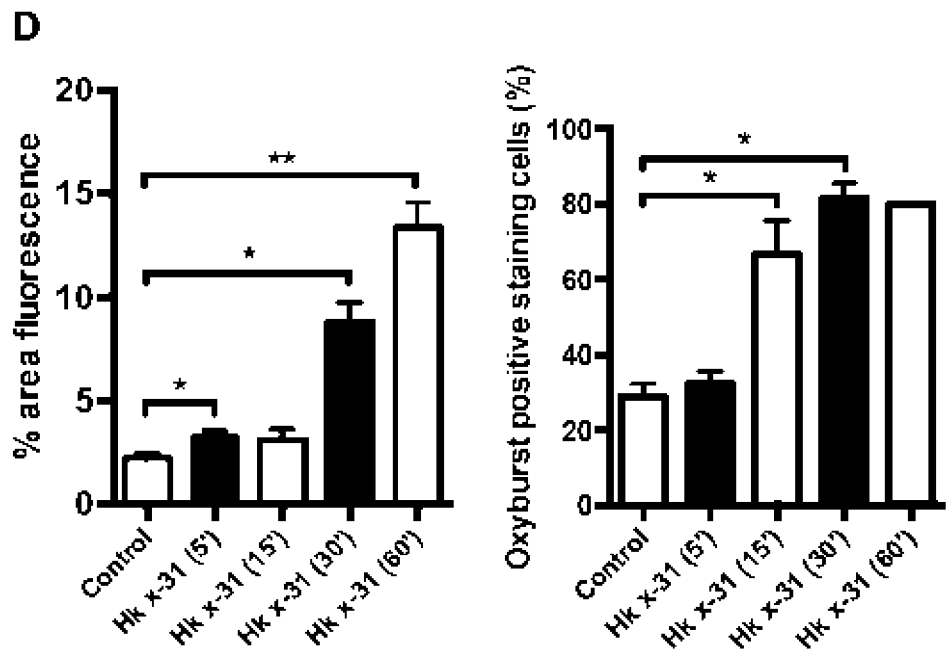
Figure 1E:
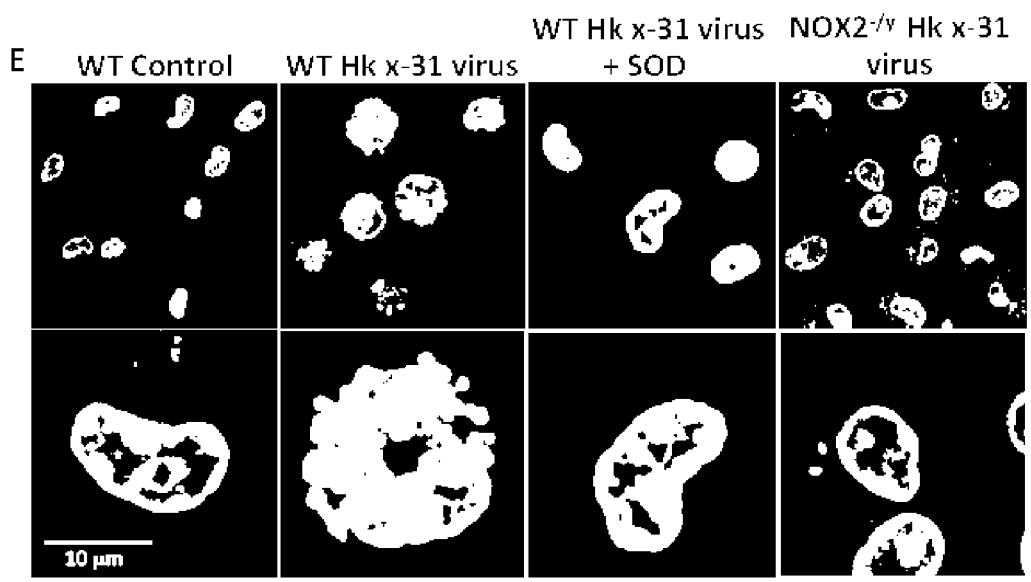
Figure 1F:
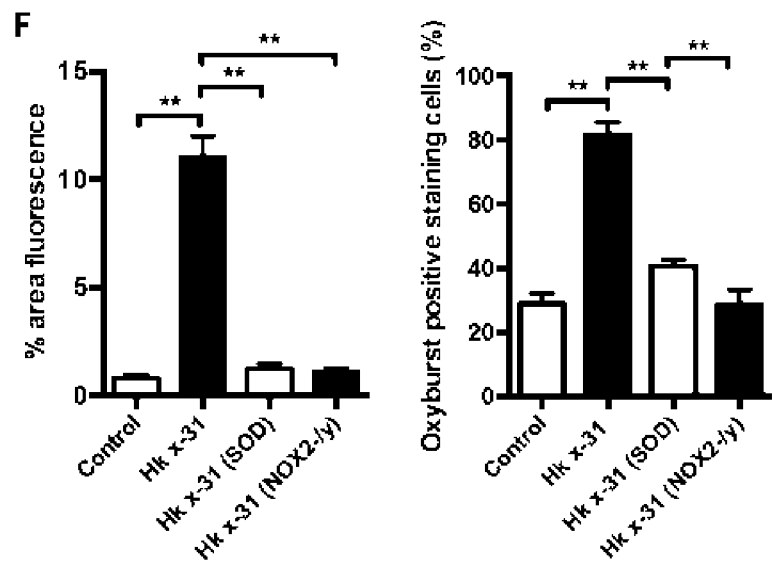
Figure 1G:
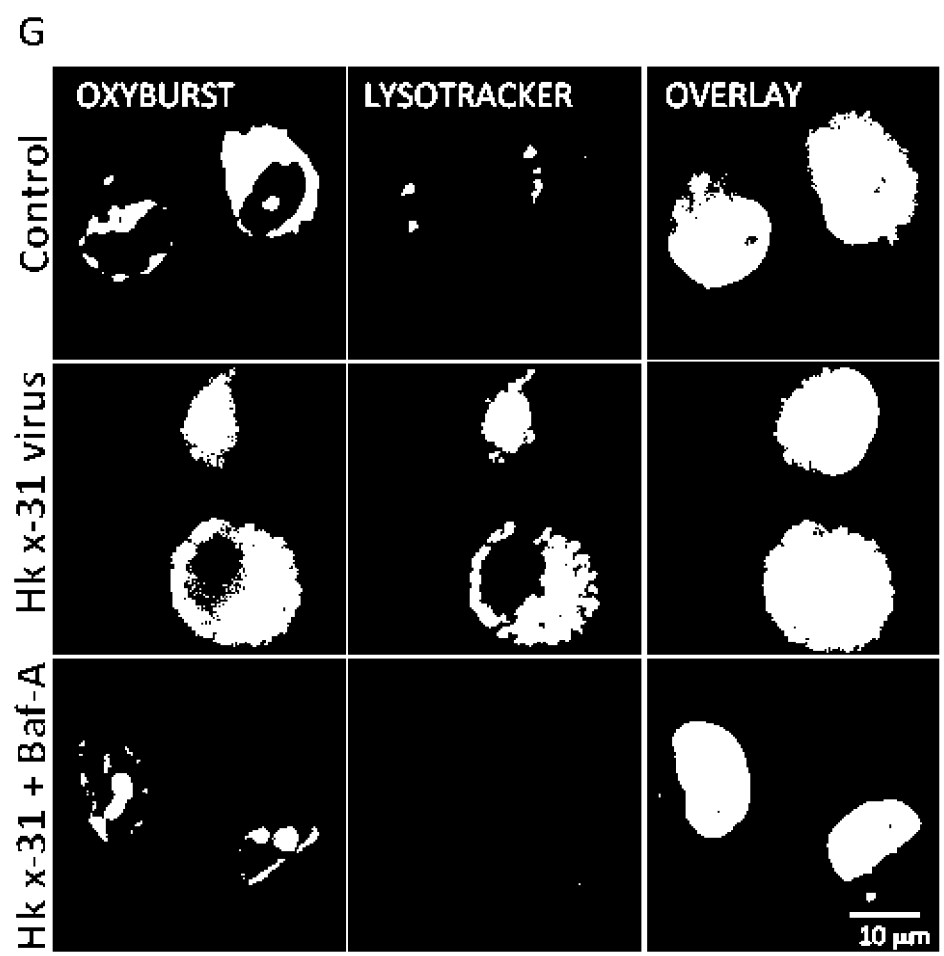
Figure 1H:
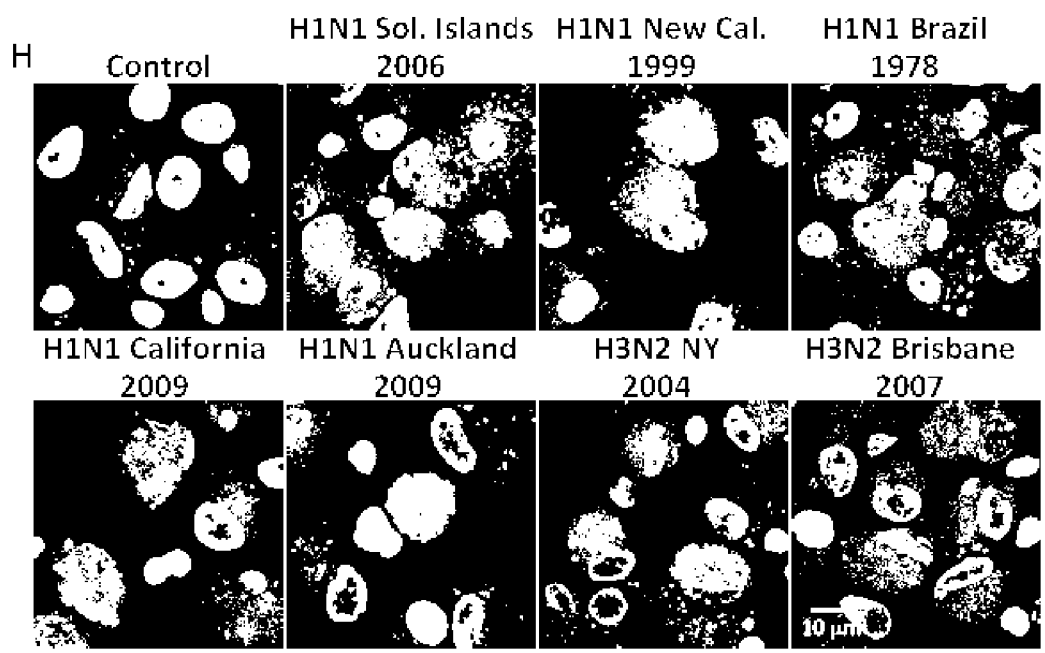
Figure 1I:
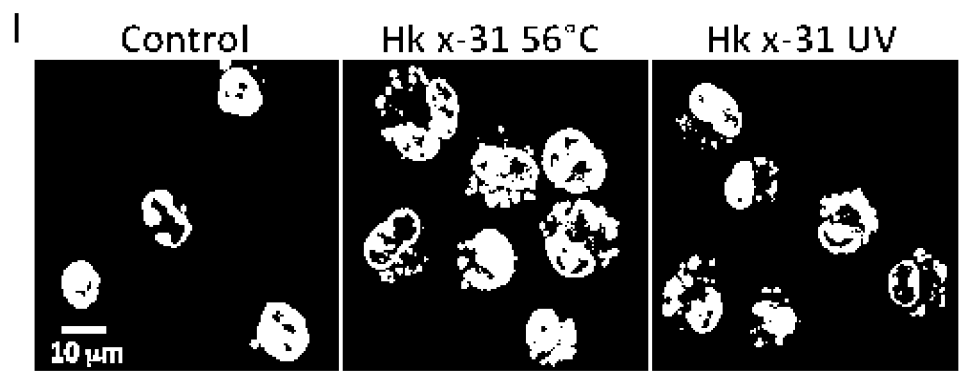
Figure 1J:
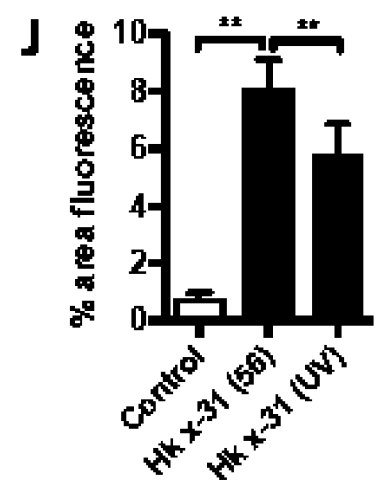

To address the potential role of endosomal ROS production in virus pathology, influenza A viruses, which belong to the Group IV negative sense, ssRNA viruses of the Orthomyxoviridae family and are internalized by endocytosis were first considered. Exposure of mouse alveolar macrophages (AMs), mouse peritoneal RAW264.7 cells or bone marrow-derived macrophages (BMDMs) to influenza A virus strain HKx31 (H3N2) resulted in a dose and time-dependent increase in influenza nucleoprotein (NP) fluorescence, which was almost abolished by the dynamin inhibitor, Dynasore (100 µM) indicating a clathrin-coated pit or caveolin-dependent mechanism of internalization. Internalized virus displayed a strong co-location with the early endosomal marker EEA1 (FIG. 1a). However, not all of the NP was co-located with EEA1 indicating that influenza A virus was not present exclusively in early endosomes (FIG. 1a) and might have already entered late endosomes and/or lysosomes. NOX2 co-located with EEA1 in control and influenza infected cells (FIG. 1b). Thus, the enzymatic machinery for ROS generation is present in early endosomes and this is significantly enhanced in influenza A virus infection, promoting co-localization with internalized virus. Endosomal ROS production in response to viral uptake was assessed with OxyBURST16. Exposure to a series of low to high pathogenic seasonal and pandemic influenza A viruses resulted in rapid and dose-dependent increases in Oxy-BURST fluorescence in mouse primary AMs (FIGS. 1c and d) and human alveolar macrophages (FIG. 1h). This Oxy- BURST-derived signal was abolished by addition of superoxide dismutase (SOD; 300 U/mL), which internalizes into the endosome along with the virus17 and converts superoxide to $H_2O_2$ (FIG. 1e,f). In contrast the ROS signal was significantly increased in AMs from mice deficient in endosomal SOD (SOD3$^{-/-}$ mice), establishing the detection of a superoxide derivative. For confirmation that ROS production occurred in acidified endosomes a co-location of Oxy-BURST fluorescence was demonstrated with LysoTracker (50 nM) in the presence of influenza virus (FIG. 1g). Inhibition of the vacuolar V-ATPase pump with bafilomycin A (100 nM), and thus inhibition of endosomal acidification, abolished the LysoTracker fluorescence and endosomal ROS production in response to influenza A virus infection (FIG. 1g). Endosomal ROS was minimal in NOX2$^{-/y}$ alveolar macrophages, but was unaffected in NOX4$^{-/-}$ macrophages and in macrophages treated with the NOX1 inhibitor ML171 (100 nM) (FIGS. 1e and f). Internalization of influenza A virus into AMs was not impaired in NOX2$^{-/y}$ cells, indicating that reduced endosomal ROS production was not due to reduced viral entry. In addition, heat- and UV-inactivated forms of influenza (replication-deficient) caused an increase in endosomal ROS production that was similar to the live virus control (FIGS. 1i and j). Therefore, influenza A viruses, irrespective of subtype, strain and pathogenicity, stimulate NOX2, but not NOX4 nor NOX1 oxidase-dependent ROS production in endosomes, and this involves endosomal acidification, but does not require viral replication.

Example 2

Endosome TLR7-NOX2 Signaling Axis

Figure 2D:
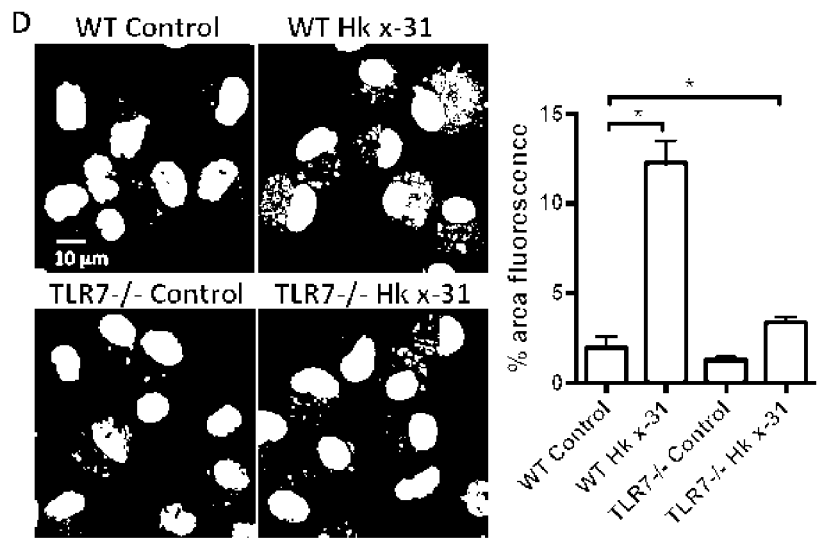
Figure 2E:
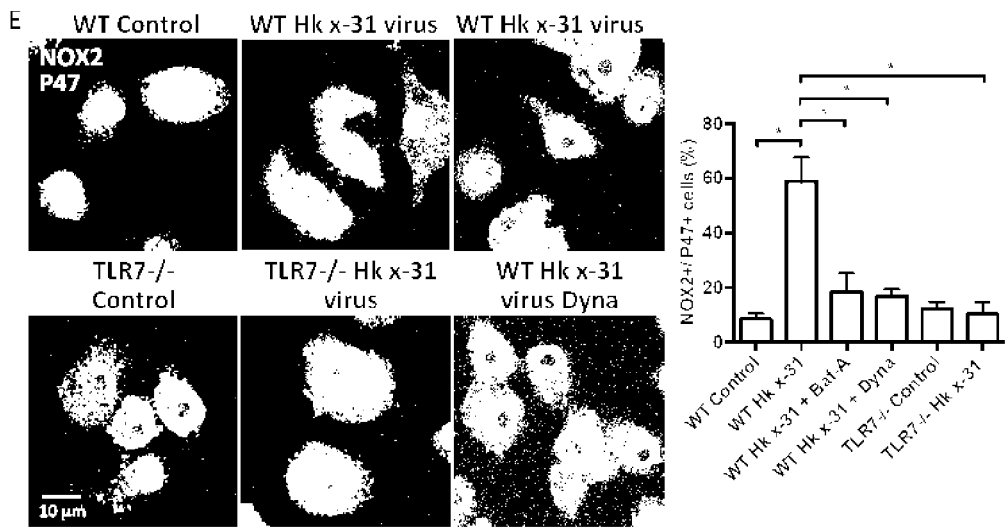
Figure 2F:
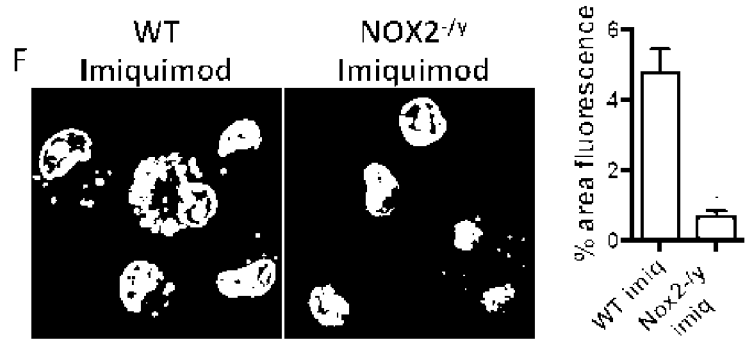
Figure 2G:
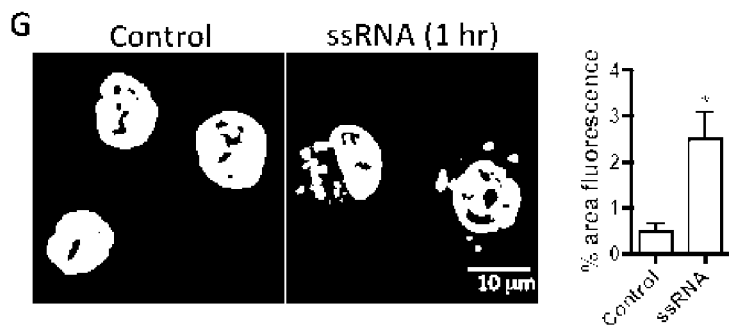

RNA viruses are recognized by endosomal TLR7 (for ssRNA viruses) [Lund et al. (2004) *Proceedings of the National Academy of Sciences of the United States of America* 101(15): 5598-5603, Diebold et al. *Science* 303 (5663):1529-1531] and TLR3 (dsRNA viruses), as well as the cytosolic sensors retinoic acid inducible gene I (RIG-I) (which can detect viral RNA bearing 5' triphosphates (Lund et al. (2004) supra) and NOD-like receptors (NLRs) [Iwasaki and Pillai (2014) supra; Ichinohe et al. (2009) *The Journal of Experimental Medicine* 206(1):79-87; Allen et al. (2009) *Immunity* 30(4):556-565]. It was hypothesized that influenza A virus entry into acidified endosomes results in the liberation of viral RNA, activation of TLR7 and stimulation of NOX2 oxidase-dependent ROS production. Consistent with this suggestion, TLR7 co-locates with influenza A virus (FIG. 2a), NOX2 (FIG. 2b) and EEA1 (FIG. 2c) and primary AMs from TLR7$^{-/-}$ mice, and TLR7- and MyD88-deficient BMDM, display minimal endosomal ROS production in response to influenza A virus (FIG. 2d). The lack of endosomal ROS production in response to virus in TLR7$^{-/-}$ and MyD88$^{-/-}$ cells was not due to a reduced capacity of the NOX2 oxidase per se, as NOX2 activation by the PKC activator phorbol dibutyrate (PDB; 10-6 M) was similar in these cells and WT control cells. As a second measure of NOX2 oxidase activity, enzyme assembly was assessed by examining the degree of association of the NOX2 catalytic subunit with the p47$^{phox}$ regulatory subunit. In unstimulated cells, there was very little colocalization of NOX2 and p47$^{phox}$ (FIG. 2e). However, influenza virus caused strong co-location of NOX2 and p47$^{phox}$, which was reduced by Dynasore or bafilomycin A pre-treatment, and almost abolished in TLR7$^{-/-}$ cells (FIG. 2e). To provide further evidence that the activation of TLR7 leads to endosomal ROS production, the specific TLR7 agonist, imiquimod (10 µg/mL) was used. Imiquimod markedly increased endosomal ROS in AMs from human and WT mice, but not from NOX2$^{-/y}$ mice (FIG. 2f) or macrophages deficient in TLR7 or MyD88. Finally, AMs or RAW264.7 cells were pulsed with a guanidine- and uridine-rich ssRNA sequence (ssRNA40; 100 µM). In concentrations capable of increasing IL-1β, IL-6 and TNF-α mRNA via a TLR7-dependent mechanism, ssRNA40 caused elevated endosomal ROS production (FIG. 2g). In contrast, endosomal ROS production in response to influenza A virus was preserved in NLRP3$^{-/-}$, TLR2$^{-/-}$ and TLR4$^{-/-}$ macrophages and in macrophages treated with the TLR3 inhibitor (50 µM).

Figure 2H:
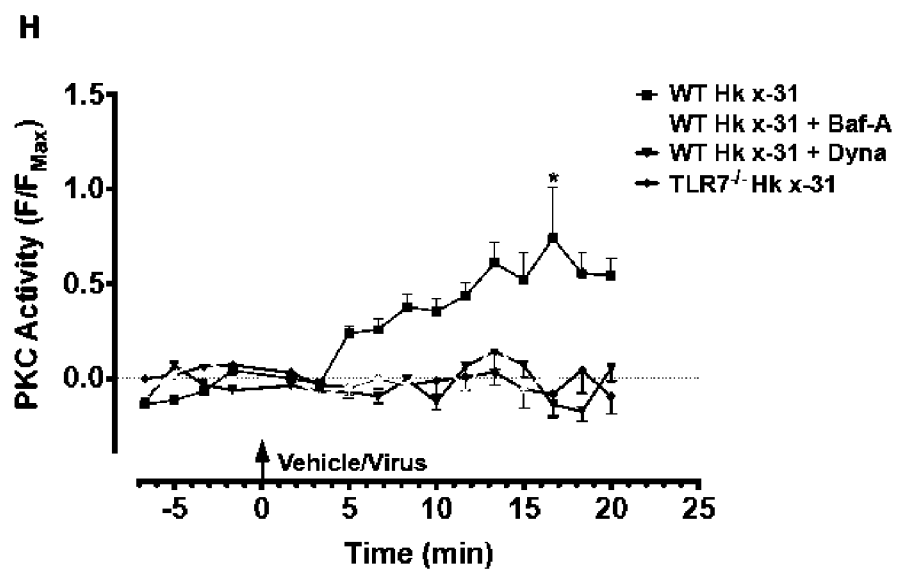

How TLR7 elicits the assembly and activation of endosomal NOX2 oxidase was then examined. NOX2 oxidase can be activated by protein kinase C, which triggers robust phosphorylation of key serine residues on p47$^{phox}$, resulting in a NOX2 oxidase-dependent oxidative burst (Drummond et al. (2011) supra). To define the spatiotemporal regulation of PKC signaling and to assess its regulation by TLR7, the FRET biosensor cytoCKAR was expressed to detect cytosolic PKC (Jensen et al. (2014) supra; Violin et al. (2003) *The Journal of Cell Biology* 161(5):899-909; Halls et al. (2015) supra) in WT and TLR7$^{-/-}$ macrophages. The treatment of WT macrophages with influenza A virus or imiquimod elevated cytosolic PKC activity within 5 min, but this response was absent in TLR7$^{-/-}$ macrophages and in WT macrophages treated with Dynasore or bafilomycin A (FIGS. 2h and i). A FRET biosensor method for cytosolic pERK1/2 activity (Allen et al. (2009) supra; Halls et al. (2015) supra) showed that both influenza virus and imiquimod increased cytosolic pERK1/2 in a TLR7-dependent manner. In contrast, blocking pERK1/2 with PD98059 (30 µM) did not influence endosomal ROS production or the association of NOX2 with p47phox in response to influenza. These data indicate that influenza A virus increases endosomal NOX2 oxidase activity via TLR7 and the downstream activation of PKC but not via pERK1/2. It is concluded that virus infection triggers a NOX2 oxidase-dependent production of ROS in endosomes using a process that is dependent on low pH. Indeed, this conclusion is supported by the following experimental evidence. First it is known that reduced endosome acidification impairs the activation of TLR7 by viral RNA 18, 19. NOX2 dependent ROS production in response to virus infection and to the TLR7 agonist imiquimod was abolished in TLR7$^{-/-}$ cells and also by pretreatment with bafilomycin A. Second, bafilomycin A suppressed PKC activation due to influenza virus and imiquimod treatment, and PKC is upstream of acute NOX2 activation (Drummond et al. (2011) supra; Bedard and Krause (2007) supra). Third, bafilomycin A suppressed the association of p47$^{phox}$-NOX2, which is a critical step for NOX2 assembly and activation.

Example 3

Viral Strain Independence of Endosomal ROS

Figure 3A:
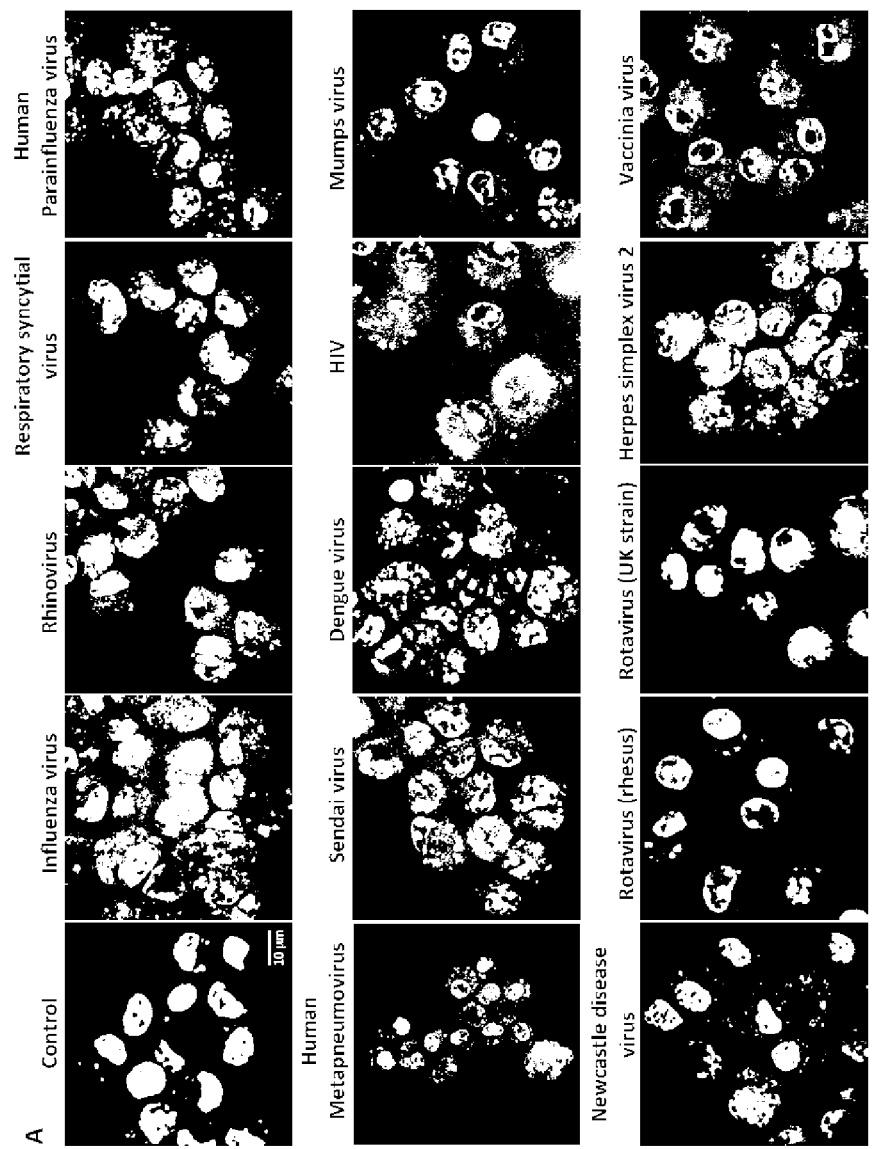
FIG. 3A and FIG. 3B are photographic and graphic representations showing endosomal ROS production to ssRNA and DNA viruses are via TLR7 and TLR9-dependent mechanisms, respectively. (A) Endosomal ROS production in WT and TLR7$^{-/-}$ bone marrow-derived macrophages as assessed by OxyBURST (100 μM) fluorescence microscopy in the absence or presence of influenza A virus (HKx31 virus), rhinovirus (rhino), respiratory synctitial virus (RSV), human parainfluenza virus (PW), human metapneumovirus (HMPV), sendai virus, dengue virus, human immunodeficiency virus (HIV), mumps virus (MuV), Newcastle disease virus (NDV), rotavirus (UK and bovine strains), herpes simplex virus 2 (HSV-2) and vaccinia virus and labeled with 4',6'-diamidino-2-phenylindole (DAPI). Also shown is the quantification of the results (n=5). (B) Endosomal ROS production in WT and TLR9$^{-/-}$ mouse primary alveolar macrophages as assessed by OxyBURST fluorescence microscopy in the absence or presence of HKx31 virus, rhinovirus, sendai virus, dengue virus, and herpes simplex virus 2 (HSV-2) and labeled with DAPI (n=5). (A and B) Images are representative of >150 cells analyzed over each experiment. Original magnification X100. All data are represented as mean±SEM. One-way ANOVA followed by Dunnett's post hoc test for multiple comparisons. #P<0.05 compared to WT control. *P<0.05 comparisons indicated by horizontal bars.
Figure 3B:
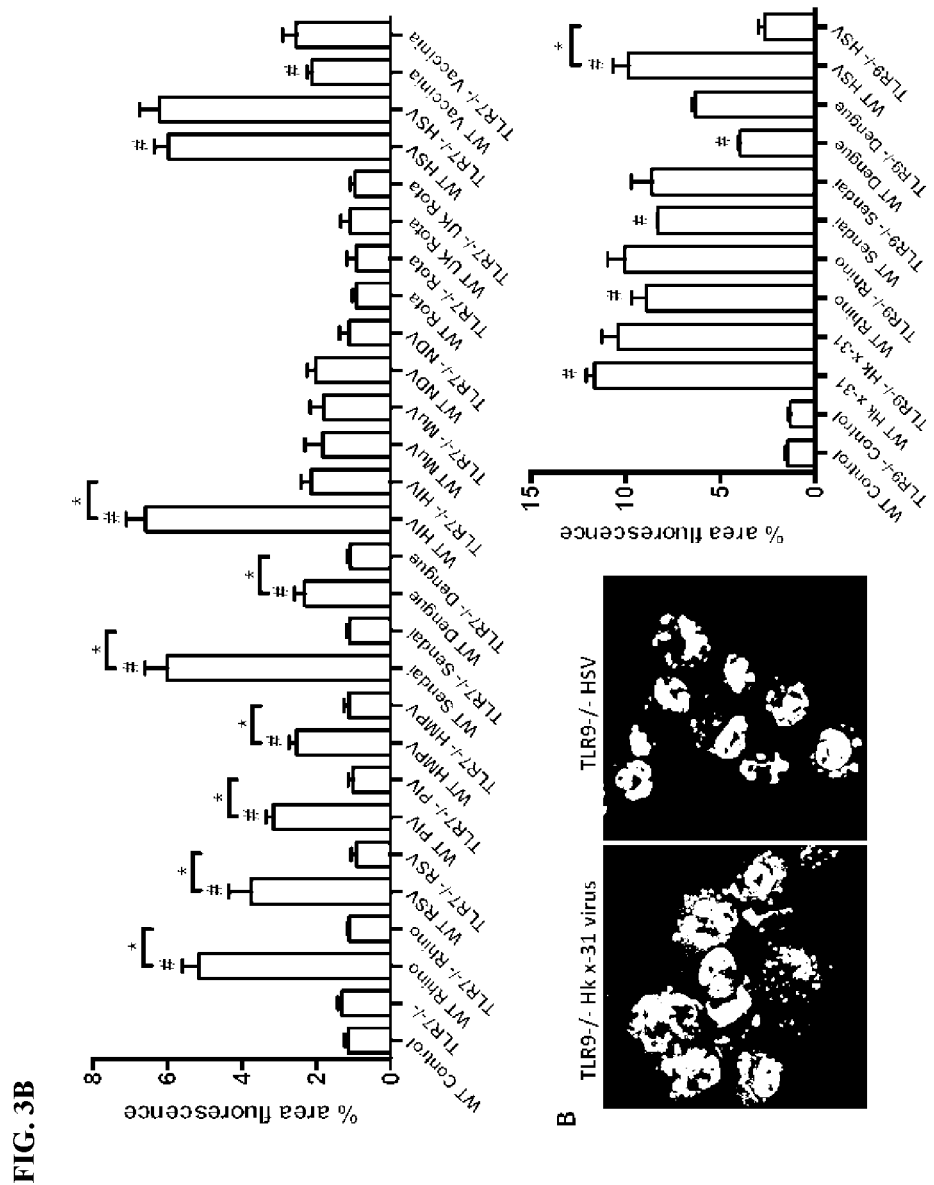
Figure 1:
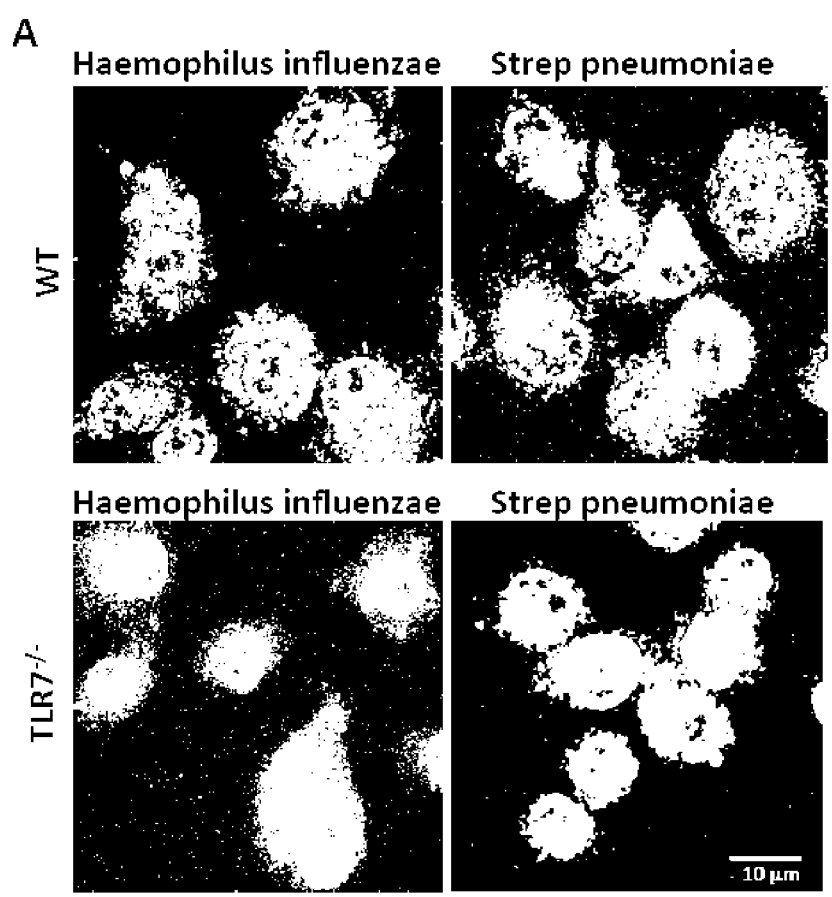

Exposure of macrophages to rhinovirus (picornaviridae, Group IV), respiratory syncytial virus (paramyxoviridae, Group V), human parainfluenza virus (paramyxoviridae, Group V), human metapneumovirus (paramyxoviridae, Group V), Sendai virus (paramyxoviridae, Group V), Dengue virus (flavoviridae Group IV), or HIV (retroviridae, Group VI, ssRNA-RT virus) resulted in a significant elevation of endosomal ROS that was markedly suppressed in TLR7$^{-/-}$ macrophages, but unaffected in TLR9$^{-/-}$ cells (FIGS. 3a and b). Both mumps virus (paramyxoviridae Group V) and Newcastle disease virus (NDV, paramyxoviridae Group V) failed to generate significant endosomal ROS (FIGS. 3a and b), and it is noteworthy that these viruses primarily enter cells by a cell membrane fusion process and not via endocytosis. Rotavirus (rhesus monkey strain or bovine UK strain, (reoviridae Group III)) exposure of macrophages also failed to generate endosomal ROS (FIGS. 3a and b). The DNA viruses Herpes simplex virus 2 (herpesviridae, Group I) and vaccinia virus (poxyviridae, Group I) each caused an elevation in endosomal ROS in WT macrophages and TLR7$^{-/-}$ macrophages, but not in TLR9$^{-/-}$ macrophages (FIGS. 3a and b). It is concluded that the specific recognition of either ssRNA viruses by TLR7, or DNA viruses by TLR9, leads to a NOX2 oxidase-dependent burst of endosomal ROS.

Example 4

Bacteria and Viruses Activate Distinct ROS Pathways

Figure 4B:
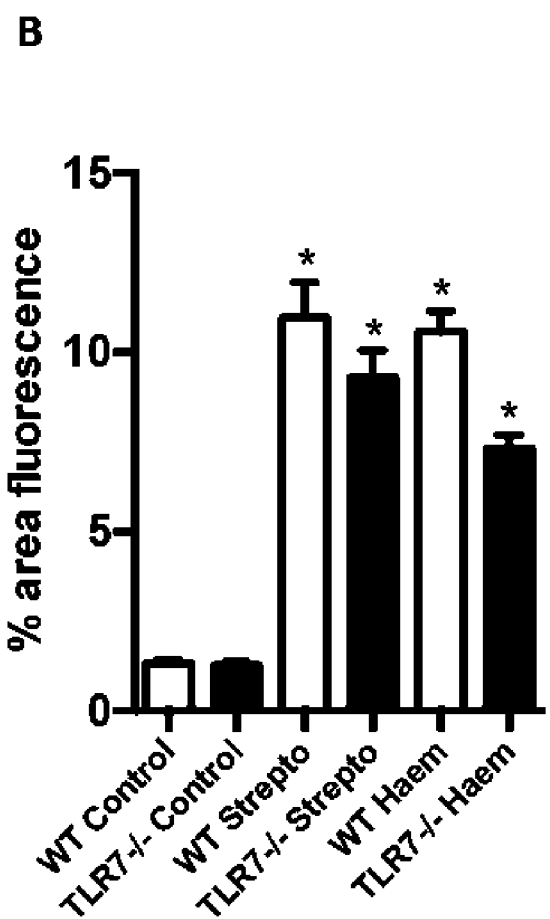

Plasma membrane TLRs, especially TLR1, TLR2 and TLR4, and not those present within endosomes (such as TLR7), sense bacteria resulting in the recruitment of mitochondria to macrophage phagosomes and mitochondrial dependent ROS production (West et al. (2011) *Nature* 472 (7344):476-480). However, the stimulation of endosomal TLRs failed to augment mitochondrial ROS (West et al. (2011) supra). TLR7 activation with imiquimod, which caused a significant elevation in endosomal ROS (FIG. 2f), failed to increase macrophage mitochondrial superoxide production. The production of phagosomal ROS was examined in response to the Gram-positive bacteria *Streptococcus pneumoniae* (SP) or gram-negative non-typeable *Haemophilus influenzae* (NTHI). Both SP and NTHI caused ROS production in WT mouse macrophages (FIG. 4), which was significantly enhanced in SOD3$^{-/-}$ cells, but unaffected in TLR7$^{-/-}$ macrophages (FIG. 4). Thus, endosomal ROS production is not a characteristic of endocytosis per se, but a 'pathogen (cargo)-specific' response. ROS produced for antibacterial purposes involves an obligatory role of mitochondria, which serves as a central hub to promote innate immune signaling. By contrast, ssRNA viruses do not employ these antibacterial ROS generating pathways.

Example 5

Endosomal H$_2$O$_2$ Suppresses TLR7 Immunity

Figure 5A:
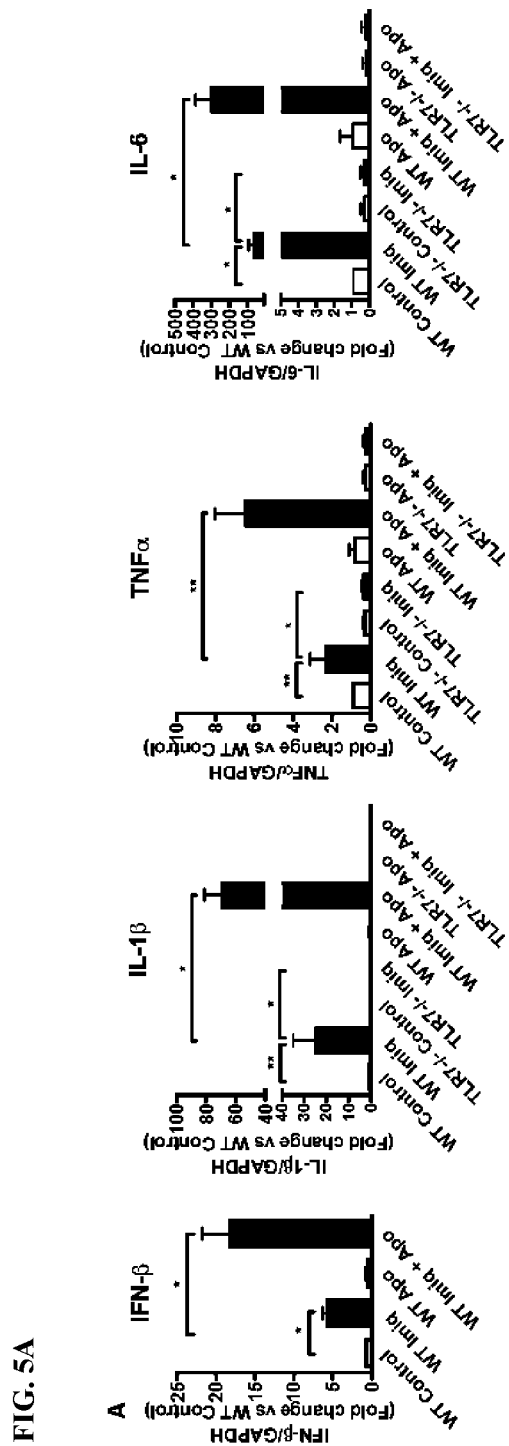
FIG. 5A, FIG. 5B, FIG. 5C, and FIG. 5D are graphic representations showing endosomal NOX2 oxidase suppresses cytokine expression in response to TLR7 activation in vitro and in vivo. (A-B) WT and TLR7$^{-/-}$ immortalized bone marrow-derived macrophages (BMDMs) were untreated or treated with imiquimod (Imiq; 10 μg/mL) in the absence or presence of A) apocynin (Apo; 300 μM) or B) bafilomycin A (Baf-A; 100 nM), and IFN-β, IL-1β, TNF-α and IL-6 mRNA expression determined by QPCR after 24 hr (n=6). (C-D) WT and NOX2$^{-/y}$ mice were administered with imiquimod (50 μg/mouse, intranasal) and C) total airway inflammation quantified by bronchoalveolar lavage fluid analysis and D) cytokine expression assessed 24 h later (n=5). (A, B, D) Responses are relative to GAPDH and then expressed as a fold-change above WT controls. (A-D) Data are represented as mean±SEM. (A, B and D) Kruskal-Wallis test with Dunn's post hoc for multiple comparisons. (C) One-way ANOVA followed by Dunnett's post hoc test for multiple comparisons. Statistical significance was accepted when P<0.05. *P<0.05; **P<0.01.
Figure 5B:
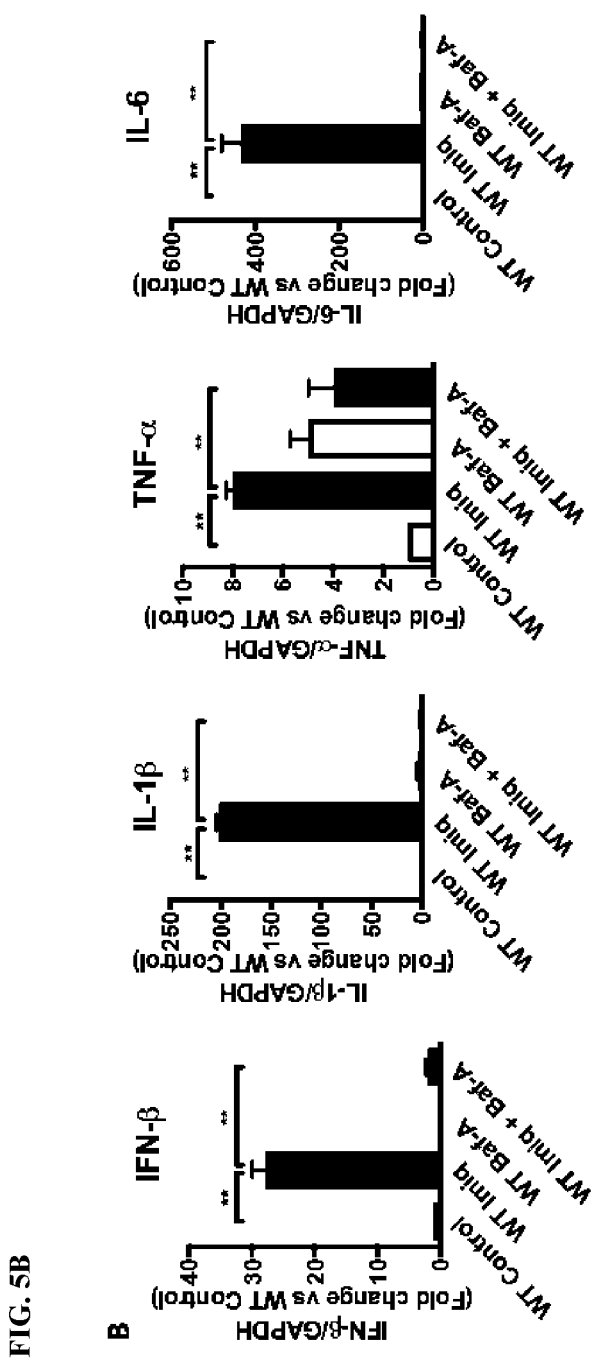
Figures 5C, 5D:
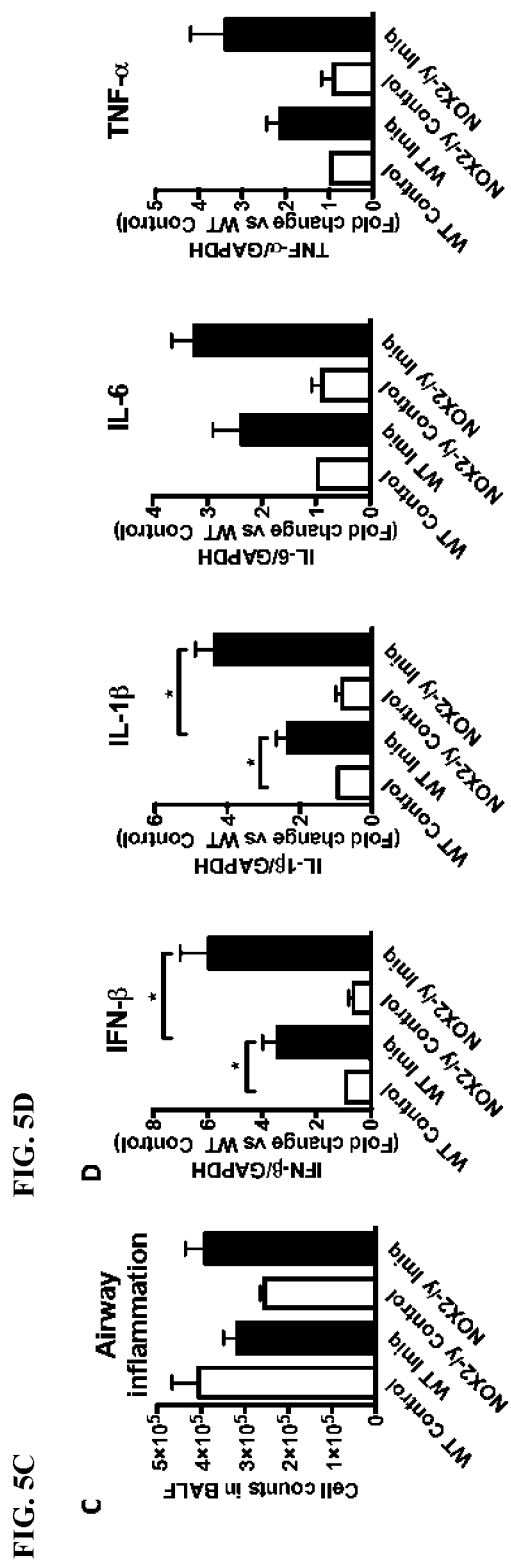

To establish the functional importance of endosomal ROS, the impact of NOX2 inhibition was assessed on the production of cytokines that are endosome TLR7-dependent and thus relevant to virus pathogenicity (Diebold et al. (2004) supra). An endosome- and TLR7-dependent signal was confirmed by showing that imiquimod caused a significant elevation in IFN-β, IL-1β, TNF-α and IL-6 expression in WT macrophages, but not in TLR7$^{-/-}$ macrophages (FIG. 5a) or in macrophages treated with bafilomycin A (100 nM) (FIG. 5b). Second, pre-treatment with the NOX2 oxidase inhibitor and H$_2$O$_2$ scavenger, apocynin (300 μM) significantly enhanced IFN-β, IL-1β, TNF-α and IL-6 expression in response to imiquimod, in WT macrophages but not in TLR7$^{-/-}$ macrophages, indicating that the suppressive effect of NOX2 oxidase-derived ROS on cytokine expression is dependent on TLR7 (FIG. 5a). In contrast, IFN-β, IL-1β, TNF-α and IL-6 expression in response to the TLR3 agonist, poly I:C (25 μg/mL), was suppressed by apocynin pre-treatment whereas increases in these same cytokines triggered by the TLR9 agonist CpG (10 μg/mL), were unaffected by apocynin. It was further tested whether NOX2 oxidase influences TLR7 immunity in vivo. WT and NOX2$^{-/y}$ mice were treated with a single dose of imiquimod (50 μg/mouse, intranasally) for measurements of lung IFN-β, IL-1β, IL-6 and TNF-α after 24 h. This time point was chosen to reflect early phases of RNA infection. There were no discernible alterations in airway inflammation in response to imiquimod (FIG. 5c), however, imiquimod treatment resulted in elevated levels of IFN-β, IL-1β, IL-6 and TNF-α in NOX2$^{-/y}$ mice (FIG. 5d).

Figure 6A:
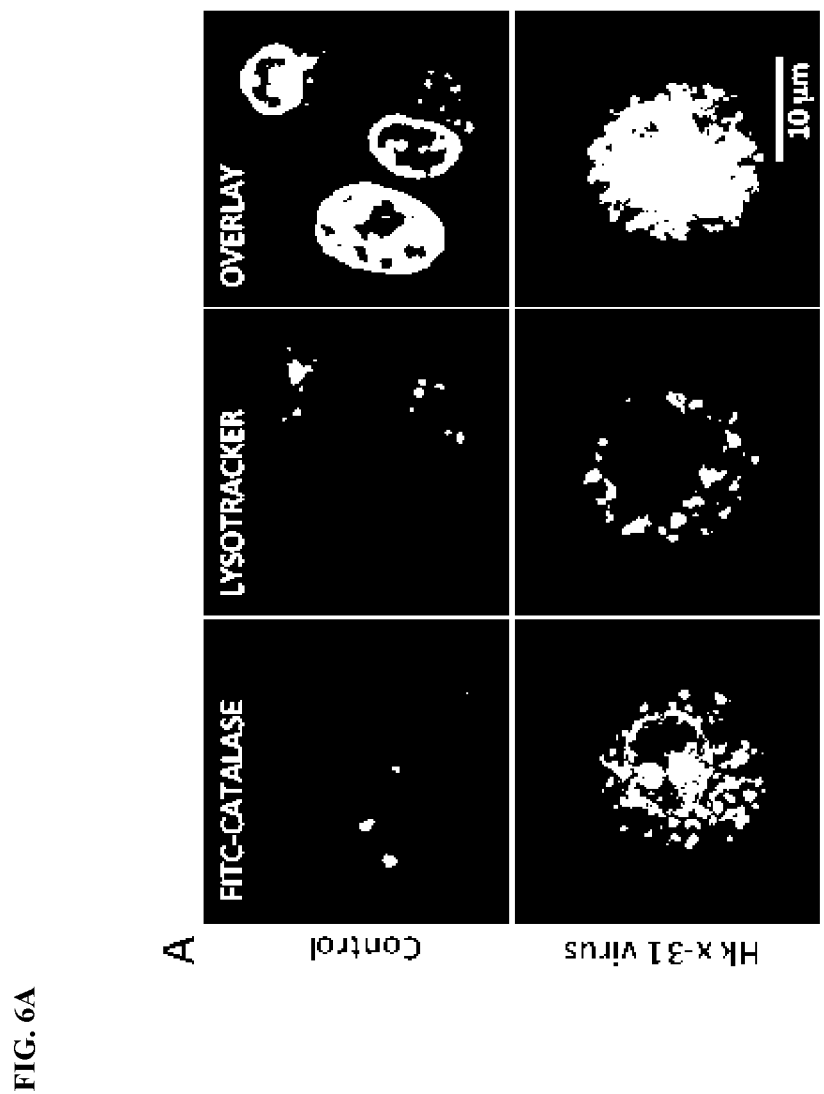
Figures 6B, 6C:
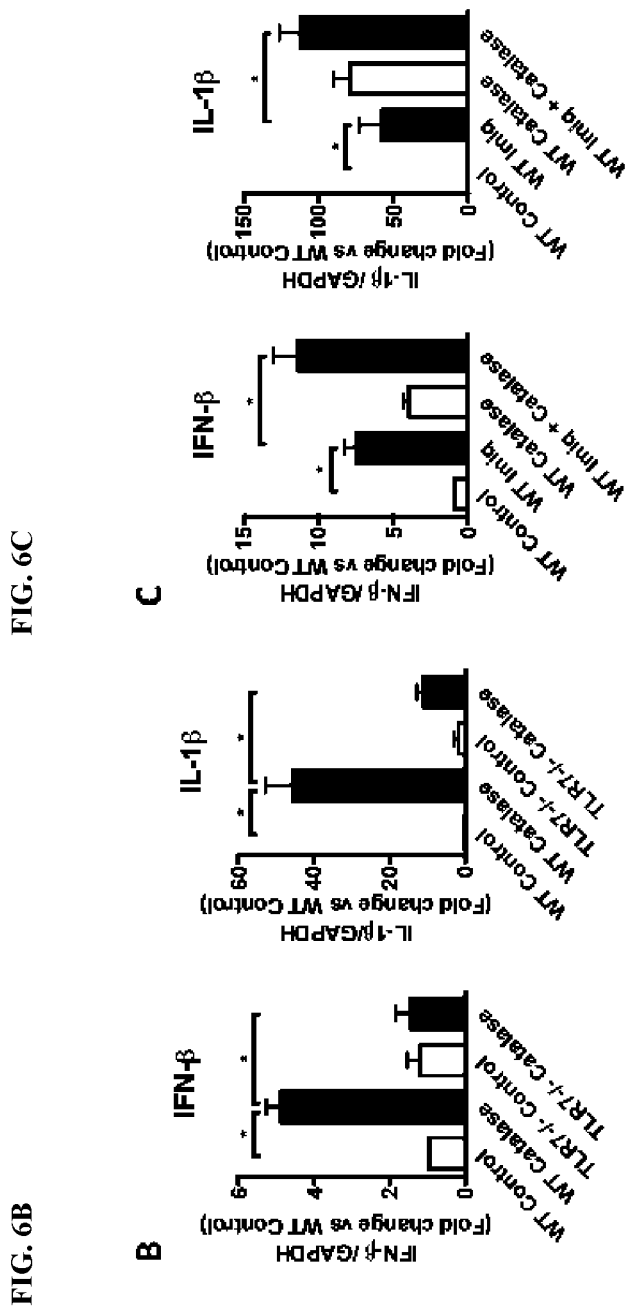
Figure 6D:
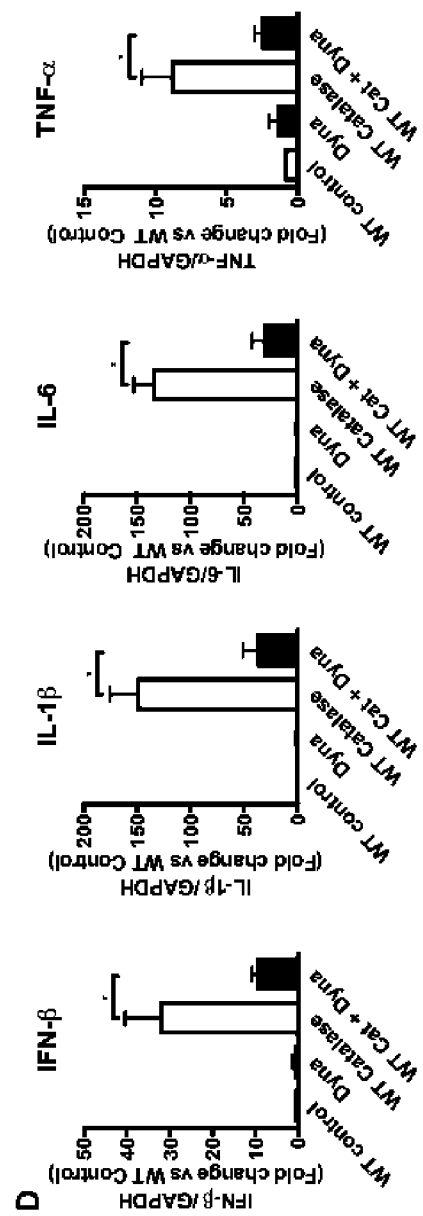
Figures 6G, 6H, 6I, 6J, 6K, 6L:
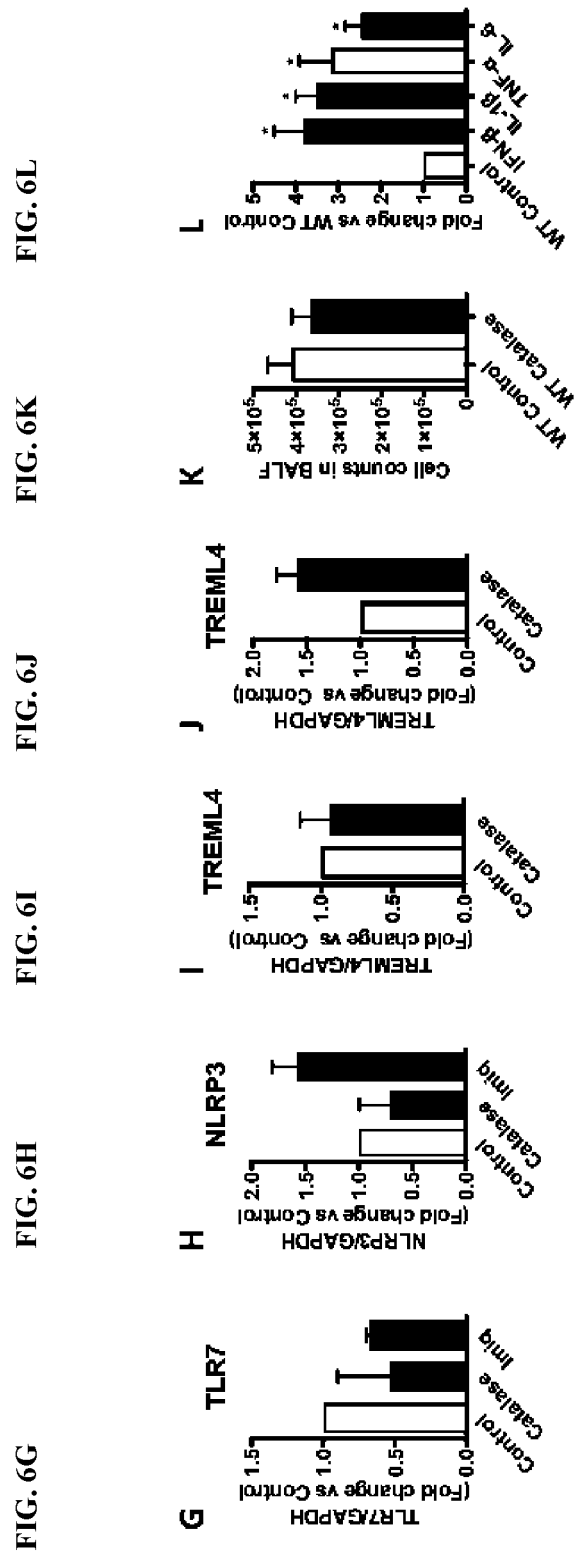

It was sought to establish how endosomal NOX2 oxidase activity results in the suppression of TLR7-dependent responses and hypothesized that the parent species superoxide and its immediate downstream product, H$_2$O$_2$ are culprit mediators. Inactivation of superoxide by adding exogenous SOD (300 U/mL) failed to influence either basal or imiquimod-stimulated expression of IFN-β, IL-1β, TNF-α and IL-6, suggesting little role for superoxide itself in modulating TLR7 responses. To examine H202, catalase was utilized to inactivate the H$_2$O$_2$ generated within endosomes. Within 30 min, it was found that exposure to a FITC-labeled catalase resulted in co-localization with LysoTracker, confirming internalization into acidified endosomal compartments (FIG. 6a). A 1 hr "pulse" exposure to catalase (1000 U/mL) resulted in significant elevations in IFN-β and IL-1β expression after 24 h in WT macrophages, but not in TLR7$^{-/-}$ macrophages (FIG. 6b). Moreover, imiquimod-dependent responses were significantly increased in the presence of catalase (FIG. 6c). The catalase-dependent increase in cytokines was significantly suppressed in WT macrophages treated with Dynasore (FIG. 6d) but unaffected in TLR2$^{-/-}$ macrophages (FIG. 6e). The translocation of TLR7 to endosomes is governed by the actions of the chaperone protein, UNCB93. Indeed in the absence of UNCB93 there are substantial signaling defects due to the failure of the nucleotide-sensing TLRs to reach the endolysosomes, where they initiate MyD88/TRIF-dependent signaling pathways. In UNCB93$^{-/-}$ cells, the increase in cytokines to catalase treatment was significantly smaller than that observed in WT cells (FIG. 6f). Thus, the suppressive actions of H$_2$O$_2$ are most likely occurring when TLR7 is located within the endosomal compartment. Catalase had no effect on TLR7, TREML4 or NLRP3 expression indicating that H$_2$O$_2$ does not modulate the expression of TLR7, a positive regulator of TLR7 activity (i.e. TREML4 26) or NLRP3 that drives similar anti-viral cytokines to TLR7 (FIGS. 6g-j). Therefore, the effect of H$_2$O$_2$ is likely to be post-translational. Whether endosomal NOX2 oxidase-derived H$_2$O$_2$ influences TLR7 responses in vivo was examined. catalase (1000 U/mouse) intranasally to WT mice and showed a 3 to 4 fold increase in lung IFN-β IL-1β, TNF-α and IL-6 after 24 h and this occurred prior to overt airway inflammation (FIGS. 6k and l).

The question arose whether H$_2$O$_2$ released by endosomal NOX2 oxidase targets cysteine residues on protein domains of TLR7 that regulate receptor activity and are exposed upon activation within endosomal compartments (Kanno et al. (2013) *International Immunology* 25(7):413-422). These include Cys260, Cys263, Cys270 and Cys273 within the leucine repeat region as well as two additional cysteines, Cys98 and Cys445 that are unique to TLR7 (FIGS. 10 and 11). Site-directed mutagenesis was performed to create a series of TLR7 mutants including: 1) a mutant with all six of these cysteine residues replaced with alanine; 2) mutants with a dual mutation of Cys98 and Cys445 (TLR$^{7C98A/C445A}$), and 3) single mutations of Cys98

Figure 7A:
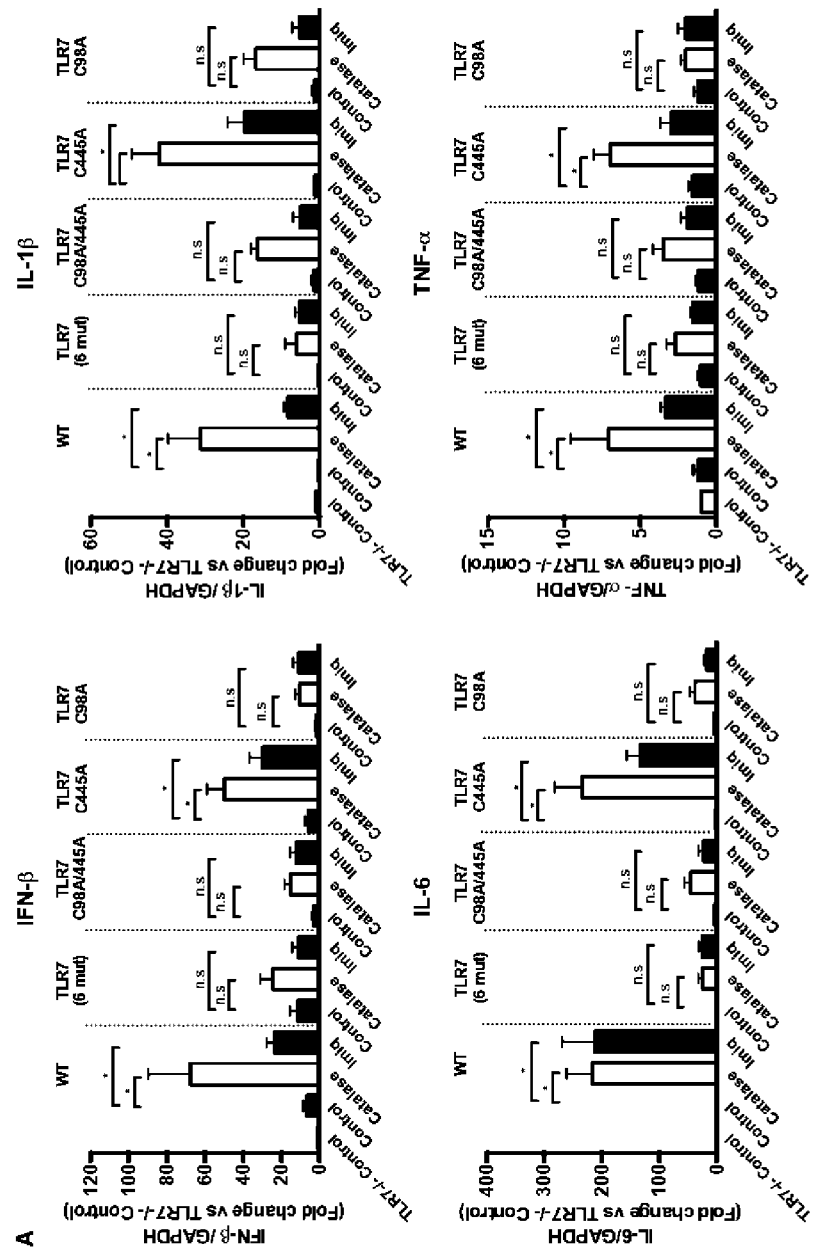

(TLR7$^{C98A}$) and Cys445 (TLR7$^{C445A}$). Transfection of WT TLR7 or TLR7$_{C445A}$ into TLR7$^{-/-}$ macrophages restored the ability of imiquimod to stimulate cytokine expression in these cells; however, transfection with the TLR7 containing the 6 mutations, the TLR7$^{C98A/C445A}$ or the TLR7$^{C98A}$ did not (FIG. 7a). Catalase (1000 U/mL) treatment had little or no effect on cytokine expression in cells expressing the mutated TLR7, TLR7$^{C98A/C445A}$ or TLR7$^{C98A}$ whereas it markedly increased cytokine expression in cells with WT TLR7 or TLR7$^{C445A}$ (FIG. 7a). Sequence analysis using both multiple sequence analysis algorithms (i.e. CLUSTAL OMEGA) and pair-wise sequence analysis (NCBI, Blast) with human TLR7 as a reference point. Using the multiple sequence analysis it was identified that Cys98 was unique to TLR7 and fully conserved in vertebrate TLR7 including from teleosts to man (FIGS. 7b, 10 and 11). Pair-wise sequence alignment showed that Cys98 was the only cysteine residue of the 27 cysteines on TLR7 that was unique to TLR7 and fully conserved in vertebrates. It is suggested here that $H_2O_2$ produced by endosomal NOX2 oxidase is likely to modify a single and evolutionary conserved unique cysteine residue i.e. Cys98, located on the endosomal face of TLR7, resulting in a dampened antiviral cytokine response. Potentially this signifies Cys98 of TLR7 as a novel redox sensor that controls immune function during viral infections.

Example 6

NOX2 Oxidase Dampens Antibody Production

Figure 8A:
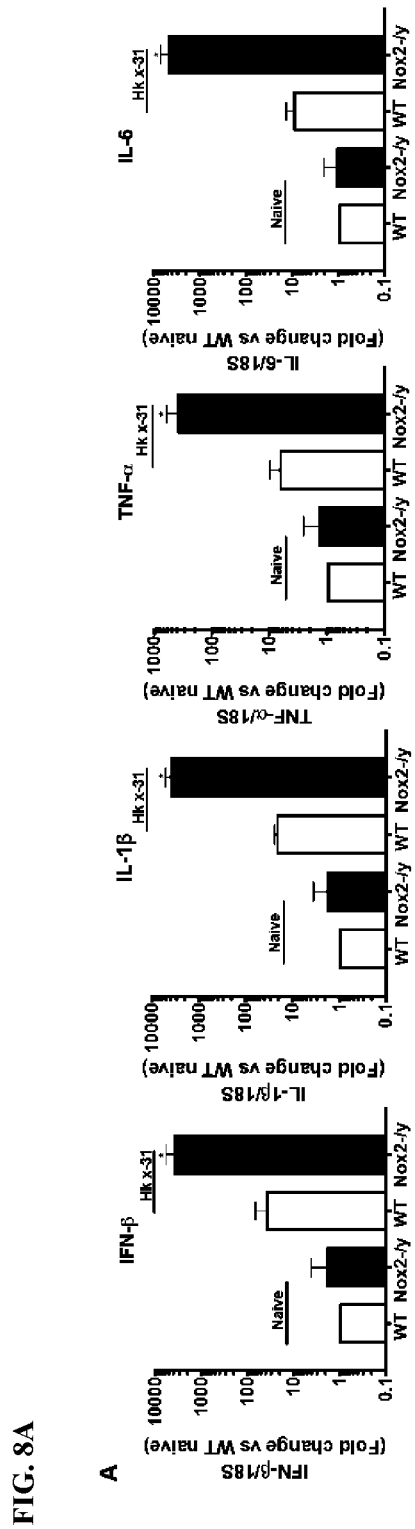
FIG. 8A, FIG. 8B, FIG. 8C, FIG. 8D, FIG. 8E, FIG. 8F, FIG. 8G, FIG. 8H, and FIG. 8I are graphic representations showing inhibition of NOX2 oxidase increases expression of Type I IFN and IL-1β, and antibody production to influenza A virus infection (A) Alveolar macrophages from WT and NOX2$^{-/y}$ mice were either left untreated (naïve) or infected with HKx31 influenza A virus (MOI of 10) for analysis of IFN-β, IL-1β, TNF-α and IL-6 mRNA expression by QPCR after 24 h (n=8). (B-C) WT and NOX2$^{-/y}$ mice were infected with live HKx31 influenza A virus (1×105 PFU per mouse) and B) cytokine mRNA expression and IFN-β protein expression in C) BALF or D) serum were assessed 3 days later (n=5). (E-I) WT and NOX2$^{-/y}$ mice were infected with inactivated HKx31 influenza A virus (equivalent to 1×104 PFU per mouse) for measurements at day 7 of: E) body weight; F) airway inflammation and differential cell counts (i.e. macrophages, neutrophils and lymphocytes); G) cytokine expression in whole lung (responses are shown as fold change relative to GAPDH) and H) serum and I) BALF antibody levels (n=6). Data are shown as mean±SE. (A) Kruskal-Wallis test with Dunn's post hoc for multiple comparisons. (B-I) Unpaired t-test; statistical significance taken when the P<0.05. *P<0.05. **P<0.01.
Figure 8E:
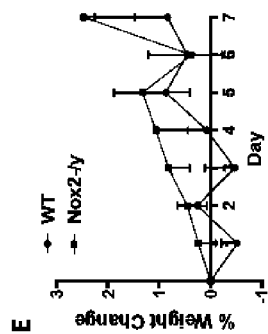
Figures 8C, 8D:
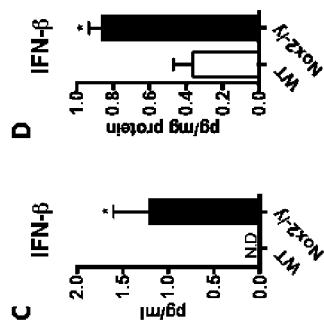
Figure 8B:
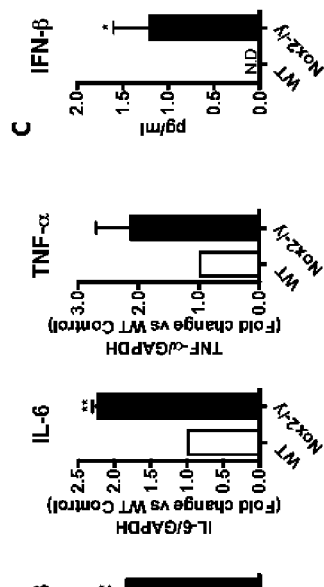
Figures 8F, 8G:
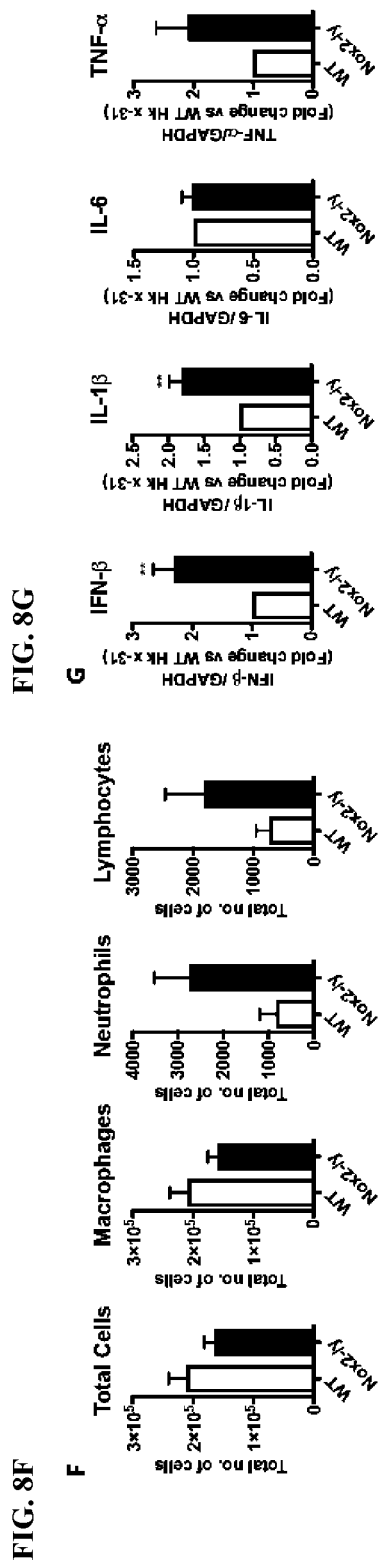
Figure 8H:
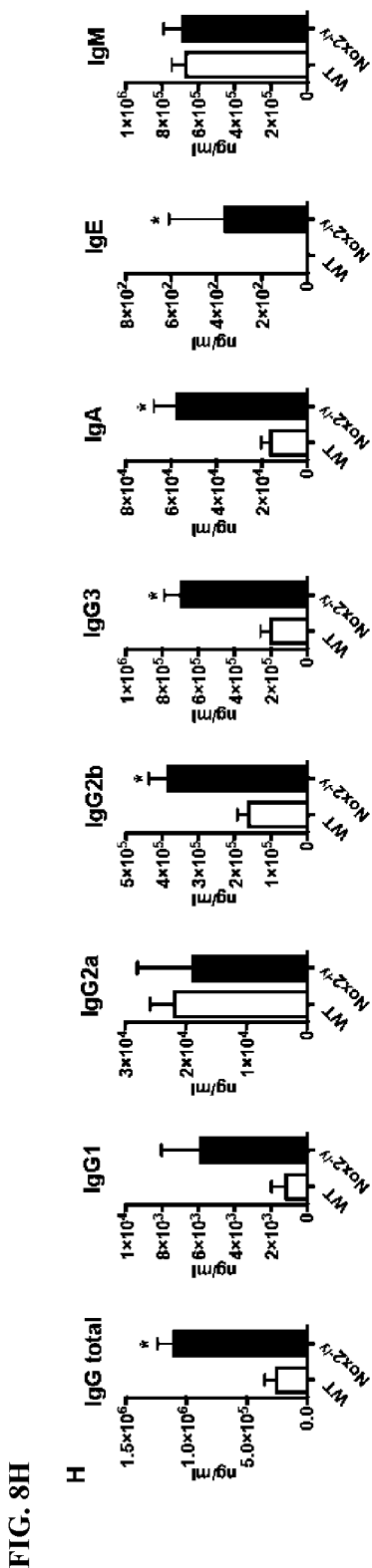
Figure 8I:
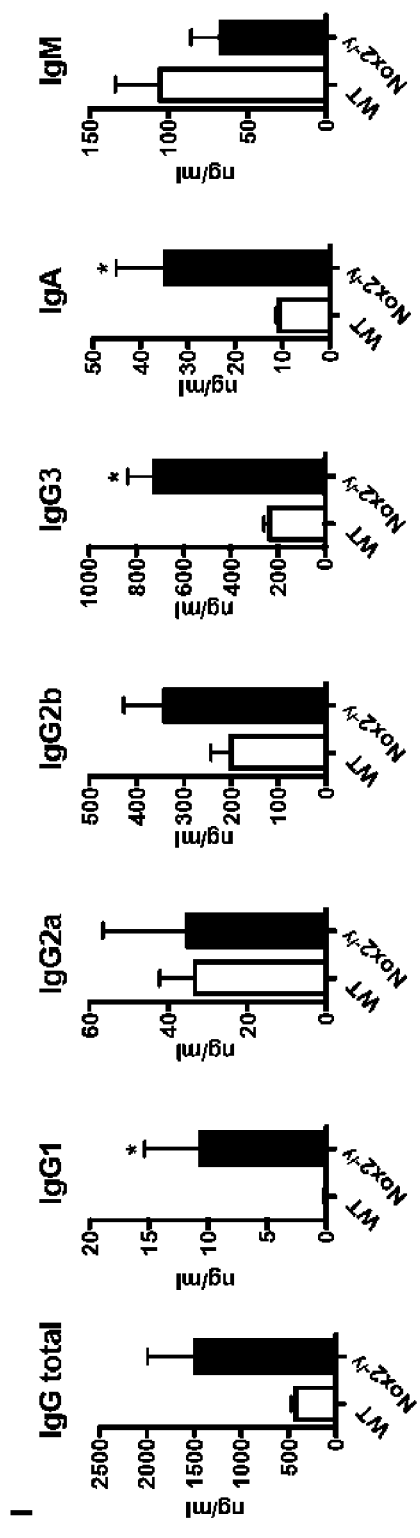

The suppressive effect of endosomal NOX2 oxidase activity was examined on Type I IFN and IL-1β expression also occurs following influenza A virus infection. First, virus triggered translocation of the transcription factor, IRF-7, to the nucleus of WT BMDMs, but not TLR7$^{-/-}$ BMDMs, indicating that influenza A virus activates TLR7-dependent antiviral signaling in macrophages. Second, virus elevated IFN-β, IL-1β, IL-6, and TNF-α expression to a greater extent in NOX2$^{-/y}$ AMs (FIG. 8a). Third, influenza A virus (Hkx31; 105 PFU/mouse) infection in mice in vivo for 24h resulted in greater increases in lung IFN-β, IL-1β, TNF-α and IL-6 mRNA (FIG. 8b), as well as serum (FIG. 8c) and lung IFN-β protein (FIG. 8d) in NOX2$^{-/y}$. Thus, a fully functional NOX2 oxidase suppresses anti-viral cytokine production triggered by influenza A virus. TLR7 is essential for the activation of B-cells and for antibody production. To test whether NOX2 oxidase suppresses TLR7-dependent immunity to influenza A virus in vivo, heat-inactivated, replication-deficient influenza A virus was used as a stimulus, and hence a form of virus expected to mainly trigger engagement of the TLR7 PRR with very little contribution of RIG-I and NLRP3 20. Intranasal inoculation with inactivated virus had no effect on weight loss over 7-days (FIG. 8e) or airways BALF inflammation (FIG. 8f). NOX2 deletion resulted in a significant elevation in lung levels of IFN-β, IL-1β and TNF-α mRNA (FIG. 8g) and in both serum and BALF levels of IgA, total IgG, IgG1, IgG2b and IgG3 (FIGS. 8h and i). Therefore, activation of endosomal NOX2 oxidase following influenza A virus infection results in the suppression of antiviral cytokines and humoral immunity via the suppression of antibody production—processes that are required for optimal clearance of the virus and resistance to re-infection.

Example 7

Endosomal Targeted NOX2 Inhibitor

Figure 9A:
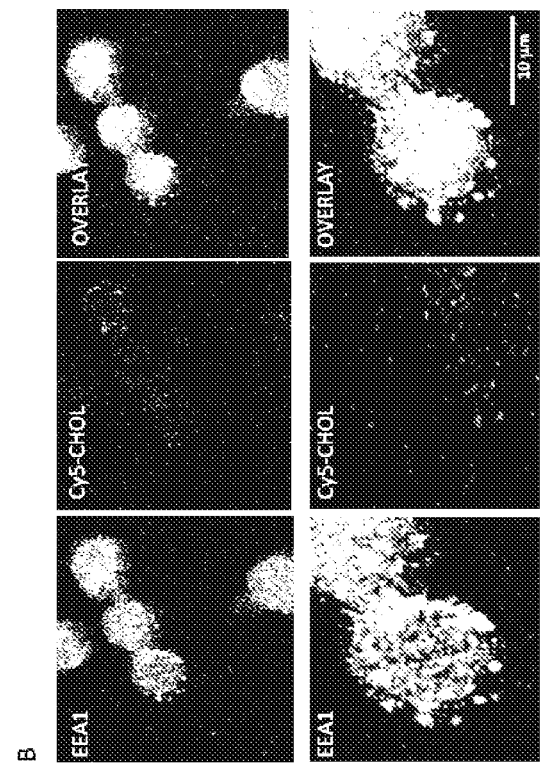
Figure 9B:
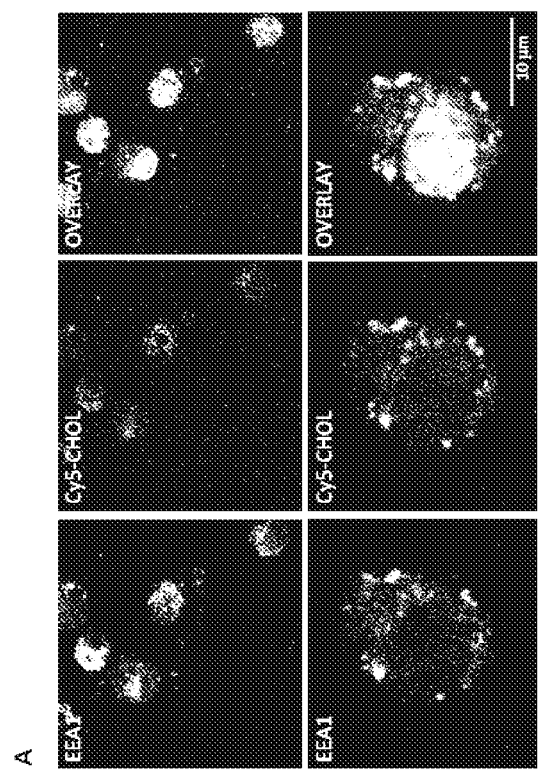
Figure 9D:
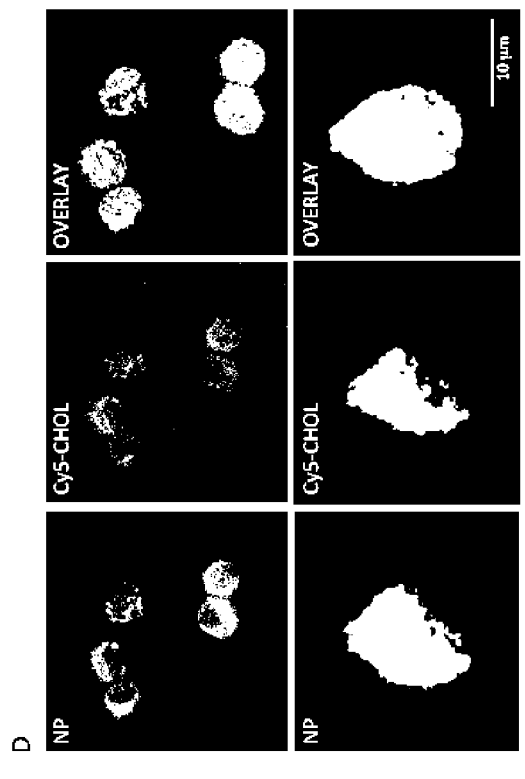
Figure 9C:
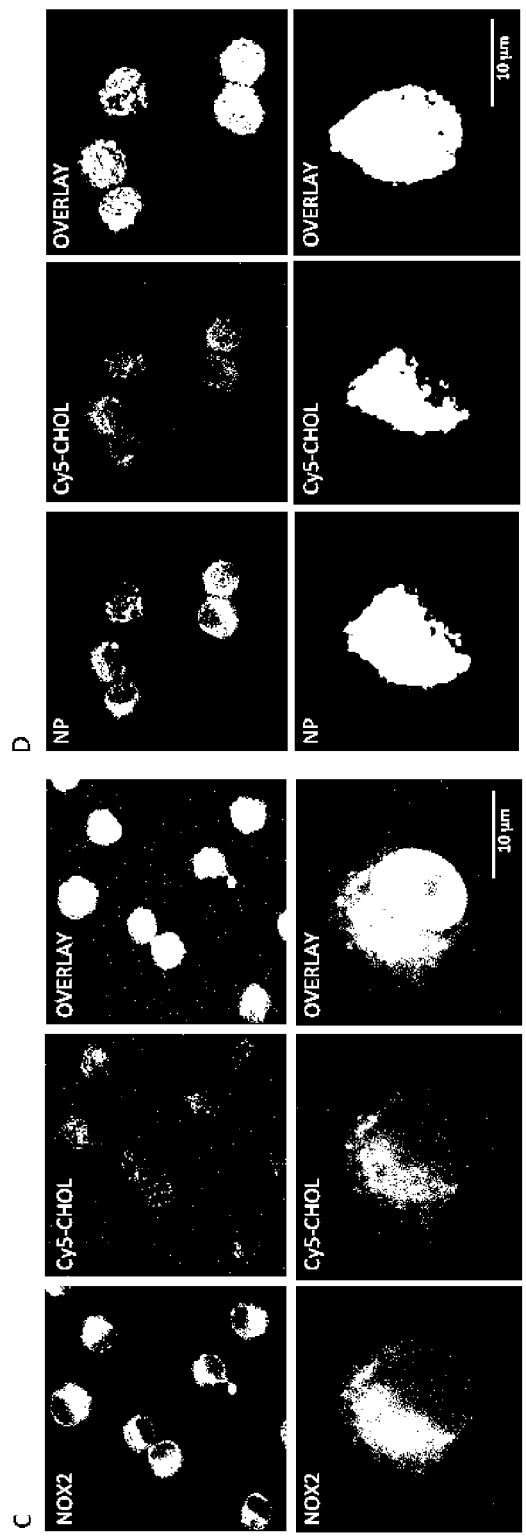
Figure 9E:
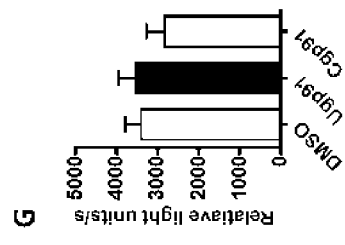
Figure 9F:
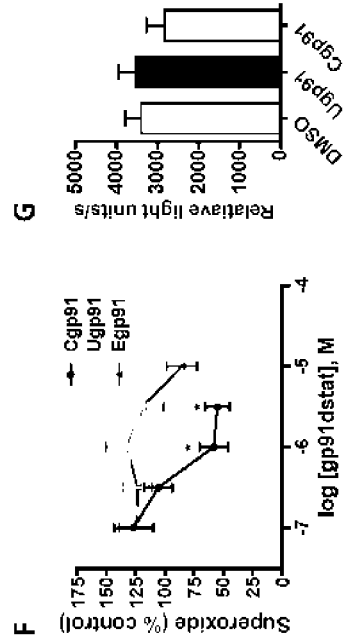
Figure 9G:
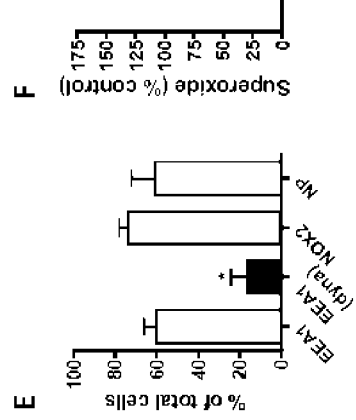

An innovative molecular targeting system was synthesized, to deliver a specific NOX2 oxidase inhibitor (i.e. gp91ds-TAT) directly to endosomes, so as to disrupt the viral signaling platform by abrogating ROS production. To do this, a tripartite structure was generated comprising gp91ds-tat conjugated to the membrane anchor cholestanol via a PEG-linker at the N-terminal region of the peptide. Similar constructs have been shown previously to enhance endosome localization for inhibitors of the enzyme beta secretase (Rajendran et al. (2008) Science 320(5875):520-523). A Cy5 fluorophore conjugated to cholestanol using the same PEG linker resulted in cytosolic fluorescence in the peri-nuclear region and co-localization with EEA1, NOX2 and influenza virus NP following viral infection in a dynasore (100 μM)-sensitive manner providing evidence for endocytosis as its primary mode of cell entry (FIGS. 9a-e). Superoxide generation in macrophages in vitro was suppressed with at least a 10-fold greater potency by cholestanol-conjugated gp91ds-TAT (Cgp91ds-TAT) when compared to the unconjugated drug (Ugp91ds-TAT; FIG. 9f), which is not attributed to enhanced ROS scavenging properties of the compound (FIG. 9g).

Figure 9H:
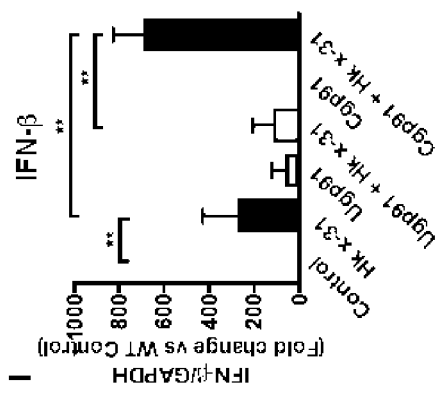
Figure 9I:
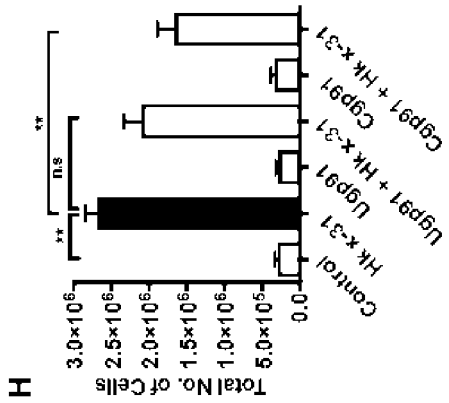

It was examined whether Cgp91ds-TAT suppresses disease severity following influenza A virus infection in vivo. Daily intranasal administration of Cgp91ds-TAT (0.02 mg/kg/d) from 1 day prior, until day 3 post-influenza A virus infection resulted in a ~40% reduction in airways inflammation (FIG. 9h), whereas Ugp91ds-TAT had no effect (FIG. 9h). Cgp91ds-TAT significantly increased lung Type I IFN-r3 mRNA levels compared to the control virus group, whereas Ugp91ds-TAT failed to do so (FIG. 9i). To eliminate the possibility that this improvement in NOX2 inhibition by cholestanol conjugation of gp91ds-TAT was attributed to cholestanol-PEG linker per se, the cholestanol PEG-linker was conjugated to a scrambled gp91ds-TAT (Sgp91ds-TAT) and examined its effect against influenza infection in vivo. Sgp91ds-TAT had no effect on airway inflammation, lung IFN-β mRNA levels and superoxide production. Increasing the dose of the Ugp91ds-TAT by 10-fold to 0.2 mg/kg/day significantly reduced the weight loss caused by influenza A virus at day 3 and almost abolished airway inflammation, as well superoxide production in BALF inflammatory cells, similar to Cgp91ds-TAT at the same dose (FIGS. 9j-l). Strikingly, both Cgp91ds-TAT (0.2 mg/kg/day) and Ugp91ds-TAT (0.2 mg/kg/day) caused an almost 10,000-fold, decrease in lung influenza A viral burden (FIG. 9m). Thus, suppression of endosome NOX2 oxidase via nasal administration of gp91ds-TAT results in a substantial reduction in influenza A virus pathogenicity. This is an innovative approach for suppressing NOX2 oxidase activity that occurs within the endosome compartment. The customer made inhibitor is specifically and preferentially delivered via the endocytic compartment owing to the cholestanol conjugation. In support of this, the findings of FIGS. 9a and b show that cholestanol conjugation results in a drug delivery system that promotes endosome delivery i.e. the drug displayed a strong degree of co-location with EEA1+ endosomes that was abolished by dynasore pretreatment. This delivery system brings a NOX2 inhibitor to the predominant site of action that relates to virus infection (FIG. 9d showed strong co-location of viral nucleoprotein and our NOX2 inhibitor). Following internalization into the endosome, it is proposed herein the drug is most likely on the luminal face of the endosome membrane and due to the TAT portion can penetrate the membrane and suppress NOX2 activity. The drug might still be able to diffuse towards other sites or locations of NOX2, however, the immediate and primary site of action is proposed to be NOX2 activity at the endosome, given that the drug appears to be selectively delivered via the endocytic pathway.

Example 8

Role of NOX2

Figure 2I:
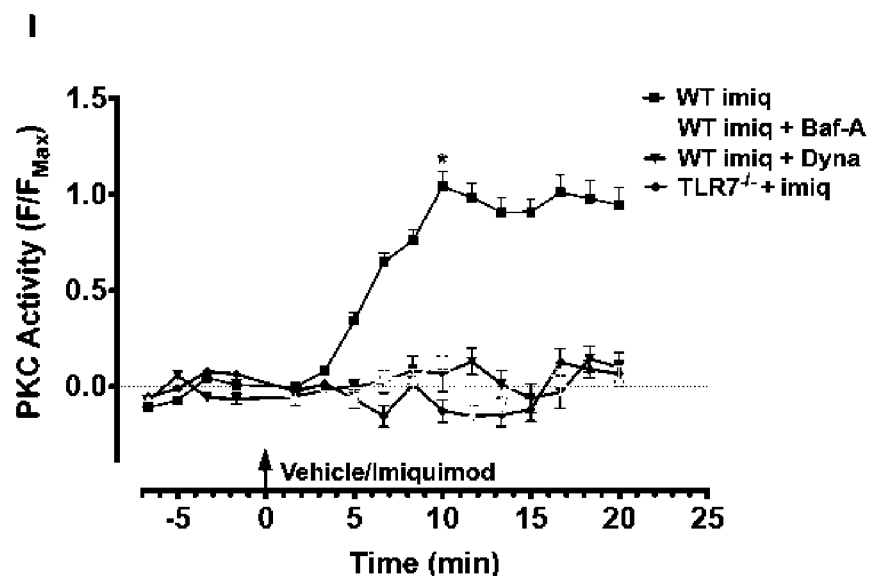

Evidence is provided here that virus entry into endosomal compartments triggers a NOX2 oxidase-dependent production of ROS in endosomes. It is proposed here that the major contributor to endosomal concentrations of superoxide is superoxide generated directly in this compartment. Superoxide is the primary product of NOX2 and it will only be generated within the endosome compartment owing to the topology of the NOX2 and the unidirectional transfer of electrons through this catalytic subunit. In keeping with this, it is well regarded that superoxide does not travel far from its site of generation due to its negative charge. By contrast to superoxide, hydrogen peroxide has some capacity to permeate membranes and diffuse, and as such, it can be envisaged that some endosome $H_2O_2$ might have been generated elsewhere by NOX2 expressed in other sites of the cell such as the plasma membrane. There are several lines of evidence that indicate that it is very likely that little remotely generated $H_2O_2$ is finding its way into the endosome compartment. PKC activation following virus infection, which is critical for NOX2 activation, is significantly impaired if: 1) the virus is prevented from entering cells (FIGS. 2H and 2I); 2) endosome acidification is blocked by Bafilomycin A (FIGS. 2H and 2I) or 3) if TLR7 is absent (i.e. TLR7$^{-/-}$ macrophages are used). Therefore, endosomal NOX2 derived ROS generation occurs only after virus has entered endosomes and activates endosome-specific pathways, lending further credence to endosome NOX2 as the predominant site of $H_2O_2$ generation.

Here, it is demonstrated that endosomal ROS are essential negative regulators of a fundamental molecular mechanism of viral pathogenicity that impacts on antiviral immunity and the capacity of the host to fight and clear viral infections. Importantly, this effect is conserved, regardless of viral classification, for all viruses that enter cells via the endocytic pathway, and is TLR7 dependent. This provides a target for antiviral therapy for a range of viruses that cause significant morbidity and mortality worldwide.

Example 9

Generation of Decoy Peptide Encompassing C98 of TLR7

A decoy peptide is generated comprising the D95 to L104 of murine TLR7 (DLRCNCVPVL—SEQ ID NO:1) operably linked to the HIV-TAT uptake peptide moiety (YGRKKRRQRRR—SEQ ID NO:2). The decoy peptide (referred to herein as C98i) prevents the disulfide bond forming between C98 and C475, thus preventing TLR7 activation.

Example 10

C98i Blocks Responses to TLR7 Agonist (Imiquimod)

Figure 12A:
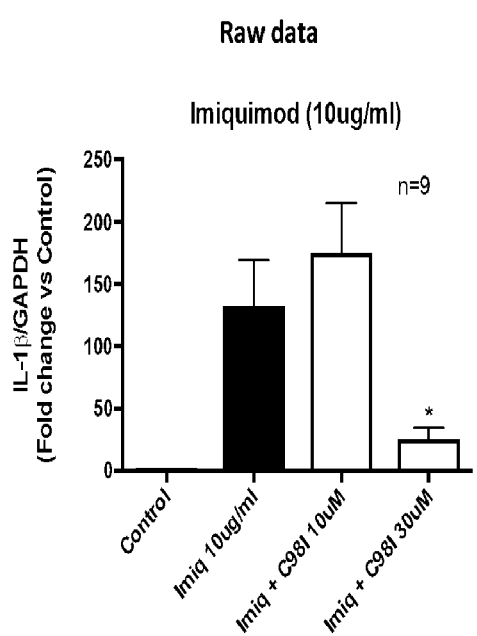
FIG. 12A and FIG. 12B are graphic representations showing data expression of IL-1β cytokine generated by bone marrow derived macrophages after exposure to the TLR7 agonist imiquimod in the absence or presence of C98i. The duration of C98i treatment was for 1 hr prior to imiquimod exposure and cytokine was measured after a 24h period with quantitative real time PCR.
Figure 12B:
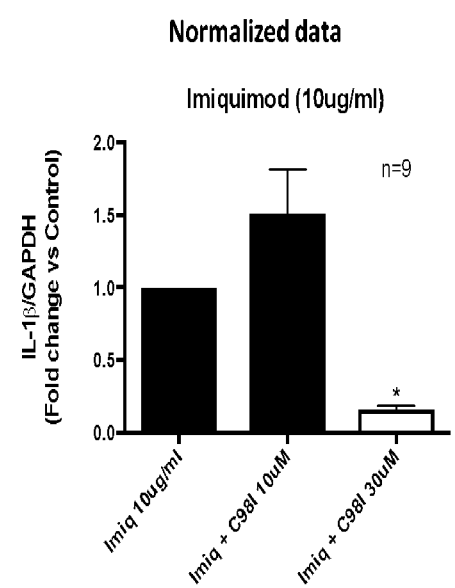
Figure 15:
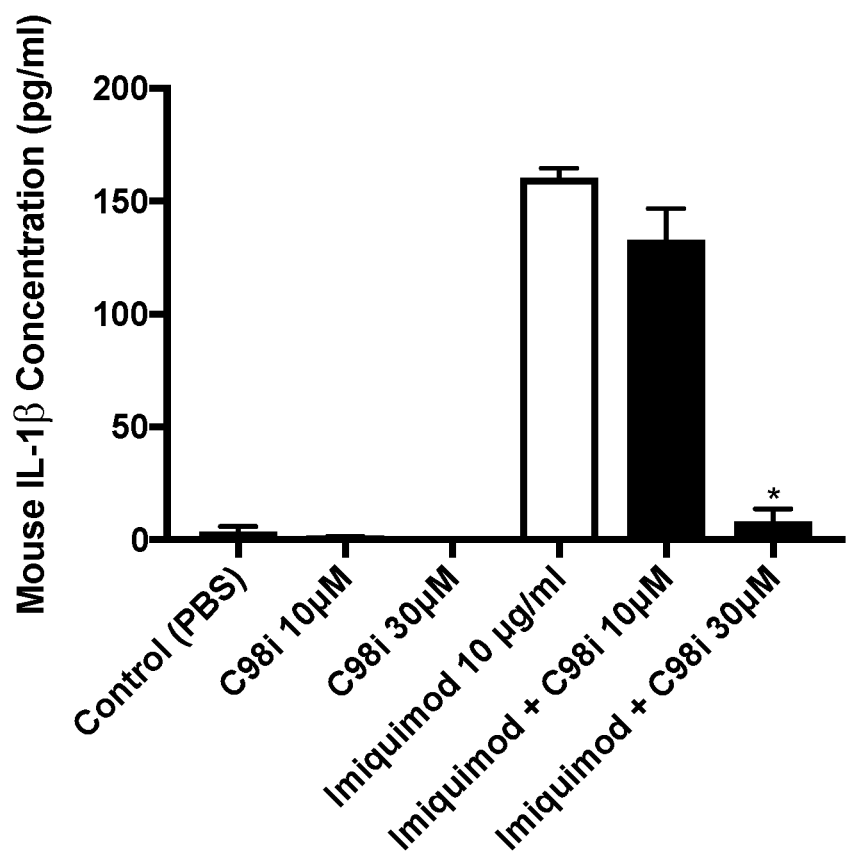
FIG. 15 is a graphical representation showing data of protein expression of IL-1β cytokine generated by bone marrow derived macrophages after exposure to TLR7 agonist, imiquimod, in the presence or absence of C98i in vitro. The duration of C98i treatment was 1 hr prior to imiquimod exposure and cytokine was measured after a 24 hr period with ELISA.

FIGS. 12a (raw data) and b (normalized data) show that cytokine IL-1β generated by bone marrow derived macrophages after exposure to imiquimod (a TLR7 agonist) is elevated in the presence of C98i. Analogous results are shown in FIG. 15. The data indicate that C98i is blocking TLR7 activity.

Example 11

C98i Blocks Responses to TLR7 Agonist (Gardiquimod)

Figure 13:
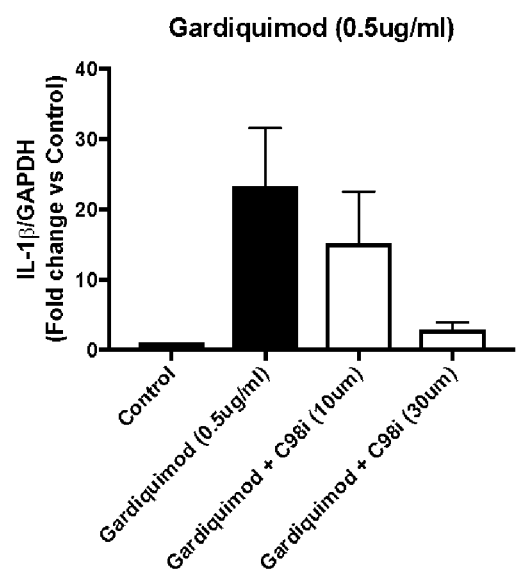
FIG. 13 is a graphic representation showing data expression of IL-1β cytokine generated by bone marrow derived macrophages after exposure to the TLR7 agonist gardiquimod in the absence or presence of C98i. The duration of C98i treatment was for 1 hr prior to imiquimod exposure and cytokine was measured after a 24h period with quantitative real time PCR.
Figure 14:
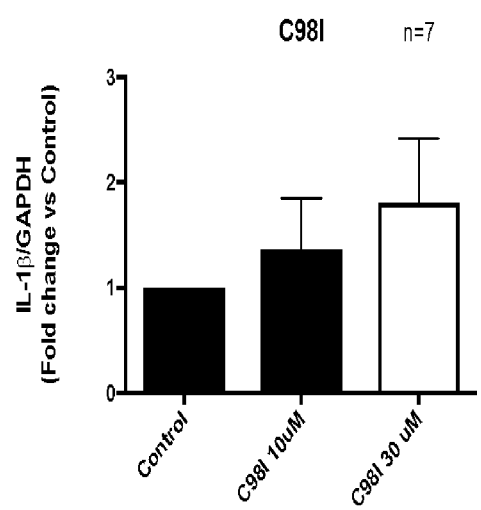
FIG. 14 is a graphic representation showing data expression of IL-1β cytokine generated by bone marrow derived macrophages after exposure C98i. The duration of C98i treatment was for 1 hr and cytokine was measured after a 24 h period with quantitative real time PCR.

FIG. 13 shows that C98i blocks TLR7 response to the TLR7 agonist, gardiquimod. No effect is shown on basal un-stimulated levels of IL-1β (FIG. 13). There was also no effect on TLR9, a closely related family member which has a tryptophan at position 98, or on TLR4 agonist response or TLR2 agonist response. There is very little sequence homology between TLR7 and TLR4 and TLR7 and TLR2.

Similar results were noted with TLR5 agonist response. C98i had no adverse effect on TLR7 expression or on cell viability.

The data show that C98i blocks TLR7 activity and does not influence TLR2, TLR4, TLR5, TLR9 activity. It is unlikely to influence the other members of the TLR family (i.e. TLR1, TLR3, TLR6 and TLR8) due to the uniqueness of the sequence. The findings that C98i does not influence the activity of TLR2, TLR4, TLR5 and TLR9 also suggests that the drug does not have non-specific properties on cell function that impact the production of the cytokine IL-1β.

TLR7 is a target that is involved in viral, autoimmune diseases and cancer. A novel drug targeting TLR7 has huge potential.

Example 12

Effect of a No TAT Version of C98i

Figure 16A:
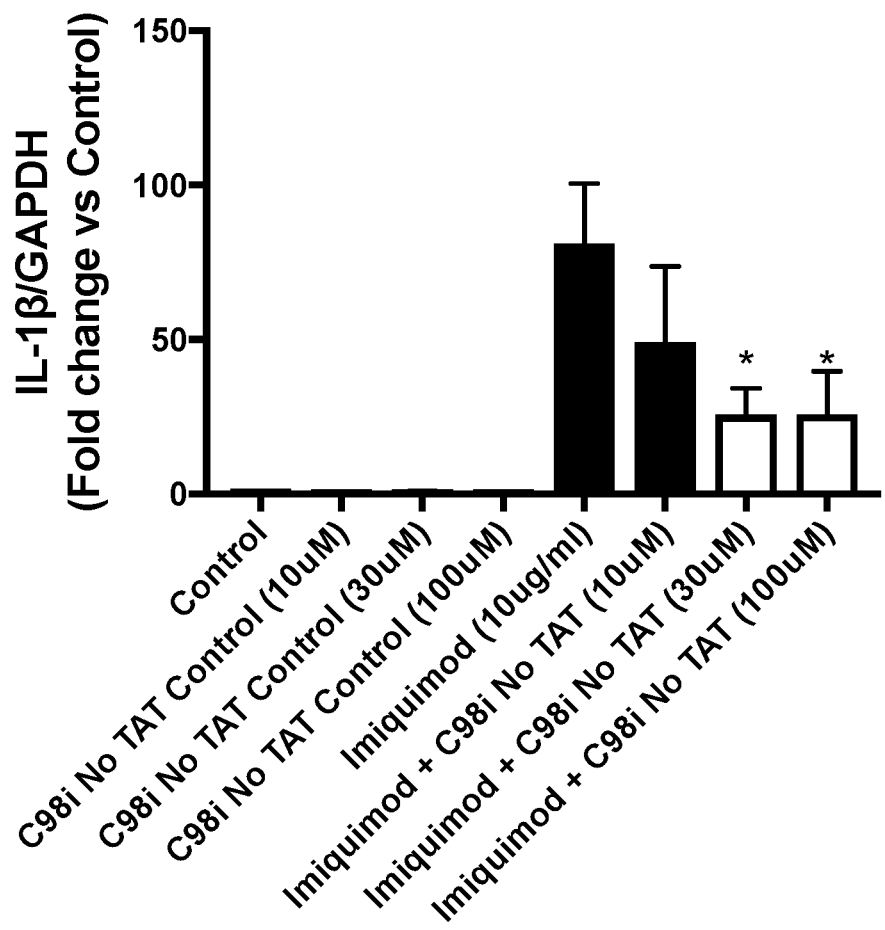
FIG. 16A and FIG. 16B are diagrammatic representations of IL-1β production (a) and cell viability (b) in response to TLR7 agonist, imiquimod, and C98i with no TAT (no TAT).
Figure 16B:
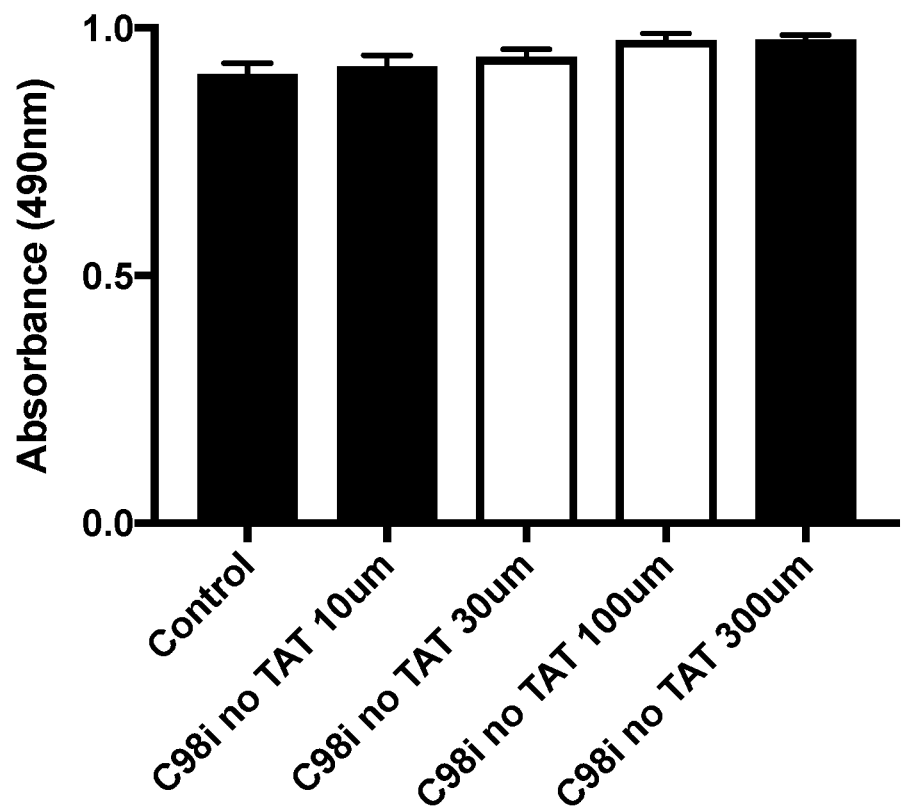

In the absence of TAT, the C98i peptide retains its ability to inhibit TLR7 agonist, imiquimod, responses in vitro. The absence of TAT is referred to as "no TAT". The results are shown in FIG. 16a. There was no adverse effect on cell viability (FIG. 16b).

Example 13

C98i Inhibits Influenza a Virus Response

Figure 17:
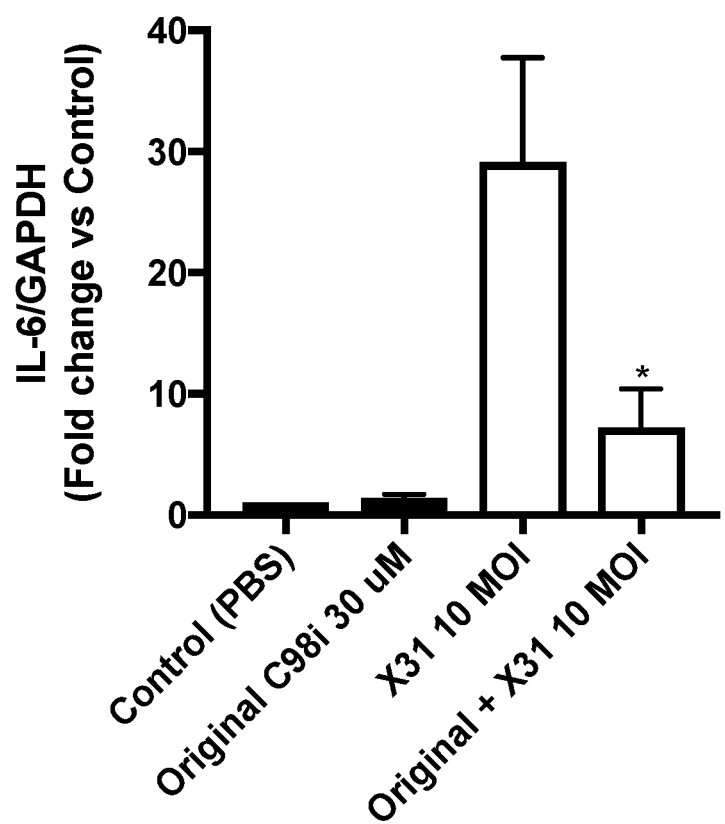
FIG. 17 is a graphical representation showing that C98i inhibits influenza A (X31) virus response (IL-6 GAPDH) in vitro (C98i 30 μM+X31-IL-6 mRNA expression).

FIG. 17 shows that C98i inhibits Influenza A virus (X31) response (IL-6-mRNA expression) in vitro. In the absence of C98i, IL-6 mRNA expression is significantly higher compared to C98i+Influenza A virus (X31).

Example 14

Effect of Scrambled C98i Amino Acid Sequence

Figure 18:
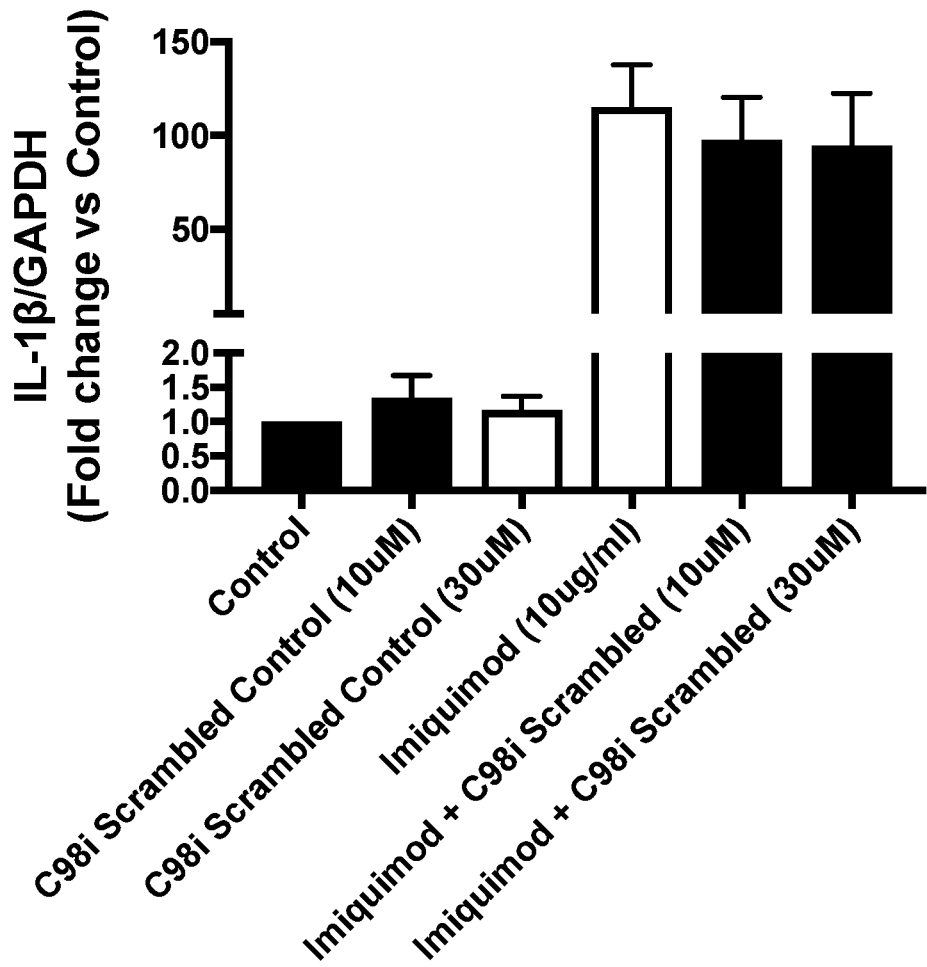
FIG. 18 is a graphical representation showing that a scrambled amino acid sequence of C98i had no effect on TLR7 agonist (imiquimod). The scrambled amino acid sequence is YGRKKRRQRRRCLVPNDCRLV-NH$_2$ (SEQ ID NO:44).

The amino acid sequence of C98i was scrambled to produce YGRKKRRQRRRCLVPNDCRLV-NH$_2$ (SEQ ID NO:44). The scrambled C98i peptide sequence was not able to inhibit TLR7 agonist (imiquimod). The results are shown in FIG. 18.

Example 15

Effects of Short Peptides on TLR7 Agonist (Imiquimod) Response

Figure 19:
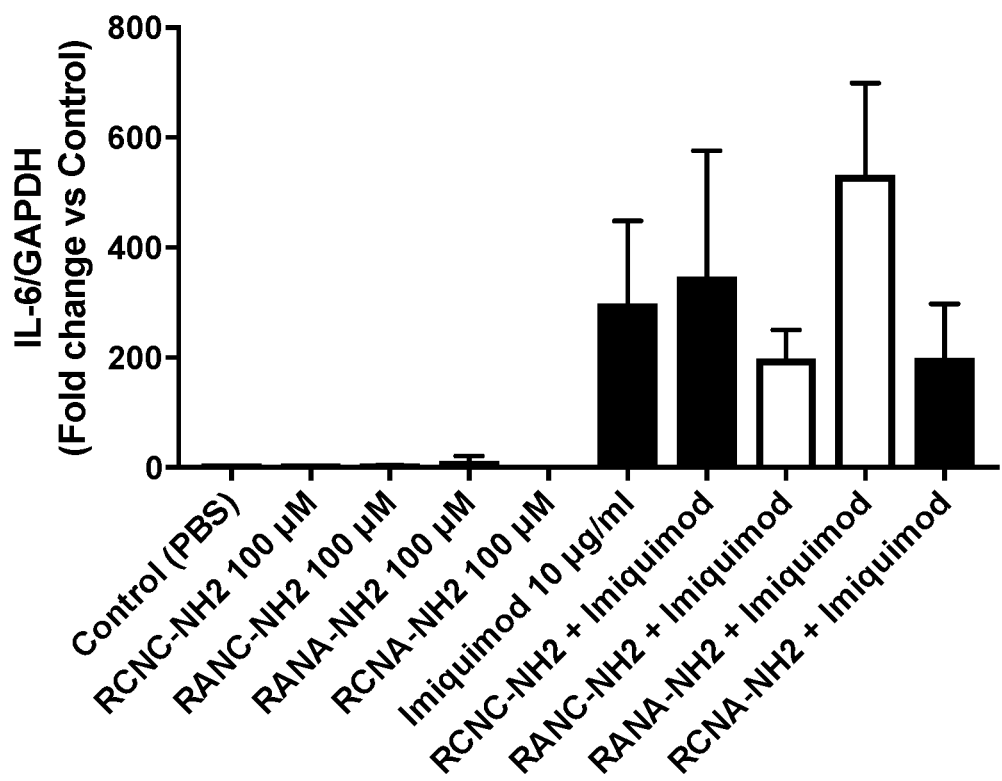
FIG. 19 is a graphical representation showing that none of the short motif in C98i RCNC (SEQ ID NO:45) nor any of its modified forms (RANC, SEQ ID NO:46; RANA, SEQ ID NO:47; or RCNA, SEQ ID NO:48) was able to inhibit TLR7 agonist (imiquimod) responses in vitro. Peptides were used at 100 μM+10 μg/ml imiquimod; IL-6 mRNA expression was measured.

The Arg-Cys-Asn-Cys (RCNC) (SEQ ID NO:45) motif of the decoy peptide in C98i, was modified to form RANC (SEQ ID NO:46), RANA (SEQ ID NO:47) and RCNA (SEQ ID NO:48). These short peptides were tested with no TAT to ascertain their effects on TLR7 agonist, imiquimod. FIG. 19 shows that none of RANC (SEQ ID NO:45), RCNC (SEQ ID NO:46), RANA (SEQ ID NO:47) or RCNA (SEQ ID NO:48) inhibited TLR7 agonist, imiquimod, response in vitro.

Example 16

Examination of Antioxidant and Immunomodulatory Effects of C98i In Vitro and In Vivo Following Virus Infection Experimentation in vitro using isolated macrophages: Assays for examining oxidative stress and viral replication in the absence or presence of C98i. The following viruses are examined: low to high pathogenic Influenza A virus, respiratory synctitial virus, rhinovirus, Dengue virus.

It is expected that there is suppression of endosome oxidative stress and viral replication by C98i.

Experimentation in vivo: Delivery of C98i intranasally in mice, followed by Influenza A virus infection (via intranasal delivery) [To et al. (2017) *Nature Communications* 8(69): 1-17]. The potential regulation of lung oxidative stress, inflammation, injury, viral burden and immune cell responses in lung and systemic circulation are assessed.

Example 17

Examination of Immunomodulatory Effect of C98i In Vivo in a Lupus Like Model-Test for Autoimmunity Wild-type C57BL/6 mice are treated with C98i and then treated with epicutaneous topical TLR7 agonist imiquimod (Aldara Cream) to the ear 3 times weekly. Following treatment, the mice are examined for serum autoantibody and creatinine levels as well as histopathology of the kidneys, spleens, livers, hearts and skin. Immunologic abnormalities are analyzed by immunohistochemistry, quantitative reverse transcription-polymerase chain reaction, and fluorescence-activated cell sorting.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

All patents, applications, publications, test methods, literature, and other materials cited herein are hereby incorporated by reference in their entirety as if physically present in this specification.

BIBLIOGRAPHY

Aguirre (2010) *Free Radical Biology and Medicine* 49(9): 1342-1353

Allen et al. (2009) *Immunity* 30(4):556-565

Altschul et al. (1997) *Nucl. Acids. Res.* 25:3389

Ausubel et al. (*In: Current Protocols in Molecular Biology*, John Wiley & Sons Inc. 1994-1998

Bedard and Krause (2007) *Physiological Reviews* 87(1): 245-313

Campbell et al. (2012) *Science Translational Medicine* 4(157):157ra141

Cossart and Helenius (2014) *Cold Spring Harbor Perspectives in Biology* 6(8)

Diebold et al. *Science* 303(5663):1529-1531

Drummond et al. (2011) *Nature Reviews Drug Discovery* 10(6):453-471

Guidotti et al. (2017) *Trends in Pharmacological Science* 38(4):406-424

Halls et al. (2015) *Methods in Molecular Biology* 1335:131-161

Ichinohe et al. (2009) *The Journal of Experimental Medicine* 206(1):79-87

Imai et al. (2008) *Cell* 133(2):235-249

Iwasaki and Pillai (2014) *Nature Reviews Immunology* 14(5):315-328

Jensen et al. (2014) *The Journal of Biological Chemistry* 289(20):20283-20294

Johnson et al. (1993) *Peptide Turn Mimetics in Biotechnology and Pharmacy*

Judkins et al. (2010) *American Journal of Physiology Heart and Circulatory Physiology* 298(1):H24-32

Kanno et al. (2013) *International Immunology* 25(7):413-422

Kawahara et al. (2007) *BMC Evolutionary Biology* 7:109

Kelkka et al. (2014)*Antioxidants & Redox Signaling* 21(16): 2231-2245

King et al. (2013) *The Journal of Allergy and Clinical Immunology* 131(5):1314-1321 e1314

Lund et al. (2004) *Proceedings of the National Academy of Sciences of the United States of America* 101(15):5598-5603

Pezzuto et al, Eds., Chapman and Hall, New York

Pollock et al. (1995) *Nature Genetics* 9(2):202-209

Rajendran et al. (2008) *Science* 320(5875):520-523

Selemidis et al. (2008) *Pharmacology & Therapeutics* 120 (3):254-291

Snelgrove et al. (2006) *Eur J Immunol* 36(6):1364-1373

To et al. (2014) *Free Radical Research* 48(8):940-947

To et al. (2017) *Nature Communications* 8(69):1-17

Violin et al. (2003) *The Journal of Cell Biology* 161(5):899-909

Vlahos et al. (2011) *PLoS pathogens* 7(2): e1001271

Vlahos et al. (2012) *Trends in Pharmacological Sciences* 33(1):308

Vlahos and Selemidis (2014) *Molecular Pharmacology* 86(6):747-759

West et al. (2011) *Nature* 472(7344):476-480

The invention claimed is:

1. A method for inhibiting TLR7-mediated immunostimulatory activity in a TLR7-expressing cell, the method comprising contacting the cell with a peptide of up to 190 amino acids in length, wherein the peptide comprises the amino acid sequence of $DX_1RCNCX_2PX_3X_4$ (SEQ ID NO:27) wherein:
$X_1$ is L, F, or M;
$X_2$ is V or I;

$X_3$ is V, I, A, or P; and $X_4$ is P, L, K, or R.

2. The method of claim 1, wherein the peptide comprises the amino acid sequence DFRCNCVPIP (SEQ ID NO:26).

3. The method of claim 1, wherein the peptide comprises the amino acid sequence DLRCNCVPVL (SEQ ID NO:1).

4. The method of claim 1, wherein the peptide further comprises a moiety attached to the N-terminal or C-terminal end of the peptide which enables uptake of the peptide into the cell.

5. The method of claim 4, wherein the moiety is a hydrophilic peptide, an amphiphilic peptide, a peptide with a periodic amino acid sequence, or a conjugate with cholestanol.

6. The method of claim 4, wherein the moiety is a hydrophilic peptide selected from the group consisting of TAT (SEQ ID NO:2), SynB1 (SEQ ID NO:3), SynB3 (SEQ ID NO:4), PTD-4 (SEQ ID NO:5), PTD-5 (SEQ ID NO:6), FHV coat (SEQ ID NO:7), BMV Gag-(7-25) (SEQ ID NO:8), HTLV-II Rex-(4-16) (SEQ ID NO:9), D-Tat (SEQ ID NO:10), and R9-Tat (SEQ ID NO:11).

7. The method of claim 4, wherein the moiety is an amphiphilic peptide selected from the group consisting of Transportan chimera (SEQ ID NO:12), MAP (SEQ ID NO:13), SBP (SEQ ID NO:14), FBP (SEQ ID NO:15), MPG [MPGac] (SEQ ID NO:16), MPG (ΔNLS) (SEQ ID NO:17), Pep-1 (SEQ ID NO:18), and Pep-2 (SEQ ID NO:19).

8. The method of claim 4, wherein the moiety is a periodic amino acid sequence comprising a polyarginine or a polylysine sequence.

9. The method of claim 1, wherein the peptide is up to 100 amino acids in length.

10. The method of claim 1, wherein the peptide is up to 40 amino acids in length.

11. The method of claim 1, wherein the cell is of a subject with an autoimmune disease, a viral pathogenesis, a microbial pathogenesis, an inflammation, or a cancer.

12. The method of claim 1, wherein the cell is of a subject with a viral pathogenesis.

13. The method of claim 1, wherein the cell is selected from macrophages, neutrophils, dendritic cells, natural killer cells, mast cells, eosinophils, basophils, B-lymphocytes, T-lymphocytes, and epithelial cells.

14. The method of claim 1, wherein the cell is a macrophage.

* * * * *

SEQUENCE LISTING

```
<160> NUMBER OF SEQ ID NOS: 57

<210> SEQ ID NO 1
<211> LENGTH: 10
<212> TYPE: PRT
```

```
<213> ORGANISM: artificial
<220> FEATURE:
<223> OTHER INFORMATION: peptide decoy D95 to L104 of murine TLR7

<400> SEQUENCE: 1

Asp Leu Arg Cys Asn Cys Val Pro Val Leu
1               5                   10

<210> SEQ ID NO 2
<211> LENGTH: 11
<212> TYPE: PRT
<213> ORGANISM: artificial
<220> FEATURE:
<223> OTHER INFORMATION: TAT

<400> SEQUENCE: 2

Thr Gly Arg Lys Lys Arg Arg Gln Arg Arg
1               5                   10

<210> SEQ ID NO 3
<211> LENGTH: 18
<212> TYPE: PRT
<213> ORGANISM: artificial
<220> FEATURE:
<223> OTHER INFORMATION: SynB1

<400> SEQUENCE: 3

Arg Gly Gly Arg Leu Ser Tyr Ser Arg Arg Arg Phe Ser Thr Ser Thr
1               5                   10                  15

Gly Arg

<210> SEQ ID NO 4
<211> LENGTH: 10
<212> TYPE: PRT
<213> ORGANISM: artificial
<220> FEATURE:
<223> OTHER INFORMATION: SynB3

<400> SEQUENCE: 4

Arg Arg Leu Ser Tyr Ser Arg Arg Arg Phe
1               5                   10

<210> SEQ ID NO 5
<211> LENGTH: 12
<212> TYPE: PRT
<213> ORGANISM: artificial
<220> FEATURE:
<223> OTHER INFORMATION: PTD-4

<400> SEQUENCE: 5

Pro Ile Arg Arg Arg Lys Lys Leu Arg Arg Leu Lys
1               5                   10

<210> SEQ ID NO 6
<211> LENGTH: 12
<212> TYPE: PRT
<213> ORGANISM: artificial
<220> FEATURE:
<223> OTHER INFORMATION: PTD-5

<400> SEQUENCE: 6

Arg Arg Gln Arg Arg Thr Ser Lys Leu Met Lys Arg
1               5                   10

<210> SEQ ID NO 7
<211> LENGTH: 15
```

```
<212> TYPE: PRT
<213> ORGANISM: artificial
<220> FEATURE:
<223> OTHER INFORMATION: FHV Coat (35-49)

<400> SEQUENCE: 7

Arg Arg Arg Arg Asn Arg Thr Arg Arg Asn Arg Arg Arg Val Arg
1               5                   10                  15

<210> SEQ ID NO 8
<211> LENGTH: 19
<212> TYPE: PRT
<213> ORGANISM: artificial
<220> FEATURE:
<223> OTHER INFORMATION: BMV Gag (70-5)

<400> SEQUENCE: 8

Lys Met Thr Arg Ala Gln Arg Arg Ala Ala Ala Arg Arg Asn Arg Trp
1               5                   10                  15

Thr Ala Arg

<210> SEQ ID NO 9
<211> LENGTH: 13
<212> TYPE: PRT
<213> ORGANISM: artificial
<220> FEATURE:
<223> OTHER INFORMATION: HTLV-II Rex (4-16)

<400> SEQUENCE: 9

Thr Arg Arg Gln Arg Thr Arg Arg Ala Arg Arg Asn Arg
1               5                   10

<210> SEQ ID NO 10
<211> LENGTH: 13
<212> TYPE: PRT
<213> ORGANISM: artificial
<220> FEATURE:
<223> OTHER INFORMATION: D-Tat

<400> SEQUENCE: 10

Gly Arg Lys Lys Arg Arg Gln Arg Arg Arg Pro Pro Gln
1               5                   10

<210> SEQ ID NO 11
<211> LENGTH: 13
<212> TYPE: PRT
<213> ORGANISM: artificial
<220> FEATURE:
<223> OTHER INFORMATION: R9-Tat

<400> SEQUENCE: 11

Gly Arg Arg Arg Arg Arg Arg Arg Arg Arg Pro Pro Gln
1               5                   10

<210> SEQ ID NO 12
<211> LENGTH: 27
<212> TYPE: PRT
<213> ORGANISM: artificial
<220> FEATURE:
<223> OTHER INFORMATION: Transportan

<400> SEQUENCE: 12

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
                20                  25
```

<210> SEQ ID NO 13
<211> LENGTH: 17
<212> TYPE: PRT
<213> ORGANISM: artificial
<220> FEATURE:
<223> OTHER INFORMATION: MAP

<400> SEQUENCE: 13

Lys Leu Ala Leu Lys Leu Ala Leu Lys Leu Ala Leu Ala Leu Lys Leu
1               5                   10                  15

Ala

<210> SEQ ID NO 14
<211> LENGTH: 27
<212> TYPE: PRT
<213> ORGANISM: artificial
<220> FEATURE:
<223> OTHER INFORMATION: SBP

<400> SEQUENCE: 14

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 15
<211> LENGTH: 27
<212> TYPE: PRT
<213> ORGANISM: artificial
<220> FEATURE:
<223> OTHER INFORMATION: FBP

<400> SEQUENCE: 15

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 16
<211> LENGTH: 27
<212> TYPE: PRT
<213> ORGANISM: artificial
<220> FEATURE:
<223> OTHER INFORMATION: MPG ac

<400> SEQUENCE: 16

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 17
<211> LENGTH: 27
<212> TYPE: PRT
<213> ORGANISM: artificial
<220> FEATURE:
<223> OTHER INFORMATION: MPG (NLS)

<400> SEQUENCE: 17

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 18
<211> LENGTH: 21
<212> TYPE: PRT
<213> ORGANISM: artificial
<220> FEATURE:
<223> OTHER INFORMATION: Pep-1

<400> SEQUENCE: 18

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 19
<211> LENGTH: 21
<212> TYPE: PRT
<213> ORGANISM: artificial
<220> FEATURE:
<223> OTHER INFORMATION: Pep-2

<400> SEQUENCE: 19

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 20
<211> LENGTH: 1048
<212> TYPE: PRT
<213> ORGANISM: artificial
<220> FEATURE:
<223> OTHER INFORMATION: TLR7

<400> SEQUENCE: 20

Met Val Phe Pro Met Trp Thr Leu Lys Arg Leu Ile Leu Ile Leu Phe
1               5                   10                  15

Asn Ile Ile Leu Ile Ser Lys Leu Leu Gly Ala Arg Trp Phe Pro Lys
                20                  25                  30

Thr Leu Pro Cys Asp Val Thr Leu Asp Val Pro Lys Asn His Val Ile
            35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190

```
Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
    210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
            340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
    370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
        435                 440                 445

Arg Thr Ser Val Glu Ser Tyr Glu Pro Gln Val Leu Glu Gln Leu His
    450                 455                 460

Tyr Phe Arg Tyr Asp Lys Tyr Arg Ser Cys Arg Phe Lys Asn Lys Glu
465                 470                 475                 480

Ala Ser Phe Met Ser Val Asn Glu Ser Cys Tyr Lys Tyr Gly Gln Thr
                485                 490                 495

Leu Asp Leu Ser Lys Asn Ser Ile Phe Phe Val Lys Ser Ser Asp Phe
            500                 505                 510

Gln His Leu Ser Phe Leu Lys Cys Leu Asn Leu Ser Gly Asn Leu Ile
        515                 520                 525

Ser Gln Thr Leu Asn Gly Ser Glu Phe Gln Pro Leu Ala Glu Leu Arg
    530                 535                 540

Tyr Leu Asp Phe Ser Asn Asn Arg Leu Asp Leu Leu His Ser Thr Ala
545                 550                 555                 560

Phe Glu Glu Leu His Lys Leu Glu Val Leu Asp Ile Ser Ser Asn Ser
                565                 570                 575

His Tyr Phe Gln Ser Glu Gly Ile Thr His Met Leu Asn Phe Thr Lys
            580                 585                 590

Asn Leu Lys Val Leu Gln Lys Leu Met Met Asn Asp Asn Asp Ile Ser
        595                 600                 605

Ser Ser Thr Ser Arg Thr Met Glu Ser Glu Ser Leu Arg Thr Leu Glu
```

```
                610                 615                 620
Phe Arg Gly Asn His Leu Asp Val Leu Trp Arg Glu Gly Asp Asn Arg
625                 630                 635                 640

Tyr Leu Gln Leu Phe Lys Asn Leu Leu Lys Leu Glu Glu Leu Asp Ile
                645                 650                 655

Ser Lys Asn Ser Leu Ser Phe Leu Pro Ser Gly Val Phe Asp Gly Met
                660                 665                 670

Pro Pro Asn Leu Lys Asn Leu Ser Leu Ala Lys Asn Gly Leu Lys Ser
                675                 680                 685

Phe Ser Trp Lys Lys Leu Gln Cys Leu Lys Asn Leu Glu Thr Leu Asp
690                 695                 700

Leu Ser His Asn Gln Leu Thr Thr Val Pro Glu Arg Leu Ser Asn Cys
705                 710                 715                 720

Ser Arg Ser Leu Lys Asn Leu Ile Leu Lys Asn Gln Ile Arg Ser
                725                 730                 735

Leu Thr Lys Tyr Phe Leu Gln Asp Ala Phe Gln Leu Arg Tyr Leu Asp
                740                 745                 750

Leu Ser Ser Asn Lys Ile Gln Met Ile Gln Lys Thr Ser Phe Pro Glu
                755                 760                 765

Asn Val Leu Asn Asn Leu Lys Met Leu Leu Leu His His Asn Arg Phe
770                 775                 780

Leu Cys Thr Cys Asp Ala Val Trp Phe Val Trp Trp Val Asn His Thr
785                 790                 795                 800

Glu Val Thr Ile Pro Tyr Leu Ala Thr Asp Val Thr Cys Val Gly Pro
                805                 810                 815

Gly Ala His Lys Gly Gln Ser Val Ile Ser Leu Asp Leu Tyr Thr Cys
                820                 825                 830

Glu Leu Asp Leu Thr Asn Leu Ile Leu Phe Ser Leu Ser Ile Ser Val
                835                 840                 845

Ser Leu Phe Leu Met Val Met Met Thr Ala Ser His Leu Tyr Phe Trp
850                 855                 860

Asp Val Trp Tyr Ile Tyr His Phe Cys Lys Ala Lys Ile Lys Gly Tyr
865                 870                 875                 880

Gln Arg Leu Ile Ser Pro Asp Cys Cys Tyr Asp Ala Phe Ile Val Tyr
                885                 890                 895

Asp Thr Lys Asp Pro Ala Val Thr Glu Trp Val Leu Ala Glu Leu Val
                900                 905                 910

Ala Lys Leu Glu Asp Pro Arg Glu Lys His Phe Asn Leu Cys Leu Glu
                915                 920                 925

Glu Arg Asp Trp Leu Pro Gly Gln Pro Val Leu Glu Asn Leu Ser Gln
930                 935                 940

Ser Ile Gln Leu Ser Lys Lys Thr Val Phe Val Met Thr Asp Lys Tyr
945                 950                 955                 960

Ala Lys Thr Glu Asn Phe Lys Ile Ala Phe Tyr Leu Ser His Gln Arg
                965                 970                 975

Leu Met Asp Glu Lys Val Asp Val Ile Ile Leu Ile Phe Leu Glu Lys
                980                 985                 990

Pro Phe Gln Lys Ser Lys Phe Leu  Gln Leu Arg Lys Arg  Leu Cys Gly
                995                 1000                1005

Ser Ser  Val Leu Glu Trp Pro  Thr Asn Pro Gln Ala  His Pro Tyr
1010                1015                1020

Phe Trp  Gln Cys Leu Lys Asn  Ala Leu Ala Thr Asp  Asn His Val
1025                1030                1035
```

Ala Tyr Ser Gln Val Phe Lys Glu Thr Val
         1040                1045

<210> SEQ ID NO 21
<211> LENGTH: 19
<212> TYPE: DNA
<213> ORGANISM: artificial
<220> FEATURE:
<223> OTHER INFORMATION: Influenza polymerase forward primer

<400> SEQUENCE: 21
cggtccaaat tcctgctga                                                   19

<210> SEQ ID NO 22
<211> LENGTH: 20
<212> TYPE: DNA
<213> ORGANISM: artificial
<220> FEATURE:
<223> OTHER INFORMATION: Influenza polymerase reverse primer

<400> SEQUENCE: 22
cattgggttc cttccatcca                                                  20

<210> SEQ ID NO 23
<211> LENGTH: 22
<212> TYPE: PRT
<213> ORGANISM: artificial
<220> FEATURE:
<223> OTHER INFORMATION: gp91 ds-tat

<400> SEQUENCE: 23

Tyr Gly Arg Lys Lys Arg Arg Gln Arg Arg Arg Cys Ser Thr Arg Ile
1               5                   10                  15

Arg Arg Gln Leu Asn His
            20

<210> SEQ ID NO 24
<211> LENGTH: 29
<212> TYPE: PRT
<213> ORGANISM: artificial
<220> FEATURE:
<223> OTHER INFORMATION: Sgp91 ds-tat

<400> SEQUENCE: 24

Pro Glu Gly Pro Glu Gly Pro Glu Gly Arg Lys Lys Arg Arg Gln Arg
1               5                   10                  15

Arg Arg Cys Leu Arg Ile Thr Arg Gln Ser Arg Asn His
            20                  25

<210> SEQ ID NO 25
<211> LENGTH: 1050
<212> TYPE: PRT
<213> ORGANISM: artificial
<220> FEATURE:
<223> OTHER INFORMATION: Mus musculus TLR7

<400> SEQUENCE: 25

Met Val Phe Ser Met Trp Thr Arg Lys Arg Gln Ile Leu Ile Phe Leu
1               5                   10                  15

Asn Met Leu Leu Val Ser Arg Val Phe Gly Phe Arg Trp Phe Pro Lys
            20                  25                  30

Thr Leu Pro Cys Glu Val Lys Val Asn Ile Pro Glu Ala His Val Ile
            35                  40                  45

-continued

Val Asp Cys Thr Asp Lys His Leu Thr Glu Ile Pro Glu Gly Ile Pro
 50                  55                  60

Thr Asn Thr Thr Asn Leu Thr Leu Thr Ile Asn His Ile Pro Ser Ile
 65                  70                  75                  80

Ser Pro Asp Ser Phe Arg Arg Leu Asn His Leu Glu Glu Ile Asp Leu
                 85                  90                  95

Arg Cys Asn Cys Val Pro Val Leu Leu Gly Ser Lys Ala Asn Val Cys
                100                 105                 110

Thr Lys Arg Leu Gln Ile Arg Pro Gly Ser Phe Ser Gly Leu Ser Asp
            115                 120                 125

Leu Lys Ala Leu Tyr Leu Asp Gly Asn Gln Leu Leu Glu Ile Pro Gln
        130                 135                 140

Asp Leu Pro Ser Ser Leu His Leu Leu Ser Leu Glu Ala Asn Asn Ile
145                 150                 155                 160

Phe Ser Ile Thr Lys Glu Asn Leu Thr Glu Leu Val Asn Ile Glu Thr
                165                 170                 175

Leu Tyr Leu Gly Gln Asn Cys Tyr Tyr Arg Asn Pro Cys Asn Val Ser
            180                 185                 190

Tyr Ser Ile Glu Lys Asp Ala Phe Leu Val Met Arg Asn Leu Lys Val
        195                 200                 205

Leu Ser Leu Lys Asp Asn Asn Val Thr Ala Val Pro Thr Thr Leu Pro
210                 215                 220

Pro Asn Leu Leu Glu Leu Tyr Leu Tyr Asn Asn Ile Ile Lys Lys Ile
225                 230                 235                 240

Gln Glu Asn Asp Phe Asn Asn Leu Asn Glu Leu Gln Val Leu Asp Leu
                245                 250                 255

Ser Gly Asn Cys Pro Arg Cys Tyr Asn Val Pro Tyr Pro Cys Thr Pro
            260                 265                 270

Cys Glu Asn Asn Ser Pro Leu Gln Ile His Asp Asn Ala Phe Asn Ser
        275                 280                 285

Leu Thr Glu Leu Lys Val Leu Arg Leu His Ser Asn Ser Leu Gln His
    290                 295                 300

Val Pro Pro Thr Trp Phe Lys Asn Met Arg Asn Leu Gln Glu Leu Asp
305                 310                 315                 320

Leu Ser Gln Asn Tyr Leu Ala Arg Glu Ile Glu Glu Ala Lys Phe Leu
                325                 330                 335

His Phe Leu Pro Asn Leu Val Glu Leu Asp Phe Ser Phe Asn Tyr Glu
            340                 345                 350

Leu Gln Val Tyr His Ala Ser Ile Thr Leu Pro His Ser Leu Ser Ser
        355                 360                 365

Leu Glu Asn Leu Lys Ile Leu Arg Val Lys Gly Tyr Val Phe Lys Glu
    370                 375                 380

Leu Lys Asn Ser Ser Leu Ser Val Leu His Lys Leu Pro Arg Leu Glu
385                 390                 395                 400

Val Leu Asp Leu Gly Thr Asn Phe Ile Lys Ile Ala Asp Leu Asn Ile
                405                 410                 415

Phe Lys His Phe Glu Asn Leu Lys Leu Ile Asp Leu Ser Val Asn Lys
            420                 425                 430

Ile Ser Pro Ser Glu Glu Ser Arg Glu Val Gly Phe Cys Pro Asn Ala
        435                 440                 445

Gln Thr Ser Val Asp Arg His Gly Pro Gln Val Leu Glu Ala Leu His
    450                 455                 460

Tyr Phe Arg Tyr Asp Glu Tyr Ala Arg Ser Cys Arg Phe Lys Asn Lys

-continued

```
            465                 470                 475                 480
        Glu Pro Pro Ser Phe Leu Pro Leu Asn Ala Asp Cys His Ile Tyr Gly
                        485                 490                 495
        Gln Thr Leu Asp Leu Ser Arg Asn Asn Ile Phe Phe Ile Lys Pro Ser
                        500                 505                 510
        Asp Phe Gln His Leu Ser Phe Leu Lys Cys Leu Asn Leu Ser Gly Asn
                        515                 520                 525
        Thr Ile Gly Gln Thr Leu Asn Gly Ser Glu Leu Trp Pro Leu Arg Glu
                        530                 535                 540
        Leu Arg Tyr Leu Asp Phe Ser Asn Asn Arg Leu Asp Leu Leu Tyr Ser
        545                 550                 555                 560
        Thr Ala Phe Glu Glu Leu Gln Ser Leu Glu Val Leu Asp Leu Ser Ser
                        565                 570                 575
        Asn Ser His Tyr Phe Gln Ala Glu Gly Ile Thr His Met Leu Asn Phe
                        580                 585                 590
        Thr Lys Lys Leu Arg Leu Leu Asp Lys Leu Met Met Asn Asp Asn Asp
                        595                 600                 605
        Ile Ser Thr Ser Ala Ser Arg Thr Met Glu Ser Asp Ser Leu Arg Ile
                        610                 615                 620
        Leu Glu Phe Arg Gly Asn His Leu Asp Val Leu Trp Arg Ala Gly Asp
        625                 630                 635                 640
        Asn Arg Tyr Leu Asp Phe Phe Lys Asn Leu Phe Asn Leu Glu Val Leu
                        645                 650                 655
        Asp Ile Ser Arg Asn Ser Leu Asn Ser Leu Pro Pro Glu Val Phe Glu
                        660                 665                 670
        Gly Met Pro Pro Asn Leu Lys Asn Leu Ser Leu Ala Lys Asn Gly Leu
                        675                 680                 685
        Lys Ser Phe Phe Trp Asp Arg Leu Gln Leu Leu Lys His Leu Glu Ile
                        690                 695                 700
        Leu Asp Leu Ser His Asn Gln Leu Thr Lys Val Pro Glu Arg Leu Ala
        705                 710                 715                 720
        Asn Cys Ser Lys Ser Leu Thr Thr Leu Ile Leu Lys His Asn Gln Ile
                        725                 730                 735
        Arg Gln Leu Thr Lys Tyr Phe Leu Glu Asp Ala Leu Gln Leu Arg Tyr
                        740                 745                 750
        Leu Asp Ile Ser Ser Asn Lys Ile Gln Val Ile Gln Lys Thr Ser Phe
                        755                 760                 765
        Pro Glu Asn Val Leu Asn Asn Leu Glu Met Leu Val Leu His His Asn
                        770                 775                 780
        Arg Phe Leu Cys Asn Cys Asp Ala Val Trp Phe Val Trp Trp Val Asn
        785                 790                 795                 800
        His Thr Asp Val Thr Ile Pro Tyr Leu Ala Thr Asp Val Thr Cys Val
                        805                 810                 815
        Gly Pro Gly Ala His Lys Gly Gln Ser Val Ile Ser Leu Asp Leu Tyr
                        820                 825                 830
        Thr Cys Glu Leu Asp Leu Thr Asn Leu Ile Leu Phe Ser Val Ser Ile
                        835                 840                 845
        Ser Ser Val Leu Phe Leu Met Val Val Met Thr Thr Ser His Leu Phe
                        850                 855                 860
        Phe Trp Asp Met Trp Tyr Ile Tyr Tyr Phe Trp Lys Ala Lys Ile Lys
        865                 870                 875                 880
        Gly Tyr Gln His Leu Gln Ser Met Glu Ser Cys Tyr Asp Ala Phe Ile
                        885                 890                 895
```

```
Val Tyr Asp Thr Lys Asn Ser Ala Val Thr Glu Trp Val Leu Gln Glu
            900                 905                 910

Leu Val Ala Lys Leu Glu Asp Pro Arg Glu Lys His Phe Asn Leu Cys
        915                 920                 925

Leu Glu Glu Arg Asp Trp Leu Pro Gly Gln Pro Val Leu Glu Asn Leu
    930                 935                 940

Ser Gln Ser Ile Gln Leu Ser Lys Lys Thr Val Phe Val Met Thr Gln
945                 950                 955                 960

Lys Tyr Ala Lys Thr Glu Ser Phe Lys Met Ala Phe Tyr Leu Ser His
                965                 970                 975

Gln Arg Leu Leu Asp Glu Lys Val Asp Val Ile Ile Leu Ile Phe Leu
            980                 985                 990

Glu Lys Pro Leu Gln Lys Ser Lys  Phe Leu Gln Leu Arg  Lys Arg Leu
        995                 1000                1005

Cys Arg  Ser Ser Val Leu Glu  Trp Pro Ala Asn Pro  Gln Ala His
    1010                1015                1020

Pro Tyr  Phe Trp Gln Cys Leu  Lys Asn Ala Leu Thr  Thr Asp Asn
    1025                1030                1035

His Val  Ala Tyr Ser Gln Met  Phe Lys Glu Thr Val
    1040                1045                1050

<210> SEQ ID NO 26
<211> LENGTH: 10
<212> TYPE: PRT
<213> ORGANISM: artificial
<220> FEATURE:
<223> OTHER INFORMATION: peptide decoy D95 to L104 of Homo sapiens TLR7

<400> SEQUENCE: 26

Asp Phe Arg Cys Asn Cys Val Pro Ile Pro
1               5                   10

<210> SEQ ID NO 27
<211> LENGTH: 10
<212> TYPE: PRT
<213> ORGANISM: artificial
<220> FEATURE:
<223> OTHER INFORMATION: peptide decoy
<220> FEATURE:
<221> NAME/KEY: MISC_FEATURE
<222> LOCATION: (2)..(2)
<223> OTHER INFORMATION: X = L, F or M
<220> FEATURE:
<221> NAME/KEY: MISC_FEATURE
<222> LOCATION: (7)..(7)
<223> OTHER INFORMATION: X = V or I
<220> FEATURE:
<221> NAME/KEY: MISC_FEATURE
<222> LOCATION: (9)..(9)
<223> OTHER INFORMATION: X = V or I or A or P
<220> FEATURE:
<221> NAME/KEY: MISC_FEATURE
<222> LOCATION: (10)..(10)
<223> OTHER INFORMATION: X = L or K or R
<220> FEATURE:
<221> NAME/KEY: MISC_FEATURE
<222> LOCATION: (10)..(10)
<223> OTHER INFORMATION: X = P or L or K or R

<400> SEQUENCE: 27

Asp Xaa Arg Cys Asn Cys Xaa Pro Xaa Xaa
1               5                   10

<210> SEQ ID NO 28
```

```
<211> LENGTH: 904
<212> TYPE: PRT
<213> ORGANISM: artificial
<220> FEATURE:
<223> OTHER INFORMATION: Homo sapiens TLR3

<400> SEQUENCE: 28
```

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
    290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

```
Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
            405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
            435                 440                 445

Gly Gln Glu Trp Arg Gly Leu Glu Asn Ile Phe Glu Ile Tyr Leu Ser
450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
            515                 520                 525

Leu Glu Lys Leu Glu Ile Leu Asp Leu Gln His Asn Asn Leu Ala Arg
530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
            595                 600                 605

Gln Val Ser Leu Lys Ser Leu Asn Leu Gln Lys Asn Leu Ile Thr Ser
            610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
                660                 665                 670

Ser His Tyr Leu Cys Asn Thr Pro Pro His Tyr His Gly Phe Pro Val
            675                 680                 685

Arg Leu Phe Asp Thr Ser Ser Cys Lys Asp Ser Ala Pro Phe Glu Leu
            690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
                740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
            770                 775                 780

Lys Phe Cys Leu Glu Glu Arg Asp Phe Glu Ala Gly Val Phe Glu Leu
785                 790                 795                 800
```

```
Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
            835                 840                 845

Leu Val Phe Leu Glu Glu Ile Pro Asp Tyr Lys Leu Asn His Ala Leu
        850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
                900
```

<210> SEQ ID NO 29
<211> LENGTH: 1032
<212> TYPE: PRT
<213> ORGANISM: artificial
<220> FEATURE:
<223> OTHER INFORMATION: Homo sapiens TLR9

<400> SEQUENCE: 29

```
Met Gly Phe Cys Arg Ser Ala Leu His Pro Leu Ser Leu Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
        195                 200                 205

Asn Asn Leu Thr Val Val Pro Arg Asn Leu Pro Ser Ser Leu Glu Tyr
210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255
```

```
Arg Cys Asp His Ala Pro Asn Pro Cys Met Glu Cys Pro Arg His Phe
                260                 265                 270

Pro Gln Leu His Pro Asp Thr Phe Ser His Leu Ser Arg Leu Glu Gly
            275                 280                 285

Leu Val Leu Lys Asp Ser Ser Leu Ser Trp Leu Asn Ala Ser Trp Phe
        290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
        355                 360                 365

Leu Asp Met His Gly Ile Phe Phe Arg Ser Leu Asp Glu Thr Thr Leu
        370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
            420                 425                 430

Leu Thr Ala Thr Met Gly Glu Ala Asp Gly Gly Glu Lys Val Trp Leu
        435                 440                 445

Gln Pro Gly Asp Leu Ala Pro Ala Pro Val Asp Thr Pro Ser Ser Glu
        450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                485                 490                 495

His Leu Gln Cys Leu Arg Leu Ser His Asn Cys Ile Ser Gln Ala Val
            500                 505                 510

Asn Gly Ser Gln Phe Leu Pro Leu Thr Gly Leu Gln Val Leu Asp Leu
        515                 520                 525

Ser His Asn Lys Leu Asp Leu Tyr His Glu His Ser Phe Thr Glu Leu
        530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
            580                 585                 590

Gln Gln Leu Cys Ser Thr Ser Leu Arg Ala Leu Asp Phe Ser Gly Asn
        595                 600                 605

Ala Leu Gly His Met Trp Ala Glu Gly Asp Leu Tyr Leu His Phe Phe
        610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Gln
```

```
                    675                 680                 685
Leu Lys Ala Leu Thr Asn Gly Ser Leu Pro Ala Gly Thr Arg Leu Arg
        690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
        755                 760                 765

Ala Phe Met Asp Phe Leu Leu Glu Val Gln Ala Ala Val Pro Gly Leu
    770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
        835                 840                 845

Leu Cys Leu Ala Trp Leu Pro Trp Arg Gly Arg Gln Ser Gly Arg Asp
    850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
            900                 905                 910

Trp Leu Pro Gly Lys Thr Leu Phe Glu Asn Leu Trp Ala Ser Val Tyr
        915                 920                 925

Gly Ser Arg Lys Thr Leu Phe Val Leu Ala His Thr Asp Arg Val Ser
    930                 935                 940

Gly Leu Leu Arg Ala Ser Phe Leu Leu Ala Gln Gln Arg Leu Leu Glu
945                 950                 955                 960

Asp Arg Lys Asp Val Val Val Leu Val Ile Leu Ser Pro Asp Gly Arg
                965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
        995                 1000                1005

Leu Gly Met Ala Leu Thr Arg Asp Asn His His Phe Tyr Asn Arg
    1010                1015                1020

Asn Phe Cys Gln Gly Pro Thr Ala Glu
    1025                1030

<210> SEQ ID NO 30
<211> LENGTH: 1059
<212> TYPE: PRT
<213> ORGANISM: artificial
<220> FEATURE:
<223> OTHER INFORMATION: Homo sapiens TLR8

<400> SEQUENCE: 30

Met Lys Glu Ser Ser Leu Gln Asn Ser Ser Cys Ser Leu Gly Lys Glu
```

-continued

```
1               5                   10                  15
Thr Lys Lys Glu Asn Met Phe Leu Gln Ser Ser Met Leu Thr Cys Ile
                20                  25                  30

Phe Leu Leu Ile Ser Gly Ser Cys Glu Leu Cys Ala Glu Glu Asn Phe
                35                  40                  45

Ser Arg Ser Tyr Pro Cys Asp Glu Lys Lys Gln Asn Asp Ser Val Ile
        50                  55                  60

Ala Glu Cys Ser Asn Arg Arg Leu Gln Glu Val Pro Gln Thr Val Gly
65                  70                  75                  80

Lys Tyr Val Thr Glu Leu Asp Leu Ser Asp Asn Phe Ile Thr His Ile
                85                  90                  95

Thr Asn Glu Ser Phe Gln Gly Leu Gln Asn Leu Thr Lys Ile Asn Leu
                100                 105                 110

Asn His Asn Pro Asn Val Gln His Gln Asn Gly Asn Pro Gly Ile Gln
                115                 120                 125

Ser Asn Gly Leu Asn Ile Thr Asp Gly Ala Phe Leu Asn Leu Lys Asn
        130                 135                 140

Leu Arg Glu Leu Leu Leu Glu Asp Asn Gln Leu Pro Gln Ile Pro Ser
145                 150                 155                 160

Gly Leu Pro Glu Ser Leu Thr Glu Leu Ser Leu Ile Gln Asn Asn Ile
                165                 170                 175

Tyr Asn Ile Thr Lys Glu Gly Ile Ser Arg Leu Ile Asn Leu Lys Asn
                180                 185                 190

Leu Tyr Leu Ala Trp Asn Cys Tyr Phe Asn Lys Val Cys Glu Lys Thr
        195                 200                 205

Asn Ile Glu Asp Gly Val Phe Glu Thr Leu Thr Asn Leu Glu Leu Leu
210                 215                 220

Ser Leu Ser Phe Asn Ser Leu Ser His Val Pro Pro Lys Leu Pro Ser
225                 230                 235                 240

Ser Leu Arg Lys Leu Phe Leu Ser Asn Thr Gln Ile Lys Tyr Ile Ser
                245                 250                 255

Glu Glu Asp Phe Lys Gly Leu Ile Asn Leu Thr Leu Leu Asp Leu Ser
                260                 265                 270

Gly Asn Cys Pro Arg Cys Phe Asn Ala Pro Phe Pro Cys Val Pro Cys
        275                 280                 285

Asp Gly Gly Ala Ser Ile Asn Ile Asp Arg Phe Ala Phe Gln Asn Leu
290                 295                 300

Thr Gln Leu Arg Tyr Leu Asn Leu Ser Ser Thr Ser Leu Arg Lys Ile
305                 310                 315                 320

Asn Ala Ala Trp Phe Lys Asn Met Pro His Leu Lys Val Leu Asp Leu
                325                 330                 335

Glu Phe Asn Tyr Leu Val Gly Glu Ile Ala Ser Gly Ala Phe Leu Thr
                340                 345                 350

Met Leu Pro Arg Leu Glu Ile Leu Asp Leu Ser Phe Asn Tyr Ile Lys
        355                 360                 365

Gly Ser Tyr Pro Gln His Ile Asn Ile Ser Arg Asn Phe Ser Lys Leu
370                 375                 380

Leu Ser Leu Arg Ala Leu His Leu Arg Gly Tyr Val Phe Gln Glu Leu
385                 390                 395                 400

Arg Glu Asp Asp Phe Gln Pro Leu Met Gln Leu Pro Asn Leu Ser Thr
                405                 410                 415

Ile Asn Leu Gly Ile Asn Phe Ile Lys Gln Ile Asp Phe Lys Leu Phe
                420                 425                 430
```

```
Gln Asn Phe Ser Asn Leu Glu Ile Ile Tyr Leu Ser Glu Asn Arg Ile
    435                 440                 445

Ser Pro Leu Val Lys Asp Thr Arg Gln Ser Tyr Ala Asn Ser Ser Ser
450                 455                 460

Phe Gln Arg His Ile Arg Lys Arg Arg Ser Thr Asp Phe Glu Phe Asp
465                 470                 475                 480

Pro His Ser Asn Phe Tyr His Phe Thr Arg Pro Leu Ile Lys Pro Gln
                485                 490                 495

Cys Ala Ala Tyr Gly Lys Ala Leu Asp Leu Ser Leu Asn Ser Ile Phe
                500                 505                 510

Phe Ile Gly Pro Asn Gln Phe Glu Asn Leu Pro Asp Ile Ala Cys Leu
            515                 520                 525

Asn Leu Ser Ala Asn Ser Asn Ala Gln Val Leu Ser Gly Thr Glu Phe
            530                 535                 540

Ser Ala Ile Pro His Val Lys Tyr Leu Asp Leu Thr Asn Asn Arg Leu
545                 550                 555                 560

Asp Phe Asp Asn Ala Ser Ala Leu Thr Glu Leu Ser Asp Leu Glu Val
                565                 570                 575

Leu Asp Leu Ser Tyr Asn Ser His Tyr Phe Arg Ile Ala Gly Val Thr
            580                 585                 590

His His Leu Glu Phe Ile Gln Asn Phe Thr Asn Leu Lys Val Leu Asn
            595                 600                 605

Leu Ser His Asn Asn Ile Tyr Thr Leu Thr Asp Lys Tyr Asn Leu Glu
            610                 615                 620

Ser Lys Ser Leu Val Glu Leu Val Phe Ser Gly Asn Arg Leu Asp Ile
625                 630                 635                 640

Leu Trp Asn Asp Asp Asp Asn Arg Tyr Ile Ser Ile Phe Lys Gly Leu
                645                 650                 655

Lys Asn Leu Thr Arg Leu Asp Leu Ser Leu Asn Arg Leu Lys His Ile
                660                 665                 670

Pro Asn Glu Ala Phe Leu Asn Leu Pro Ala Ser Leu Thr Glu Leu His
            675                 680                 685

Ile Asn Asp Asn Met Leu Lys Phe Phe Asn Trp Thr Leu Leu Gln Gln
            690                 695                 700

Phe Pro Arg Leu Glu Leu Leu Asp Leu Arg Gly Asn Lys Leu Leu Phe
705                 710                 715                 720

Leu Thr Asp Ser Leu Ser Asp Phe Thr Ser Ser Leu Arg Thr Leu Leu
                725                 730                 735

Leu Ser His Asn Arg Ile Ser His Leu Pro Ser Gly Phe Leu Ser Glu
            740                 745                 750

Val Ser Ser Leu Lys His Leu Asp Leu Ser Ser Asn Leu Leu Lys Thr
            755                 760                 765

Ile Asn Lys Ser Ala Leu Glu Thr Lys Thr Thr Thr Lys Leu Ser Met
            770                 775                 780

Leu Glu Leu His Gly Asn Pro Phe Glu Cys Thr Cys Asp Ile Gly Asp
785                 790                 795                 800

Phe Arg Arg Trp Met Asp Glu His Leu Asn Val Lys Ile Pro Arg Leu
                805                 810                 815

Val Asp Val Ile Cys Ala Ser Pro Gly Asp Gln Arg Gly Lys Ser Ile
                820                 825                 830

Val Ser Leu Glu Leu Thr Thr Cys Val Ser Asp Val Thr Ala Val Ile
            835                 840                 845
```

```
Leu Phe Phe Thr Phe Phe Ile Thr Thr Met Val Met Leu Ala Ala
    850             855                 860

Leu Ala His His Leu Phe Tyr Trp Asp Val Trp Phe Ile Tyr Asn Val
865             870                 875                 880

Cys Leu Ala Lys Val Lys Gly Tyr Arg Ser Leu Ser Thr Ser Gln Thr
                885                 890                 895

Phe Tyr Asp Ala Tyr Ile Ser Tyr Asp Thr Lys Asp Ala Ser Val Thr
                900                 905                 910

Asp Trp Val Ile Asn Glu Leu Arg Tyr His Leu Glu Glu Ser Arg Asp
            915                 920                 925

Lys Asn Val Leu Leu Cys Leu Glu Glu Arg Asp Trp Asp Pro Gly Leu
    930                 935                 940

Ala Ile Ile Asp Asn Leu Met Gln Ser Ile Asn Gln Ser Lys Lys Thr
945                 950                 955                 960

Val Phe Val Leu Thr Lys Lys Tyr Ala Lys Ser Trp Asn Phe Lys Thr
                965                 970                 975

Ala Phe Tyr Leu Ala Leu Gln Arg Leu Met Asp Glu Asn Met Asp Val
                980                 985                 990

Ile Ile Phe Ile Leu Leu Glu Pro Val Leu Gln His Ser Gln Tyr Leu
            995                 1000                1005

Arg Leu Arg Gln Arg Ile Cys Lys Ser Ser Ile Leu Gln Trp Pro
    1010                1015                1020

Asp Asn Pro Lys Ala Glu Gly Leu Phe Trp Gln Thr Leu Arg Asn
    1025                1030                1035

Val Val Leu Thr Glu Asn Asp Ser Arg Tyr Asn Asn Met Tyr Val
    1040                1045                1050

Asp Ser Ile Lys Gln Tyr
    1055

<210> SEQ ID NO 31
<211> LENGTH: 858
<212> TYPE: PRT
<213> ORGANISM: artificial
<220> FEATURE:
<223> OTHER INFORMATION: Homo sapiens TLR5

<400> SEQUENCE: 31

Met Gly Asp His Leu Asp Leu Leu Gly Val Val Leu Met Ala Gly
1               5                   10                  15

Pro Val Phe Gly Ile Pro Ser Cys Ser Phe Asp Gly Arg Ile Ala Phe
                20                  25                  30

Tyr Arg Phe Cys Asn Leu Thr Gln Val Pro Gln Val Leu Asn Thr Thr
            35                  40                  45

Glu Arg Leu Leu Leu Ser Phe Asn Tyr Ile Arg Thr Val Thr Ala Ser
    50                  55                  60

Ser Phe Pro Phe Leu Glu Gln Leu Gln Leu Leu Glu Leu Gly Ser Gln
65                  70                  75                  80

Tyr Thr Pro Leu Thr Ile Asp Lys Glu Ala Phe Arg Asn Leu Pro Asn
                85                  90                  95

Leu Arg Ile Leu Asp Leu Gly Ser Ser Lys Ile Tyr Phe Leu His Pro
                100                 105                 110

Asp Ala Phe Gln Gly Leu Phe His Leu Phe Glu Leu Arg Leu Tyr Phe
            115                 120                 125

Cys Gly Leu Ser Asp Ala Val Leu Lys Asp Gly Tyr Phe Arg Asn Leu
130                 135                 140
```

```
Lys Ala Leu Thr Arg Leu Asp Leu Ser Lys Asn Gln Ile Arg Ser Leu
145                 150                 155                 160

Tyr Leu His Pro Ser Phe Gly Lys Leu Asn Ser Leu Lys Ser Ile Asp
                165                 170                 175

Phe Ser Ser Asn Gln Ile Phe Leu Val Cys Glu His Glu Leu Glu Pro
            180                 185                 190

Leu Gln Gly Lys Thr Leu Ser Phe Phe Ser Leu Ala Ala Asn Ser Leu
        195                 200                 205

Tyr Ser Arg Val Ser Val Asp Trp Gly Lys Cys Met Asn Pro Phe Arg
    210                 215                 220

Asn Met Val Leu Glu Ile Leu Asp Val Ser Gly Asn Gly Trp Thr Val
225                 230                 235                 240

Asp Ile Thr Gly Asn Phe Ser Asn Ala Ile Ser Lys Ser Gln Ala Phe
                245                 250                 255

Ser Leu Ile Leu Ala His His Ile Met Gly Ala Gly Phe Gly Phe His
            260                 265                 270

Asn Ile Lys Asp Pro Asp Gln Asn Thr Phe Ala Gly Leu Ala Arg Ser
        275                 280                 285

Ser Val Arg His Leu Asp Leu Ser His Gly Phe Val Phe Ser Leu Asn
    290                 295                 300

Ser Arg Val Phe Glu Thr Leu Lys Asp Leu Lys Val Leu Asn Leu Ala
305                 310                 315                 320

Tyr Asn Lys Ile Asn Lys Ile Ala Asp Glu Ala Phe Tyr Gly Leu Asp
                325                 330                 335

Asn Leu Gln Val Leu Asn Leu Ser Tyr Asn Leu Leu Gly Glu Leu Tyr
            340                 345                 350

Ser Ser Asn Phe Tyr Gly Leu Pro Lys Val Ala Tyr Ile Asp Leu Gln
        355                 360                 365

Lys Asn His Ile Ala Ile Ile Gln Asp Gln Thr Phe Lys Phe Leu Glu
    370                 375                 380

Lys Leu Gln Thr Leu Asp Leu Arg Asp Asn Ala Leu Thr Thr Ile His
385                 390                 395                 400

Phe Ile Pro Ser Ile Pro Asp Ile Phe Leu Ser Gly Asn Lys Leu Val
                405                 410                 415

Thr Leu Pro Lys Ile Asn Leu Thr Ala Asn Leu Ile His Leu Ser Glu
            420                 425                 430

Asn Arg Leu Glu Asn Leu Asp Ile Leu Tyr Phe Leu Leu Arg Val Pro
        435                 440                 445

His Leu Gln Ile Leu Ile Leu Asn Gln Asn Arg Phe Ser Ser Cys Ser
    450                 455                 460

Gly Asp Gln Thr Pro Ser Glu Asn Pro Ser Leu Glu Gln Leu Phe Leu
465                 470                 475                 480

Gly Glu Asn Met Leu Gln Leu Ala Trp Glu Thr Glu Leu Cys Trp Asp
                485                 490                 495

Val Phe Glu Gly Leu Ser His Leu Gln Val Leu Tyr Leu Asn His Asn
            500                 505                 510

Tyr Leu Asn Ser Leu Pro Pro Gly Val Phe Ser His Leu Thr Ala Leu
        515                 520                 525

Arg Gly Leu Ser Leu Asn Ser Asn Arg Leu Thr Val Leu Ser His Asn
    530                 535                 540

Asp Leu Pro Ala Asn Leu Glu Ile Leu Asp Ile Ser Arg Asn Gln Leu
545                 550                 555                 560

Leu Ala Pro Asn Pro Asp Val Phe Val Ser Leu Ser Val Leu Asp Ile
```

565                 570                 575
Thr His Asn Lys Phe Ile Cys Glu Cys Glu Leu Ser Thr Phe Ile Asn
                580                 585                 590

Trp Leu Asn His Thr Asn Val Thr Ile Ala Gly Pro Pro Ala Asp Ile
            595                 600                 605

Tyr Cys Val Tyr Pro Asp Ser Phe Ser Gly Val Ser Leu Phe Ser Leu
        610                 615                 620

Ser Thr Glu Gly Cys Asp Glu Glu Val Leu Lys Ser Leu Lys Phe
625                 630                 635                 640

Ser Leu Phe Ile Val Cys Thr Val Thr Leu Thr Leu Phe Leu Met Thr
                645                 650                 655

Ile Leu Thr Val Thr Lys Phe Arg Gly Phe Cys Phe Ile Cys Tyr Lys
            660                 665                 670

Thr Ala Gln Arg Leu Val Phe Lys Asp His Pro Gln Gly Thr Glu Pro
        675                 680                 685

Asp Met Tyr Lys Tyr Asp Ala Tyr Leu Cys Phe Ser Ser Lys Asp Phe
    690                 695                 700

Thr Trp Val Gln Asn Ala Leu Leu Lys His Leu Asp Thr Gln Tyr Ser
705                 710                 715                 720

Asp Gln Asn Arg Phe Asn Leu Cys Phe Glu Glu Arg Asp Phe Val Pro
                725                 730                 735

Gly Glu Asn Arg Ile Ala Asn Ile Gln Asp Ala Ile Trp Asn Ser Arg
            740                 745                 750

Lys Ile Val Cys Leu Val Ser Arg His Phe Leu Arg Asp Gly Trp Cys
        755                 760                 765

Leu Glu Ala Phe Ser Tyr Ala Gln Gly Arg Cys Leu Ser Asp Leu Asn
    770                 775                 780

Ser Ala Leu Ile Met Val Val Val Gly Ser Leu Ser Gln Tyr Gln Leu
785                 790                 795                 800

Met Lys His Gln Ser Ile Arg Gly Phe Val Gln Lys Gln Gln Tyr Leu
                805                 810                 815

Arg Trp Pro Glu Asp Leu Gln Asp Val Gly Trp Phe Leu His Lys Leu
            820                 825                 830

Ser Gln Gln Ile Leu Lys Lys Glu Lys Glu Lys Lys Lys Asp Asn Asn
        835                 840                 845

Ile Pro Leu Gln Thr Val Ala Thr Ile Ser
    850                 855

<210> SEQ ID NO 32
<211> LENGTH: 839
<212> TYPE: PRT
<213> ORGANISM: artificial
<220> FEATURE:
<223> OTHER INFORMATION: Homo sapiens TLR4

<400> SEQUENCE: 32

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
                20                  25                  30

Val Pro Asn Ile Thr Tyr Gln Cys Met Glu Leu Asn Phe Tyr Lys Ile
            35                  40                  45

Pro Asp Asn Leu Pro Phe Ser Thr Lys Asn Leu Asp Leu Ser Phe Asn
        50                  55                  60

Pro Leu Arg His Leu Gly Ser Tyr Ser Phe Phe Ser Phe Pro Glu Leu

-continued

```
                65                  70                  75                  80
        Gln Val Leu Asp Leu Ser Arg Cys Glu Ile Gln Thr Ile Glu Asp Gly
                            85                  90                  95

Ala Tyr Gln Ser Leu Ser His Leu Ser Thr Leu Ile Leu Thr Gly Asn
                        100                 105                 110

Pro Ile Gln Ser Leu Ala Leu Gly Ala Phe Ser Gly Leu Ser Ser Leu
                    115                 120                 125

Gln Lys Leu Val Ala Val Glu Thr Asn Leu Ala Ser Leu Glu Asn Phe
                130                 135                 140

Pro Ile Gly His Leu Lys Thr Leu Lys Glu Leu Asn Val Ala His Asn
        145                 150                 155                 160

Leu Ile Gln Ser Phe Lys Leu Pro Glu Tyr Phe Ser Asn Leu Thr Asn
                            165                 170                 175

Leu Glu His Leu Asp Leu Ser Ser Asn Lys Ile Gln Ser Ile Tyr Cys
                        180                 185                 190

Thr Asp Leu Arg Val Leu His Gln Met Pro Leu Leu Asn Leu Ser Leu
                    195                 200                 205

Asp Leu Ser Leu Asn Pro Met Asn Phe Ile Gln Pro Gly Ala Phe Lys
        210                 215                 220

Glu Ile Arg Leu His Lys Leu Thr Leu Arg Asn Asn Phe Asp Ser Leu
        225                 230                 235                 240

Asn Val Met Lys Thr Cys Ile Gln Gly Leu Ala Gly Leu Glu Val His
                            245                 250                 255

Arg Leu Val Leu Gly Glu Phe Arg Asn Glu Gly Asn Leu Glu Lys Phe
                        260                 265                 270

Asp Lys Ser Ala Leu Glu Gly Leu Cys Asn Leu Thr Ile Glu Glu Phe
                    275                 280                 285

Arg Leu Ala Tyr Leu Asp Tyr Tyr Leu Asp Asp Ile Ile Asp Leu Phe
                290                 295                 300

Asn Cys Leu Thr Asn Val Ser Ser Phe Ser Leu Val Ser Val Thr Ile
        305                 310                 315                 320

Glu Arg Val Lys Asp Phe Ser Tyr Asn Phe Gly Trp Gln His Leu Glu
                            325                 330                 335

Leu Val Asn Cys Lys Phe Gly Gln Phe Pro Thr Leu Lys Leu Lys Ser
                        340                 345                 350

Leu Lys Arg Leu Thr Phe Thr Ser Asn Lys Gly Gly Asn Ala Phe Ser
                    355                 360                 365

Glu Val Asp Leu Pro Ser Leu Glu Phe Leu Asp Leu Ser Arg Asn Gly
                370                 375                 380

Leu Ser Phe Lys Gly Cys Cys Ser Gln Ser Asp Phe Gly Thr Thr Ser
        385                 390                 395                 400

Leu Lys Tyr Leu Asp Leu Ser Phe Asn Gly Val Ile Thr Met Ser Ser
                            405                 410                 415

Asn Phe Leu Gly Leu Glu Gln Leu Glu His Leu Asp Phe Gln His Ser
                        420                 425                 430

Asn Leu Lys Gln Met Ser Glu Phe Ser Val Phe Leu Ser Leu Arg Asn
                    435                 440                 445

Leu Ile Tyr Leu Asp Ile Ser His Thr His Thr Arg Val Ala Phe Asn
                450                 455                 460

Gly Ile Phe Asn Gly Leu Ser Ser Leu Glu Val Leu Lys Met Ala Gly
        465                 470                 475                 480

Asn Ser Phe Gln Glu Asn Phe Leu Pro Asp Ile Phe Thr Glu Leu Arg
                            485                 490                 495
```

```
Asn Leu Thr Phe Leu Asp Leu Ser Gln Cys Gln Leu Glu Gln Leu Ser
            500                 505                 510

Pro Thr Ala Phe Asn Ser Leu Ser Leu Gln Val Leu Asn Met Ser
        515                 520                 525

His Asn Asn Phe Phe Ser Leu Asp Thr Phe Pro Tyr Lys Cys Leu Asn
530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835

<210> SEQ ID NO 33
<211> LENGTH: 784
<212> TYPE: PRT
<213> ORGANISM: artificial
<220> FEATURE:
<223> OTHER INFORMATION: Homo sapiens TLR2

<400> SEQUENCE: 33

Met Pro His Thr Leu Trp Met Val Trp Val Leu Gly Val Ile Ile Ser
1               5                   10                  15
```

```
Leu Ser Lys Glu Glu Ser Ser Asn Gln Ala Ser Leu Ser Cys Asp Arg
        20              25                  30

Asn Gly Ile Cys Lys Gly Ser Ser Gly Ser Leu Asn Ser Ile Pro Ser
            35              40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65              70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
            115                 120                 125

Leu Asn Leu Leu Gly Asn Pro Tyr Lys Thr Leu Gly Glu Thr Ser Leu
            130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
            195                 200                 205

Gln His Ile Leu Leu Leu Glu Ile Phe Val Asp Val Thr Ser Ser Val
        210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
            275                 280                 285

Leu Asn Gly Val Gly Asn Phe Arg Ala Ser Asp Asn Asp Arg Val Ile
            290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
            355                 360                 365

Glu Asn Leu Met Val Glu Glu Tyr Leu Lys Asn Ser Ala Cys Glu Asp
            370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430
```

```
Gln Trp Pro Glu Lys Met Lys Tyr Leu Asn Leu Ser Ser Thr Arg Ile
            435                 440                 445

His Ser Val Thr Gly Cys Ile Pro Lys Thr Leu Glu Ile Leu Asp Val
450                 455                 460

Ser Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
            580                 585                 590

Gly Met Cys Cys Ala Leu Phe Leu Leu Ile Leu Leu Thr Gly Val Leu
        595                 600                 605

Cys His Arg Phe His Gly Leu Trp Tyr Met Lys Met Met Trp Ala Trp
610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
                645                 650                 655

Asn Leu Met Val Gln Glu Leu Glu Asn Phe Asn Pro Pro Phe Lys Leu
            660                 665                 670

Cys Leu His Lys Arg Asp Phe Ile Pro Gly Lys Trp Ile Ile Asp Asn
        675                 680                 685

Ile Ile Asp Ser Ile Glu Lys Ser His Lys Thr Val Phe Val Leu Ser
690                 695                 700

Glu Asn Phe Val Lys Ser Glu Trp Cys Lys Tyr Glu Leu Asp Phe Ser
705                 710                 715                 720

His Phe Arg Leu Phe Asp Glu Asn Asn Asp Ala Ala Ile Leu Ile Leu
                725                 730                 735

Leu Glu Pro Ile Glu Lys Lys Ala Ile Pro Gln Arg Phe Cys Lys Leu
            740                 745                 750

Arg Lys Ile Met Asn Thr Lys Thr Tyr Leu Glu Trp Pro Met Asp Glu
        755                 760                 765

Ala Gln Arg Glu Gly Phe Trp Val Asn Leu Arg Ala Ala Ile Lys Ser
770                 775                 780

<210> SEQ ID NO 34
<211> LENGTH: 811
<212> TYPE: PRT
<213> ORGANISM: artificial
<220> FEATURE:
<223> OTHER INFORMATION: Homo sapiens TLR10

<400> SEQUENCE: 34

Met Arg Leu Ile Arg Asn Ile Tyr Ile Phe Cys Ser Ile Val Met Thr
1               5                   10                  15
```

-continued

```
Ala Glu Gly Asp Ala Pro Glu Leu Pro Glu Arg Glu Leu Met Thr
         20                  25                  30
Asn Cys Ser Asn Met Ser Leu Arg Lys Val Pro Ala Asp Leu Thr Pro
         35                  40                  45
Ala Thr Thr Thr Leu Asp Leu Ser Tyr Asn Leu Leu Phe Gln Leu Gln
 50                  55                  60
Ser Ser Asp Phe His Ser Val Ser Lys Leu Arg Val Leu Ile Leu Cys
 65                  70                  75                  80
His Asn Arg Ile Gln Gln Leu Asp Leu Lys Thr Phe Glu Phe Asn Lys
                 85                  90                  95
Glu Leu Arg Tyr Leu Asp Leu Ser Asn Asn Arg Leu Lys Ser Val Thr
             100                 105                 110
Trp Tyr Leu Leu Ala Gly Leu Arg Tyr Leu Asp Leu Ser Phe Asn Asp
             115                 120                 125
Phe Asp Thr Met Pro Ile Cys Glu Glu Ala Gly Asn Met Ser His Leu
130                 135                 140
Glu Ile Leu Gly Leu Ser Gly Ala Lys Ile Gln Lys Ser Asp Phe Gln
145                 150                 155                 160
Lys Ile Ala His Leu His Leu Asn Thr Val Phe Leu Gly Phe Arg Thr
                 165                 170                 175
Leu Pro His Tyr Glu Glu Gly Ser Leu Pro Ile Leu Asn Thr Thr Lys
             180                 185                 190
Leu His Ile Val Leu Pro Met Asp Thr Asn Phe Trp Val Leu Leu Arg
             195                 200                 205
Asp Gly Ile Lys Thr Ser Lys Ile Leu Glu Met Thr Asn Ile Asp Gly
210                 215                 220
Lys Ser Gln Phe Val Ser Tyr Glu Met Gln Arg Asn Leu Ser Leu Glu
225                 230                 235                 240
His Ala Lys Thr Ser Val Leu Leu Asn Lys Val Asp Leu Leu Trp
                 245                 250                 255
Asp Asp Leu Phe Leu Ile Leu Gln Phe Val Trp His Thr Ser Val Glu
             260                 265                 270
His Phe Gln Ile Arg Asn Val Thr Phe Gly Gly Lys Ala Tyr Leu Asp
             275                 280                 285
His Asn Ser Phe Asp Tyr Ser Asn Thr Val Met Arg Thr Ile Lys Leu
290                 295                 300
Glu His Val His Phe Arg Val Phe Tyr Ile Gln Gln Asp Lys Ile Tyr
305                 310                 315                 320
Leu Leu Leu Thr Lys Met Asp Ile Glu Asn Leu Thr Ile Ser Asn Ala
                 325                 330                 335
Gln Met Pro His Met Leu Phe Pro Asn Tyr Pro Thr Lys Phe Gln Tyr
             340                 345                 350
Leu Asn Phe Ala Asn Asn Ile Leu Thr Asp Glu Leu Phe Lys Arg Thr
             355                 360                 365
Leu Gln Leu Pro His Leu Lys Thr Leu Ile Leu Asn Gly Asn Lys Leu
370                 375                 380
Glu Thr Leu Ser Leu Val Ser Cys Phe Ala Asn Asn Thr Pro Leu Glu
385                 390                 395                 400
His Leu Asp Leu Ser Gln Asn Leu Leu Gln His Lys Asn Asp Glu Asn
                 405                 410                 415
Cys Ser Trp Pro Glu Thr Val Val Asn Met Asn Leu Ser Tyr Asn Lys
             420                 425                 430
Leu Ser Asp Ser Val Phe Arg Cys Leu Pro Lys Ser Ile Gln Ile Leu
```

435                 440                 445
Asp Leu Asn Asn Asn Gln Ile Gln Thr Val Pro Lys Glu Thr Ile His
450                     455                 460

Leu Met Ala Leu Arg Glu Leu Asn Ile Ala Phe Asn Phe Leu Thr Asp
465                     470                 475                 480

Leu Pro Gly Cys Ser His Phe Ser Arg Leu Ser Val Leu Asn Ile Glu
                    485                 490                 495

Met Asn Phe Ile Leu Ser Pro Ser Leu Asp Phe Val Gln Ser Cys Gln
                500                 505                 510

Glu Val Lys Thr Leu Asn Ala Gly Arg Asn Pro Phe Arg Cys Thr Cys
            515                 520                 525

Glu Leu Lys Asn Phe Ile Gln Leu Glu Thr Tyr Ser Glu Val Met Met
        530                 535                 540

Val Gly Trp Ser Asp Ser Tyr Thr Cys Glu Tyr Pro Leu Asn Leu Arg
545                 550                 555                 560

Gly Thr Arg Leu Lys Asp Val His Leu His Glu Leu Ser Cys Asn Thr
                565                 570                 575

Ala Leu Leu Ile Val Thr Ile Val Val Ile Met Leu Val Leu Gly Leu
                580                 585                 590

Ala Val Ala Phe Cys Cys Leu His Phe Asp Leu Pro Trp Tyr Leu Arg
            595                 600                 605

Met Leu Gly Gln Cys Thr Gln Thr Trp His Arg Val Arg Lys Thr Thr
        610                 615                 620

Gln Glu Gln Leu Lys Arg Asn Val Arg Phe His Ala Phe Ile Ser Tyr
625                 630                 635                 640

Ser Glu His Asp Ser Leu Trp Val Lys Asn Glu Leu Ile Pro Asn Leu
                645                 650                 655

Glu Lys Glu Asp Gly Ser Ile Leu Ile Cys Leu Tyr Glu Ser Tyr Phe
                660                 665                 670

Asp Pro Gly Lys Ser Ile Ser Glu Asn Ile Val Ser Phe Ile Glu Lys
            675                 680                 685

Ser Tyr Lys Ser Ile Phe Val Leu Ser Pro Asn Phe Val Gln Asn Glu
        690                 695                 700

Trp Cys His Tyr Glu Phe Tyr Phe Ala His His Asn Leu Phe His Glu
705                 710                 715                 720

Asn Ser Asp His Ile Ile Leu Ile Leu Leu Glu Pro Ile Pro Phe Tyr
                725                 730                 735

Cys Ile Pro Thr Arg Tyr His Lys Leu Lys Ala Leu Leu Glu Lys Lys
                740                 745                 750

Ala Tyr Leu Glu Trp Pro Lys Asp Arg Arg Lys Cys Gly Leu Phe Trp
            755                 760                 765

Ala Asn Leu Arg Ala Ala Ile Asn Val Asn Val Leu Ala Thr Arg Glu
        770                 775                 780

Met Tyr Glu Leu Gln Thr Phe Thr Glu Leu Asn Glu Glu Ser Arg Gly
785                 790                 795                 800

Ser Thr Ile Ser Leu Met Arg Thr Asp Cys Leu
                805                 810

<210> SEQ ID NO 35
<211> LENGTH: 786
<212> TYPE: PRT
<213> ORGANISM: artificial
<220> FEATURE:
<223> OTHER INFORMATION: Homo sapiens TLR1

```
<400> SEQUENCE: 35

Met Thr Ser Ile Phe His Phe Ala Ile Ile Phe Met Leu Ile Leu Gln
1               5                   10                  15

Ile Arg Ile Gln Leu Ser Glu Glu Ser Glu Phe Leu Val Asp Arg Ser
            20                  25                  30

Lys Asn Gly Leu Ile His Val Pro Lys Asp Leu Ser Gln Lys Thr Thr
            35                  40                  45

Ile Leu Asn Ile Ser Gln Asn Tyr Ile Ser Glu Leu Trp Thr Ser Asp
50                  55                  60

Ile Leu Ser Leu Ser Lys Leu Arg Ile Leu Ile Ser His Asn Arg
65                  70                  75                  80

Ile Gln Tyr Leu Asp Ile Ser Val Phe Lys Phe Asn Gln Leu Glu
                85                  90                  95

Tyr Leu Asp Leu Ser His Asn Lys Leu Val Lys Ile Ser Cys His Pro
                100                 105                 110

Thr Val Asn Leu Lys His Leu Asp Leu Ser Phe Asn Ala Phe Asp Ala
                115                 120                 125

Leu Pro Ile Cys Lys Glu Phe Gly Asn Met Ser Gln Leu Lys Phe Leu
130                 135                 140

Gly Leu Ser Thr Thr His Leu Glu Lys Ser Ser Val Leu Pro Ile Ala
145                 150                 155                 160

His Leu Asn Ile Ser Lys Val Leu Leu Val Leu Gly Glu Thr Tyr Gly
                165                 170                 175

Glu Lys Glu Asp Pro Gly Gly Leu Gln Asp Phe Asn Thr Glu Ser Leu
                180                 185                 190

His Ile Val Phe Pro Thr Asn Lys Glu Phe His Phe Ile Leu Asp Val
                195                 200                 205

Ser Val Lys Thr Val Ala Asn Leu Glu Leu Ser Asn Ile Lys Cys Val
                210                 215                 220

Leu Glu Asp Ser Lys Cys Ser Tyr Phe Leu Ser Ile Leu Ala Lys Leu
225                 230                 235                 240

Gln Thr Asn Pro Lys Leu Ser Ser Leu Thr Leu Asn Asn Ile Glu Thr
                245                 250                 255

Thr Trp Asn Ser Phe Ile Arg Ile Leu Gln Leu Val Trp His Thr Thr
                260                 265                 270

Val Trp Tyr Ser Ser Ile Ser Asn Val Lys Leu Gln Gly Gln Leu Asp
                275                 280                 285

Phe Arg Asp Phe Asp Tyr Ser Gly Thr Ser Leu Lys Ala Leu Ser Ile
290                 295                 300

His Gln Val Val Ser Asp Val Phe Gly Phe Pro Gln Ser Tyr Ile Tyr
305                 310                 315                 320

Glu Ile Phe Ser Asn Met Asn Ile Lys Asn Phe Thr Val Ser Gly Thr
                325                 330                 335

Arg Met Val His Met Leu Cys Pro Ser Lys Ile Ser Pro Phe Leu His
                340                 345                 350

Leu Asp Phe Ser Asn Asn Leu Leu Thr Asp Thr Val Phe Glu Asn Cys
                355                 360                 365

Gly His Leu Thr Glu Leu Glu Thr Leu Ile Leu Gln Met Asn Gln Leu
                370                 375                 380

Lys Glu Leu Ser Lys Ile Ala Glu Met Thr Thr Gln Met Lys Ser Leu
385                 390                 395                 400

Gln Gln Leu Asp Ile Ser Gln Asn Ser Val Ser Tyr Asp Glu Lys Lys
                405                 410                 415
```

Gly Asp Cys Ser Trp Thr Lys Ser Leu Leu Ser Leu Asn Met Ser Ser
            420                 425                 430

Asn Ile Leu Thr Asp Thr Ile Phe Arg Cys Leu Pro Pro Arg Ile Lys
        435                 440                 445

Val Leu Asp Leu His Ser Asn Lys Ile Lys Ser Ile Pro Lys Gln Val
450                 455                 460

Val Lys Leu Glu Ala Leu Gln Glu Leu Asn Val Ala Phe Asn Ser Leu
465                 470                 475                 480

Thr Asp Leu Pro Gly Cys Gly Ser Phe Ser Ser Leu Ser Val Leu Ile
                485                 490                 495

Ile Asp His Asn Ser Val Ser His Pro Ser Ala Asp Phe Phe Gln Ser
                500                 505                 510

Cys Gln Lys Met Arg Ser Ile Lys Ala Gly Asp Asn Pro Phe Gln Cys
            515                 520                 525

Thr Cys Glu Leu Gly Glu Phe Val Lys Asn Ile Asp Gln Val Ser Ser
        530                 535                 540

Glu Val Leu Glu Gly Trp Pro Asp Ser Tyr Lys Cys Asp Tyr Pro Glu
545                 550                 555                 560

Ser Tyr Arg Gly Thr Leu Leu Lys Asp Phe His Met Ser Glu Leu Ser
                565                 570                 575

Cys Asn Ile Thr Leu Leu Ile Val Thr Ile Val Ala Thr Met Leu Val
                580                 585                 590

Leu Ala Val Thr Val Thr Ser Leu Cys Ile Tyr Leu Asp Leu Pro Trp
            595                 600                 605

Tyr Leu Arg Met Val Cys Gln Trp Thr Gln Thr Arg Arg Arg Ala Arg
        610                 615                 620

Asn Ile Pro Leu Glu Glu Leu Gln Arg Asn Leu Gln Phe His Ala Phe
625                 630                 635                 640

Ile Ser Tyr Ser Gly His Asp Ser Phe Trp Met Lys Asn Glu Leu Leu
                645                 650                 655

Pro Asn Leu Glu Lys Glu Gly Met Gln Ile Cys Leu His Glu Arg Asn
                660                 665                 670

Phe Val Pro Gly Lys Ser Ile Val Glu Asn Ile Ile Thr Cys Ile Glu
            675                 680                 685

Lys Ser Tyr Lys Ser Ile Phe Val Leu Ser Pro Asn Phe Val Gln Ser
        690                 695                 700

Glu Trp Cys His Tyr Glu Leu Tyr Phe Ala His His Asn Leu Phe His
705                 710                 715                 720

Glu Gly Ser Asn Ser Leu Ile Leu Ile Leu Leu Glu Pro Ile Pro Gln
                725                 730                 735

Tyr Ser Ile Pro Ser Ser Tyr His Lys Leu Lys Ser Leu Met Ala Arg
                740                 745                 750

Arg Thr Tyr Leu Glu Trp Pro Lys Glu Lys Ser Lys Arg Gly Leu Phe
            755                 760                 765

Trp Ala Asn Leu Arg Ala Ala Ile Asn Ile Lys Leu Thr Glu Gln Ala
        770                 775                 780

Lys Lys
785

<210> SEQ ID NO 36
<211> LENGTH: 796
<212> TYPE: PRT
<213> ORGANISM: artificial
<220> FEATURE:

<223> OTHER INFORMATION: Homo sapiens TLR6

<400> SEQUENCE: 36

```
Met Thr Lys Asp Lys Glu Pro Ile Val Lys Ser Phe His Phe Val Cys
1               5                   10                  15

Leu Met Ile Ile Ile Val Gly Thr Arg Ile Gln Phe Ser Asp Gly Asn
            20                  25                  30

Glu Phe Ala Val Asp Lys Ser Lys Arg Gly Leu Ile His Val Pro Lys
        35                  40                  45

Asp Leu Pro Leu Lys Thr Lys Val Leu Asp Met Ser Gln Asn Tyr Ile
    50                  55                  60

Ala Glu Leu Gln Val Ser Asp Met Ser Phe Leu Ser Glu Leu Thr Val
65                  70                  75                  80

Leu Arg Leu Ser His Asn Arg Ile Gln Leu Leu Asp Leu Ser Val Phe
                85                  90                  95

Lys Phe Asn Gln Asp Leu Glu Tyr Leu Asp Leu Ser His Asn Gln Leu
            100                 105                 110

Gln Lys Ile Ser Cys His Pro Ile Val Ser Phe Arg His Leu Asp Leu
        115                 120                 125

Ser Phe Asn Asp Phe Lys Ala Leu Pro Ile Cys Lys Glu Phe Gly Asn
    130                 135                 140

Leu Ser Gln Leu Asn Phe Leu Gly Leu Ser Ala Met Lys Leu Gln Lys
145                 150                 155                 160

Leu Asp Leu Leu Pro Ile Ala His Leu His Leu Ser Tyr Ile Leu Leu
                165                 170                 175

Asp Leu Arg Asn Tyr Tyr Ile Lys Glu Asn Glu Thr Glu Ser Leu Gln
            180                 185                 190

Ile Leu Asn Ala Lys Thr Leu His Leu Val Phe His Pro Thr Ser Leu
        195                 200                 205

Phe Ala Ile Gln Val Asn Ile Ser Val Asn Thr Leu Gly Cys Leu Gln
    210                 215                 220

Leu Thr Asn Ile Lys Leu Asn Asp Asp Asn Cys Gln Val Phe Ile Lys
225                 230                 235                 240

Phe Leu Ser Glu Leu Thr Arg Gly Pro Thr Leu Leu Asn Phe Thr Leu
                245                 250                 255

Asn His Ile Glu Thr Thr Trp Lys Cys Leu Val Arg Val Phe Gln Phe
            260                 265                 270

Leu Trp Pro Lys Pro Val Glu Tyr Leu Asn Ile Tyr Asn Leu Thr Ile
        275                 280                 285

Ile Glu Ser Ile Arg Glu Glu Asp Phe Thr Tyr Ser Lys Thr Thr Leu
    290                 295                 300

Lys Ala Leu Thr Ile Glu His Ile Thr Asn Gln Val Phe Leu Phe Ser
305                 310                 315                 320

Gln Thr Ala Leu Tyr Thr Val Phe Ser Glu Met Asn Ile Met Met Leu
                325                 330                 335

Thr Ile Ser Asp Thr Pro Phe Ile His Met Leu Cys Pro His Ala Pro
            340                 345                 350

Ser Thr Phe Lys Phe Leu Asn Phe Thr Gln Asn Val Phe Thr Asp Ser
        355                 360                 365

Ile Phe Glu Lys Cys Ser Thr Leu Val Lys Leu Glu Thr Leu Ile Leu
    370                 375                 380

Gln Lys Asn Gly Leu Lys Asp Leu Phe Lys Val Gly Leu Met Thr Lys
385                 390                 395                 400
```

-continued

Asp Met Pro Ser Leu Glu Ile Leu Asp Val Ser Trp Asn Ser Leu Glu
                405                 410                 415
Ser Gly Arg His Lys Glu Asn Cys Thr Trp Val Glu Ser Ile Val Val
            420                 425                 430
Leu Asn Leu Ser Ser Asn Met Leu Thr Asp Ser Val Phe Arg Cys Leu
        435                 440                 445
Pro Pro Arg Ile Lys Val Leu Asp Leu His Ser Asn Lys Ile Lys Ser
450                 455                 460
Val Pro Lys Gln Val Lys Leu Glu Ala Leu Gln Glu Leu Asn Val
465                 470                 475                 480
Ala Phe Asn Ser Leu Thr Asp Leu Pro Gly Cys Gly Ser Phe Ser Ser
                485                 490                 495
Leu Ser Val Leu Ile Ile Asp His Asn Ser Val Ser His Pro Ser Ala
            500                 505                 510
Asp Phe Phe Gln Ser Cys Gln Lys Met Arg Ser Ile Lys Ala Gly Asp
        515                 520                 525
Asn Pro Phe Gln Cys Thr Cys Glu Leu Arg Glu Phe Val Lys Asn Ile
    530                 535                 540
Asp Gln Val Ser Ser Glu Val Leu Glu Gly Trp Pro Asp Ser Tyr Lys
545                 550                 555                 560
Cys Asp Tyr Pro Glu Ser Tyr Arg Gly Ser Pro Leu Lys Asp Phe His
                565                 570                 575
Met Ser Glu Leu Ser Cys Asn Ile Thr Leu Leu Ile Val Thr Ile Gly
            580                 585                 590
Ala Thr Met Leu Val Leu Ala Val Thr Val Thr Ser Leu Cys Ile Tyr
        595                 600                 605
Leu Asp Leu Pro Trp Tyr Leu Arg Met Val Cys Gln Trp Thr Gln Thr
    610                 615                 620
Arg Arg Arg Ala Arg Asn Ile Pro Leu Glu Glu Leu Gln Arg Asn Leu
625                 630                 635                 640
Gln Phe His Ala Phe Ile Ser Tyr Ser Glu His Asp Ser Ala Trp Val
                645                 650                 655
Lys Ser Glu Leu Val Pro Tyr Leu Glu Lys Glu Asp Ile Gln Ile Cys
            660                 665                 670
Leu His Glu Arg Asn Phe Val Pro Gly Lys Ser Ile Val Glu Asn Ile
        675                 680                 685
Ile Asn Cys Ile Glu Lys Ser Tyr Lys Ser Ile Phe Val Leu Ser Pro
    690                 695                 700
Asn Phe Val Gln Ser Glu Trp Cys His Tyr Glu Leu Tyr Phe Ala His
705                 710                 715                 720
His Asn Leu Phe His Glu Gly Ser Asn Asn Leu Ile Leu Ile Leu Leu
                725                 730                 735
Glu Pro Ile Pro Gln Asn Ser Ile Pro Asn Lys Tyr His Lys Leu Lys
            740                 745                 750
Ala Leu Met Thr Gln Arg Thr Tyr Leu Gln Trp Pro Lys Glu Lys Ser
        755                 760                 765
Lys Arg Gly Leu Phe Trp Ala Asn Ile Arg Ala Ala Phe Asn Met Lys
    770                 775                 780
Leu Thr Leu Val Thr Glu Asn Asn Asp Val Lys Ser
785                 790                 795

<210> SEQ ID NO 37
<211> LENGTH: 1063
<212> TYPE: PRT

<213> ORGANISM: artificial
<220> FEATURE:
<223> OTHER INFORMATION: Salmo salar TLR7

<400> SEQUENCE: 37

```
Met Leu Ser Arg Met Thr Arg Ser Glu Cys Ala Ser Phe His Val Cys
1               5                   10                  15

Gly Val Ile Leu Leu Gly Leu Trp Cys Ser Ser Val Leu Ala Ala Gly
            20                  25                  30

Ser Trp Tyr Pro Lys Thr Leu Pro Cys Asp Val Thr Leu Asp Ser Asn
        35                  40                  45

Asp Thr Met Val Asn Val Asp Cys Thr Glu Arg Gly Leu Leu Glu Val
    50                  55                  60

Pro Lys Asp Ile Pro Arg Asn Thr Thr Asn Leu Thr Leu Thr Ile Asn
65                  70                  75                  80

His Ile Pro His Ile Asn Ser Thr Ser Phe Gln Gly Leu Glu Asn Leu
                85                  90                  95

Thr Glu Ile Asp Met Arg Cys Asn Cys Val Pro Ile Lys Ile Gly Pro
            100                 105                 110

Lys Asp Arg Met Cys Thr Glu Ser Val Thr Ile Lys Thr Asn Thr Phe
        115                 120                 125

Lys Asp Leu Arg Asn Leu Lys Ala Leu Tyr Leu Asp Gly Asn Gln Leu
    130                 135                 140

Ser Ser Ile Pro Lys Gly Leu Pro Pro Asn Leu Ile Leu Leu Ser Leu
145                 150                 155                 160

Glu Val Asn Lys Ile Tyr Thr Ile Leu Lys Arg Asn Leu Ser Asp Ile
                165                 170                 175

Thr Asn Val Gln Ile Leu Tyr Leu Gly Gln Asn Cys Tyr Tyr Arg Asn
            180                 185                 190

Pro Cys Asn Val Ser Tyr Gln Ile Glu Glu Gly Ala Phe Leu Gln Leu
        195                 200                 205

Gly Asn Met Thr Leu Leu Ser Leu Lys Ser Asn Asn Leu Ser Tyr Ile
    210                 215                 220

Pro Pro Arg Leu Pro Thr Ser Leu Arg Glu Leu Tyr Leu Tyr Asn Asn
225                 230                 235                 240

Lys Ile Glu Met Val Thr Asp Lys Asp Phe His Asn Leu Thr Gln Leu
                245                 250                 255

Glu Ile Leu Asp Leu Cys Gly Asn Cys Pro Arg Cys Tyr Asn Ala Pro
            260                 265                 270

Phe Pro Cys Ile Pro Cys Pro Asn Asn Ser Leu Gln Ile Asp Pro Ser
        275                 280                 285

Thr Phe Lys Thr Leu Thr Lys Leu Arg Ile Leu Arg Leu His Ser Asn
    290                 295                 300

Ser Leu Thr Tyr Val Leu Arg Glu Trp Phe Gln Asn Cys Lys Glu Leu
305                 310                 315                 320

Arg Val Leu Asp Leu Ser Thr Asn Phe Leu Ala Arg Glu Ile Ala Ile
                325                 330                 335

Thr Tyr Phe Pro Arg Ala Leu Pro Asn Leu Glu Glu Leu Asp Leu Ser
            340                 345                 350

Phe Asn Tyr Glu Leu Gln Arg Tyr Pro Ala Thr Leu His Leu Ser Pro
        355                 360                 365

Ser Phe Ser Ser Leu Lys Ser Leu Lys Val Leu Arg Ile Arg Ala Phe
    370                 375                 380

Val Phe Gln Gln Leu Thr Leu Glu Asp Ile Ser Pro Leu Ile His Leu
```

```
385                 390                 395                 400

Lys Asn Leu Glu Val Ile Asp Leu Gly Thr Asn Phe Ile Lys Ile Thr
                405                 410                 415

Asn Leu Ser Ile Leu Met Glu Leu Lys Ser Phe Lys Ile Ile Asn Leu
                420                 425                 430

Ser Asp Asn Lys Ile Ser Ser Pro Ser Glu Ser Gly Gln Ser Val Ala
                435                 440                 445

Phe Ser Gly Gly Glu Ala Ile His Gly Ser Pro Met Ser Asp Ala Gly
                450                 455                 460

His Asn Arg Asn Gly Glu Val Arg Glu Ile His Tyr Phe Arg Tyr Asp
465                 470                 475                 480

Glu Tyr Ala Arg Ser Cys Lys Tyr Lys Asp Lys Glu Asp Gly Thr Leu
                485                 490                 495

Asn Ser Phe Val Asn Thr Gln Cys Ser Lys Phe Gly Lys Thr Leu Asp
                500                 505                 510

Ile Ser Arg Asn Asn Ile Phe Phe Leu His Ser Arg Phe Leu Asn Leu
                515                 520                 525

Ala Asp Leu Arg Cys Leu Asn Leu Ser Gly Asn Ala Met Ser Gln Ser
                530                 535                 540

Leu Asn Gly Ser Glu Phe Thr Phe Leu Thr Lys Leu Gln Tyr Leu Asp
545                 550                 555                 560

Phe Ser Phe Asn Arg Leu Asp Leu Leu Tyr Ser Ser Ala Phe Gln Glu
                565                 570                 575

Leu Glu Asn Leu Val Ile Leu Asp Ile Ser Asn Asn Asn His Tyr Phe
                580                 585                 590

Glu Ser Glu Gly Leu Thr His Met Leu Asn Phe Thr Lys Asn Leu Thr
                595                 600                 605

Lys Leu Lys Ile Leu Leu Met Asn Tyr Asn Lys Ile Ser Thr Ser Thr
                610                 615                 620

Asn Thr Glu Leu Glu Ser Arg Ser Leu Glu Lys Leu Glu Phe Lys Gly
625                 630                 635                 640

Asn Arg Leu Asp Met Leu Trp Arg Asp Gly Asp Thr Arg Tyr Ile Asp
                645                 650                 655

Tyr Phe Lys Lys Leu Leu Asn Leu Arg Val Leu Asp Ile Ser His Asn
                660                 665                 670

Asn Leu Asn Phe Ile Pro Gln Gln Val Phe Gln Gly Leu Pro Asp Lys
                675                 680                 685

Leu Thr Asn Leu Tyr Ile Asn Asn Asn Arg Leu Lys Ile Phe Ser Trp
                690                 695                 700

Glu Lys Leu Ile Ile Leu Gln Tyr Leu Glu Val Leu Asp Leu Ser Ser
705                 710                 715                 720

Asn Ser Ile Ser Thr Val Pro Pro Glu Leu Ser Asn Cys Thr Lys Ser
                725                 730                 735

Leu Lys Thr Leu Leu Leu Arg Arg Asn Gln Ile Ser Lys Leu Ser Ala
                740                 745                 750

Tyr Phe Leu Lys Asp Ala Phe Ser Leu Lys Tyr Leu Asp Leu Ser Phe
                755                 760                 765

Asn His Ile Gln Asn Ile Glu Gln Thr Ser Ile Pro Asp Asp Val Val
                770                 775                 780

Asp Gln Met Asp Thr Leu Val Leu Asn Asn Lys Phe Met Cys Asn
785                 790                 795                 800

Cys Asn Ala Leu Met Phe Val Met Trp Leu Asn Arg Thr Met Val Asn
                805                 810                 815
```

```
Ile Pro Arg Leu Ala Thr Ala Val Val Cys Ala Ala Pro Gly Ala Gln
            820                 825                 830

Arg Gly His Pro Val Ile Ser Leu Asp Leu Glu Leu Gln Ala Cys Gln
            835                 840                 845

His Asn Tyr Leu Ser Ile Ile Leu Tyr Ile Leu Leu Thr Ser Leu Val
            850                 855                 860

Leu Ser Phe Val Thr Leu Pro Ile Ser Ser His Leu Phe Leu Trp Asp
865                 870                 875                 880

Val Trp Tyr Leu Tyr His Phe Leu Leu Ala Lys Phe Lys Gly Tyr Arg
                885                 890                 895

Arg Leu Ser Ser Pro Ser Ala Ala Tyr Asp Ala Phe Val Tyr Asp
            900                 905                 910

Lys Lys Asp Pro Glu Val Ser Glu Trp Val Leu Lys Glu Leu Leu Val
            915                 920                 925

Gln Leu Glu Glu His Gly Asp His Pro Leu Gln Leu Cys Leu Glu Glu
            930                 935                 940

Arg Asp Trp Ile Pro Gly Cys Pro Leu Ile Asp Asn Leu Ser Gln Ser
945                 950                 955                 960

Ile His Gln Ser Lys Arg Thr Val Phe Ile Leu Thr Asn Lys Tyr Ile
                965                 970                 975

Lys Ser Gly Asp Phe Lys Thr Ala Phe Tyr Met Ala His Gln Arg Leu
            980                 985                 990

Met Asp Glu Arg Asp Asp Val Ile  Val Leu Ile Phe Leu  Glu Lys Val
            995                 1000                1005

Pro Ser  His Ser Lys Tyr Leu  Arg Leu Arg Lys Arg  Leu Tyr Arg
         1010                 1015                 1020

Arg Ser  Val Ile Glu Trp Pro  Thr Asn Pro Gln Ala  Gln Gln Tyr
         1025                 1030                 1035

Phe Trp  Phe Ser Leu Arg Ser  Val Leu Val Thr Asp  Ser Gln Lys
         1040                 1045                 1050

Gln Tyr  Ser Asn Leu Phe Lys  Glu Thr Arg
         1055                 1060

<210> SEQ ID NO 38
<211> LENGTH: 1054
<212> TYPE: PRT
<213> ORGANISM: artificial
<220> FEATURE:
<223> OTHER INFORMATION: Xenopus tropicalis TLR7

<400> SEQUENCE: 38

Met His Gly Lys Thr Phe Lys Val Phe Tyr Phe Gly Met Arg Arg Gln
1               5                   10                  15

Leu Leu Phe Phe Leu Ile Ser Ile Leu Ser Phe Ser Gly Leu Leu Ala
            20                  25                  30

Thr Asn Trp Phe Pro Lys Ser Leu Pro Cys Asp Val Glu Gln Asn Ala
            35                  40                  45

Lys Gly Asn Val Ile Val Val Asp Cys Ser Asp Arg His Leu Thr Ser
        50                  55                  60

Ile Pro Trp Gly Ile Pro Thr Asn Val Thr Asn Leu Thr Leu Thr Ile
65                  70                  75                  80

Asn His Ile Pro Arg Ile Ser Val Asp Ser Phe Ala Glu Phe Thr Asn
                85                  90                  95

Leu Val Glu Leu Asp Phe Arg Cys Asn Cys Val Pro Ala Lys Val Gly
            100                 105                 110
```

```
Pro Lys Asp His Val Cys Thr Lys Arg Leu Asp Val Glu Asp Arg Ser
            115                 120                 125

Phe Ala Ser Leu Tyr Asn Leu Arg Ser Leu Tyr Leu Asp Gly Asn Gln
130                 135                 140

Leu Ile Glu Phe Pro Lys Gly Leu Pro Pro Asn Leu Gln Leu Leu Ser
145                 150                 155                 160

Leu Glu Ile Asn Asn Ile Ile Ser Ile Ser Arg Asn Asn Leu Ser Glu
            165                 170                 175

Leu Ser Asn Ile Gln Met Leu Tyr Leu Gly Gln Asn Cys Tyr His Arg
            180                 185                 190

Asn Pro Cys Ser Asp Ser Phe Lys Ile Glu Lys Asp Ala Phe Lys Asp
            195                 200                 205

Leu Lys Asn Leu Ser Ile Leu Ser Met Lys Ser Asn Asn Leu Ser Phe
210                 215                 220

Val Pro Gly Gly Leu Ser Asp Ser Leu Lys Glu Leu Tyr Leu Tyr Asn
225                 230                 235                 240

Asn Ala Ile Gln Tyr Ile Glu Glu His Asp Leu Glu Asn Leu Ile Asn
            245                 250                 255

Leu Glu Ile Leu Asp Leu Ser Gly Asn Cys Pro Arg Cys Tyr Asn Ser
            260                 265                 270

Pro Phe Pro Cys Thr Pro Cys Pro Asn Asn Ala Pro Ile Gln Ile His
            275                 280                 285

Pro Lys Ala Phe Ser Ser Leu Lys Asn Leu Gln Val Leu Arg Leu His
            290                 295                 300

Ser Asn Ser Leu Arg Ser Ile Pro Glu Gln Trp Phe Lys Asn Asn Arg
305                 310                 315                 320

Asn Leu Gln Val Leu Asp Leu Ser Glu Asn Phe Leu Ala Ser Glu Ile
            325                 330                 335

Ser Thr Ala Asn Phe Leu Lys Tyr Ile Pro Ser Leu Lys Ser Leu Asp
            340                 345                 350

Leu Ser Phe Asn Phe Glu Leu Gln Val Tyr Pro Ser Asp Leu Lys Leu
            355                 360                 365

Ser Ser Ile Phe Ser Ser Leu Ala Ser Leu Glu Thr Leu Arg Ile Arg
            370                 375                 380

Gly Tyr Val Phe Gln Asn Leu Lys Lys Asn Asn Leu Met Pro Leu Val
385                 390                 395                 400

His Leu Pro Asn Leu Thr Leu Leu Asp Leu Ser Thr Asn Phe Ile Lys
            405                 410                 415

Val Ala Asp Phe Ser Leu Phe Pro Lys Phe Lys Ser Leu Gln Thr Ile
            420                 425                 430

Ile Leu Ser Asn Asn Lys Ile Ser Pro Ser Ser Glu Ala Asn Ile Asp
            435                 440                 445

Ser Cys Ser Ala Ser Gln Val Ser Ser Gly His Tyr Ile Gly Arg Thr
450                 455                 460

Phe Gln Glu Val His Tyr Phe Glu Tyr Asp Glu Asn Ala Arg Lys Cys
465                 470                 475                 480

Lys Ala Lys Asp Lys Glu Asn Phe Thr Phe Lys Leu Phe Leu Asn Glu
            485                 490                 495

Ser Cys Gln Ala Tyr Gly Gln Ser Leu Asp Leu Ser Gln Asn Asn Ile
            500                 505                 510

Phe Phe Val Lys Ala Thr Asp Phe Thr Asn Leu Ser Phe Leu Lys Cys
            515                 520                 525
```

```
Leu Asn Leu Ser Gly Asn Ala Ile Ser Gln Thr Leu Asn Gly Ser Glu
        530                 535                 540

Phe Arg Asn Leu Asn Arg Leu Lys Tyr Leu Asp Phe Ser Asn Asn Arg
545                 550                 555                 560

Ile Asp Leu Leu Tyr Ser Thr Ala Phe Gln Glu Leu Thr Glu Leu Glu
                565                 570                 575

Val Leu Asp Ile Ser Asn Asn Asp His Tyr Phe Leu Ala Glu Gly Ile
            580                 585                 590

Thr His Val Phe Asn Phe Thr Lys Asn Leu Glu Lys Leu Thr Lys Leu
        595                 600                 605

Met Met Asn Asn Asn Gln Ile Ser Thr Ser Thr Asn Arg His Leu Val
610                 615                 620

Ser Gln Ser Leu Arg Ile Leu Glu Phe Lys Gly Asn Tyr Leu Asn Ile
625                 630                 635                 640

Leu Trp Lys Asp Gly Asp Thr Arg Tyr Leu Asn Phe Phe Lys Asn Leu
                645                 650                 655

Asn Lys Leu Tyr Lys Leu Asp Ile Ser Glu Asn Ser Leu Thr Phe Val
                660                 665                 670

Pro Pro Gly Val Phe Glu Gly Met Pro Pro Asp Leu Leu Glu Leu Tyr
            675                 680                 685

Leu Ala Arg Asn Lys Leu Lys Thr Phe Ser Trp Asp Lys Leu His Leu
690                 695                 700

Leu Glu Lys Leu Ser Val Leu Asp Leu Ser Asn Asn Tyr Leu Thr Thr
705                 710                 715                 720

Val Pro Arg Glu Leu Ser Asn Cys Thr Ser Ile Lys Lys Leu Ile
                725                 730                 735

Leu Ser Asn Asn Lys Ile Lys Lys Leu Thr Pro Phe Phe Leu Arg Gly
                740                 745                 750

Ser Val Ser Leu Lys Tyr Leu Asp Leu Ser Asp Asn Leu Ile Gln Asn
            755                 760                 765

Ile Gly His Ser Ser Phe Pro Glu Asp Val Leu Asp Asn Leu Thr Glu
            770                 775                 780

Leu Leu Leu Gln Gly Asn Pro Phe Lys Cys Asn Cys Asn Leu Val Trp
785                 790                 795                 800

Leu Val Ser Trp Ile Asn Gln Thr Lys Val Tyr Ile Pro Asn Leu Val
                805                 810                 815

Thr Gly Val Thr Cys Ser Gly Pro Gly Ala His Arg Gly Gln Ser Leu
            820                 825                 830

Val Leu Leu Asp Leu Tyr Thr Cys Glu Gln Tyr His Leu Asn Leu Ile
            835                 840                 845

Leu Gln Ala Leu Ser Ala Ser Phe Ile Ile Cys Leu Met Val Val Ser
850                 855                 860

Val Ser Ser His Leu Phe Tyr Trp Asp Phe Trp Phe Ile Tyr His Leu
865                 870                 875                 880

Phe Lys Ala Lys Ile His Gly Tyr Lys Arg Phe Pro Lys Cys Cys Tyr
                885                 890                 895

Asp Ala Leu Ile Met Tyr Asp Thr Lys Asp Ser Ala Val Ser Asp Trp
                900                 905                 910

Val Phe Asn Asp Leu Val Asn Ile Leu Glu Lys Gln Gly Asn Lys Met
            915                 920                 925

Leu Asn Leu Cys Leu Glu Glu Arg Asp Phe Leu Ala Gly Gln Pro Phe
930                 935                 940

Leu Asp Asn Leu Ser Glu Ser Ile Gln Ile Ser Arg Lys Thr Val Phe
```

```
945                 950                 955                 960
Val Leu Thr Arg Lys Tyr Val Lys Gly His Phe Lys Thr Ala Phe
                965                 970                 975
Tyr Met Ala His Gln Arg Leu Ile Glu Glu Lys Val Asp Val Ile Ile
                980                 985                 990
Leu Ile Leu Leu Glu Lys Thr Leu Gln Arg Ser Arg Tyr Leu Arg Leu
                995                1000                1005
Arg Lys Arg Leu Cys Ala Asn Ser Val Leu Tyr Trp Pro Ser Asn
    1010                1015                1020
Pro Asn Ser Gln Ser Tyr Phe Trp His Cys Leu Lys Ser Ala Ile
        1025                1030                1035
Ala Thr Glu Asn Gln Met Ala Tyr Asp Lys Leu Phe Lys Asp His
        1040                1045                1050
Thr

<210> SEQ ID NO 39
<211> LENGTH: 1059
<212> TYPE: PRT
<213> ORGANISM: artificial
<220> FEATURE:
<223> OTHER INFORMATION: Gallus gallus TLR7

<400> SEQUENCE: 39

Met Thr Asn Leu Ser Glu Val Ala Ala His Arg Lys Met Val His His
1               5                  10                  15
Ala Arg Thr Ser Asn Ala Leu Leu Phe Val Leu Leu Phe Leu Phe Pro
                20                  25                  30
Met Leu Leu Ser Gly Arg Trp Phe Pro Lys Thr Leu Pro Cys Asp Val
            35                  40                  45
Glu Ala Phe Glu Ser Thr Val Arg Val Asp Cys Ser Asp Arg Arg Leu
        50                  55                  60
Lys Glu Val Pro Arg Gly Ile Pro Gly Asn Ala Thr Asn Leu Thr Leu
65                  70                  75                  80
Thr Ile Asn His Ile Pro Arg Ile Ser Pro Ala Ser Phe Thr Gln Leu
                85                  90                  95
Glu Asn Leu Val Glu Ile Asp Phe Arg Cys Asn Cys Val Pro Pro Arg
                100                 105                 110
Leu Gly Pro Lys Asp Asn Val Cys Val Thr Pro Pro Ser Ile Glu Asn
            115                 120                 125
Gly Ser Phe Ala Ala Leu Thr Arg Leu Lys Ser Leu Tyr Leu Asp Ala
        130                 135                 140
Asn Gln Leu Ser Lys Ile Pro Arg Gly Leu Pro Ala Thr Leu Arg Leu
145                 150                 155                 160
Leu Ser Leu Glu Ala Asn Ile Phe Ser Ile Lys Lys Asn Thr Phe
                165                 170                 175
Ser Glu Leu Arg Asn Ile Glu Leu Leu Tyr Leu Gly Gln Asn Cys Tyr
                180                 185                 190
Tyr Arg Asn Pro Cys Asn Val Ser Phe Glu Ile Glu Glu Thr Ala Phe
            195                 200                 205
Leu Asn Leu Lys Asn Leu Thr Val Leu Ser Leu Lys Ser Asn Asn Leu
        210                 215                 220
Thr Phe Ile Pro Pro Asn Leu Ser Ser Thr Leu Lys Glu Leu Tyr Ile
225                 230                 235                 240
Tyr Asn Asn Arg Ile Gln Glu Val Gln Glu His Asp Leu Ser Asn Leu
                245                 250                 255
```

```
Tyr Asn Leu Glu Ile Leu Asp Leu Ser Gly Asn Cys Pro Arg Cys Tyr
            260                 265                 270

Asn Ala Pro Tyr Pro Cys Thr Pro Cys Pro Asn Ile Ser Ile Lys Ile
            275                 280                 285

His Ser Lys Ala Phe Tyr Ser Leu Lys Lys Leu Arg Ile Leu Arg Leu
            290                 295                 300

His Ser Asn Ser Leu Gln Ser Ile Pro Ser Ser Trp Phe Lys Asn Ile
305                 310                 315                 320

Lys Asn Leu Lys Asn Leu Asp Leu Ser Gln Asn Phe Leu Ile Lys Glu
                325                 330                 335

Ile Gly Asp Ala Glu Phe Leu Lys Leu Ile Pro Ser Leu Val Glu Leu
            340                 345                 350

Asp Leu Ser Phe Asn Phe Glu Leu Gln Met Tyr Ser Pro Phe Leu Asn
            355                 360                 365

Leu Ser Lys Thr Phe Ser Cys Leu Ser Asn Leu Glu Thr Leu Arg Ile
            370                 375                 380

Lys Gly Tyr Val Phe Lys Glu Leu Arg Glu Glu Asn Leu Asp Pro Leu
385                 390                 395                 400

Leu Asn Leu Arg Asn Leu Thr Val Leu Asp Leu Gly Thr Asn Phe Ile
                405                 410                 415

Lys Ile Ala Asp Leu Arg Val Phe Lys Lys Phe Arg Ser Leu Lys Ile
            420                 425                 430

Ile Asp Leu Ser Met Asn Lys Ile Ser Pro Ser Ser Gly Glu Gly Asn
            435                 440                 445

Phe Tyr Gly Phe Cys Ser Asp His Arg Ile Thr Val Glu Gln Tyr Ser
            450                 455                 460

Arg His Val Leu Gln Glu Met His Tyr Phe Arg Tyr Asp Glu Tyr Gly
465                 470                 475                 480

Arg Ser Cys Lys Ser Lys Asp Lys Glu Ala Asp Ser Tyr Gln Pro Leu
                485                 490                 495

Val Asn Gly Asp Cys Met Ser Tyr Gly Glu Thr Leu Asp Leu Ser Arg
            500                 505                 510

Asn Asn Ile Phe Phe Val Asn Ser Ile Asp Phe Gln Asp Leu Ser Phe
            515                 520                 525

Leu Lys Cys Leu Asn Leu Ser Gly Asn Ala Ile Ser Gln Thr Leu Asn
            530                 535                 540

Gly Ser Glu Phe Tyr Tyr Leu Ser Gly Leu Lys Tyr Leu Asp Phe Ser
545                 550                 555                 560

Asn Asn Arg Ile Asp Leu Leu Tyr Ser Thr Ala Phe Lys Glu Leu Lys
                565                 570                 575

Phe Leu Glu Ile Leu Asp Leu Ser Asn Asn Lys His Tyr Phe Leu Ala
            580                 585                 590

Glu Gly Val Ser His Val Leu Ser Phe Met Lys Asn Leu Ala Tyr Leu
            595                 600                 605

Lys Lys Leu Met Met Asn Glu Asn Glu Ile Ser Thr Ser Ile Ser Thr
            610                 615                 620

Gly Met Glu Ser Gln Ser Leu Gln Thr Leu Glu Phe Arg Gly Asn Arg
625                 630                 635                 640

Leu Asp Ile Phe Trp Ser Asp Gly Lys Lys Glu Tyr Leu Ser Phe Phe
                645                 650                 655

Lys Asn Leu Thr Asn Leu Glu Gln Leu Asp Ile Ser Ser Asn Met Leu
            660                 665                 670
```

```
Asn Phe Leu Pro Pro Asp Val Phe Glu Ala Met Pro Pro Glu Leu Lys
            675                 680                 685

Ile Leu Asn Leu Thr Ser Asn Arg Leu His Thr Phe Asn Trp Gly Lys
690                 695                 700

Leu His Leu Leu Thr Lys Leu Ile Thr Leu Asp Leu Ser Asn Asn Leu
705                 710                 715                 720

Leu Thr Thr Val Pro Arg Lys Leu Ser Asn Cys Thr Ser Thr Leu Gln
            725                 730                 735

Glu Leu Ile Leu Arg Asn Asn Arg Ile Thr Arg Ile Thr Lys Tyr Phe
            740                 745                 750

Leu Arg Gly Ala Ile Gln Leu Thr Tyr Leu Asp Leu Ser Ser Asn Lys
        755                 760                 765

Ile Gln Ile Ile Lys Lys Ser Ser Phe Pro Glu Asn Ile Ile Asn Asn
        770                 775                 780

Leu Arg Met Leu Leu Leu His Asn Asn Pro Phe Lys Cys Asn Cys Asp
785                 790                 795                 800

Ala Val Trp Phe Val Gly Trp Ile Asn Gln Thr Gln Val Ala Ile Pro
                805                 810                 815

Leu Leu Ala Thr Asp Val Thr Cys Ala Gly Pro Gly Ala His Lys Gly
            820                 825                 830

Arg Ser Leu Val Phe Leu Asp Leu Asn Thr Cys Glu Leu Asp Thr Ser
        835                 840                 845

Tyr Phe Ile Met Tyr Ala Leu Ser Thr Ser Ala Val Leu Cys Leu Met
    850                 855                 860

Met Phe Ala Val Met Ser His Leu Tyr Phe Trp Asp Val Trp Tyr Ser
865                 870                 875                 880

Tyr His Tyr Cys Thr Ala Lys Leu Lys Gly Tyr Arg Arg Ile Pro Leu
                885                 890                 895

Pro Asp Ala Cys Tyr Asp Ala Phe Ile Ala Tyr Asp Asn Thr Asp Leu
            900                 905                 910

Ala Val Asn Glu Trp Val Met Thr Glu Leu Val Glu Lys Leu Glu Asp
        915                 920                 925

Gln Lys Ala Arg Gln Phe Asn Leu Cys Leu Glu Glu Arg Asp Trp Leu
    930                 935                 940

Pro Gly Gln Pro Val Phe Asp Asn Leu Ser Gln Ser Ile Gln Leu Ser
945                 950                 955                 960

Lys Lys Thr Ile Phe Val Leu Thr Asn Lys Tyr Ile Lys Ser Gly Thr
                965                 970                 975

Phe Lys Thr Thr Phe Tyr Met Ala His Gln Arg Leu Leu Asp Glu Lys
            980                 985                 990

Ile Asp Val Ile Ile Leu Ile Phe  Leu Glu Lys Val Leu  Gln Lys Ser
        995                 1000                1005

Arg Tyr  Val Gln Leu Arg Lys  Arg Leu Cys Arg Ser   Ser Val Leu
    1010                1015                1020

Glu Trp  Pro Thr Asn Pro Arg  Ser Gln Pro Tyr Phe   Trp Gln Arg
    1025                1030                1035

Leu Lys  Asn Ala Ile Ala Met  Asn Asn Thr Leu Ser   Tyr Asn Lys
    1040                1045                1050

Leu Leu  Gln Glu Thr Val
    1055

<210> SEQ ID NO 40
<211> LENGTH: 1050
<212> TYPE: PRT
```

<213> ORGANISM: artificial
<220> FEATURE:
<223> OTHER INFORMATION: Rattus norvegius TLR7

<400> SEQUENCE: 40

```
Met Val Phe Pro Met Trp Thr Leu Lys Arg Gln Ser Phe Ile Phe Leu
1               5                   10                  15

Asn Met Ile Leu Val Ser Arg Val Leu Gly Phe Arg Trp Tyr Pro Lys
            20                  25                  30

Thr Leu Pro Cys Asp Val Ser Leu Asp Ser Thr Asn Thr His Val Ile
        35                  40                  45

Val Asp Cys Thr Asp Lys His Leu Thr Glu Ile Pro Glu Gly Ile Pro
50                  55                  60

Thr Asn Thr Thr Asn Leu Thr Leu Thr Ile Asn His Ile Pro Ser Ile
65                  70                  75                  80

Ser Pro Asp Ser Phe His Arg Leu Lys His Leu Glu Glu Leu Asp Leu
                85                  90                  95

Arg Cys Asn Cys Val Pro Ile Leu Leu Gly Ser Lys Ala Asn Val Cys
            100                 105                 110

Thr Lys Arg Leu Gln Ile Arg Pro Gly Ser Phe Ser Gly Leu Ser Asp
        115                 120                 125

Leu Lys Ser Leu Tyr Leu Asp Gly Asn Gln Leu Leu Glu Ile Pro Gln
130                 135                 140

Asp Leu Pro Ser Ser Leu Gln Leu Leu Ser Leu Glu Ala Asn Asn Ile
145                 150                 155                 160

Phe Ser Ile Thr Lys Glu Asn Leu Ser Glu Leu Val Asn Ile Glu Ser
                165                 170                 175

Leu Tyr Leu Gly Gln Asn Cys Tyr Tyr Arg Asn Pro Cys Asn Val Ser
            180                 185                 190

Tyr Ser Ile Glu Lys Asp Ala Phe Leu Val Met Lys Asn Leu Lys Val
        195                 200                 205

Leu Ser Leu Lys Asp Asn Asn Val Thr Ala Val Pro Thr Ile Leu Pro
210                 215                 220

Pro Asn Leu Leu Glu Leu Tyr Leu Tyr Asn Asn Ile Ile Lys Arg Ile
225                 230                 235                 240

Gln Glu His Asp Phe Asn Lys Leu Ser Gln Leu Gln Val Leu Asp Leu
                245                 250                 255

Ser Gly Asn Cys Pro Arg Cys Tyr Asn Val Pro Tyr Pro Cys Thr Pro
            260                 265                 270

Cys Glu Asn Asn Ser Pro Leu Gln Ile His Asp Asn Ala Phe Asp Ser
        275                 280                 285

Leu Thr Glu Leu Lys Val Leu Arg Leu His Ser Asn Ser Leu Gln His
290                 295                 300

Val Pro Ala Glu Trp Phe Lys Asn Met Ser Asn Leu Gln Glu Leu Asp
305                 310                 315                 320

Leu Ser Gln Asn Tyr Leu Ala Arg Glu Ile Glu Ala Lys Phe Leu
                325                 330                 335

Asn Ser Leu Pro Asn Leu Val Gln Leu Asp Leu Ser Phe Asn Tyr Glu
            340                 345                 350

Leu Gln Val Tyr His Ala Ser Ile Thr Leu Pro His Ser Leu Ser Ser
        355                 360                 365

Leu Thr Lys Leu Lys Asn Leu Tyr Ile Lys Gly Tyr Val Phe Lys Glu
370                 375                 380

Leu Lys Asp Ser Ser Leu Ser Val Leu His Asn Leu Ser Asn Leu Glu
```

-continued

```
             385                 390                 395                 400
        Val Leu Asp Leu Gly Thr Asn Phe Ile Lys Ile Ala Asp Leu Asn Ile
                        405                 410                 415

Phe Gln Gln Phe Glu Asn Leu Lys Phe Ile Asp Leu Ser Val Asn Lys
                        420                 425                 430

Ile Ser Pro Ser Glu Glu Ser Arg Glu Val Gly Leu Cys Pro Asn Ala
                        435                 440                 445

Gln Thr Ser Val Asp Trp His Gly Pro Gln Val Leu Glu Ala Leu His
                450                 455                 460

Tyr Phe Arg Tyr Asp Glu Tyr Ala Arg Ser Cys Arg Phe Lys Asn Lys
        465                 470                 475                 480

Glu Pro Pro Thr Phe Leu Pro Leu Asn Ala Asp Cys His Thr Tyr Gly
                        485                 490                 495

Lys Thr Leu Asp Leu Ser Arg Asn Asn Ile Phe Phe Ile Lys Pro Ser
                        500                 505                 510

Asp Phe Lys His Leu Ser Phe Leu Lys Cys Leu Asn Leu Ser Gly Asn
                        515                 520                 525

Ala Ile Gly Gln Thr Leu Asn Gly Ser Glu Leu Gln Pro Leu Arg Glu
                530                 535                 540

Leu Arg Tyr Leu Asp Phe Ser Asn Asn Arg Leu Asp Leu Leu Tyr Ser
        545                 550                 555                 560

Thr Ala Phe Glu Glu Leu Gln Asn Leu Glu Ile Leu Asp Leu Ser Ser
                        565                 570                 575

Asn Ser His Tyr Phe Gln Ala Glu Gly Ile Thr His Met Leu Asn Phe
                        580                 585                 590

Thr Lys Lys Leu Arg His Leu Glu Lys Leu Met Met Asn Asp Asn Asp
                        595                 600                 605

Ile Ser Thr Ser Ala Ser Arg Thr Met Glu Ser Glu Ser Leu Arg Val
                        610                 615                 620

Leu Glu Phe Arg Gly Asn His Leu Asp Val Leu Trp Arg Asp Gly Asp
        625                 630                 635                 640

Asn Arg Tyr Leu Asp Phe Phe Lys Asn Leu Leu Asn Leu Glu Glu Leu
                        645                 650                 655

Asp Ile Ser Arg Asn Ser Leu Asn Ser Val Pro Pro Gly Val Phe Glu
                        660                 665                 670

Gly Met Pro Pro Asn Leu Thr Thr Leu Ser Leu Ala Lys Asn Gly Leu
                        675                 680                 685

Arg Ser Phe Ser Trp Gly Arg Leu Gln Leu Leu Lys His Leu Lys Asn
                        690                 695                 700

Leu Asp Leu Ser His Asn Gln Leu Thr Thr Val Pro Ala Arg Leu Ala
        705                 710                 715                 720

Asn Cys Ser Lys Ser Leu Thr Lys Leu Ile Leu Asn His Asn Gln Ile
                        725                 730                 735

Arg Gln Leu Thr Lys Tyr Phe Leu Glu Asp Ala Leu Gln Leu Arg Tyr
                        740                 745                 750

Leu Asp Ile Ser Ser Asn Lys Ile Gln Val Ile Gln Lys Thr Ser Phe
                        755                 760                 765

Pro Glu Asn Val Leu Asn Asn Leu Asn Met Leu Leu Leu His His Asn
                        770                 775                 780

Arg Phe Leu Cys Asn Cys Asp Ala Val Trp Phe Val Trp Trp Val Asn
        785                 790                 795                 800

His Thr Asp Val Thr Ile Pro Tyr Leu Ala Thr Asp Val Thr Cys Ala
                        805                 810                 815
```

-continued

```
Gly Pro Gly Ala His Lys Gly Gln Ser Val Ile Ser Leu Asp Leu Tyr
            820                 825                 830

Thr Cys Glu Leu Asp Leu Thr Asn Leu Ile Leu Phe Ser Val Ser Ile
            835                 840                 845

Ser Ser Val Leu Phe Leu Met Ile Val Met Thr Thr Ser His Leu Phe
850                 855                 860

Phe Trp Asp Met Trp Tyr Ile Tyr Tyr Phe Trp Lys Ala Lys Ile Lys
865                 870                 875                 880

Gly Tyr Gln His Leu Gln Ser Met Glu Ser Cys Tyr Asp Ala Phe Ile
                885                 890                 895

Val Tyr Asp Thr Lys Asn Ser Ala Val Thr Glu Trp Val Leu Gln Glu
            900                 905                 910

Leu Val Val Lys Leu Glu Asp Pro Arg Glu Lys His Phe Asn Leu Cys
            915                 920                 925

Leu Glu Glu Arg Asp Trp Leu Pro Gly Gln Pro Val Leu Glu Asn Leu
930                 935                 940

Ser Gln Ser Ile Gln Leu Ser Arg Lys Thr Val Phe Val Met Thr Gln
945                 950                 955                 960

Lys Tyr Ala Lys Thr Glu Ser Phe Lys Met Ala Phe Tyr Leu Ser His
                965                 970                 975

Gln Arg Leu Met Asp Glu Lys Val Asp Val Ile Ile Leu Ile Phe Leu
            980                 985                 990

Glu Lys Pro Leu Gln Lys Ser Lys Phe Leu Gln Leu Arg Lys Arg Leu
            995                1000                1005

Cys Ser Ser Ser Val Leu Glu Trp Pro Thr Asn Pro Gln Ala His
        1010                1015                1020

Pro Tyr Phe Trp Gln Cys Leu Lys Asn Ala Leu Thr Thr Asp Asn
        1025                1030                1035

His Val Ala Tyr Ser Gln Met Phe Lys Glu Thr Val
        1040                1045                1050

<210> SEQ ID NO 41
<211> LENGTH: 1049
<212> TYPE: PRT
<213> ORGANISM: artificial
<220> FEATURE:
<223> OTHER INFORMATION: Homo sapiens TLR7

<400> SEQUENCE: 41

Met Val Phe Pro Met Trp Thr Leu Lys Arg Leu Ile Leu Ile Leu Phe
1               5                  10                  15

Asn Ile Ile Leu Ile Ser Lys Leu Leu Gly Ala Arg Trp Phe Pro Lys
                20                  25                  30

Thr Leu Pro Cys Asp Val Thr Leu Asp Val Pro Lys Asn His Val Ile
            35                  40                  45

Val Asp Cys Thr Asp Lys His Leu Thr Glu Ile Pro Gly Gly Ile Pro
        50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125
```

```
Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190

Tyr Ser Ile Glu Lys Asp Ala Phe Leu Asn Leu Thr Lys Leu Lys Val
        195                 200                 205

Leu Ser Leu Lys Asp Asn Val Thr Ala Val Pro Thr Val Leu Pro
    210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
            340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
    370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
        435                 440                 445

Arg Thr Ser Val Glu Ser Tyr Glu Pro Gln Val Leu Glu Gln Leu His
    450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Phe Val Lys Ser Ser Asp
            500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
    530                 535                 540
```

```
Arg Tyr Leu Asp Phe Ser Asn Asn Arg Leu Asp Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Lys Leu Glu Glu Leu Asp
                645                 650                 655

Ile Ser Lys Asn Ser Leu Ser Phe Leu Pro Ser Gly Val Phe Asp Gly
                660                 665                 670

Met Pro Pro Asn Leu Lys Asn Leu Ser Leu Ala Lys Asn Gly Leu Lys
                675                 680                 685

Ser Phe Ser Trp Lys Lys Leu Gln Cys Leu Lys Asn Leu Glu Thr Leu
690                 695                 700

Asp Leu Ser His Asn Gln Leu Thr Thr Val Pro Glu Arg Leu Ser Asn
705                 710                 715                 720

Cys Ser Arg Ser Leu Lys Asn Leu Ile Leu Lys Asn Asn Gln Ile Arg
                725                 730                 735

Ser Leu Thr Lys Tyr Phe Leu Gln Asp Ala Phe Gln Leu Arg Tyr Leu
                740                 745                 750

Asp Leu Ser Ser Asn Lys Ile Gln Met Ile Gln Lys Thr Ser Phe Pro
            755                 760                 765

Glu Asn Val Leu Asn Asn Leu Lys Met Leu Leu Leu His His Asn Arg
            770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
            835                 840                 845

Val Ser Leu Phe Leu Met Val Met Met Thr Ala Ser His Leu Tyr Phe
850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
            915                 920                 925

Glu Glu Arg Asp Trp Leu Pro Gly Gln Pro Val Leu Glu Asn Leu Ser
            930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
```

```
                        965                 970                 975
Arg Leu Met Asp Glu Lys Val Asp Val Ile Ile Leu Ile Phe Leu Glu
                980                 985                 990

Lys Pro Phe Gln Lys Ser Lys Phe Leu Gln Leu Arg Lys Arg Leu Cys
            995                1000                1005

Gly Ser Ser Val Leu Glu Trp Pro Thr Asn Pro Gln Ala His Pro
           1010                1015                1020

Tyr Phe Trp Gln Cys Leu Lys Asn Ala Leu Ala Thr Asp Asn His
           1025                1030                1035

Val Ala Tyr Ser Gln Val Phe Lys Glu Thr Val
           1040                1045

<210> SEQ ID NO 42
<211> LENGTH: 1050
<212> TYPE: PRT
<213> ORGANISM: artificial
<220> FEATURE:
<223> OTHER INFORMATION: Sus scrofa TLR7

<400> SEQUENCE: 42

Met Val Phe Pro Val Trp Thr Leu Lys Arg Gln Phe Leu Ile Leu Phe
1               5                  10                  15

Asn Ile Val Leu Ile Ser Glu Leu Leu Gly Ala Arg Trp Phe Pro Lys
            20                  25                  30

Thr Leu Pro Cys Asp Val Ser Leu Asp Ala Pro Asn Ala His Val Ile
        35                  40                  45

Val Asp Cys Thr Asp Lys His Leu Thr Ala Ile Pro Gly Gly Ile Pro
    50                  55                  60

Thr Asn Ala Thr Asn Leu Thr Leu Thr Ile Asn His Ile Ala Ser Ile
65                  70                  75                  80

Thr Pro Ala Ser Phe Gln Gln Leu Asp His Leu Val Glu Ile Asp Phe
                85                  90                  95

Arg Cys Asn Cys Ile Pro Val Arg Leu Gly Pro Lys Asn Leu Cys
            100                 105                 110

Thr Arg Arg Leu Gln Ile Lys Pro Ser Ser Phe Ser Lys Leu Thr Tyr
        115                 120                 125

Leu Lys Ala Leu Tyr Leu Asp Gly Asn Gln Leu Leu Glu Ile Pro Arg
    130                 135                 140

Asp Leu Pro Pro Ser Leu Gln Leu Leu Ser Leu Glu Ala Asn Asn Ile
145                 150                 155                 160

Phe Trp Ile Met Lys Glu Asn Leu Thr Glu Leu Ala Asn Leu Glu Met
                165                 170                 175

Leu Tyr Leu Gly Gln Asn Cys Tyr Tyr Arg Asn Pro Cys Asn Val Ser
            180                 185                 190

Phe Ser Ile Glu Lys Asp Ala Phe Leu Ser Leu Arg Asn Leu Lys Leu
        195                 200                 205

Leu Ser Leu Lys Asp Asn Asn Ile Ser Ala Val Pro Thr Val Leu Pro
    210                 215                 220

Ser Thr Leu Thr Glu Leu Phe Leu Tyr Asn Asn Ile Ile Ala Lys Ile
225                 230                 235                 240

Gln Glu Asp Asp Phe Asn Asn Leu Ser Gln Leu Gln Val Leu Asp Leu
                245                 250                 255

Ser Gly Asn Cys Pro Arg Cys Tyr Asn Val Pro Phe Pro Cys Thr Pro
            260                 265                 270

Cys Glu Asn Asn Ala Pro Leu Gln Ile His Leu His Ala Phe Asp Ala
```

```
            275                 280                 285
Leu Thr Glu Leu Gln Val Leu Arg Leu His Ser Asn Ser Leu Gln Tyr
290                 295                 300

Val Pro Gln Arg Trp Phe Gln Asn Leu Asn Lys Leu Lys Glu Leu Asp
305                 310                 315                 320

Leu Ser Gln Asn Phe Leu Ala Lys Glu Ile Gly Asp Ala Lys Phe Leu
                325                 330                 335

His Leu Leu Pro Asn Leu Val Lys Leu Asp Leu Ser Phe Asn Tyr Glu
            340                 345                 350

Leu Gln Val Tyr His Thr Phe Met Asn Leu Ser Asp Ser Phe Ser Ser
                355                 360                 365

Leu Lys Asn Leu Lys Val Leu Arg Ile Lys Gly Tyr Val Phe Lys Glu
            370                 375                 380

Leu Lys Ser Leu Asn Leu Ser Pro Leu Arg Asn Leu Pro Asn Leu Glu
385                 390                 395                 400

Val Leu Asp Leu Gly Thr Asn Phe Ile Lys Ile Ala Asn Leu Ser Ile
                405                 410                 415

Phe Lys Gln Phe Lys Thr Leu Lys Phe Ile Asp Leu Ser Val Asn Lys
                420                 425                 430

Ile Ser Pro Ser Gly Asp Ser Glu Ser Gly Phe Cys Ser Gly Met
            435                 440                 445

Arg Thr Ser Ala Glu Ser His Gly Pro Gln Val Leu Glu Ser Leu His
            450                 455                 460

Tyr Phe Arg Tyr Asp Glu Tyr Ala Arg Ser Cys Arg Phe Lys Asn Lys
465                 470                 475                 480

Glu Pro Ser Ser Ser Leu Pro Leu Asn Glu Asp Cys Ser Met Tyr Gly
                485                 490                 495

Gln Thr Leu Asp Leu Ser Arg Asn Asn Ile Phe Phe Ile Arg Ser Ser
            500                 505                 510

Glu Phe Gln His Leu Thr Phe Leu Lys Cys Leu Asn Leu Ser Gly Asn
            515                 520                 525

Ser Ile Ser Gln Ala Leu Asn Gly Ser Glu Phe Gln Pro Leu Val Glu
530                 535                 540

Leu Lys Tyr Leu Asp Phe Ser Asn Asn Arg Leu Asp Leu Leu His Ser
545                 550                 555                 560

Thr Ala Phe Glu Glu Leu Arg Asn Leu Glu Val Leu Asp Ile Ser Ser
                565                 570                 575

Asn Ser His Tyr Phe Gln Ser Glu Gly Ile Thr His Met Leu Asp Phe
                580                 585                 590

Thr Lys Asn Leu Lys Val Leu Lys Lys Leu Met Met Asn Asn Asn Asp
            595                 600                 605

Ile Ala Thr Ser Thr Ser Thr Thr Met Glu Ser Glu Ser Leu Arg Ile
            610                 615                 620

Leu Glu Phe Arg Gly Asn His Leu Asp Ile Leu Trp Arg Asp Gly Asp
625                 630                 635                 640

Asn Arg Tyr Leu Lys Phe Phe Lys Asn Leu His Lys Leu Glu Glu Leu
                645                 650                 655

Asp Ile Ser Glu Asn Ser Leu Ser Phe Leu Pro Ser Gly Val Phe Asp
            660                 665                 670

Gly Met Pro Pro Asn Leu Lys Thr Leu Ser Leu Ala Lys Asn Gly Leu
            675                 680                 685

Lys Ser Phe Asn Trp Gly Lys Leu Gln Tyr Leu Gln Asn Leu Glu Thr
690                 695                 700
```

Leu Asp Leu Ser Tyr Asn Gln Leu Lys Thr Val Pro Glu Arg Leu Ser
705                 710                 715                 720

Asn Cys Ser Arg Ser Leu Lys Lys Leu Ile Leu Lys Asn Asn Glu Ile
            725                 730                 735

Arg Asn Leu Thr Lys Tyr Phe Leu Gln Asp Ala Phe Gln Leu Arg His
        740                 745                 750

Leu Asp Leu Ser Ser Asn Lys Ile Gln Val Ile Gln Lys Thr Ser Phe
    755                 760                 765

Pro Glu Asn Val Leu Asn Asn Leu Gln Ile Leu Phe Leu His His Asn
770                 775                 780

Arg Phe Leu Cys Asn Cys Asp Ala Val Trp Leu Val Trp Trp Val Asn
785                 790                 795                 800

His Thr Glu Val Thr Ile Pro Phe Leu Ala Thr Asp Val Thr Cys Met
                805                 810                 815

Gly Pro Gly Ala His Lys Gly Gln Ser Val Val Ser Leu Asp Leu Tyr
            820                 825                 830

Thr Cys Glu Leu Asp Leu Thr Asn Phe Val Leu Phe Ser Leu Ser Leu
        835                 840                 845

Ser Ala Val Leu Phe Leu Ile Val Ile Thr Ile Ala Asn His Leu Tyr
    850                 855                 860

Phe Trp Asp Val Trp Tyr Ser Tyr His Phe Cys Lys Ala Lys Ile Lys
865                 870                 875                 880

Gly Tyr Gln Arg Leu Ile Ser Pro Asn Ser Cys Tyr Asp Ala Phe Ile
                885                 890                 895

Val Tyr Asp Thr Lys Asp Pro Ala Val Thr Glu Trp Val Leu Asp Glu
            900                 905                 910

Leu Val Ala Lys Leu Glu Asp Pro Arg Glu Lys His Phe Asn Leu Cys
        915                 920                 925

Leu Glu Glu Arg Asp Trp Leu Pro Gly Gln Pro Val Leu Glu Asn Leu
    930                 935                 940

Ser Gln Ser Ile Gln Leu Ser Lys Lys Thr Val Phe Val Met Thr Asp
945                 950                 955                 960

Lys Tyr Ala Lys Thr Glu Lys Phe Lys Ile Ala Phe Tyr Leu Ser His
                965                 970                 975

Gln Arg Leu Met Asp Glu Lys Val Asp Val Ile Ile Leu Ile Phe Leu
            980                 985                 990

Glu Lys Pro Leu Gln Lys Ser Lys Phe Phe Gln Leu Arg Lys Arg Leu
        995                 1000                1005

Cys Gly Ser Ser Val Leu Glu Trp Pro Thr Asn Pro Gln Ala His
    1010                1015                1020

Pro Tyr Phe Trp Gln Cys Leu Lys Asn Ala Leu Ala Thr Asp Asn
    1025                1030                1035

His Val Thr Tyr Ser Gln Val Phe Lys Glu Thr Ala
    1040                1045                1050

<210> SEQ ID NO 43
<211> LENGTH: 1058
<212> TYPE: PRT
<213> ORGANISM: artificial
<220> FEATURE:
<223> OTHER INFORMATION: Bos Taurus TLR7

<400> SEQUENCE: 43

Met Gly Asp Leu Phe Leu Tyr Phe Gln Val Phe Pro Met Trp Thr Leu
1               5                   10                  15

```
Lys Arg Gln Phe Pro Ile Leu Phe Asn Met Ile Leu Ile Ser Gly Leu
                20                  25                  30

Leu Gly Ala Arg Trp Phe Pro Lys Thr Leu Pro Cys Asp Val Thr Leu
            35                  40                  45

Asp Ala Pro Asn Thr His Val Ile Val Asp Cys Thr Asp Lys His Leu
 50                  55                  60

Thr Glu Ile Pro Gly Gly Ile Pro Ala Asn Ala Thr Asn Leu Thr Leu
 65                  70                  75                  80

Thr Ile Asn His Ile Ala Gly Ile Ser Pro Ala Ser Phe His Arg Leu
                85                  90                  95

Asp His Leu Val Glu Ile Asp Phe Arg Cys Asn Cys Val Pro Val Arg
                100                 105                 110

Leu Gly Pro Lys Asp Asn Val Cys Thr Lys Arg Leu Gln Ile Lys Pro
            115                 120                 125

Asn Ser Phe Ser Lys Leu Thr Tyr Leu Lys Ser Leu Tyr Leu Asp Gly
130                 135                 140

Asn Gln Leu Leu Glu Ile Pro Gln Asp Leu Pro Pro Ser Leu Gln Leu
145                 150                 155                 160

Leu Ser Leu Glu Ala Asn Asn Ile Phe Leu Ile Met Lys Glu Asn Leu
                165                 170                 175

Thr Glu Leu Ala Asn Leu Glu Ile Leu Tyr Leu Gly Gln Asn Cys Tyr
            180                 185                 190

Tyr Arg Asn Pro Cys Asn Val Ser Phe Thr Ile Glu Lys Asp Ala Phe
            195                 200                 205

Leu Asn Met Arg Asn Leu Lys Leu Leu Ser Leu Lys Asp Asn Asn Ile
            210                 215                 220

Ser Ala Val Pro Thr Val Leu Pro Ser Ser Leu Thr Glu Leu Tyr Leu
225                 230                 235                 240

Tyr Asn Asn Ile Ile Thr Lys Ile Gln Glu Asp Asp Phe Asn Asn Leu
                245                 250                 255

Ser Gln Leu Gln Val Leu Asp Leu Ser Gly Asn Cys Pro Arg Cys Tyr
            260                 265                 270

Asn Val Pro Phe Pro Cys Thr Pro Cys Glu Asn Asn Ser Pro Leu Gln
            275                 280                 285

Ile Asp Pro Asn Ala Phe Asp Ala Leu Thr Glu Leu Gln Val Leu Arg
290                 295                 300

Leu His Ser Asn Ser Leu Gln His Val Pro Gln Arg Trp Phe Lys Asn
305                 310                 315                 320

Ile Asn Lys Leu Lys Glu Leu Asp Leu Ser Gln Asn Phe Leu Ala Lys
            325                 330                 335

Glu Ile Gly Asp Ala Lys Phe Leu His Leu Leu His Asn Leu Val Asn
            340                 345                 350

Leu Asp Leu Ser Phe Asn Tyr Asp Leu Gln Val Tyr His Ala Val Ile
            355                 360                 365

Asn Leu Ser Asp Ala Phe Ser Ser Leu Lys Lys Leu Lys Val Leu Arg
            370                 375                 380

Ile Lys Gly Tyr Val Phe Lys Glu Leu Asn Ser Leu Asn Leu Phe Pro
385                 390                 395                 400

Leu His Asn Leu Pro Asn Leu Glu Val Leu Asp Leu Gly Thr Asn Phe
                405                 410                 415

Ile Lys Ile Ala Asn Leu Ser Ile Phe Asn Gln Phe Lys Thr Leu Lys
            420                 425                 430
```

```
Phe Ile Asp Leu Ser Val Asn Lys Ile Ser Pro Ser Gly Asp Ser Pro
            435                 440                 445

Glu Gly Gly Phe Cys Ser Asn Arg Arg Thr Ser Val Glu Gly His Gly
    450                 455                 460

Pro Gln Val Leu Glu Thr Leu His Tyr Phe Arg Tyr Asp Glu Tyr Ala
465                 470                 475                 480

Arg Ser Cys Arg Ser Lys Ser Lys Glu Pro Pro Ser Phe Leu Pro Leu
                485                 490                 495

Asn Glu Asp Cys Tyr Met Tyr Gly Gln Thr Leu Asp Leu Ser Arg Asn
            500                 505                 510

Asn Ile Phe Phe Ile Lys Pro Ser Asp Phe Gln His Leu Ser Phe Leu
        515                 520                 525

Lys Cys Leu Asn Leu Ser Gly Asn Ser Ile Ser Gln Thr Leu Asn Gly
    530                 535                 540

Ser Glu Phe Gln Pro Leu Val Glu Leu Lys Tyr Leu Asp Phe Ser Asn
545                 550                 555                 560

Asn Arg Leu Asp Leu Leu Tyr Ser Thr Ala Phe Glu Glu Leu His Asn
                565                 570                 575

Leu Glu Val Leu Asp Ile Ser Ser Asn Ser His Tyr Phe Gln Ser Glu
            580                 585                 590

Gly Ile Thr His Met Leu Asn Phe Thr Lys Asn Leu Lys Val Leu Arg
        595                 600                 605

Lys Leu Met Met Asn Tyr Asn Asp Ile Ala Thr Ser Thr Ser Arg Thr
    610                 615                 620

Met Glu Ser Glu Ser Leu Gln Ile Leu Glu Phe Arg Gly Asn His Leu
625                 630                 635                 640

Asp Ile Leu Trp Arg Asp Gly Asp Asn Arg Tyr Leu Lys Phe Phe Lys
                645                 650                 655

Asn Leu Leu Asn Leu Glu Glu Leu Asp Ile Ser Glu Asn Ser Leu Ser
            660                 665                 670

Phe Leu Pro Leu Gly Val Phe Asp Ser Met Pro Pro Asn Leu Lys Thr
        675                 680                 685

Leu Ser Leu Ala Lys Asn Gly Leu Lys Ser Phe Ser Trp Glu Arg Leu
    690                 695                 700

Gln Ser Leu Lys Asn Leu Glu Thr Leu Asp Leu Ser Phe Asn Gln Leu
705                 710                 715                 720

Lys Thr Val Pro Glu Arg Leu Ser Asn Cys Ser Arg Ser Leu Lys Lys
                725                 730                 735

Leu Ile Leu Lys Asn Asn Gln Ile Arg Cys Leu Thr Lys Tyr Phe Leu
            740                 745                 750

Gln Gly Ala Phe Gln Leu Arg His Leu Asp Leu Ser Ser Asn Lys Ile
        755                 760                 765

Gln Val Ile Gln Lys Thr Ser Phe Pro Glu Asn Val Leu Asn Asn Leu
    770                 775                 780

Asn Ile Leu Phe Leu His His Asn Arg Phe Leu Cys Asn Cys Asp Ala
785                 790                 795                 800

Val Trp Phe Val Trp Trp Val Asn His Thr Glu Val Thr Ile Pro Tyr
                805                 810                 815

Leu Ala Thr Asp Val Thr Cys Met Gly Pro Gly Ala His Lys Gly Gln
            820                 825                 830

Ser Val Val Ser Leu Asp Leu Tyr Thr Cys Glu Leu Asp Leu Thr Asn
        835                 840                 845

Phe Ile Leu Phe Ser Leu Ser Ile Ser Ala Val Leu Ser Leu Met Met
```

Ile Thr Ile Ala Asn His Leu Tyr Phe Trp Asp Val Trp Tyr Ser Tyr
865                 870                 875                 880

His Phe Cys Lys Ala Lys Ile Lys Gly Tyr Arg Arg Leu Ile Ser Pro
                885                 890                 895

Asn Ser Cys Tyr Asp Ala Phe Ile Val Tyr Asp Thr Lys Asp Pro Ala
            900                 905                 910

Val Thr Glu Trp Val Leu Asp Glu Leu Val Ala Lys Leu Glu Asp Pro
        915                 920                 925

Arg Glu Lys Cys Phe Asn Leu Cys Leu Glu Glu Arg Asp Trp Leu Pro
    930                 935                 940

Gly Gln Pro Val Leu Glu Asn Leu Ser Gln Ser Ile Gln Leu Ser Lys
945                 950                 955                 960

Lys Thr Val Phe Val Met Thr Asp Lys Tyr Ala Lys Thr Glu Asn Phe
                965                 970                 975

Lys Ile Ala Phe Tyr Leu Ser His Gln Arg Leu Met Asp Glu Lys Val
            980                 985                 990

Asp Val Ile Ile Leu Ile Phe Leu Glu Lys Pro Leu Gln Lys Ser Lys
        995                 1000                1005

Phe Leu Gln Leu Arg Lys Arg Leu Cys Gly Ser Ser Val Leu Glu
    1010                1015                1020

Trp Pro Thr Asn Pro Gln Ala His Pro Tyr Phe Trp Gln Cys Leu
    1025                1030                1035

Lys Asn Ala Leu Ala Thr Asp Asn His Val Thr Tyr Ser Gln Val
    1040                1045                1050

Phe Lys Glu Thr Ala
    1055

<210> SEQ ID NO 44
<211> LENGTH: 23
<212> TYPE: PRT
<213> ORGANISM: artificial
<220> FEATURE:
<223> OTHER INFORMATION: scarmbled C98i

<400> SEQUENCE: 44

Tyr Gly Arg Lys Lys Arg Arg Gln Arg Arg Cys Leu Val Pro Asn
1               5                   10                  15

Asp Cys Arg Leu Val Asn His
            20

<210> SEQ ID NO 45
<211> LENGTH: 4
<212> TYPE: PRT
<213> ORGANISM: artificial
<220> FEATURE:
<223> OTHER INFORMATION: C98i motif RCNC

<400> SEQUENCE: 45

Arg Cys Asn Cys
1

<210> SEQ ID NO 46
<211> LENGTH: 4
<212> TYPE: PRT
<213> ORGANISM: artificial
<220> FEATURE:
<223> OTHER INFORMATION: RANC

<400> SEQUENCE: 46

Arg Ala Asn Cys
1

<210> SEQ ID NO 47
<211> LENGTH: 4
<212> TYPE: PRT
<213> ORGANISM: artificial
<220> FEATURE:
<223> OTHER INFORMATION: RANA

<400> SEQUENCE: 47

Arg Ala Asn Ala
1

<210> SEQ ID NO 48
<211> LENGTH: 4
<212> TYPE: PRT
<213> ORGANISM: artificial
<220> FEATURE:
<223> OTHER INFORMATION: RCNA

<400> SEQUENCE: 48

Arg Cys Asn Ala
1

<210> SEQ ID NO 49
<211> LENGTH: 7
<212> TYPE: PRT
<213> ORGANISM: artificial
<220> FEATURE:
<223> OTHER INFORMATION: Homo sapiens TLR7

<400> SEQUENCE: 49

Asp Phe Arg Cys Asn Cys Val
1               5

<210> SEQ ID NO 50
<211> LENGTH: 7
<212> TYPE: PRT
<213> ORGANISM: artificial
<220> FEATURE:
<223> OTHER INFORMATION: Mus TLR7

<400> SEQUENCE: 50

Asp Leu Arg Cys Asn Cys Val
1               5

<210> SEQ ID NO 51
<211> LENGTH: 7
<212> TYPE: PRT
<213> ORGANISM: artificial
<220> FEATURE:
<223> OTHER INFORMATION: Rattus TLR7

<400> SEQUENCE: 51

Asp Leu Arg Cys Asn Cys Val
1               5

<210> SEQ ID NO 52
<211> LENGTH: 7
<212> TYPE: PRT
<213> ORGANISM: artificial
<220> FEATURE:
<223> OTHER INFORMATION: Pullum TLR7

<400> SEQUENCE: 52

```
Asp Leu Arg Cys Asn Cys Val
1               5

<210> SEQ ID NO 53
<211> LENGTH: 7
<212> TYPE: PRT
<213> ORGANISM: artificial
<220> FEATURE:
<223> OTHER INFORMATION: Ranae TLR7

<400> SEQUENCE: 53

Asp Phe Arg Cys Asn Cys Val
1               5

<210> SEQ ID NO 54
<211> LENGTH: 7
<212> TYPE: PRT
<213> ORGANISM: artificial
<220> FEATURE:
<223> OTHER INFORMATION: Porcus TLR7

<400> SEQUENCE: 54

Asp Phe Arg Cys Asn Cys Ile
1               5

<210> SEQ ID NO 55
<211> LENGTH: 7
<212> TYPE: PRT
<213> ORGANISM: artificial
<220> FEATURE:
<223> OTHER INFORMATION: Salmo TLR7

<400> SEQUENCE: 55

Asp Phe Arg Cys Asn Cys Ile
1               5

<210> SEQ ID NO 56
<211> LENGTH: 7
<212> TYPE: PRT
<213> ORGANISM: artificial
<220> FEATURE:
<223> OTHER INFORMATION: Danio rerio TLR7

<400> SEQUENCE: 56

Asp Leu Arg Cys Asn Cys Val
1               5

<210> SEQ ID NO 57
<211> LENGTH: 21
<212> TYPE: PRT
<213> ORGANISM: artificial
<220> FEATURE:
<223> OTHER INFORMATION: C98i with TAT

<400> SEQUENCE: 57

Tyr Gly Arg Lys Lys Arg Arg Gln Arg Arg Asp Leu Arg Cys Asn
1               5                   10                  15

Cys Val Pro Val Leu
            20
```